(12) United States Patent
Martel et al.

(10) Patent No.: US 9,518,064 B2
(45) Date of Patent: Dec. 13, 2016

(54) IMIDAZOTHIADIAZOLE AND IMIDAZOPYRIDAZINE DERIVATIVES AS PROTEASE ACTIVATED RECEPTOR 4 (PAR4) INHIBITORS FOR TREATING PLATELET AGGREGATION

(71) Applicants: BRISTOL-MYERS SQUIBB COMPANY, Princeton, NJ (US); Universite De Montreal, Montreal (CA)

(72) Inventors: Alain Martel, Delson (CA); François Tremblay, Laval (CA); Anne Marinier, Kirkland (CA); Eldon Scott Priestley, Yardley, PA (US); Shoshana L. Posy, Highland Park, NJ (US); R. Michael Lawrence, Yardley, PA (US); Michael M. Miller, Pennington, NJ (US)

(73) Assignees: Bristol-Myers Squibb Company, Princeton, NJ (US); Universite De Montreal, Quebec (CA)

( * ) Notice: Subject to any disclaimer, the term of this patent is extended or adjusted under 35 U.S.C. 154(b) by 38 days.

(21) Appl. No.: 14/396,831

(22) PCT Filed: Apr. 24, 2013

(86) PCT No.: PCT/US2013/037884
§ 371 (c)(1),
(2) Date: Oct. 24, 2014

(87) PCT Pub. No.: WO2013/163241
PCT Pub. Date: Oct. 31, 2013

(65) Prior Publication Data
US 2015/0119390 A1    Apr. 30, 2015

Related U.S. Application Data

(60) Provisional application No. 61/638,567, filed on Apr. 26, 2012.

(51) Int. Cl.
| | | |
|---|---|---|
| *C07D 513/04* | (2006.01) | |
| *C07D 487/04* | (2006.01) | |
| *A61K 38/12* | (2006.01) | |
| *A61K 31/433* | (2006.01) | |
| *A61K 31/437* | (2006.01) | |
| *A61K 31/4439* | (2006.01) | |
| *A61K 31/497* | (2006.01) | |
| *A61K 31/506* | (2006.01) | |
| *A61K 31/513* | (2006.01) | |
| *A61K 31/5377* | (2006.01) | |

(52) U.S. Cl.
CPC ........... *C07D 513/04* (2013.01); *C07D 487/04* (2013.01); *A61K 31/433* (2013.01); *A61K 31/437* (2013.01); *A61K 31/4439* (2013.01); *A61K 31/497* (2013.01); *A61K 31/506* (2013.01); *A61K 31/513* (2013.01); *A61K 31/5377* (2013.01); *A61K 38/12* (2013.01)

(58) Field of Classification Search
CPC .......................... C07D 513/04; C07D 487/04
See application file for complete search history.

(56) References Cited

U.S. PATENT DOCUMENTS

| | | | |
|---|---|---|---|
| 6,673,815 B2 | 1/2004 | Devasthale et al. | |
| 7,230,019 B2* | 6/2007 | Jaquith | C07D 513/04 |
| | | | 424/451 |
| 2007/0155779 A1 | 7/2007 | Verhoest | |

FOREIGN PATENT DOCUMENTS

| | | |
|---|---|---|
| CA | 2 584 745 A1 | 10/2007 |
| CN | 102372701 | 3/2012 |

(Continued)

OTHER PUBLICATIONS

Abdel-Wahab, B.F. et al., "Synthesis of New 2-Naphthyl Ethers and Their Protective Activities against DNA Damage Induced by Bleomycin-Iron", Chem. Pharm. Bull., vol. 57, No. 12, pp. 1348-1351 (2009).

Barlin, G.B. et al., "Imidazo[1,2-*b*]pyridazines. XIII. Syntheses and Central Nervous System Activities of Some 2-Benzyl(phenethyl, biphenyl-4'-yl, 6'-methylnaphthalen-2'-yl, t-butyl and cyclohexyl)-3-methoxy(acylaminomethyl and dimethylaminomethyl)-6-(variously substituted)imidazo[1,2-*b*]pyridazines", Aust. J. Chem., vol. 45, pp. 1281-1300 (1992).

Bhovi, V.K. et al., "Synthesis of Some Mannich Bases and Novel Benzofuran Derivatives Containing Imidazo[2,1-b][1,3,4]thiadiazoles as Biological Agents", Current Chemical Biology, vol. 4, No. 2, pp. 145-150 (2010).

CAS Registry No. 1096958-08-5, Entered STN: Jan. 28, 2009.
CAS Registry No. 1097016-53-9, Entered STN: Jan. 28, 2009.
CAS Registry No. 1097037-01-8, Entered STN: Jan. 28, 2009.
CAS Registry No. 1097163-93-3, Entered STN: Jan. 28, 2009.

Rani, R. et al., "Microwave Assisted Facile Synthesis and Antimicrobial Activity of Some New Imidazo[2,1-*b*]-1,3,4-thiadiazoles", Indian Journal of Heterocyclic Chemistry, vol. 18, pp. 121-124 (2008).

(Continued)

*Primary Examiner* — Matthew Coughlin
(74) *Attorney, Agent, or Firm* — Hoffman & Baron, LLP

(57) ABSTRACT

The present invention provides imidazothiadiazole compounds of Formula (I); Wherein W, Y, $R^0$, $R^2$, $R^4$, $R^a$, $R^b$, $X^1$, $X^2$, $X^3$ and $X^4$ are as defined herein, or a stereoisomer, tautomer, pharmaceutically acceptable salt, prodrug ester or solvate form thereof, wherein all of the variables are as defined herein. These compounds are inhibitors of platelet aggregation and thus can be used as medicaments for treating or preventing thromboembolic disorders.

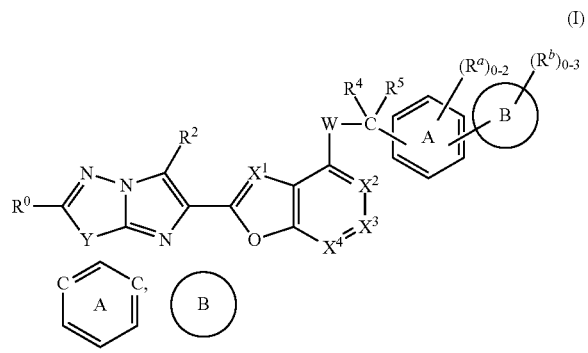

18 Claims, 1 Drawing Sheet

(56) References Cited

FOREIGN PATENT DOCUMENTS

| | | |
|---|---|---|
| DE | 2823686 | 12/1979 |
| DE | 102006054757 | 5/2008 |
| EP | 0 005 783 A1 | 12/1979 |
| EP | 0041215 | 12/1981 |
| EP | 0 158 012 A1 | 10/1985 |
| EP | 0 185 345 A1 | 6/1986 |
| EP | 0 299 209 A2 | 1/1989 |
| EP | 0 379 979 A1 | 8/1990 |
| EP | 0497258 | 8/1992 |
| EP | 2 518 066 A1 | 10/2012 |
| IN | 903/MUM/2004 | 6/2007 |
| WO | WO 99/46232 | 9/1999 |
| WO | WO 01/27118 | 4/2001 |
| WO | WO 01/27119 | 4/2001 |
| WO | WO 01/81344 | 11/2001 |
| WO | WO 03/040114 | 5/2003 |
| WO | WO 03/051890 | 6/2003 |
| WO | WO 2004/063159 | 7/2004 |
| WO | WO 2004/111060 | 12/2004 |
| WO | WO 2004/111061 | 12/2004 |
| WO | WO 2005/048948 | 6/2005 |
| WO | WO 2005/048953 | 6/2005 |
| WO | WO 2005/080355 | 9/2005 |
| WO | WO 2007/002540 | 1/2007 |
| WO | WO 2007/039177 | 4/2007 |
| WO | WO 2007/106469 | 9/2007 |
| WO | WO 2007/118318 | 10/2007 |
| WO | WO 2008/083238 | 7/2008 |
| WO | WO 2008/104279 | 9/2008 |
| WO | WO 2008/141249 | 11/2008 |
| WO | WO 2009/017954 | 2/2009 |
| WO | WO 2009/023179 | 2/2009 |
| WO | WO 2009/027733 | 3/2009 |
| WO | WO 2009/040507 | 4/2009 |
| WO | WO 2009/079683 | 7/2009 |
| WO | WO 2009/123992 | 10/2009 |
| WO | WO 2010/036629 | 4/2010 |
| WO | WO 2010/075376 | 7/2010 |
| WO | WO 2011/074658 | 6/2011 |
| WO | WO 2012/021696 | 2/2012 |
| WO | WO 2013/028670 | 2/2013 |
| WO | WO 2013/163244 | 10/2013 |
| WO | WO 2013/163279 | 10/2013 |
| WO | WO 2014/015167 | 1/2014 |

OTHER PUBLICATIONS

Tegginamath, G. et al., "Synthesis of novel imidazo[2,1-b][1,3,4]thiadiazoles appended to sydnone as anticancer agents", Medicinal Chemistry Research, vol. 22, pp. 4367-4375 (2013).

Banville et al., U.S. Appl. No. 14/396,771, filed Oct. 24, 2014.
Lawrence et al., U.S. Appl. No. 14/396,807, filed Oct. 24, 2014.
Beresneva, Tatjana, et al., "Palladium-catalyzed synthesis of novel tetra-and penta-cyclic biologically active benzopyran-and pyridopyran-containing heterocyclic systems"; Arkivoc 2013 (ix) pp. 185-194.
Terme, Thierry, et al., "Synthesis of 2-Substituted-3-nitroimidazo[1,2-b]pyridazines as Potential Biologically Active Agents", J. Heterocyclic Chem., 39, pp. 173-177, 2002.
Barlin, Gordon B. et al., "Imidazo[1,2-b]pyridazines: Syntheses and Interaction with Central and Peripheral-Type (Mitochondrial) Benzodiazepine Receptors", J. Heterocyclic Chem., 35, pp. 1205-1217, 1998.
Barlin, Gordon B. et al., "Imidazo[1,2-b]pyridazines. XX Syntheses of Some 3-Acylaminomethyl-6-(chloro, fluoro, methoxy, methylthio, phenoxy and phenylthio)-2-(phenyl,4-t-butylphenyl, 4-cyclohexylphenyl, β-naphthyl and styryl)imidazo[1,2-b]pyridazines and Their Interaction with Central and Peripheral-Type Benzodiazepine Receptors", Aust. J. Chem, 1996, 49 pp. 451-461.
Barlin, Gordon B. et al., Imidazo[1,2-b]pyridazines. XIX Syntheses and Central Nervous System Activities of Some 6-Arylthio(aryloxy and alkylthio)-3-(acetamidomethyl, benzamidomethyl, methoxy and unsubstituted)-2-arylimidazo[1,2-b]pyridazines, Aust. J. Chem, 1996, 49 pp. 443-449.
Matyus, Peter, et al., "Ligands for the Central Benzodiazepine Receptor: Structure-Affinity Relationship Studies on Imidazo[1,2-b]pyridazines", Aust. J. Chem, 1996, 49 pp. 435-442.
Davies, Les P., et al., "New Imidazo[1,2-b]Pyridazine Ligands for Peripheral Type Benzodiazepine Receptors on Mitochondria and Monocytes", Life Sciences, vol. 57, No. 25, pp. 381-386, 1995.
Barlin, Gordon B. et al., "Imidazo[1,2-b]pyridazines. XVI Synthesis and Central Nervous System Activities of Some 6-(Chloro, Alkylthio, Phenylthio, Benzylthio or Pyridinylmethylthio)-3-(unsubstituted, benzamidomethyl or methoxy)-2-(styryl or benzoyl)imidazo[1,2-b]pyridazines", Aust. J. Chem, 1994, 47 pp. 1989-1999.
STN Database Record for RN 1177489-39-2, database entry date Aug. 28, 2009.
STN Database Record for RN 1177349-45-9, database entry date Aug. 28, 2009.
STN Database Record for RN 1097163-93-3, database entry date Jan. 28, 2009.
STN Database Record for RN 1096958-09-6, database entry date Jan. 28, 2009.
STN Database Record for RN 1096958-08-5, database entry date Jan. 28, 2009.

\* cited by examiner

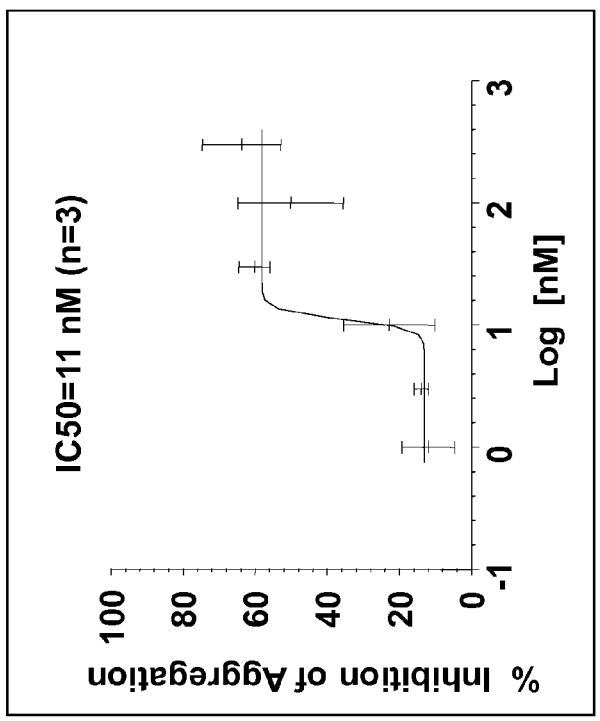
Fig 2. Inhibition of Platelet Aggregation Dose-Response Curve
Example 13
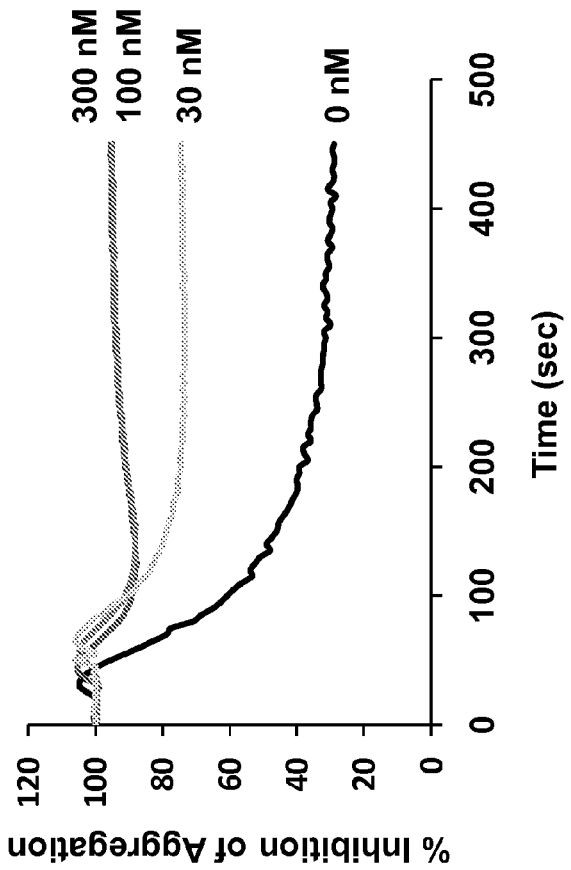
Fig 1. Human Washed Platelet Aggregation Induced by 1.5 nM Alpha-Thrombin
Example 13

IMIDAZOTHIADIAZOLE AND IMIDAZOPYRIDAZINE DERIVATIVES AS PROTEASE ACTIVATED RECEPTOR 4 (PAR4) INHIBITORS FOR TREATING PLATELET AGGREGATION

CROSS REFERENCES TO RELATED APPLICATIONS

This application is a 371 of International Application No. PCT/US2013/037884, filed on Apr. 24, 2013, which claims the benefit of U.S. Provisional Application Ser. No. 61/638,567, filed on Apr. 26, 2012, which is hereby incorporated by reference in its entirety.

FIELD OF THE INVENTION

The present invention provides novel imidazothiadiazoles and analogues thereof, which are inhibitors of platelet aggregation and which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., Nature, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4 Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., N. Eng. J. Med., 366(1):20-33 (2012). Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", J. Med. Chem., 44(22):3746-3749 (2001) discloses in the abstract that the compound

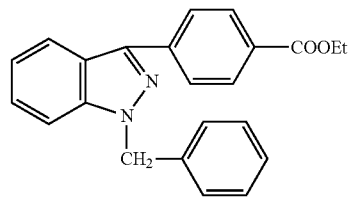

"was found to be a selective and potent inhibitor or protease-activated receptor type 4 (PAR4)-dependent platelet activation."

Compound 58 is also referred to as YD-3 in Wu, C-C. et al., "Selective Inhibition of Protease-activated Receptor 4-dependent Platelet Activation by YD-3", Thromb. Haemost., 87:1026-1033 (2002). Also, see Chen, H. S. et al., "Synthesis and platelet activity", J. Bioorg. Med. Chem., 16:1262-1278 (2008).

EP1166785 A1 and EP0667345 disclose various pyrazole derivatives which are useful as inhibitors of platelet aggregation.

SUMMARY OF THE INVENTION

In has been found that imidazothiadiazole compounds in accordance with the present invention are PAR4 antagonists which inhibit platelet aggregation in gamma-thrombin induced platelet aggregation assays. Moreover, a compound(s) of the present invention has been shown to inhibit platelet aggregation in an alpha-thrombin induced platelet aggregation assay.

Accordingly, the present invention provides novel imidazothiadiazoles, and analogues thereof, which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

BRIEF DESCRIPTION OF THE FIGURES

FIG. 1 is a graph which shows effectiveness of the Example 13 compound in inhibiting aggregation of human washed platelets stimulated by 1.5 nM alpha-thrombin over time; and FIG. 2 is a graph which shows the $IC_{50}$ of the Example 13 compound in inhibiting alpha-thrombin-induced platelet aggregation.

DETAILED DESCRIPTION

In one embodiment, the present invention provides imidazothiadiazole compounds, stereoisomers, tautomers, salts, solvates or prodrugs thereof, of Formula I having the structure:

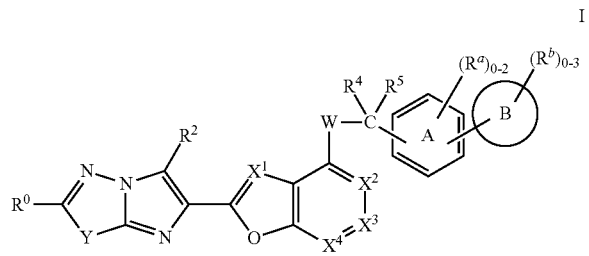

I or a stereoisomer, tautomer, pharmaceutically acceptable salt, solvate or prodrug ester thereof, wherein:
W is O or S;
$R^0$ is $R^1$ or $R^{1a}$;
Y is S or $—CR^8=CR^9—$;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
$C_1$-$C_4$ alkylthio,
$C_1$-$C_4$ alkylNH—,
$(C_1$-$C_4$ alkyl$)_2$N—,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl,
halo-$C_1$-$C_2$ alkoxy,
CN, and
OH;
provided that at least one of $R^{1a}$, $R^8$ and $R^9$ is other than H;
$R^2$ is selected from the group consisting of:
H,
halo,
$C_1$-$C_4$ alkyl,
$C_1$-$C_4$ alkoxy, and
cyano;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, which contains 1 to 5 halogens, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and $—(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H, $C_1$-$C_6$ alkyl, halo-$C_1$-$C_3$ alkyl, hydroxy-$C_1$-$C_3$ alkyl, and $C_1$-$C_3$ alkoxy-$C_1$-$C_3$ alkyl; or $R^4$ and $R^5$ can be taken together with the carbon to which they are attached to form a $C_3$-$C_7$ cycloalkyl ring;

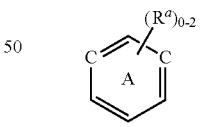

is phenyl or a 6-membered heteroaryl ring, at least one ring member of which is a nitrogen, which

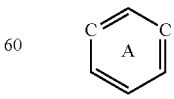

ring is substituted with 0 to 2 $R^a$ groups;
B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2$ $NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2$ $NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, $(C=O)OR^{14}$, $C_6$-$C_{10}$ aryl, 5-6-membered heteroaryl, 4- to 10-membered heterocyclyloxy and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
$C_2$-$C_4$ alkynyl,
—$(CR^{14}R^{14})_n{}^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n{}^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n{}^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n{}^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
$C_1$-$C_4$-alkylcarbonylamino-$C_1$-$C_4$-alkyl,
di-$C_1$-$C_4$-alkoxy-$C_1$-$C_4$-alkyl,
di-$C_1$-$C_4$-alkylaminophenyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_n{}^1$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^{10}$ is selected from the group consisting of $C_1$-$C_4$ alkyl, halo, $C_1$-$C_4$ alkoxy, and halo-$C_1$-$C_2$-alkyl, which contains 1 to 5 halogens, where halo is F or Cl;

$n^1$, at each occurrence, is selected from 0, 1, 2, 3, 4 or 5; and p, at each occurrence, is selected from 0, 1 and 2.

In one embodiment, the present invention provides compounds, stereoisomers, tautomers, salts, solvates or prodrugs thereof, wherein the compounds are compounds of Formula IAA:

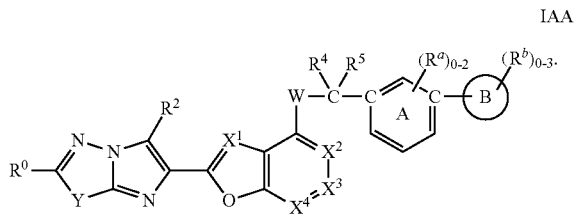

IAA

In another embodiment, the present invention provides compounds, stereoisomers, tautomers, salts, solvates or prodrugs thereof, wherein W is O.

In another embodiment, the present invention provides compounds, stereoisomers, tautomers, salts, solvates or prodrugs thereof, wherein:

W is O;
$R^0$ is $R^1$ or $R^{1a}$;
Y is S or —$CR^8$=$CR^9$—;

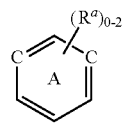

is phenyl or a 6-membered heteroaryl ring, at least one ring member of which is a nitrogen, which

ring is substituted with 0 to 2 $R^a$ groups;

 is attached at the meta position of

and is selected from the group consisting of $C_6$-$C_{10}$ aryl ring, a 5- to 10-membered heteroaryl ring, a 4- to 10-membered heterocyclyl ring or a $C_3$-$C_6$-membered cycloalkyl ring, wherein each  rings is substituted with 0 to 3 $R^b$ groups;

$R^1$ is selected from the group consisting of:
halo,
$C_1$-$C_4$ alkyl,
$C_1$-$C_4$ alkoxy,
halo-$C_1$-$C_2$-alkyl, which contains 1 to 5 halogens, where halo is F or Cl, and $C_1$-$C_4$ alkylthio;

$R^{1a}$ is selected from the group consisting of:
H,
halo,
$C_1$-$C_4$ alkyl,
$C_1$-$C_4$ alkoxy,
halo-$C_1$-$C_2$-alkyl, which contains 1 to 5 halogens, and
$C_1$-$C_4$ alkylthio;

$R^8$ and $R^9$ are independently selected from the group consisting of:
H,
$C_1$-$C_4$ alkyl,
halo,
$C_1$-$C_4$ alkoxy,
$CF_3$,
$CF_3O$,
$CHF_2$, and
OH;
provided that at least one of $R^{1a}$, $R^8$ and $R^9$ is other than H;

$R^2$ is selected from the group consisting of:
H,
halo,
$C_1$-$C_4$ alkyl,
$C_1$-$C_4$ alkoxy, and
cyano;

$X^1$ is selected from the group consisting of CH, N or $CR^{10}$;

$X^2$, $X^3$ and $X^4$ are independently selected from $CR^3$ or N;

$R^3$ is selected from the group consisting of H, $C_1$-$C_4$ alkoxy, halo, $CF_3O$, $CHF_2O$, and halo-$C_1$-$C_2$-alkyl, which contains 1 to 5 halogens;

$R^4$ and $R^5$ are independently selected from H and $C_1$-$C_6$ alkyl, or $R^4$ and $R^5$ can be taken together with the carbon to which they are attached to form a $C_3$-$C_6$ cycloalkyl ring;

$R^a$ is, at each occurrence, independently selected from the group consisting of:
H, halo, $OCF_3$, $NR^6R^7$, $OCHF_2$, halo-$C_1$-$C_2$-alkyl substituted with 1 to 5 fluorines, $CF_3$,
$C_1$-$C_4$ alkyl,
$C_1$-$C_4$ alkoxy,
$C_1$-$C_4$ alkylthio,
OH,
CN,
$NO_2$,
COOH,
$C_1$-$C_4$ alkoxycarbonyl,
$C(=O)NR^6R^7$,
$C_1$-$C_4$ alkylsulfonyl, and
$S(=O)_2NR^6R^7$;

$R^b$ is, at each occurrence, independently selected from the group consisting of:
H, halo, $OCF_3$, $NR^6R^7$, $OCHF_2$, halo-$C_1$-$C_2$-alkyl substituted with 1 to 5 fluorines, $CF_3$,
$C_1$-$C_4$ alkyl,
$C_1$-$C_4$ alkoxy,
$C_1$-$C_4$ alkylthio,
OH,
CN,
$NO_2$,
COOH,
$C_1$-$C_4$ alkoxycarbonyl,
$C(=O)NR^6R^7$,
$C_1$-$C_4$ alkylsulfonyl, and
$S(=O)_2NR^6R^7$; or $R^6$ and $R^7$ are, independently, at each occurrence, selected from the group consisting of:
H,
$C_1$-$C_4$ alkyl, and
—$(CH_2)_{n^1}$phenyl,
alternatively, $R^6$ and $R^7$, when attached to the same nitrogen, combine to form a 4- to 6-membered heterocyclic ring containing carbon atoms and 1 to 2 additional heteroatoms selected from N, $NR^{13}$, O and $S(O)_p$;

$R^{13}$ is independently, at each occurrence, selected from the group consisting of H, $C_1$-$C_4$ alkyl and —$(CH_2)$phenyl;

$n^1$, at each occurrence, is selected from 0, 1, 2, 3, 4 and 5; and p, at each occurrence, is selected from 0, 1 and 2.

In yet another embodiment, the present invention provides compounds, stereoisomers, tautomers, salts, solvates or prodrugs thereof, wherein:

Y is S or CH=CH—;
$X^1$ is CH or N;
$X^2$, $X^3$ and $X^4$ are each independently $CR^3$;
$R^0$ is $R^1$ or $R^{1a}$;
$R^1$ and $R^{1a}$ are independently selected from the group consisting of:
$C_1$-$C_4$ alkyl,
$C_1$-$C_4$ alkylthio,
$C_1$-$C_4$ alkoxy, and
halo-$C_1$-$C_2$-alkyl which contains 1 to 5 halogens;
$R^2$ is H;
$R_3$ is selected from the group consisting of:
$C_1$-$C_4$ alkoxy,
H, and
halo; and
$R^4$ and $R^5$ are each H.

In still yet another embodiment, the present invention provides compounds, stereoisomers, tautomers, salts, solvates or prodrugs thereof, wherein the compounds are compounds of Formula IA and IB:

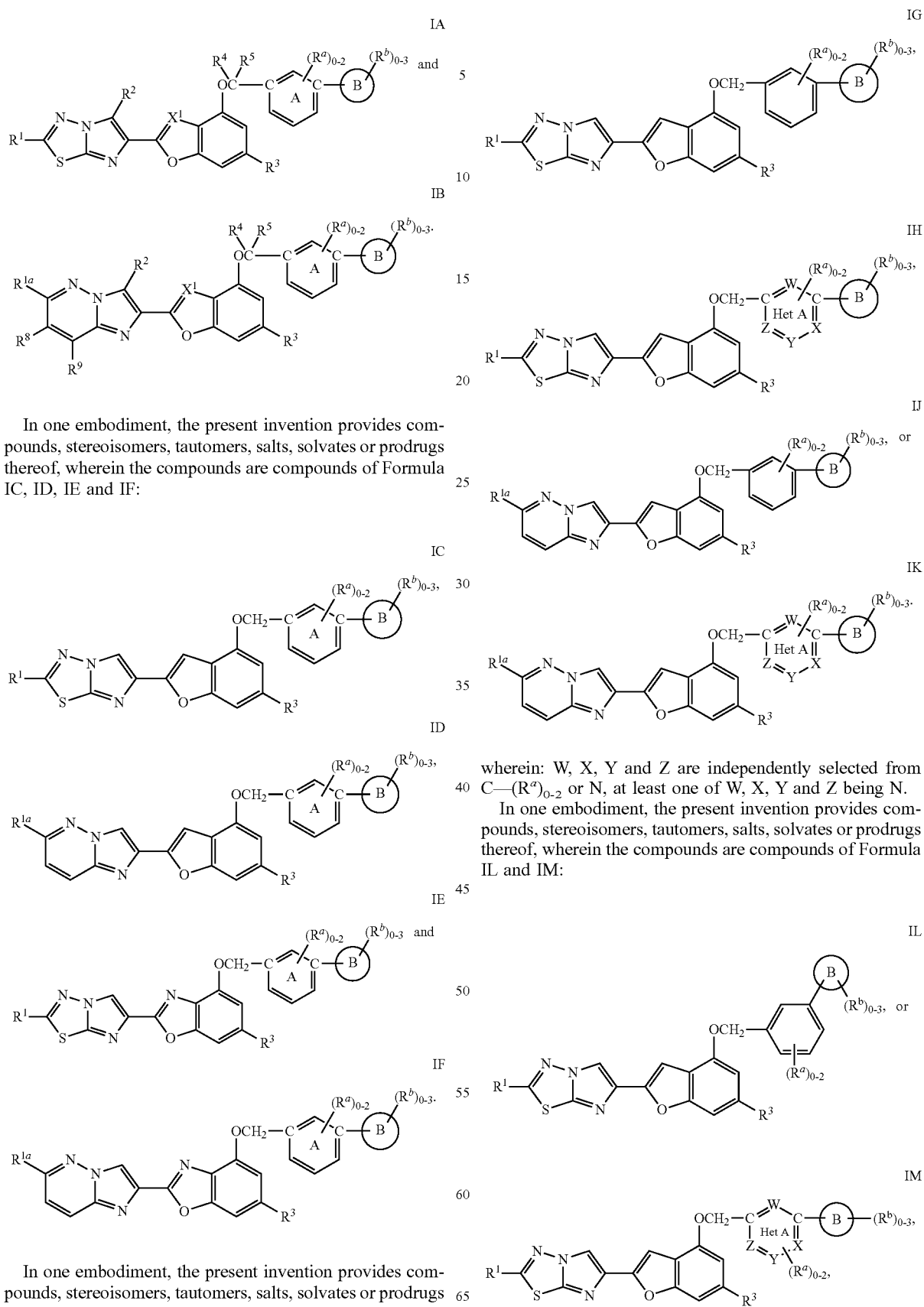

In one embodiment, the present invention provides compounds, stereoisomers, tautomers, salts, solvates or prodrugs thereof, wherein the compounds are compounds of Formula IC, ID, IE and IF:

In one embodiment, the present invention provides compounds, stereoisomers, tautomers, salts, solvates or prodrugs thereof, wherein the compounds are compounds of Formula IG, IH, IJ and IK:

wherein: W, X, Y and Z are independently selected from $C-(R^a)_{0-2}$ or N, at least one of W, X, Y and Z being N.

In one embodiment, the present invention provides compounds, stereoisomers, tautomers, salts, solvates or prodrugs thereof, wherein the compounds are compounds of Formula IL and IM:

wherein:

Het A is selected from the group consisting of pyridyl, pyrazinyl, pyrimidinyl, pyridazinyl, and triazinyl; and Ⓑ is selected from the group consisting of phenyl, naphthyl, pyridyl, pyrimidinyl, pyrrolyl, pyrazolyl, thienyl, thiazolyl,

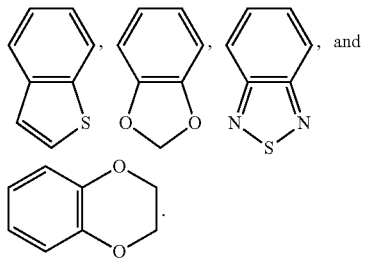

In one embodiment, the present invention provides compounds, stereoisomers, tautomers, salts, solvates or prodrugs thereof, wherein the compounds are compounds of Formula IP and IQ:

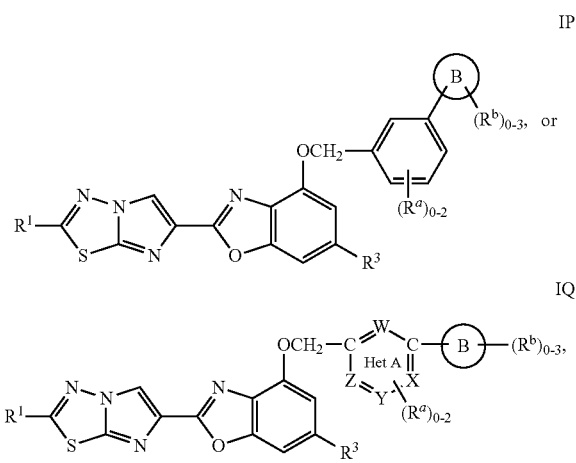

wherein:

Het A is selected from the group consisting of pyridyl, pyrazinyl, pyrimidinyl, pyridazinyl, and triazinyl; and Ⓑ is selected from the group consisting of phenyl, naphthyl pyridyl, pyrimidinyl, pyrrolyl, pyrazolyl, thienyl, thiazolyl,

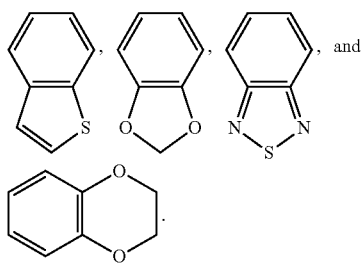

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IB.

In one embodiment, the present invention provides compounds, stereoisomers, tautomers, salts, solvates or prodrugs thereof, wherein the compounds are compounds of Formula IC.

In one embodiment, the present invention provides compounds, stereoisomers, tautomers, salts, solvates or prodrugs thereof, wherein the compounds are compounds of Formula ID.

In one embodiment, the present invention provides compounds, stereoisomers, tautomers, salts, solvates or prodrugs thereof, wherein the compounds are compounds of Formula IE.

In one embodiment, the present invention provides compounds, stereoisomers, tautomers, salts, solvates or prodrugs thereof, wherein the compounds are compounds of Formula IF.

In one embodiment, the present invention provides compounds, stereoisomers, tautomers, salts, solvates or prodrugs thereof, wherein the compounds are compounds of Formula IG.

In one embodiment, the present invention provides compounds, stereoisomers, tautomers, salts, solvates or prodrugs thereof, wherein the compounds are compounds of Formula IH.

In one embodiment, the present invention provides compounds, stereoisomers, tautomers, salts, solvates or prodrugs thereof, wherein the compounds are compounds of Formula IJ.

In one embodiment, the present invention provides compounds, stereoisomers, tautomers, salts, solvates or prodrugs thereof, wherein the compounds are compounds of Formula IK.

In one embodiment, the present invention provides compounds, stereoisomers, tautomers, salts, solvates or prodrugs thereof, wherein the compounds are compounds of Formula IL.

In one embodiment, the present invention provides compounds, stereoisomers, tautomers, salts, solvates or prodrugs thereof, wherein the compounds are compounds of Formula IM.

In one embodiment, the present invention provides compounds, stereoisomers, tautomers, salts, solvates or prodrugs thereof, wherein the compounds are compounds of Formula IP.

In one embodiment, the present invention provides compounds, stereoisomers, tautomers, salts, solvates or prodrugs thereof, wherein the compounds are compounds of Formula IQ.

In yet another embodiment, the present invention provides compounds, stereoisomers, tautomers, salts, solvates or prodrugs thereof, wherein:

$R^a$ is selected from the group consisting of H, halo, $OCF_3$, $OCHF_2$, $NR^6R^7$, $C_1$-$C_4$ alkoxycarbonyl, (C=O)$NR^6R^7$, $C_1$-$C_4$ alkylsulfonyl, S(=O)$_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, and $C_3$-$C_6$-cycloalkyl; and $R^b$ is selected from the group consisting of H, halo, $OCF_3$, $OCHF_2$, $NR^6R^7$, $C_1$-$C_4$ alkoxycarbonyl, (C=O)$NR^6R^7$, $C_1$-$C_4$ alkylsulfonyl, S(=O)$_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, and $C_3$-$C_6$-cycloalkyl, In yet another embodiment, the present invention provides compounds, stereoisomers, tautomers, salts, solvates or prodrugs thereof, wherein $R^a$ and $R^b$ are independently selected from the group consisting of:

OH;
CN;
$NO_2$;
$NR^6R^7$;
carboxy;
halo;
$OCF_3$;
$OCHF_2$;
$C_1$-$C_4$ alkyl;
halo-$C_1$-$C_2$-alkyl substituted with 1 to 5 fluorines;
$C_1$-$C_4$ alkoxy;
$C_1$-$C_4$ alkoxycarbonyl;
C(=O)$NR^6R^7$;
$C_1$-$C_4$ alkylsulfonyl;
S(=O)$_2NR^6R^7$;
aryl substituted by 0 to 3 groups independently selected from the group consisting of halo, $C_1$-$C_4$ alkoxy, $C_1$-$C_4$ alkyl, cyclopropyl, $CF_3$, $OCF_3$, $CF_2CH_3$, $OCHF_2$, and cyano;
aryloxy, wherein the aryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;
arylthio, wherein the aryl is substituted by 0 to 3 groups independently selected from the group consisting of the group consisting of halo, $C_1$-$C_4$ alkoxy, $C_1$-$C_4$ alkyl, cyclopropyl, $CF_3$, $OCF_3$, $OCHF_2$, and cyano;
aryl-$C_1$-$C_4$-alkoxy, wherein the aryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;
$C_3$-$C_6$ cycloalkyl substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;
$C_3$-$C_6$ cycloalkoxy substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;
5- to 10-membered heteroaryl-$C_1$-$C_4$-alkyl, wherein the heteroaryl is substituted by 0 to 3 groups independently selected from the group consisting of halo, $C_1$-$C_4$ alkoxy, $C_1$-$C_3$ alkyl, cyclopropyl, $CF_3$, $OCF_3$, $OCHF_2$, and cyano;
5- to 10-membered heteroaryl-$C_1$-$C_4$-alkoxy, wherein the heteroaryl is substituted by 0 to 3 groups independently selected from the group consisting of halo, $C_1$-$C_4$ alkoxy, $C_1$-$C_3$ alkyl, cyclopropyl, $CF_3$, $OCF_3$, $OCHF_2$, and cyano;
aryl-$C_1$-$C_4$-alkyl, wherein the aryl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;
4- to 10-membered heterocyclylcarbonyl, wherein the heterocyclyl is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;

4- to 10-membered heterocyclyl which is substituted by 0 to 3 groups independently selected from the group consisting of halo, $C_1$-$C_4$ alkoxy, $C_1$-$C_4$ alkyl, cyclopropyl, $CF_3$, $OCF_3$, $OCHF_2$, and cyano;

4- to 10-membered heterocyclyl-$C_1$-$C_4$-alkyl, wherein the heterocyclyl is substituted by 0 to 3 groups independently selected from the group consisting of halo, $C_1$-$C_4$ alkoxy, $C_1$-$C_3$ alkyl, cyclopropyl, $CF_3$, $OCF_3$, $OCHF_2$, and cyano; and 4- to 10-membered heterocyclyl-$C_1$-$C_4$-alkoxy, wherein the heterocyclyl is substituted by 0 to 3 groups independently selected from the group consisting of halo, $C_1$-$C_4$ alkoxy, $C_1$-$C_3$ alkyl, cyclopropyl, $CF_3$, $OCF_3$, $OCHF_2$, and cyano.

In yet another embodiment, the present invention provides compounds, stereoisomers, tautomers, salts, solvates or prodrugs thereof, wherein

is selected from the group consisting of phenyl, pyridyl, pyrazinyl, pyrimidinyl, pyridazinyl, and triazinyl.

In still yet another embodiment, the present invention provides compounds, stereoisomers, tautomers, salts, solvates or prodrugs thereof, wherein  is selected from the group consisting of phenyl, naphthyl pyridyl, pyrimidinyl, pyrrolyl, pyrazolyl, thienyl, thiazolyl,

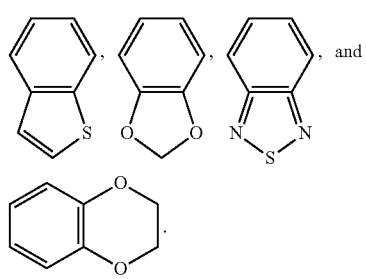

In one embodiment, the present invention provides compounds, stereoisomers, tautomers, salts, solvates or prodrugs thereof, wherein:

is selected from the group consisting of phenyl, pyridyl, pyrazinyl, pyrimidinyl, pyridazinyl, and triazinyl; and

 is selected from the group consisting of phenyl, naphthyl pyridyl, pyrimidinyl, pyrrolyl, pyrazolyl, thienyl, thiazolyl,

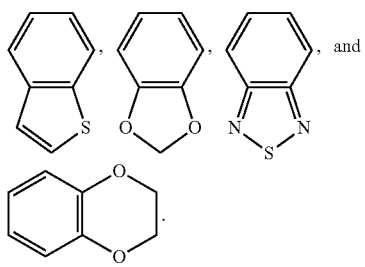

In another embodiment, the present invention provides compounds, stereoisomers, tautomers, salts, solvates or prodrugs thereof, wherein:

W is O or S;
$R^0$ is $R^1$ or $R^{1a}$;
Y is S or $-CR^8=CR^9-$;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
halo-$C_1$-$C_2$-alkyl, which contains 1 to 5 halogens, where halo is F or Cl,
halo-$C_3$-$C_4$ cycloalkyl, and
halo-$C_1$-$C_2$ alkoxy;
$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
halo-$C_1$-$C_2$-alkyl, which contains 1 to 5 halogens, where halo is F or Cl,
halo-$C_3$-$C_4$ cycloalkyl, and
halo-$C_1$-$C_2$ alkoxy;
$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl,
halo-$C_1$-$C_2$ alkoxy, and
OH;
provided that at least one of $R^{1a}$, $R^8$ and $R^9$ is other than H;
$R^2$ is selected from the group consisting of:
H,
halo,
$C_1$-$C_4$ alkyl, and
$C_1$-$C_4$ alkoxy;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, which contains 1 to 5 halogens, and $-(CH_2)_n{}^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H, $C_1$-$C_6$ alkyl, halo-$C_1$-$C_3$ alkyl, hydroxy-$C_1$-$C_3$ alkyl, and $C_1$-$C_3$ alkoxy-$C_1$-$C_3$ alkyl, or $R^4$ and $R^5$ can be taken together with the carbon to which they are attached to form a $C_3$-$C_7$ cycloalkyl ring;

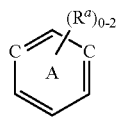

is phenyl or a 6-membered heteroaryl ring, at least one ring member of which is a nitrogen, which

ring is substituted with 0 to 2 $R^a$ groups;

B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, $(C=O)NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, $(C=O)NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, $(C=O)OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:

H,
C$_1$-C$_4$ alkyl,
halo-C$_1$-C$_4$-alkyl,
C$_1$-C$_4$ alkyleneoxy-C$_1$-C$_4$-alkylene,
C$_2$-C$_4$ alkenyl,
C$_2$-C$_4$ alkynyl,
—(CR$^{14}$R$^{14}$)$_n^1$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
—(CHR$^{13}$)$_n^1$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_n^1$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl,
—(CHR$^{13}$)$_n^1$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
C$_1$-C$_4$-alkylcarbonylamino-C$_1$-C$_4$-alkyl,
di-C$_1$-C$_4$-alkoxy-C$_1$-C$_4$-alkyl,
di-C$_1$-C$_4$-alkylaminophenyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl; and
alternatively, R$^6$ and R$^7$, when attached to the same nitrogen, combine to form a 4- to 6-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;
R$^{13}$ is independently, at each occurrence, selected from the group consisting of H, C$_1$-C$_6$ alkyl and —(CH$_2$)phenyl;
R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino, (C$_6$-C$_{10}$ arylcarbonylamino), and —(CH$_2$)$_n^1$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
R$^{10}$ is selected from the group consisting of C$_1$-C$_4$ alkyl, halo, C$_1$-C$_4$ alkoxy, and halo-C$_1$-C$_2$-alkyl, which contains 1 to 5 halogens, where halo is F or Cl;
n$^1$, at each occurrence, is selected from 0, 1, 2, 3, 4 or 5; and
p, at each occurrence, is selected from 0, 1 and 2.
In yet another embodiment, the present invention provides compounds, stereoisomers, tautomers, salts, solvates or prodrugs thereof, wherein:
W is O or S;
R$^0$ is R$^1$ or R$^{1a}$;
Y is S or —CR$^8$=CR$^9$—;
R$^1$ is independently selected from the group consisting of:
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_2$ alkoxy-C$_1$-C$_2$ alkyl,
tetrahydrofuran-2-yl;
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;
R$^{1a}$ is independently selected from the group consisting of:
H,
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_2$ alkoxy-C$_1$-C$_2$ alkyl,
tetrahydrofuran-2-yl;
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;
R$^8$ and R$^9$ are independently selected from the group consisting of:
H,
halo,
C$_1$-C$_4$ alkyl,
C$_1$-C$_4$ alkoxy,
halo-C$_1$-C$_2$ alkyl, and
halo-C$_1$-C$_2$ alkoxy;
provided that at least one of R$^{1a}$, R$^8$ and R$^9$ is other than H;
R$^2$ is selected from the group consisting of:
H,
halo,
C$_1$-C$_3$ alkyl, and
C$_1$-C$_2$ alkoxy;
X$^1$ is selected from the group consisting of CH, N or CR$^{10}$;
X$^2$, X$^3$ and X$^4$ are independently selected from CR$^3$ or N;
R$^3$ is selected from the group consisting of H, C$_1$-C$_4$ alkyl, C$_2$-C$_4$ alkenyl, C$_2$-C$_4$ alkynyl, C$_1$-C$_4$ alkoxy, C$_1$-C$_4$ alkylthio, halo, OH, CN, OCF$_3$, C$_1$-C$_2$-alkoxy-C$_1$-C$_2$-alkoxy, halo-C$_1$-C$_3$-alkyl, which contains 1 to 5 halogens, benzyloxy substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, and —(CH$_2$)$_n^1$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano;
R$^4$ and R$^5$ are independently selected from H, C$_1$-C$_6$ alkyl, halo-C$_1$-C$_3$ alkyl, hydroxy-C$_1$-C$_3$ alkyl, and C$_1$-C$_3$ alkoxy- $C_1$-$C_3$ alkyl, or $R^4$ and $R^5$ can be taken together with the carbon to which they are attached to form a $C_3$-$C_7$ cycloalkyl ring;

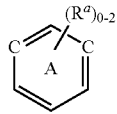

is phenyl or a 6-membered heteroaryl ring, at least one ring member of which is a nitrogen, which

ring is substituted with 0 to 2 $R^a$ groups;

B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2$ $NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2$ $NR^6R^7$, $N(R^{13})$(C=O)$NR^6R^7$, $N(R^{13})$(C=O)$OR^{14}$, $N(R^{13})$ (C=O)$R^{14}$, $NR^{13}S(O)R^{14}$, $NR^{13}SO_2R^{14}$, O(C=O)$NR^6R^7$, O(C=O)$OR^{14}$, O(C=O)$R^{14}$, (C=O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
$C_2$-$C_4$ alkynyl,
—(CR$^{14}$R$^{14}$)$_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—(CHR$^{13}$)$_n^1$—$C_3$-$C_6$-cycloalkyl substituted by 0 to 3 groups independently selected from the group consist-
ing of halo, $CF_3$, $OCF_3$, 5- or 6-membered heteroaryl, OH, hydroxy-$C_1$-$C_4$-alkyl, and $C_1$-$C_4$ alkyl,
—(CHR$^{13}$)$_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—(CHR$^{13}$)$_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —(CH$_2$)phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —(CH$_2$)$_n^1$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^{10}$ is selected from the group consisting of $C_1$-$C_4$ alkyl, halo, $C_1$-$C_4$ alkoxy, and halo-$C_1$-$C_2$-alkyl, which contains 1 to 5 halogens, where halo is F or Cl;

$n^1$, at each occurrence, is selected from 0, 1, 2, 3, 4 or 5; and p, at each occurrence, is selected from 0, 1 and 2.

In yet another embodiment, the present invention provides compounds, stereoisomers, tautomers, salts, solvates or prodrugs thereof, wherein:
W is O or S;
$R^O$ is $R^1$ or $R^{1a}$;
Y is S or —CR$^8$=CR$^9$—;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;

$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl, and
halo-$C_1$-$C_2$ alkoxy;
provided that at least one of $R^{1a}$, $R^8$ and $R^9$ is other than H;
$R^2$ is selected from the group consisting of:
H,
fluoro,
chloro, and
$CH_3$;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_3$ alkyl, $C_2$-$C_3$ alkenyl, $C_2$-$C_3$ alkynyl, $C_1$-$C_3$ alkoxy, $C_1$-$C_3$ alkylthio, halo, OH, CN, $OCF_3$, and halo-$C_1$-$C_3$-alkyl, which contains 1 to 5 halogens;
$R^4$ and $R^5$ are independently selected from H, $C_1$-$C_3$ alkyl, halo-$C_1$-$C_3$ alkyl, hydroxy-$C_1$-$C_3$ alkyl, and $C_1$-$C_3$ alkoxy-$C_1$-$C_3$ alkyl, or $R^4$ and $R^5$ can be taken together with the carbon to which they are attached to form a $C_3$-$C_7$ cycloalkyl ring;

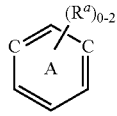

is phenyl or a 6-membered heteroaryl ring, at least one ring member of which is a nitrogen, which

ring is substituted with 0 to 2 $R^a$ groups;
B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;
$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2$ $NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;
$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2$ $NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, $(C=O)OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;
$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —($CH_2$)phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino) and —$(CH_2)_n^1$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^{10}$ is selected from the group consisting of $C_1$-$C_4$ alkyl, halo, and halo-$C_1$-$C_2$-alkyl, which contains 1 to 5 halogens, where halo is F or Cl;

$n^1$, at each occurrence, is selected from 0, 1, 2, 3 or 4; and p, at each occurrence, is selected from 0, 1 and 2.

In still yet another embodiment, the present invention provides compounds, stereoisomers, tautomers, salts, solvates or prodrugs thereof, wherein:

W is O;
$R^0$ is $R^1$ or $R^{1a}$;
Y is S or —$CR^8$=$CR^9$—;
$R^1$ is independently selected from the group consisting of:
halo,
$C_1$-$C_2$ alkyl,
cyclopropyl,
$C_1$-$C_2$ alkoxy,
$C_1$-$C_2$ alkylthio,
halo-$C_1$-$C_2$-alkyl, which contains 1 to 5 halogens, where halo is F or Cl, and
halo-$C_3$-$C_4$ cycloalkyl;

$R^{1a}$ is independently selected from the group consisting of:
H,
halo,
$C_1$-$C_2$ alkyl,
cyclopropyl,
$C_1$-$C_2$ alkoxy,
$C_1$-$C_2$ alkylthio,
halo-$C_1$-$C_2$-alkyl, which contains 1 to 5 halogens, where halo is F or Cl, and
halo-$C_3$-$C_4$ cycloalkyl;

$R^8$ and $R^9$ are independently selected from the group consisting of:
H,
fluoro,
chloro,
$C_1$-$C_3$ alkyl,
$C_1$-$C_2$ alkoxy, and
halo-$C_1$-$C_2$ alkyl;
provided that at least one of $R^{1a}$, $R^8$ and $R^9$ is other than H;

$R^2$ is H;
$X^1$ is selected from the group consisting of CH or N;
$X^2$, $X^3$ and $X^4$ are independently selected from $CR^3$;
$R^3$ is selected from the group consisting of H, $C_1$-$C_3$ alkyl, $C_1$-$C_3$ alkoxy, fluoro, chloro, $OCF_3$, and halo-$C_1$-$C_2$-alkyl, which contains 1 to 5 halogens;

$R^4$ and $R^5$ are independently selected from H, $C_1$-$C_6$ alkyl, halo-$C_1$-$C_3$ alkyl, hydroxy-$C_1$-$C_3$ alkyl and $C_1$-$C_3$ alkoxy-$C_1$-$C_3$ alkyl;

is selected from the group consisting of phenyl, pyridyl, pyrazinyl, pyrimidinyl, pyridazinyl, and triazinyl;

B is selected from the group consisting of a $C_6$-$C_{10}$ aryl, a 5- to 10-membered heteroaryl, a 4- to 10-membered heterocyclyl containing carbon atoms and 1 to 2 additional heteroatoms selected from N, O, and S, and a $C_3$-$C_6$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, (C=O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
$C_2$-$C_4$ alkenyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl, C$_1$-C$_4$-alkylcarbonyl,
phenylcarbonyl;
C$_1$-C$_4$-alkoxycarbonylamino-C$_1$-C$_4$-alkylcarbonyl, and
di-C$_1$-C$_4$-alkylamino-C$_1$-C$_4$-alkylcarbonyl,
alternatively, R$^6$ and R$^7$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H, C$_1$-C$_6$ alkyl and —(CH$_2$)phenyl;

R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino and —(CH$_2$)$_{n^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, n$^1$, at each occurrence, is selected from 0, 1, 2 or 3; and
p, at each occurrence, is selected from 0, 1 and 2.

In one embodiment, the present invention provides compounds, stereoisomers, tautomers, salts, solvates or prodrugs thereof, wherein:

W is O;
R$^0$ is R$^1$ or R$^{1a}$;
Y is S or —CR$^8$═CR$^9$—;
R$^1$ is independently selected from the group consisting of:
C$_1$-C$_2$ alkyl,
C$_1$-C$_2$ alkoxy,
C$_1$-C$_2$ alkylthio, and
halo-C$_1$-C$_2$-alkyl, which contains 1 to 5 halogens, where halo is F or Cl;
R$^{1a}$ is independently selected from the group consisting of:
H,
fluoro,
chloro,
C$_1$-C$_2$ alkyl,
C$_1$-C$_2$ alkoxy,
C$_1$-C$_2$ alkylthio, and
halo-C$_1$-C$_2$-alkyl, which contains 1 to 5 halogens, where halo is F or Cl;
R$^8$ and R$^9$ are independently selected from the group consisting of:
H,
fluoro,
chloro,
CH$_3$,
OCH$_3$,
CF$_3$, and
CHF$_2$;
provided that at least one of R$^{1a}$, R$^8$ and R$^9$ is other than H;
R$^2$ is H;
X$^1$ is selected from the group consisting of CH or N;
X$^2$ and X$^4$ are CH;
X$^3$ is CR$^3$;
R$^3$ is selected from the group consisting of H, C$_1$-C$_3$ alkyl, C$_1$-C$_3$ alkoxy, fluoro, chloro, OCF$_3$, and halo-C$_1$-C$_2$-alkyl, which contains 1 to 5 halogens;

R$^4$ and R$^5$ are independently selected from H and C$_1$-C$_6$ alkyl;

is selected from the group consisting of phenyl, pyridyl, pyrazinyl, pyrimidinyl, pyridazinyl, and triazinyl;

 is selected from the group consisting of phenyl, naphthyl pyridyl, pyrimidinyl, pyrrolyl, pyrazolyl, thienyl, thiazolyl,

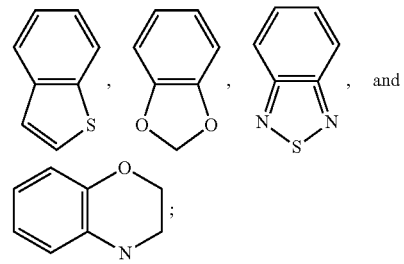, and

R$^a$, at each occurrence, is independently selected from the group consisting of H, halo, halo-C$_1$-C$_4$ alkoxy, OH, CN, NO$_2$, NR$^6$R$^7$, COOH, C$_1$-C$_4$ alkoxy, C$_1$-C$_4$ alkylthio, C$_1$-C$_4$ alkoxycarbonyl, (C═O)NR$^6$R$^7$, C$_1$-C$_4$ alkoxy-C$_1$-C$_4$ alkoxy, C$_1$-C$_4$ alkylsulfonyl, C$_1$-C$_4$ alkylsulfinyl, S(═O)$_2$NR$^6$R$^7$, and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, phenyl, and C$_1$-C$_4$ alkylthio;

R$^b$, at each occurrence, is independently selected from the group consisting of H, halo, halo-C$_1$-C$_4$ alkoxy, OH, CN, NO$_2$, NR$^6$R$^7$, COOH, C$_1$-C$_4$ alkoxy, C$_1$-C$_4$ alkylthio, C$_1$-C$_4$ alkoxycarbonyl, (C═O)NR$^6$R$^7$, C$_1$-C$_4$ alkoxy-C$_1$-C$_4$ alkoxy, C$_1$-C$_4$ alkylsulfonyl, C$_1$-C$_4$ alkylsulfinyl, S(═O)$_2$NR$^6$R$^7$, N(R$^{13}$)(C═O)NR$^6$R$^7$, N(R$^{13}$)(C═O)OR$^{14}$, N(R$^{13}$)(C═O)R$^{14}$, NR$^{13}$S(O)R$^{14}$, NR$^{13}$SO$_2$R$^{14}$, O(C═O)NR$^6$R$^7$, O(C═O)OR$^{14}$, O(C═O)R$^{14}$, (C═O)OR$^{14}$, 5-6-membered heteroaryl, and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cyclo alkyl, phenyl, and C$_1$-C$_4$ alkylthio;

R$^6$ and R$^7$ are independently, at each occurrence, selected from the group consisting of:
H,
C$_1$-C$_4$ alkyl,
halo-C$_1$-C$_4$-alkyl,
C$_2$-C$_4$ alkenyl,
—(CR$^{14}$R$^{14}$)$_{n^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
—(CHR$^{13}$)$_{n^1}$—C$_3$-C$_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, —$(CHR^{13})_{n^1}$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl, —$(CHR^{13})_{n^1}$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl, and
phenylcarbonyl;

alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, and $C_1$-$C_3$ alkyl;

$R^{14}$ is independently, at each occurrence, selected from the group consisting of H, $C_1$-$C_3$ alkyl, and halo-$C_1$-$C_2$-alkyl;

$n^1$, at each occurrence, is selected from 0, 1, 2 or 3; and
p, at each occurrence, is selected from 0, 1 and 2.

In another embodiment, the present invention provides compounds, stereoisomers, tautomers, salts, solvates or prodrugs thereof, wherein:

W is O;
$R^0$ is $R^1$ or $R^{1a}$;
Y is S or —CH═CH—;
$R^1$ is independently selected from the group consisting of:
$CH_3$,
$OCH_3$,
$SCH_3$,
$CHFCH_3$, and
$CF_2CH_3$;

$R^{1a}$ is independently selected from the group consisting of:
chloro,
$CH_3$, and
$OCH_3$, $R^2$ is H;
$X^1$ is CH;
$X^2$ and $X^4$ are CH;
$X^3$ is $CR^3$;
$R^3$ is selected from the group consisting of $OCH_3$, fluoro, and chloro; $R^4$ and $R^5$ are independently selected from H and $CH_3$;

is selected from the group consisting of phenyl, pyridyl, pyrazinyl, pyrimidinyl, pyridazinyl, and triazinyl;

Ⓑ is selected from the group consisting of phenyl, naphthyl pyridyl, pyrimidinyl, pyrrolyl, pyrazolyl, thienyl, thiazolyl,

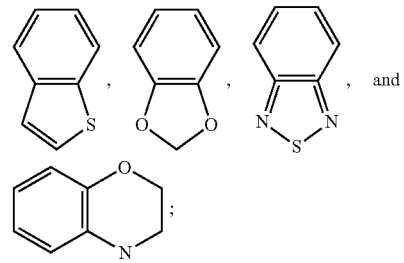

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C═O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(═O)_2$$NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C═O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(═O)_2$$NR^6R^7$, $N(R^{13})$(C═O)$NR^6R^7$, $N(R^{13})$(C═O)$OR^{14}$, $N(R^{13})$(C═O)$R^{14}$, $NR^{13}S(O)R^{14}$, $NR^{13}SO_2R^{14}$, O(C═O)$NR^6R^7$, O(C═O)$OR^{14}$, O(C═O)$R^{14}$, (C═O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cyclo alkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl, and
$C_1$-$C_4$-alkoxycarbonyl;

alternatively, $R^6$ and $R^7$, when attached to the same nitrogen, combine to form a 4- to 7-membered heterocyclic ring containing carbon atoms substituted by 0 to 2 groups independently selected from the group consisting of halo, $CF_3$, $CHF_2$, $OCF_3$, $OCHF_2$, $OCH_2F$, OH, oxo, hydroxy-$C_1$-$C_2$-alkyl, $C_1$-$C_3$ alkyl and $C_1$-$C_3$ alkoxy, and 0 to 2 additional heteroatoms selected from N, $NR^{13}$, O and $S(O)_p$;

$R^{13}$ is independently, at each occurrence, selected from the group consisting of H and $C_1$-$C_3$ alkyl;

R[14] is independently, at each occurrence, selected from the group consisting of H and $C_1$-$C_3$ alkyl $n^1$, at each occurrence, is selected from 0, 1, 2 or 3; and p, at each occurrence, is selected from 0, 1 and 2.

In yet another embodiment, the present invention provides compounds, stereoisomers, tautomers, salts, solvates or prodrugs thereof, wherein:

$X_1$ is CH or N;

$R^1$ is $C_1$-$C_3$ alkoxy or halo-$C_1$-$C_2$-alkyl which contains 1 to 5 halogens;

$R^2$ is H;

$R^3$ is H, $C_1$-$C_4$ alkoxy or halogen;

is selected from the group consisting of phenyl, pyridyl and pyrimidinyl, all of which are substituted with 0 to 2 $R^a$ groups;

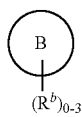

is selected from the group consisting of:
a) phenyl;
b) phenyl substituted with 1 to 2 $R^b$ substituents selected from halo, OH. halo-$C_1$-$C_2$-alkyl, which contains 1 to 5 halogens, CN, $NO_2$,

N(alkyl)$_2$, $CF_3$,
$C_1$-$C_4$ alkyl, and $C_1$-$C_4$ alkoxy;
c) phenyl fused to a heterocyclo group;
d) monocyclic heteroaryl containing 5 or 6 ring members which contain:
1 oxygen atom,
2 nitrogen atoms,
2 sulfur atoms,
1 nitrogen atom,
1 sulfur atom,
1 oxygen atom,
or combinations thereof, which monocyclic heteroaryl is substituted with 0 to 2 $R^{1p}$ substituents selected from halo, CN, $NO_2$, OH, $C_1$-$C_4$ alkyl, halo-$C_1$-$C_4$ alkyl, $C_1$-$C_4$ alkoxy, halo-$C_1$-$C_4$ alkoxy,

N(alkyl)$_2$, $C_1$-$C_4$ alkoxy-$C_1$-$C_4$ alkoxy, COOH, $C_1$-$C_4$ alkoxycarbonyl, heterocyclyl, or heterocyclylcarbonyl; and
e) bicyclic heteroaryl containing 8 or 9 ring members and which contains a sulfur atom, nitrogen atoms or combinations thereof in the ring.

In yet another embodiment, the present invention provides compounds, stereoisomers, tautomers, salts, solvates or prodrugs thereof, wherein the compounds are selected from the examples, preferably a compound selected from Examples 3 to 114.

In still yet another embodiment, the present invention provides compounds, stereoisomers, tautomers, salts, solvates or prodrugs thereof, wherein the compounds are selected from:

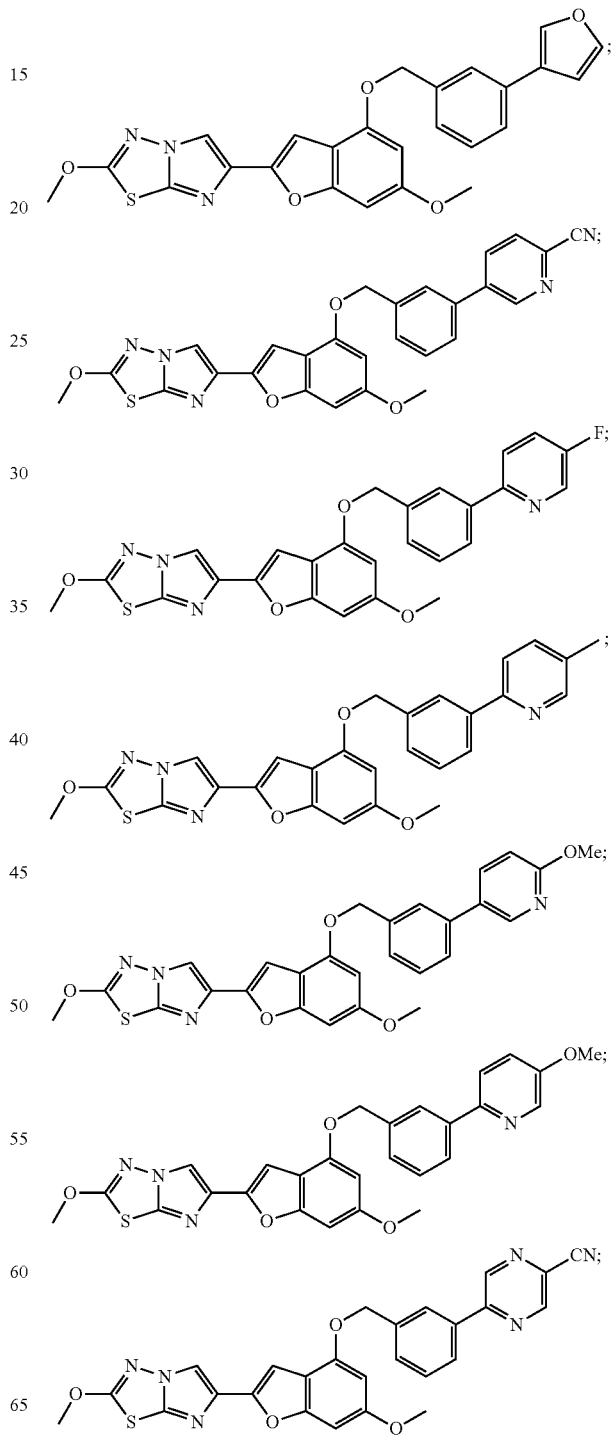

31
-continued
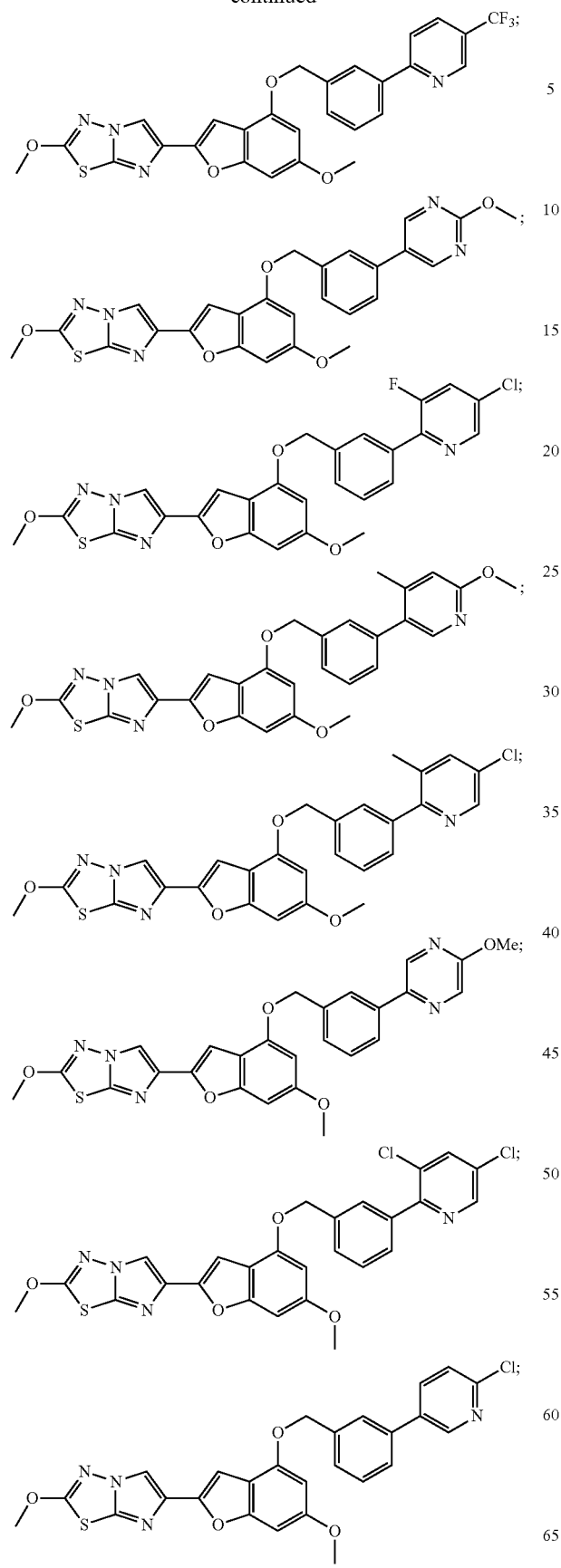
32
-continued
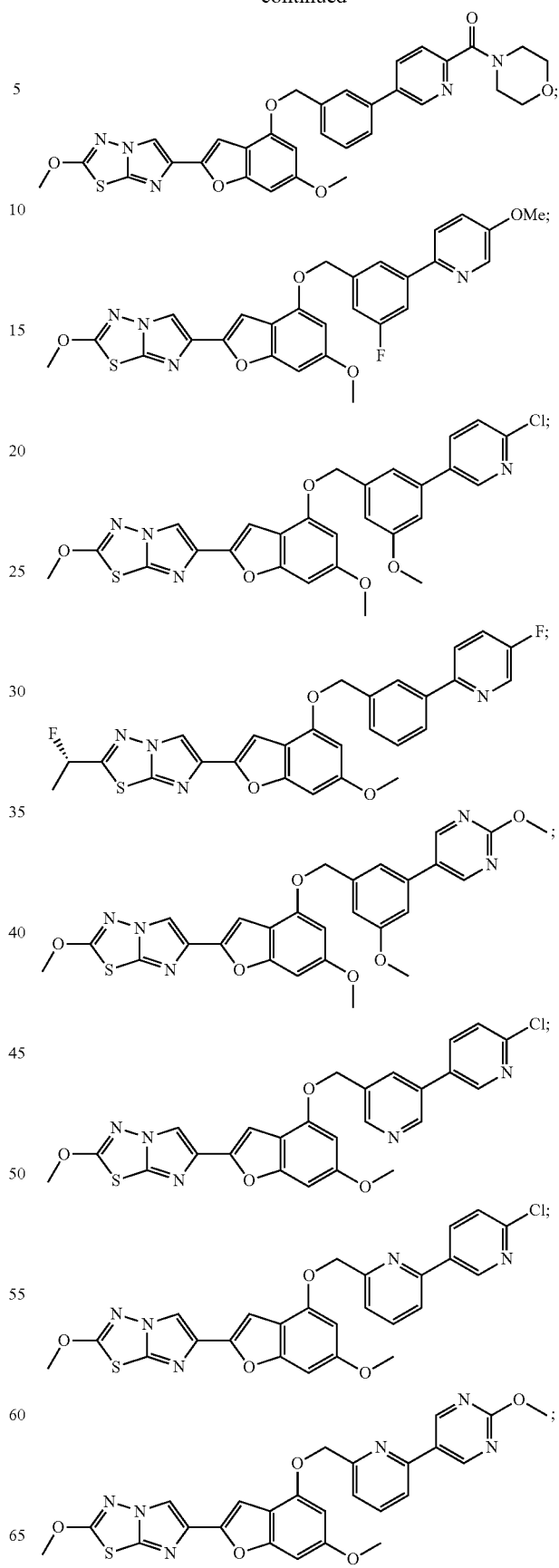

-continued

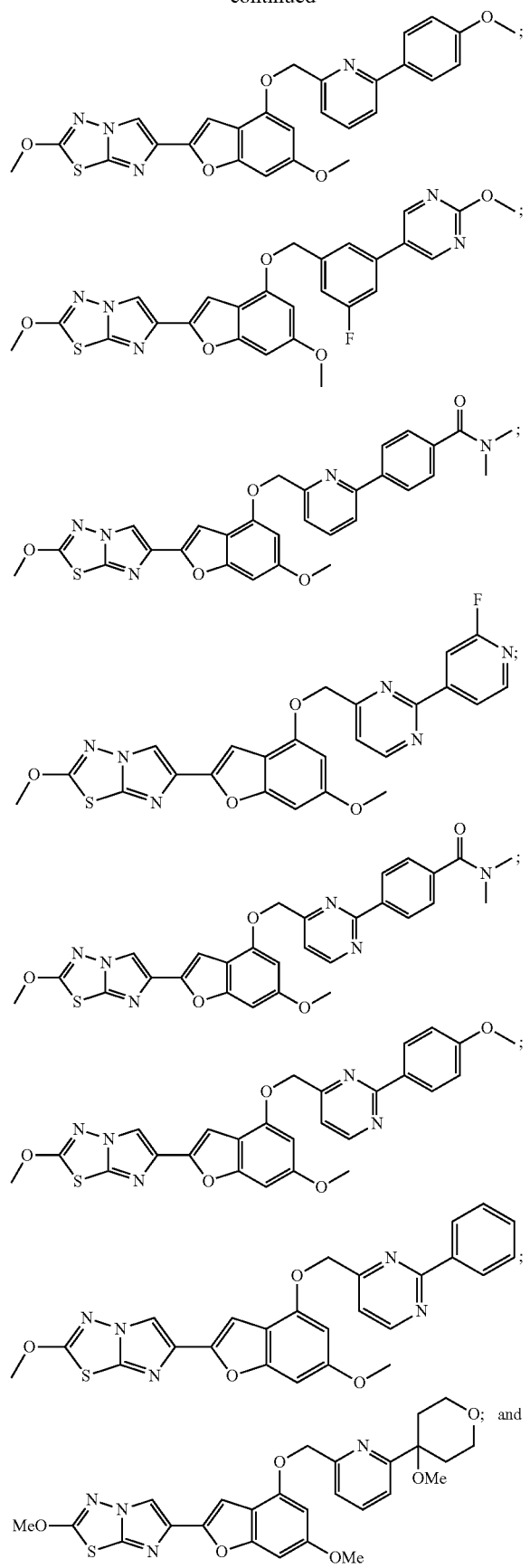

Preferably, PAR4 compounds of the invention have $IC_{50}$s in the FLIPR Assay (described hereinafter) of about 10 μM, preferably 5 μM or less, more preferably 500 nM or less, and even more preferably 10 nM or less. Activity data for a number of these compounds is presented in the table in Example F.

In some embodiments, the present invention provides at least one compound of the present invention or a stereoisomer, tautomer, pharmaceutically acceptable salt, solvate, or prodrug esters thereof.

In some embodiments, the present invention provides a pharmaceutical composition, which includes a pharmaceutically acceptable carrier and a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors, FXIa inhibitors or thrombin inhibitors. Preferably, the FXa inhibitors are apixaban or rivaroxaban. Preferably, the thrombin inhibitor is dabigatran. For examples of FXIa inhibitors that may be useful in the present invention see International Patent Application Publication No. WO 2011/10040.

In some embodiments, the present invention provides a method for the treatment or prophylaxis of a thromboembolic disorder which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, of the invention.

Other Embodiments of the Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of a compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis-, trans- or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The molecular weight of compounds of the present invention is preferably less than about 800 grams per mole.

As used herein, the term "alkyl" or "alkylene", alone or as part of another group, is intended to include both branched- and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_a$, $SR_a$, (=S), —$NR_aR_b$, —N(alkyl)$_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_1$-$C_4$ alkylene)N-$R_aR_b$, —$C(=O)NR_a(SO_2)R_b$, —$CO_2(C_1$-$C_4$ alkylene) $NR_aR_b$, —$NR_aC(=O)R_b$, —$NR_aCO_2R_b$, —$NR_a(C_1$-$C_4$ alkylene)$CO_2R_b$, =N—OH, =N—O-alkyl, wherein $R_a$ and $R_b$ are the same or different and are independently selected from hydrogen, alkyl, alkenyl, $CO_2H$, $CO_2$(alkyl), $C_3$-$C_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of ($C_1$-$C_6$)alkyl, ($C_2$-$C_6$)alkenyl, hydroxy, halogen, cyano, nitro, $CF_3$, O($C_1$-$C_6$ alkyl), $OCF_3$, C(=O)H, C(=O)($C_1$-$C_6$ alkyl), $CO_2H$, $CO_2$($C_1$-$C_6$ alkyl), $NHCO_2$($C_1$-$C_6$ alkyl), —S($C_1$-$C_6$ alkyl), —$NH_2$, NH($C_1$-$C_6$ alkyl), N($C_1$-$C_6$ alkyl)$_2$, N($CH_3$)$_3^+$, $SO_2$($C_1$-$C_6$ alkyl), C(=O)($C_1$-$C_4$ alkylene)$NH_2$, C(=O)($C_1$-$C_4$ alkylene)NH(alkyl), C(=O)($C_1$-$C_4$ alkylene)N($C_1$-$C_4$ alkyl)$_2$, $C_3$-$C_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

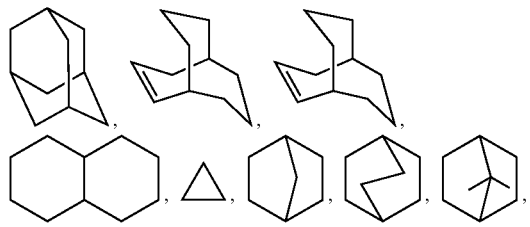

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $C_1$-$C_3$ alkyl, $CO_2H$, and $CO_2CH_3$.

As used herein, the term "heterocycle", "heterocyclo" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $=O$, $C(=O)CH_3$, $SCH_3$, $S(=O)CH_3$, $S(=O)_2CH_3$, $C_1$-$C_3$ alkyl, $CO_2H$ and $CO_2CH_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

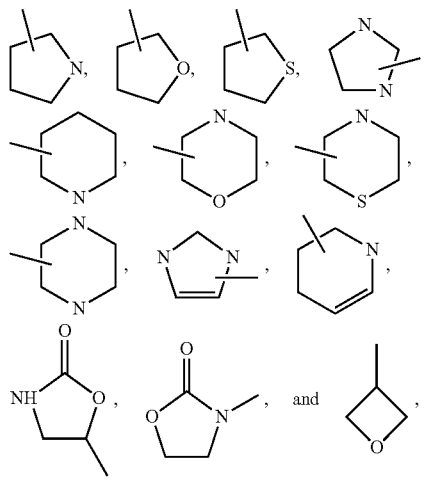

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, C$_1$-C$_3$ alkyl, CO$_2$H and CO$_2$CH$_3$. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include

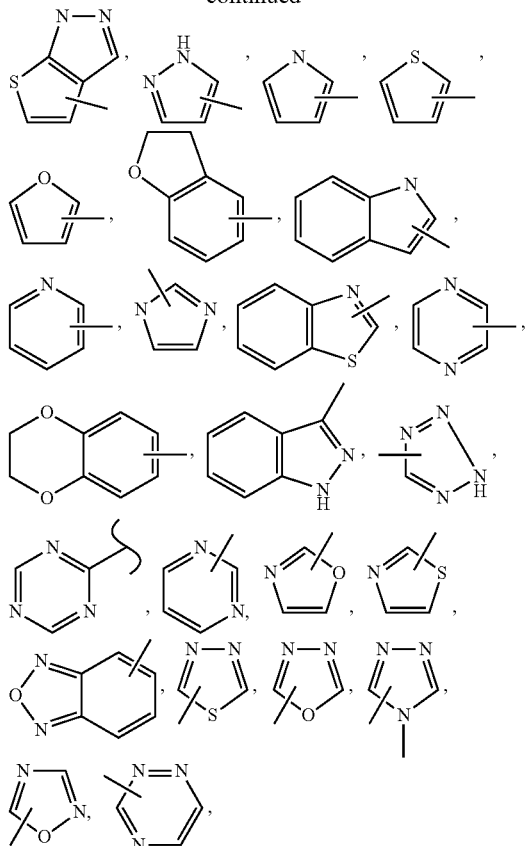

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)R$_e$, as well as the bivalent groups —C(=O)— or —C(=O)R$_e$—, which are linked to organic radicals. The group R$_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation "⌇" or

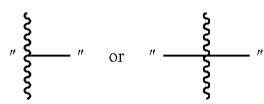

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V. Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or EDCI (or EDCI•HCl) or EDAC | 3-ethyl-3'-(dimethylamino)propyl-carbodiimide hydrochloride or 1-(3-dimethylaminopropyl)-3-ethylcarbodiimide hydrochloride |

-continued

| | |
|---|---|
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperazine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meto-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidino-phosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| K$_3$PO$_4$ | potassium phosphate |
| MgSO$_4$ | magnesium sulfate |
| NaCl | sodium chloride |
| NaH | sodium hydride |
| NaHCO$_3$ | sodium bicarbonate |
| NaOH | sodium hydroxide |
| Na$_2$SO$_3$ | sodium sulfite |
| Na$_2$SO$_4$ | sodium sulfate |
| NH$_3$ | ammonia |
| NH$_4$Cl | ammonium chloride |
| NH$_4$OH | ammonium hydroxide |
| OTs | tosylate, para-toluenesulfonate |
| PBr$_3$ | phosphorous tribromide |
| Pd(PPh$_3$)$_4$ | tetrakis(triphenylphosphine) palladium (0) |
| (S,S)-EtDuPhosRh(I) | (+)-1,2-bis((2S,5S)-2,5-diethyl-phospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Compounds of formula I of this invention can be obtained by condensation of an amine of formula III with a ketone of formula IV which contains a leaving group Z such as a bromide, iodide or tosylate and a protecting group PG such as benzyl as shown in Scheme 1. Both compounds of formula III and IV are commercially available or can be prepared by means known to one skilled in the art. This condensation is promoted by heating, either thermally or preferably by microwave irradiation. The protecting group can be removed by methods known in the art, such as BCl$_3$ at −78° C. in the presence of pentamethylbenzene. Subsequent alkylation using either an alcohol VI under Mitsunobu conditions or a bromide VII in the presence of base such as potassium carbonate provides the compounds of Formula I. Alcohols and bromides VI and VII are commercially available or can be prepared by methods known in the art.

Scheme 1

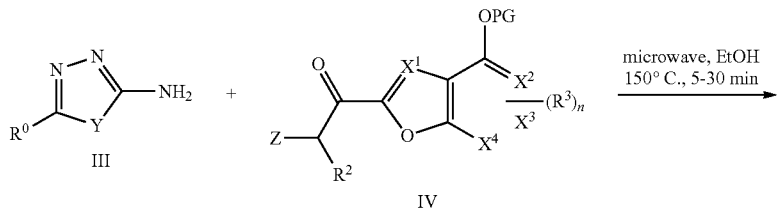

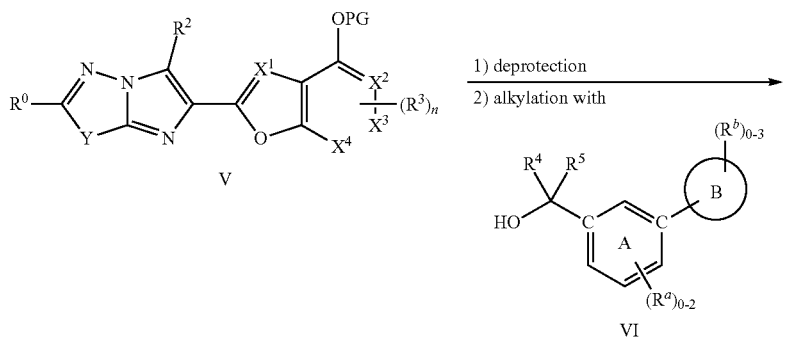

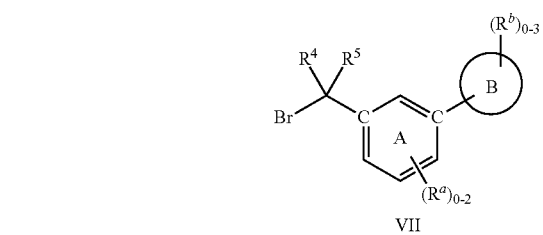

or

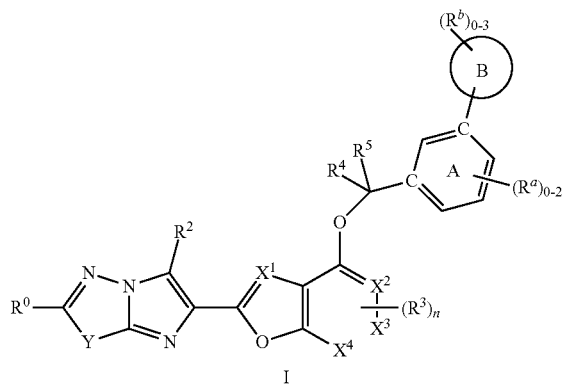

Alternatively, compounds of Formula I can be prepared from compounds of formula IX upon activation of the thiomethyl group by oxidation to a sulfone X as shown in Scheme 2. This allows introduction of a variety of nucleophiles as groups $R^0$ such as alcohols, thiols and amines in the presence of a base such as potassium carbonate or sodium hydride either neat or in a polar, aprotic solvent such as dimethylformamide to give compounds XI. Compounds XI can be converted to compounds of Formula I (where $X^3$ is $CR^3$) by removal of the protecting group (PG) and alkylation as discussed in Scheme 1.

Substituted benzofurans bearing α-bromoketone substituents at the 2-position (XV) can be prepared as shown in Scheme 3. o-Hydroxy benzaldehydes XII can be prepared by methods known to one skilled in the art of organic synthesis, and can be condensed with ketones of formula XIII bearing a leaving group Q such as chloro, bromo or tosyloxy, to give benzofurans XIV. Bromination of compounds of formula XIV affords bromoketones XV, which can be condensed with a substituted aminoheterocycle III according to Scheme 1 to give compounds of Formula I. Bromoketones XV are a specific subset of compounds IV in Scheme 1.

Scheme 2

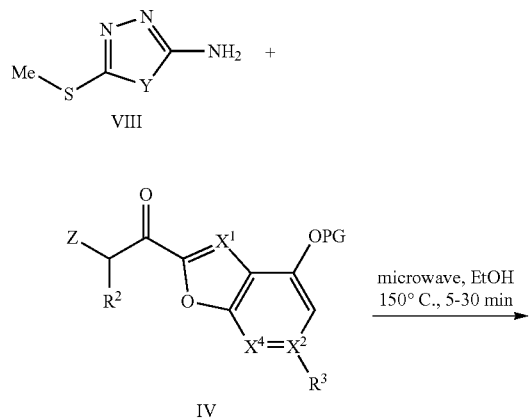

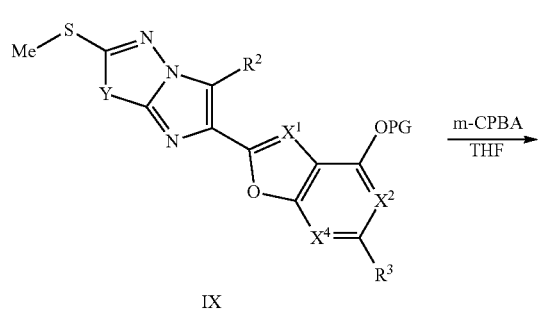

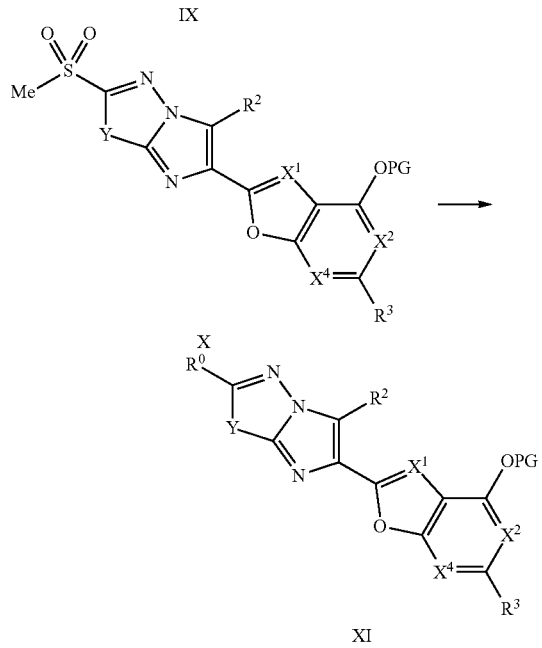

Scheme 3

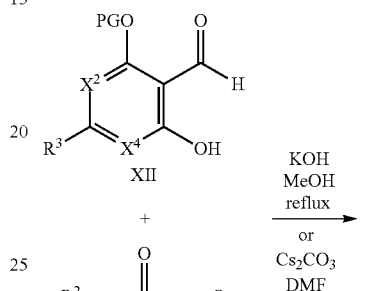

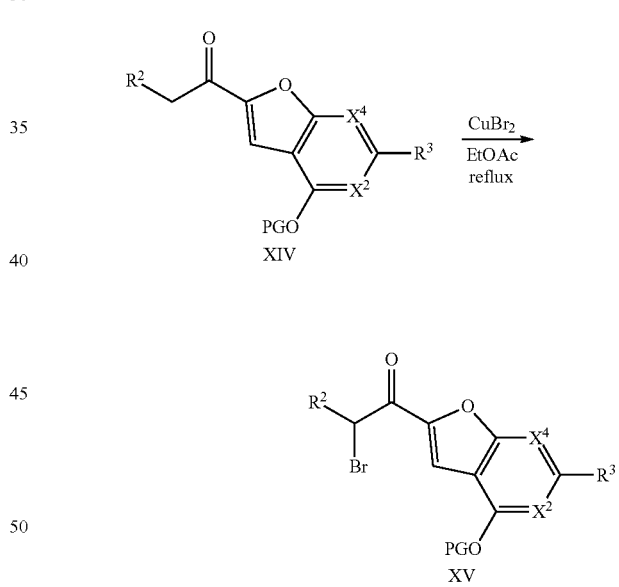

Benzoxazole compounds of Formula I can be prepared starting from substituted aminoheterocycle III and pyruvate esters of formula XVI which contain a leaving group Z such as a bromide, iodide or tosylate as shown in Scheme 4. Both compounds of formula III and XVI are commercially available or are available by means known to one skilled in the art. Following condensation and saponification of the ester XVII to form acid XVIII, amino phenols of formula XIX are coupled to form amides of the formula XX, which can be cyclized under acid catalysis to form benzoxazole compounds of formula XXI. These can be deprotected and alkylated as shown in Scheme 1 to provide compounds of Formula I (where $X^3$ is $CR^3$).

Scheme 4

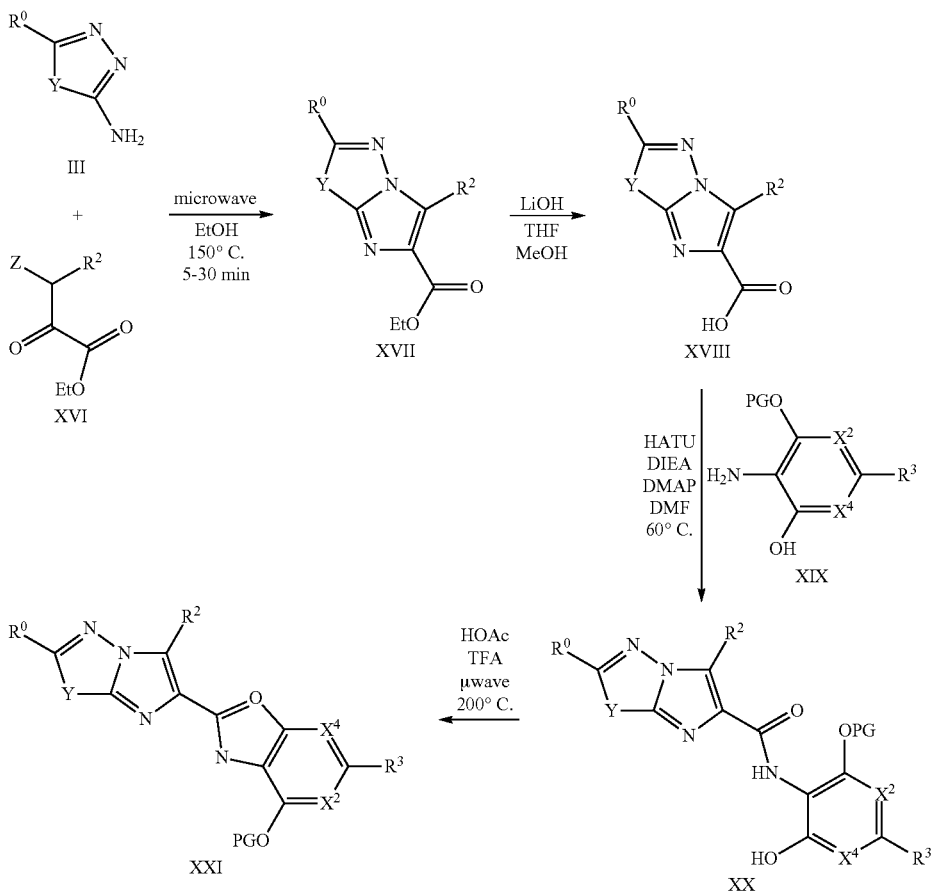

Aminoheterocycles XXIV can be prepared from carbon disulfide (XXII) via the thioxanthate intermediate XXIII. These aminoheterocycles are useful for the preparation of compounds of Formula I.

Scheme 5

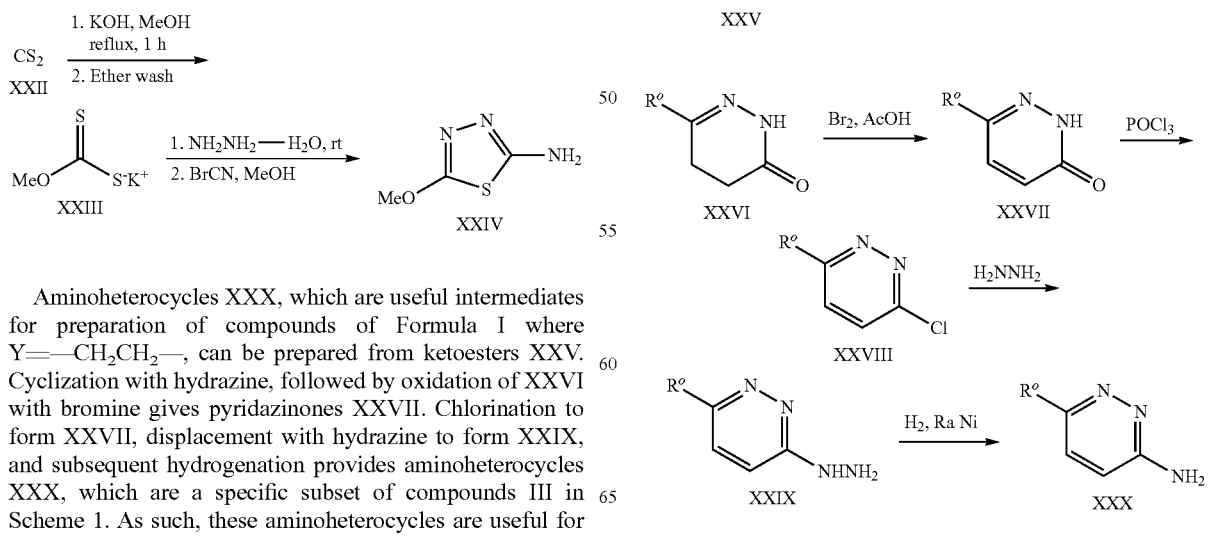

Aminoheterocycles XXX, which are useful intermediates for preparation of compounds of Formula I where Y=—CH$_2$CH$_2$—, can be prepared from ketoesters XXV. Cyclization with hydrazine, followed by oxidation of XXVI with bromine gives pyridazinones XXVII. Chlorination to form XXVII, displacement with hydrazine to form XXIX, and subsequent hydrogenation provides aminoheterocycles XXX, which are a specific subset of compounds III in Scheme 1. As such, these aminoheterocycles are useful for the preparation of compounds of Formula I.

EXAMPLES

The following compounds of the invention have been prepared, isolated and characterized using the methods disclosed herein. They demonstrate a partial scope of the invention and are not meant to be limiting of the scope of the invention. In the experimental procedures, solution ratios express a volume relationship, unless stated otherwise. NMR chemical shifts (δ) are reported in parts per million (ppm). Products were analyzed by reverse phase analytical HPLC using the following methods:

Method A: Column: Waters Xbridge 19×100 mm, 5 um C18, Mobile Phase: A=5:95 Acetonitrile:Water, B=95:5 Acetonitrile:Water, Modifier=0.05% TFA, Wavelength: 220 nm.

Method B: Column ZORBAX® XDB-C18 3.5 microns, 4.6×30 mm; Mobile Phase: A=MeOH:H$_2$O:TFA (95:5:05), B=MeOH:H$_2$O:TFA (5:95:05).

Method C: SunfireC18 3.5 microns column (4.6×30 mm) eluted at 3 mL/min with a 2 min. gradient from 100% A to 100% B (A: 5% methanol, 94.95% water, 0.05% TFA; B: 5% water, 94.95% methanol, 0.05% TFA, UV 220 nm).

Method D: Eclipse XDB-C18 3.5 microns column (4.6×30 mm) eluted at 3 mL/min with a 2 min gradient from 100% A to 100% B (A: 5% methanol, 94.95% water, 0.05% TFA; B: 5% water, 94.95% methanol, 0.05% TFA, UV 220 nm).

Method E: Eclipse XDB-C18 3.5 microns column (4.6×30 mm) eluted at 3 mL/min with a 2 min gradient from 100% A to 100% B (A: 5% acetonitrile, 94.95% water, 0.05% TFA; B: 5% water, 94.95% acetonitrile, 0.05% TFA, UV 220 nm).

Example 1

2-Methoxy-6-(6-methoxy-4-((3-(pyrimidin-5-yl)benzyl)oxy)benzofuran-2-yl)imidazo[2,1-b][1,3,4]thiadiazole

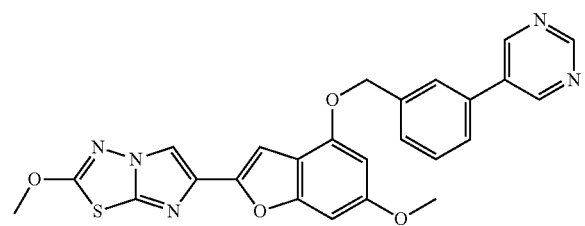 [SMILES: COc1cc(OCc2cccc(-c3cncnc3)c2)c2cc(-c3cn4nc(OC)sc4n3)oc2c1]

1A. 5-(Benzyloxy)-7-methoxy-2,2-dimethyl-4H-benzo[d][1,3]dioxin-4-one

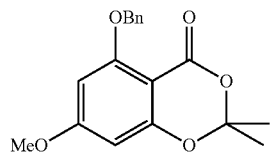 [SMILES: COc1cc(OCc2ccccc2)c2c(c1)OC(C)(C)OC2=O]

A solution of 5-hydroxy-7-methoxy-2,2-dimethyl-4H-benzo[d][1,3]dioxin-4-one (30.00 g, 0.134 mol) in N,N-dimethylformamide (400 mL) was treated with powdered anhydrous potassium carbonate (19.41 g, 0.14 mol) added all at once. The resulting mixture was stirred in vacuo for 10 min. and then flushed with nitrogen. The reaction flask was placed in a water bath (22° C.) an treated with benzyl bromide (24.03 g, 0.14 mol) added dropwise over 15 min. The resulting mixture was then stirred at 22° C. for 18 h (no starting material left by tlc). The solid was filtered and washed with N,N-dimethylformamide. The filtrate was evaporated in vacuo and the residual oil was diluted with ethyl acetate (500 mL), washed with cold 0.1 N hydrochloric acid, saturated sodium bicarbonate and brine. After drying over anhydrous magnesium sulfate, evaporation of the solvent gave a thick syrup. Crystallization form ethyl acetate (50 mL) and hexane (150 mL) gave 35.17 g of 5-(benzyloxy)-7-methoxy-2,2-dimethyl-4H-benzo[d][1,3]dioxin-4-one as large colorless prisms. Chromatography of the mother liquors on silica gel (4×13 cm, elution toluene-ethyl acetate 0-5%) gave 6.64 g of additional material to afford a total yield of 41.81 g (99%). HRMS(ESI) calcd for C$_{18}$H$_{19}$O$_5$ [M+H]$^+$ m/z 315.1227. found 315.1386. $^1$H NMR (CDCl$_3$, 600 MHz) δ 1.68 (s, 6H), 3.77 (s, 3H), 5.19 (s, 2H), 5.19 (s, 2H), 6.04 (d, J=2.03 Hz, 1H), 6.15 (d, J=2.03 Hz, 1H), 7.27 (broad t, 1H), 7.36 (broad t, 2H), 7.52 (broad d, 2H).

1B. 2-(Benzyloxy)-6-hydroxy-4-methoxybenzaldehyde

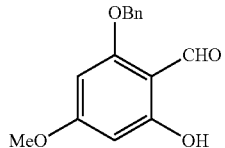

A solution of 5-(benzyloxy)-7-methoxy-2,2-dimethyl-4H-benzo[d][1,3]dioxin-4-one (Example 1A, 6.76 g, 21.5 mmol) in dichloromethane (120 mL) was cooled to −78° C. and treated with 43 mL (64.5 mmol) of a 1.5 M solution of diisobutylaluminum hydride in toluene added dropwise over 20 min. The resulting mixture was then stirred at −78° C. for 3 h. The reaction mixture was quenched by the careful addition of methanol (5 mL) added dropwise over 15 min, followed by 1N hydrochloric acid (50 mL) added dropwise over 15 min. The cooling bath was then removed and an additional 150 mL of 1N hydrochloric acid was added over 20 min. The mixture was then stirred at 22° C. for 2 h and diluted with dichloromethane (400 mL). The organic phase was collected and the aqueous phase (pH~1) was extracted with dichloromethane (3×50 mL). The combined organic extracts were washed with brine, dried over anhydrous magnesium sulfate and concentrated in vacuo. The residual oil was diluted with tetrahydrofuran (70 mL), treated with 10 mL of 0.1N hydrochloric acid and stirred at 20° C. for 2 h. The reaction mixture was diluted with ethyl acetate (300 mL), washed with brine, dried over anhydrous magnesium sulfate, evaporated in vacuo to give a clear oil. Chromatography on silica gel (4×13 cm, elution toluene) gave 4.08 g (73% yield) of the title aldehyde as a clear oil which solidified on standing. LC (Method C): 2.237 min. HRMS (ESI) calcd for C$_{15}$H$_{15}$O$_4$ [M+H]$^+$ m/z 259.0965. found 259.1153. $^1$H NMR (CDCl$_3$, 600 MHz) δ 3.80 (s, 3H), 5.07 (s, 2H), 5.97 (d, J=2.1 Hz, 1H), 6.01 (d, J=2.1 Hz, 1H), 7.3-7.4 (m, 5H), 10.15 (s, 1H), 12.49 (s, 1H).

1C. 1-(4-(Benzyloxy)-6-methoxybenzofuran-2-yl)ethanone

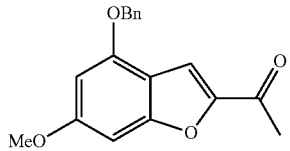 [SMILES: COc1cc(OCc2ccccc2)c2cc(C(C)=O)oc2c1]

A solution of 2-(benzyloxy)-6-hydroxy-4-methoxybenzaldehyde (Example 1B, 3.46 g, 13.4 mmol) in N,N-dimethylformamide (50 mL) was treated with powdered anhydrous cesium carbonate (4.58 g, 14.05 mmol) added all at once. The resulting mixture was stirred in vacuo for 10 min. and then flushed with nitrogen. The reaction flask was placed in a water bath (22° C.) an treated with chloroacetone (1.74 g, 18.7 mmol) added dropwise over 5 min. The resulting mixture was then stirred at 22° C. for 18 h (no starting aldehyde left by tlc and formation of the intermediate alkylated aldehyde). The solid was filtered and washed with N,N-dimethylformamide. The filtrate was evaporated in vacuo and the residual oil was diluted with ethyl acetate (300 mL), washed with cold 0.1 N hydrochloric acid, saturated sodium bicarbonate and brine. After drying over anhydrous magnesium sulfate, evaporation of the solvent gave a thick syrup. This syrup was diluted with tetrahydrofuran (50 mL) and ethyl acetate (50 mL), treated p-toluenesulfonic acid monohydrate (0.2 g) and stirred at 20° C. for 1 h (tlc indicated complete cyclization of the intermediate alkylated aldehyde to the benzofuran). The reaction mixture was diluted with ethyl acetate (300 mL), washed with saturated sodium bicarbonate and brine. After drying over anhydrous magnesium sulfate, evaporation of the solvent gave a thick syrup. Chromatography on silica gel (4×12 cm, elution toluene-ethyl acetate 2-4%) gave 3.51 g (88% yield) of the title benzofuran as a yellow solid. Recrystallization from ethyl acetate (10 mL) and hexane (20 mL) gave the title material as large yellow prisms (3.15 g). LC (Method A): 2.148 min. HRMS(ESI) calcd for $C_{18}H_{17}O_4$ [M+H]$^+$ m/z 297.1121. found 297.1092. $^1$H NMR (CDCl$_3$, 600 MHz) δ 2.51 (s, 3H), 3.82 (s, 3H), 5.13 (s, 2H), 6.37 (d, J=1.77 Hz, 1H), 6.63 (broad s, 1H), 7.34 (broad t, 1H), 7.39 (broad t, 2H), 7.44 (broad d, 2H), 7.55 (d, J=0.7 Hz, 1H).

1D. 1-(4-(Benzyloxy)-6-methoxybenzofuran-2-yl)-2-bromoethanone

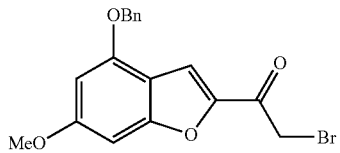 [SMILES: COc1cc(OCc2ccccc2)c2cc(C(=O)CBr)oc2c1]

A 250-mL, three-necked flask is equipped with a magnetic stirring bar and purged with a nitrogen atmosphere was charged with anhydrous tetrahydrofuran (25 mL) followed by 9.3 mL (9.3 mmol) of a 1M solution of lithium bis(trimethylsilyl)amide in tetrahydrofuran. The mixture was cooled to −78° C. and treated with a solution of 1-(4-(benzyloxy)-6-methoxybenzofuran-2-yl)ethanone (Example 1C, 2.40 g, 8.1 mmole) in tetrahydrofuran (20 mL) added dropwise over 10 min. The resulting mixture was then stirred at −78° C. for 45 min. Then chlorotrimethylsilane (1.18 mL, 9.31 mmol) was added dropwise over 5 min and the resulting solution was stirred at −78° C. for another 20 min. The cooling bath was then removed and the mixture is allowed to warm to room temperature over 30 min. The reaction mixture was then quenched by addition to a cold solution of ethyl acetate (200 mL), saturated sodium bicarbonate (30 mL) and ice. The organic phase was rapidly dried over anhydrous magnesium sulfate (magnetic stirring) and evaporated in vacuo to give the silyl enol ether as an oil which is co-evaporated with toluene (20 mL). The silyl enol ether was then dissolved in dry tetrahydrofuran (40 mL), cooled to −20° C. and treated with solid sodium bicarbonate (0.10 g) followed by N-bromosuccinimide (1.44 g, 8.1 mmol) added in small portions over 15 min. The reaction mixture was allowed to warm to 0° C. over 2 h and then quenched by addition of ethyl acetate (300 mL) and saturated sodium bicarbonate. The organic phase was washed with brine, dried over anhydrous magnesium sulfate and evaporated to give an orange oil. Chromatography on silica gel (4×12 cm, elution toluene-ethyl acetate 0-5%) gave 2.62 g (86% yield) of the title bromomethylketone as a yellow solid. Recrystallization from ethyl acetate (10 mL) and hexane (20 mL) gave yellow prisms (2.30 g). LC (Method B): 1.977 min. HRMS(ESI) calcd for $C_{18}H_{16}BrO_4$ [M+H]$^+$ m/z 375.0226. found 375.0277. $^1$H NMR (CDCl$_3$, 600 MHz) δ 3.84 (s, 3H), 4.33 (s, 2H), 5.14 (s, 2H), 6.38 (d, J=1.76 Hz, 1H), 6.64 (broad s, 1H), 7.35 (broad t, 1H), 7.40 (broad t, 2H), 7.44 (broad d, 2H), 7.70 (s, 1H).

1E. 6-(4-(Benzyloxy)-6-methoxybenzofuran-2-yl)-2-bromoimidazo[2,1-b][1,3,4]thiadiazole

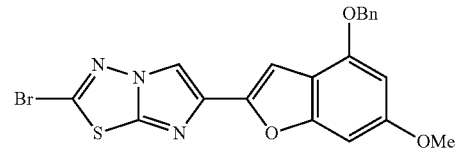 [SMILES: COc1cc(OCc2ccccc2)c2cc(-c3cn4nc(Br)sc4n3)oc2c1]

A mixture of 1-(4-(benzyloxy)-6-methoxybenzofuran-2-yl)-2-bromoethanone (Example 1D, 3.00 g, 8.0 mmol) and 5-bromo-1,3,4-thiadiazol-2-amine (1.65 g, 9.16 mmol) in isopropanol (100 mL) was heated is a pressure flask equipped with a magnetic stirring bar at 78-80° C. for 18 h (homogeneous after 20 min and then formation of a precipitate after 2 h). The cooled mixture is then transferred into five 20 mL microwave vials and then heated in a microwave apparatus to 150° C. for 30 min. Each vial was then diluted with dichloromethane (250 mL) washed with saturated sodium bicarbonate (25 mL) and brine (25 mL), dried over anhydrous magnesium sulfate. The fractions were combined and concentrated in vacuo. Chromatography of the orange-brown residual solid on silica gel (4×10 cm, slow elution with dichloromethane due to poor solubility) gave 2.96 g of the title imidazothiadiazole contaminated with some 1-(4-(benzyloxy)-6-methoxybenzofuran-2-yl)ethanone. The solid material was triturated with ethyl acetate (20 mL), filtered, washed with ethyl acetate (10 ml) and dried in vacuo to give 2.34 g (64% yield) of pure title imidazothiadiazole as an off white solid which is used as such for the next step. LC (Method B): 2.188 min. HRMS(ESI) calcd for $C_{20}H_{15}BrN_3O_3S$ [M+H]$^+$ m/z 456.00175. found 456.00397. $^1$H NMR (CDCl$_3$, 600 MHz) δ 3.82 (s, 3H), 5.16 (s, 2H), 6.38 (d, J=1.67 Hz, 1H), 6.66 (broad s, 1H), 7.15 (s, 1H), 7.31 (broad t, 1H), 7.38 (broad t, 2H), 7.45 (broad d, 2H), 8.02 (s, 1H).

1F. 6-(4-(Benzyloxy)-6-methoxybenzofuran-2-yl)-2-methoxyimidazo[2,1-b][1,3,4]thiadiazole

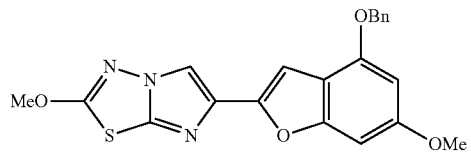 [SMILES: COc1cc(OCc2ccccc2)c2cc(-c3cn4nc(OC)sc4n3)oc2c1]

A solution of 6-(4-(benzyloxy)-6-methoxybenzofuran-2-yl)-2-bromoimidazo[2,1-b][1,3,4]thiadiazole (Example 1E, 2.30 g, 5.04 mmol) in a mixture of dichloromethane (180 mL) and methanol (45 mL) was treated at 22° C. with 4.2 mL of a 25 wt. % solution of sodium methoxide in methanol (0.2 mmol) added in one portion. More methanol (45 mL) was added and the mixture was stirred for 1 h. The reaction mixture was quenched by the addition of 25 mL of 1N hydrochloric acid followed by 20 ml of saturated sodium bicarbonate. The solvent was evaporated under reduced pressure and the residue was diluted with dichloromethane (400 mL), washed with brine, dried over anhydrous magnesium sulfate and evaporated in vacuo. Chromatography of the residue on silica gel (3×10 cm, elution with dichloromethane-ethyl acetate 0-4%) gave 1.70 g (83% yield) of the title compound as a white solid. This material was recrystallized from ethyl acetate (30 mL per gram, 80% recovery) to give white needles. LC (Method A): 2.293 min. HRMS(ESI) calcd for $C_{21}H_{18}N_3O_4S$ [M+H]$^+$ m/z 408.1013. found 408.1024. $^1$H NMR (CDCl$_3$, 600 MHz) δ 3.81 (s, 3H), 4.18 (s, 3H), 5.16 (s, 2H), 6.37 (d, J=1.75 Hz, 1H), 6.67 (broad s, 1H), 7.07 (s, 1H), 7.31 (broad t, 1H), 7.37 (broad t, 2H), 7.45 (broad d, 2H), 7.81 (s, 1H).

1G. 6-Methoxy-2-(2-methoxyimidazo[2,1-b][1,3,4]thiadiazol-6-yl)benzofuran-4-ol

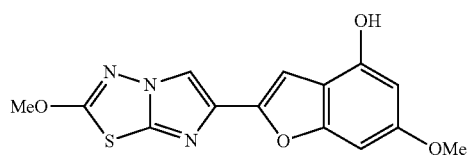 [SMILES: COc1cc(O)c2cc(-c3cn4nc(OC)sc4n3)oc2c1]

A mixture of 6-(4-(benzyloxy)-6-methoxybenzofuran-2-yl)-2-methoxyimidazo[2,1-b][1,3,4]thiadiazole (Example 1F, 1.250 g, 3.06 mmol) and pentamethylbenzene (3.17 g, 21.4 mmol) in dichloromethane (200 mL) was cooled to −78° C. under a nitrogen atmosphere and then treated immediately (to avoid crystallization) with 8 mL (8 mmol) of a 1 M solution of boron trichloride in dichloromethane added dropwise over 3 min. The resulting mixture was stirred at −78° C. for 1 h. The reaction mixture was then quenched by the addition of a solution of sodium bicarbonate (6 g) in water (100 mL) added in one portion. The cooling bath was removed and the resulting mixture was stirred at room temperature for 1 h. The solid formed was filtered, washed successively with water (50 m) and dichloromethane (50 mL). The filter cake was allowed to soak with anhydrous ethanol (15 ml) and then sucked dry. The white solid obtained was then dried under vacuum for 24 h to give 0.788 g (80% yield) of pure title material (>95% by hplc). The combined filtrate and washings were diluted with dichloromethane (600 mL) and stirred in a warm water bath till the organic phase was clear with no apparent solid in suspension. The organic phase was collected, dried over anhydrous magnesium sulfate and rapidly filtered while still warm. The filtrate was evaporated and the residue (product and hexamethylbenzene) was triturated with toluene (20 mL), the solid collected and washed with toluene (20 mL) to give 0.186 g (19% yield, 99% combined yield) of title material as a tan solid (>95% by hplc). LC (Method B): 1.444 min. HRMS(ESI) calcd for $C_{14}H_{12}N_3O_4S$ [M+H]$^+$ m/z 318.0543. found 318.0578. $^1$H NMR (DMSO-d$_6$, 600 MHz) δ 3.71 (s, 3H), 4.16 (s, 3H), 6.21 (d, J=1.87 Hz, 1H), 6.61 (broad s, 1H), 6.95 (s, 1H), 8.29 (s, 1H), 9.96 (s, 1H).

Example 1

2-Methoxy-6-(6-methoxy-4-((3-(pyrimidin-5-yl)benzyl)oxy)benzofuran-2-yl)imidazo[2,1-b][1,3,4]thiadiazole

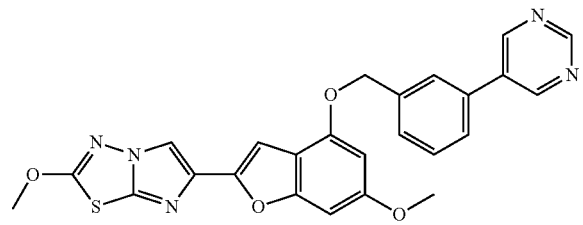 [SMILES: COc1cc(OCc2cccc(-c3cncnc3)c2)c2cc(-c3cn4nc(OC)sc4n3)oc2c1]

Into a 16×100 mm Wheaton tube was added (3-(pyrimidin-5-yl)phenyl)methanol (28 mg, 0.150 mmol) followed with 6-methoxy-2-(2-methoxyimidazo[2,1-b][1,3,4]thiadiazol-6-yl)benzofuran-4-ol (Example 1G, 16 mg, 0.050 mmol) and triphenylphosphine (26 mg, 0.100 mmol). The vial was capped with septum cap. Air was then evacuated and the vial was purged with N$_2$. To the reaction mixture was then added DIAD (39 µL, 0.200 mmol) via syringe followed with THF (0.5 mL, 0.1M). The reaction was stirred at room temperature overnight, then placed in SPEEDVAC® to dry for 2 h at 40° C. The crude material was dissolved in DMF (1.5 mL) and purified on Prep HPLC (HPLC Waters System, Column: Waters Xbridge 19×100 mm, 5 um C18, Mobile Phase:A=5:95 Acetonitrile:Water, B=95:5 Acetonitrile:Water, Modifier=0.05% TFA, Wavelength: 220 nm) to give the title material (0.63 mg, 2%). LC (Method A): 2.75 min. MS(ESI) calcd for $C_{25}H_{19}N_5O_4S$ [M+H]$^+$ m/z 485.1158. found 486.04.

Example 2

2-Methoxy-6-(6-methoxy-4-((3'-(trifluoromethyl)-[1,1'-biphenyl]-3-yl)methoxy)benzofuran-2-yl)imidazo[2,1-b][1,3,4]thiadiazole

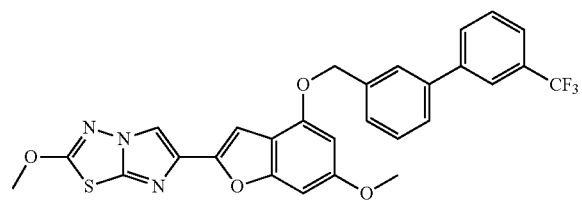 [SMILES: COc1cc(OCc2cccc(-c3cccc(C(F)(F)F)c3)c2)c2cc(-c3cn4nc(OC)sc4n3)oc2c1]

2A. (3'-(Trifluoromethyl)-[1,1'-biphenyl]-3-yl)methanol

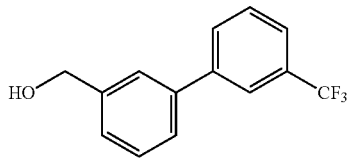 [SMILES: OCc1cccc(-c2cccc(C(F)(F)F)c2)c1]

In a 4 mL vial, palladium(II) acetate (1.3 mg, 5.79 μmol), triphenylphosphine (4 mg, 0.015 mmol), 2M aqueous solution of sodium carbonate (0.56 mL, 1.120 mmol) and water (0.37 mL, 20.54 mmol) were successively added to a mixture of (3-(trifluoromethyl)phenyl)boronic acid (161 mg, 0.848 mmol) and (3-iodophenyl)methanol (0.1 mL, 0.787 mmol) in 1-propanol (1.5 mL, 19.97 mmol) under nitrogen. The mixture was stirred at 95° C. for 4 h. The mixture was quenched with water and the product was extracted three times with AcOEt. The combined organic layers were washed twice with 1:1 sat. NaHCO$_3$:water, once with brine, dried over anh. MgSO$_4$ and concentrated. The residue was purified on ISCO using a REDISEP® Gold 12 g column (Hex/EtOAc) to give the title material (192 mg, 97%) as a clear oil. LC (Method B): 2.099 min. MS(ESI) calcd for C$_{14}$H$_{10}$F$_3$ [M+H]$^+$—H$_2$O m/z 235.0813. found 235.0753. $^1$H NMR (400 MHz, acetone-d$_6$) ppm 7.91-8.01 (m, 2H) 7.67-7.78 (m, 3H) 7.61 (dt, J=7.4, 1.8 Hz, 1H) 7.45-7.50 (m, 1H) 7.41-7.45 (m, 1H) 4.74 (d, J=5.9 Hz, 2H) 4.30 (t, J=5.9 Hz, 1H).

Example 2

2-Methoxy-6-(6-methoxy-4-((3'-(trifluoromethyl)-[1,1'-biphenyl]-3-yl)methoxy)benzofuran-2-yl)imidazo[2,1-b][1,3,4]thiadiazole

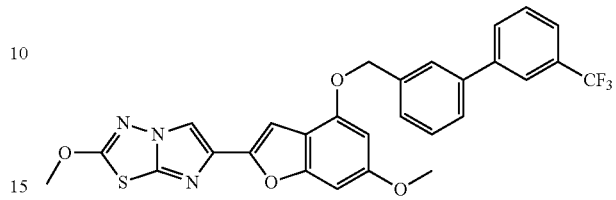

In a 10 mL round-bottomed flask, benzene was added to 6-methoxy-2-(2-methoxyimidazo[2,1-b][1,3,4]thiadiazol-6-yl)benzofuran-4-ol (Example 1G, 28 mg, 0.088 mmol) and the mixture was sonificated 30 sec. and concentrated in vacuo. The procedure was repeated once to remove traces of water in the starting material. Triphenylphosphine (58 mg, 0.221 mmol) was added and the mixture was dried on high vacuum for 10 min. To this mixture (3'-(trifluoromethyl)-[1,1'-biphenyl]-3-yl)methanol (Example 3A, 70 mg, 0.278 mmol) and THF (1.5 mL) were added and the mixture was sonificated for 5 min. A solution of diisopropyl azodicarboxylate (0.045 ml, 0.231 mmol) in THF (1 mL) was then added dropwise on 5 min. and the yellow solution was sonificated for 30 min. and stirred 18 h at room temperature. The reaction mixture was diluted in CH$_2$Cl$_2$ and washed once with sat. NaHCO$_3$, once with brine, dried on anhydrous Na$_2$SO$_4$ and concentrated. The residue was purified on ISCO using a REDISEP® Gold 12 g column (CH$_2$Cl$_2$/EtOAc) to give the title material (28 mg, 58%) as a light beige solid after lyophilization in ACN/water. LC (Method B): 2.59 min. MS(ESI) calcd for C$_{28}$H$_{21}$F$_3$N$_3$O$_4$S [M+H]$^+$ m/z 552.1199, 553.123. found 552.1221, 552.1241. $^1$H NMR (400 MHz, DMSO-d$_6$) ppm 8.38 (s, 1H) 8.01-8.04 (m, 1H) 8.00 (s, 1H) 7.90 (s, 1H) 7.70-7.78 (m, 3H) 7.53-7.61 (m, 2H) 7.00 (d, J=0.8 Hz, 1H) 6.84 (dd, J=2.0, 0.8 Hz, 1H) 6.57 (d, J=1.6 Hz, 1H) 5.35 (s, 2H) 4.20 (s, 3H) 3.80 (s, 3H).

Preparation of Benzylic Alcohols

The following benzylic alcohols were prepared according to the procedure described in Example 2A using (3-iodophenyl)methanol and the corresponding boronic acids and were employed in preparing compounds of the Examples as indicated.

| Structure (Employed in preparation of Example compound as indicated) | Formula | Calc. [M + H]$^+$ m/z | Calc. [M + H]$^+$ − H$_2$O m/z | LCMS [M + H]$^+$ m/z | LCMS [M + H]$^+$ − H$_2$O m/z | HPLC Retention Time (Min)/Method | NMR |
|---|---|---|---|---|---|---|---|
| ![structure] (4) | C$_{15}$H$_{12}$OS | 241.0682 | 223.0576 | 241.07 | 223.0596 | 2.153/B | $^1$H NMR (400 MHz, acetone) ppm 7.90-7.96 (m, 1 H) 7.83-7.88 (m, 1 H) 7.81 (dt, J = 2.4, 0.9 Hz, 1 H) 7.78 (d, J = 0.8 Hz, 1 H) 7.65-7.71 (m, 1H) 7.44 (t, J = 7.5 Hz, 1 H) 7.32-7.41 (m, 3 H) 4.72 (d, J = 5.9 Hz, 2 H) 4.34 (t, J = 5.7 Hz, 1 H) |

-continued

| Structure (Employed in preparation of Example compound as indicated) | Formula | Calc. [M + H]⁺ m/z | Calc. [M + H]⁺ − H₂O m/z | LCMS [M + H]⁺ m/z | LCMS [M + H]⁺ − H₂O m/z | HPLC Retention Time (Min)/ Method | NMR |
|---|---|---|---|---|---|---|---|
| (5) | $C_{12}H_{13}NO_2$ | 204.1019 | | 204.1052 | | 1.621/B | ¹H NMR (400 MHz, acetone) ppm 7.40-7.48 (m, 1 H) 7.33-7.40 (m, 2 H) 7.24 (dt, J = 7.2, 1.7 Hz, 1 H) 4.62-4.73 (m, 2 H) 4.25-4.32 (m, 1 H) 2.40 (s, 3 H) 2.22 (s, 3 H) |
| (6) | $C_{11}H_{10}O_2$ | 175.0754 | 157.0648 | 175.0779 | 157.0678 | 1.701/B | ¹H NMR (400 MHz, acetone) ppm 7.96-8.05 (m, 1H) 7.62-7.65 (m, 1H) 7.57-7.61 (m, 1 H) 7.47 (dt, J = 7.4, J = 7.4, 1. Hz, 1 H) 7.34 (t, J = 7.6 Hz, 1H) |
| (59) | $C_{16}H_{18}N_2O_2$ | 271.14 | | 271.2 | | 1.163/B | ¹H NMR (400 MHz, acetone) δ ppm 8.46 (dd, J = 2.7, 0.8 Hz, 1H) 7.85 (dd, J = 8.8, 2.5 Hz, 1H) 7.58-7.62 (m, 1H) 7.45-7.50 (m, 1H) 7.39 (t, J = 7.6 Hz, 1H) 7.28-7.34 (m, 1H) 6.88 (dd, J = 8.6, 0.8 Hz, 1H) 4.69 (d, J = 6.3 Hz, 2H) 4.21 (t, J = 5.9 Hz, 1H) 3.73-3.79 (m, 4H) 3.51-3.58 (m, 4H) |

Example 3

2-Methoxy-6-(6-methoxy-4-((3-(pyrimidin-2-yl)benzyl)oxy)benzofuran-2-yl)imidazo[2,1-b][1,3,4]thiadiazole

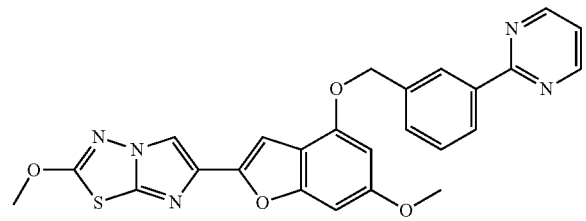 [SMILES: COc1cc(OCc2cccc(-c3ncccn3)c2)c2cc(-c3cn4nc(OC)sc4n3)oc2c1]

3A. (3-(Pyrimidin-2-yl)phenyl)methanol

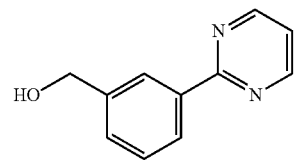 [SMILES: OCc1cccc(-c2ncccn2)c1]

In a 4 mL vial, palladium(II) acetate (0.9 mg, 4.01 μmol), triphenylphosphine (2.7 mg, 10.29 μmol), 2M aqueous solution of sodium carbonate (0.55 ml, 1.100 mmol) and water (0.3 ml, 16.65 mmol) were successively added to a mixture of 2-bromopyrimidine (120 mg, 0.755 mmol) and (3-(hydroxymethyl)phenyl)boronic acid (121 mg, 0.796 mmol) in 1-propanol (1.5 ml, 19.97 mmol) under nitrogen. The mixture was stirred at 95° C. for 2.5 hours. The mixture was quenched with water and the product was extracted three times with AcOEt. The combined organic layers were washed once with sat. NaHCO₃, once with brine, dried over anh. Na₂SO₄ and concentrated. The residue was purified on ISCO using a REDISEP® Gold 12 g column (Hex/EtOAc) to give the title material (52 mg, 37%) as a clear oil. LC (Method B): 1.372 min. MS(ESI) calcd for $C_{11}H_{12}N_2O$ [M+H]⁺ m/z 187.0866. found 187.0898. ¹H NMR (400 MHz, acetone) ppm 8.87 (d, J=5.1 Hz, 2H) 8.47-8.55 (m, 1H) 8.37 (dt, J=7.4, 1.6 Hz, 1H) 7.42-7.56 (m, 2H) 7.38 (t, J=4.7 Hz, 1H) 4.68-4.79 (m, 2H) 4.31 (t, J=5.9 Hz, 1H).

Example 3

2-Methoxy-6-(6-methoxy-4-((3-(pyrimidin-2-yl)benzyl)oxy)benzofuran-2-yl)imidazo[2,1-b][1,3,4]thiadiazole

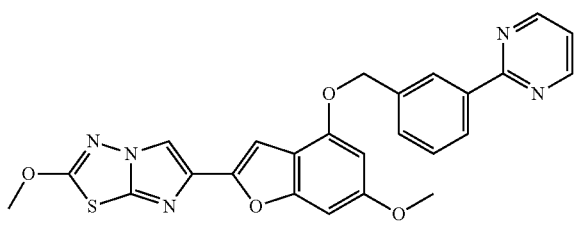

In a 10 mL round-bottomed flask, benzene was added to 6-methoxy-2-(2-methoxyimidazo[2,1-b][1,3,4]thiadiazol-6-yl)benzofuran-4-ol (Example 1G, 30 mg, 0.095 mmol) and the mixture was sonificated for 30 sec. and concentrated in vacuo to remove traces of water in the starting material. Triphenylphosphine (62 mg, 0.236 mmol) was added and the mixture was dried under high vacuum for 10 min. (3-(Pyrimidin-2-yl)phenyl)methanol (Example 4A, 50 mg, 0.269 mmol) and THF (1.5 mL) were added and the mixture was sonificated for 5 min. Diisopropyl azodicarboxylate (0.045 ml, 0.231 mmol) in THF (1 mL) was added dropwise over 5 min. and the yellow solution was sonificated for 30 min. and stirred over weekend at room temperature. The reaction mixture was then diluted in $CH_2Cl_2$, washed once with sat. $NaHCO_3$, once with brine, dried over anh. $Na_2SO_4$ and concentrated. The residue was purified on ISCO using a REDISEP® Gold 12 g column ($CH_2Cl_2$/EtOAc). The material (92% purity) was dissolved in DMF and purified on a reverse-phase ZORBAX® SB-C18 column 21.2×100 mm and was eluted with MeOH-water-0.1% TFA with a gradient of 50% to 100% MeOH over 6 minutes. The fractions were collected, concentrated in vacuo and lyophilized in ACN/water to give the title material (20 mg, 44%) as a yellowish solid. LC (Method B): 2.384 min. MS(ESI) calcd for $C_{25}H_{20}N_5O_4S$ $[M+H]^+$ m/z 486.1231. found 486.1251. $^1H$ NMR (400 MHz, DMSO-$d_6$) ppm 8.93 (d, J=5.1 Hz, 2H) 8.50-8.60 (m, 1H) 8.33-8.42 (m, 2H) 7.65-7.73 (m, 1H) 7.59 (t, J=7.6 Hz, 1H) 7.47 (t, J=4.7 Hz, 1H) 7.00 (d, J=0.8 Hz, 1H) 6.84 (dd, J=1.8, 1.0 Hz, 1H) 6.56 (d, J=1.6 Hz, 1H) 5.38 (s, 2H) 4.20 (s, 3H) 3.79 (s, 3H).

Preparation of Benzylic Alcohols

The following benzylic alcohols were prepared according to the procedure described in Example 3A using (3-(hydroxymethyl)phenyl)boronic acid and the corresponding bromides or iodides and were employed in preparing compounds of the Examples as indicated.

| Structure (Employed in preparation of compound as indicated) | Formula | Calc. [M + H]+ m/z | Calc. [M + H]+ - H2O m/z | LCMS [M + H]+ m/z | LCMS [M + H]+ - H2O m/z | HPLC Retention Time (Min)/ Method | NMR |
|---|---|---|---|---|---|---|---|
| 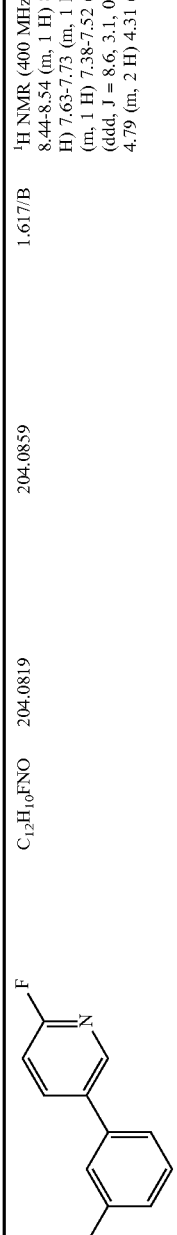 (7) | $C_{12}H_{10}FNO$ | 204.0819 | | 204.0859 | | 1.617/B | 1H NMR (400 MHz, acetone) δ ppm 8.44-8.54 (m, 1 H) 8.16-8.29 (m, 1 H) 7.63-7.73 (m, 1 H) 7.53-7.61 (m, 1 H) 7.38-7.52 (m, 2 H) 7.18 (ddd, J = 8.6, 3.1, 0.8 Hz, 1 H) 4.64-4.79 (m, 2 H) 4.31 (t, J = 5.9 Hz, 1 H) |
| 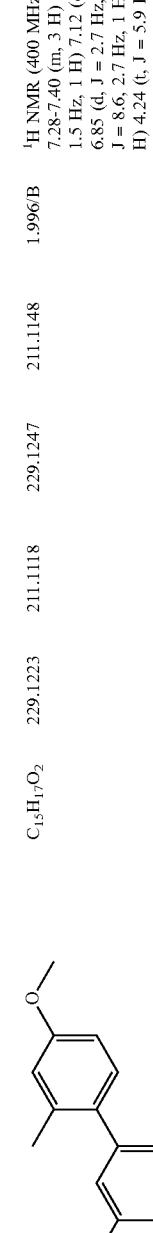 (8) | $C_{15}H_{17}O_2$ | 229.1223 | 211.1118 | 229.1247 | 211.1148 | 1.996/B | 1H NMR (400 MHz, acetone) δ ppm 7.28-7.40 (m, 3 H) 7.17 (dt, J = 7.2, 1.5 Hz, 1 H) 7.12 (d, J = 8.2 Hz, 1 H) 6.85 (d, J = 2.7 Hz, 1 H) 6.81 (dd, J = 8.6, 2.7 Hz, 1 H) 4.61-4.74 (m, 2 H) 4.24 (t, J = 5.9 Hz, 1 H) 3.81 (s, 3 H) 2.23 (s, 3 H) |
| 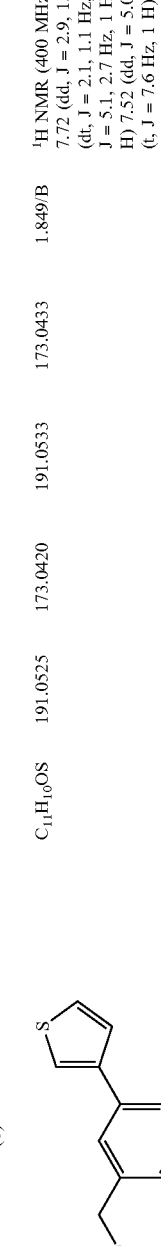 (9) | $C_{11}H_{10}OS$ | 191.0525 | 173.0420 | 191.0533 | 173.0433 | 1.849/B | 1H NMR (400 MHz, acetone) δ ppm 7.72 (dd, J = 2.9, 1.4 Hz, 1 H) 7.70 (dt, J = 2.1, 1.1 Hz, 1 H) 7.56 (dd, J = 5.1, 2.7 Hz, 1 H) 7.54-7.60 (m, 1 H) 7.52 (dd, J = 5.0, 1.6 Hz, 1 H) 7.37 (t, J = 7.6 Hz, 1 H) 7.27-7.32 (m, 1 H) 4.62-4.72 (m, 2 H) 4.25 (t, J = 5.9 Hz, 1 H) |
|  (10) | $C_{11}H_{12}N_2O$ | 189.1022 | | 189.1049 | | 1.439/B | 1H NMR (400 MHz, acetone) δ ppm 7.95 (s, 1 H) 7.77 (d, J = 0.8 Hz, 1 H) 7.51-7.60 (m, 1 H) 7.43 (dt, J = 7.4, 1.8 Hz, 1 H) 7.29 (t, J = 7.6 Hz, 1 H) 7.14-7.23 (m, 1 H) 4.58-4.68 (m, 2 H) 4.20 (t, J = 5.9 Hz, 1 H) 3.90 (s, 3 H) |

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/Method | NMR |
|---|---|---|---|---|---|---|---|
| (12) | C15H12OS | 241.0682 | 223.0576 | 241.0682 | 223.058 | 2.117/B | 1H NMR (400 MHz, acetone) δ ppm 7.99-8.07 (m, 1 H) 7.90-7.98 (m, 1 H) 7.60-7.70 (m, 2 H) 7.40-7.55 (m, 5 H) 4.74 (d, J = 5.9 Hz, 2 H) 4.29 (t, J = 5.9 Hz, 1 H) |
| (13) | C13H10N2O | 211.0866 | | 211.0882 | | 1.561/B | 1H NMR (400 MHz, acetone) δ ppm 9.05 (dd, J = 2.3, 0.8 Hz, 1H) 8.31 (dd, J = 7.8, 2.3 Hz, 1H) 8.02 (dd, J = 8.0, 1.0 Hz, 1H) 7.76-7.85 (m, 1H) 7.62-7.74 (m, 1H) 7.44-7.58 (m, 2H) 4.75 (d, J = 5.9 Hz, 2H) 4.35 (t, J = 5.7 Hz, 1H) |
| (14) | C12H10FNO | 204.0819 | | 204.0836 | | 1.561/B | 1H NMR (400 MHz, acetone) δ ppm 8.57 (d, J = 2.7 Hz, 1H) 8.06-8.12 (m, 1H) 7.97-8.05 (m, 1H) 7.89-7.97 (m, 1H) 7.62-7.76 (m, 1H) 7.37-7.50 (m, 2H) 4.27 (t, J = 5.9 Hz, 2H) 4.27 (t, J = 5.9 Hz, 1H) |
| (15) | C12H11NO | 186.0913 | | 186.092 | | 0.937/B | 1H NMR (400 MHz, acetone) δ ppm 8.87 (dd, J = 2.3, 0.8 Hz, 1H) 8.57 (dd, J = 4.9, 1.8 Hz, 1H) 8.02 (dq, J = 7.8, 1.3 Hz, 1H) 7.64-7.73 (m, 1H) 7.58 (dt, J = 7.6, 1.7 Hz, 1H) 7.37-7.52 (m, 3H) 4.73 (d, J = 6.3 Hz, 2H) 4.29 (t, J = 5.9 Hz, 1H) |

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 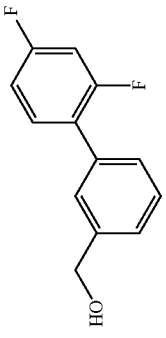 (17) | $C_{13}H_{10}F_2O$ | | 203.0667 | | 203.0655 | 1.974/B | 1H NMR (400 MHz, acetone) δ ppm 7.51-7.62 (m, 2H) 7.33-7.48 (m, 3 H) 7.05-7.20 (m, 2H) 4.71 (d, J = 6.3 Hz, 2 H) 4.27 (t, J = 5.9 Hz, 1H) |
| 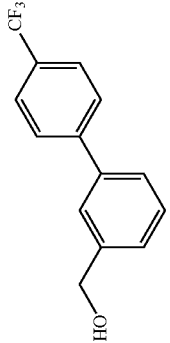 (16) | $C_{14}H_{11}F_3O$ | | 235.0730 | | 235.0720 | 2.110/B | 1H NMR (400 MHz, acetone) δ ppm 7.89 (m, J = 8.6 Hz, 2H) 7.81 (m, J = 8.6 Hz, 2H) 7.73 (s, 1H) 7.56-7.64 (m, 1H) 7.38-7.52 (m, 2H) 4.73 (d, J = 5.5 Hz, 2H) 4.31 (t, J = 5.7 Hz, 1H) |
| 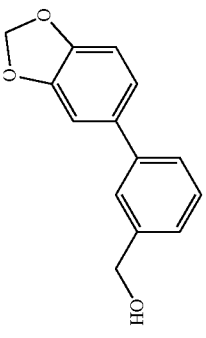 (18) | $C_{14}H_{12}O_3$ | 229.0859 | 211.0754 | 229.0847 | 211.0749 | 1.869/B | 1H NMR (400 MHz, acetone) δ ppm 7.59 (s, 1H) 7.42-7.50 (m, 1H) 7.38 (t, J = 7.6 Hz, 1 H) 7.27-7.34 (m, 1H) 7.07-7.20 (m, 2H) 6.88-6.98 (m, 1H) 6.04 (s, 2H) 4.69 (d, J = 5.9 Hz, 2H) 4.21 (t, J = 5.9 Hz, 1H) |
| 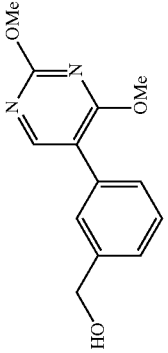 (19) | $C_{13}H_{14}N_2O_3$ | 247.1077 | | 247.109 | | 1.543/B | 1H NMR (400 MHz, acetone) δ ppm 8.30 (s, 1H) 7.50-7.58 (m, 1H) 7.31-7.47 (m, 3H) 4.68 (d, J = 5.5 Hz, 2H) 4.23 (t, J = 5.9 Hz, 1H) 3.99 (s, 3H) 3.98 (s, 3H) |

| Structure (Employed in preparation of compound as indicated) | Formula | Calc. [M + H]+ m/z | Calc. [M + H]+ - H2O m/z | LCMS [M + H]+ m/z | LCMS [M + H]+ - H2O m/z | HPLC Retention Time (Min)/ Method | NMR |
|---|---|---|---|---|---|---|---|
| (20) | $C_{13}H_{10}N_2OS$ | 243.0587 | | 243.0595 | | 1.916/B | 1H NMR (400 MHz, acetone) δ ppm 8.26 (dd, J = 1.6, 0.8 Hz, 1H) 8.02-8.19 (m, 2H) 7.85 (s, 1H) 7.73 (dt, J = 7.3, 1.6 Hz, 1H) 7.40-7.60 (m, 2H) 4.77 (d, J = 5.9 Hz, 2H) 4.33 (t, J = 5.9 Hz, 1H) |
| (21) | $C_{14}H_{12}N_2O$ | 225.1022 | | 225.1038 | | 1.010/B | 1H NMR (400 MHz, acetone) δ ppm 8.55 (dt, J = 7.0, 1.2 Hz, 1H) 7.69 (s, 1H) 7.66-7.68 (m, 1H) 7.60 (dt, J = 9.0, 1.2 Hz, 1H) 7.49-7.56 (m, 2H) 7.42-7.46 (m, 1H) 7.28 (ddd, J = 9.0, 6.6, 1.2 Hz, 1H) 6.94 (td, J = 6.8, 1.2 Hz, 1H) 4.74 (d, J = 5.9 Hz, 2H) 4.35 (t, J = 5.9 Hz, 1H) |
| (23) | $C_{14}H_{13}N_2O$ | 225.1022 | | 225.1055 | | 1.076/B | 1H NMR (400 MHz, acetone) δ ppm 8.79 (dd, J = 1.8, 1.0 Hz, 1H) 7.87-7.98 (m, 1H) 7.67-7.73 (m, 1H) 7.51-7.65 (m, 4H) 7.45 (t, J = 7.6 Hz, 1H) 7.37-7.42 (m, 1H) 4.73 (d, J = 5.9 Hz, 2H) 4.29 (t, J = 5.9 Hz, 1H) |

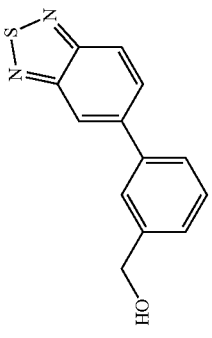

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 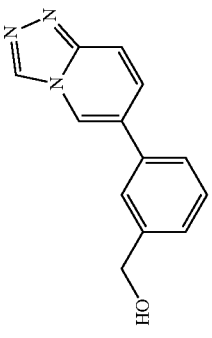 (22) | $C_{13}H_{11}N_3O$ | 226.0975 | | 226.0996 | | 1.129/B | 1H NMR (400 MHz, DMSO-d6) δ ppm 9.26 (d, J = 0.8 Hz, 1H) 8.86-8.98 (m, 1H) 7.87 (dt, J = 9.4, 1.0 Hz, 1H) 7.74 (dd, J = 9.6, 1.8 Hz, 1H) 7.65-7.70 (m, 1H) 7.59 (dq, J = 7.8, 1.0 Hz, 1H) 7.48 (t, J = 7.6 Hz, 1H) 7.33-7.43 (m, 1H) 5.30 (br. s., 1H) 4.59 (s, 2H) |
| 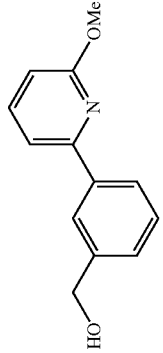 (24) | $C_{13}H_{13}NO_2$ | 216.1019 | | 216.1048 | | 1.764/B | 1H NMR (400 MHz, acetone) δ ppm 8.12 (s, 1H) 7.97-8.05 (m, 1H) 7.75 (t, J = 7.8 Hz, 1H) 7.51 (d, J = 7.4 Hz, 1H) 7.38-7.47 (m, 2H) 6.72 (d, J = 8.2 Hz, 1H) 4.72 (d, J = 5.9 Hz, 2H) 4.25 (t, J = 5.9 Hz, 1H) 4.00 (s, 3H) |
| 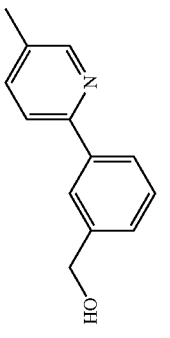 (25) | $C_{13}H_{13}NO$ | 200.1070 | | 200.1091 | | 0.992/B | 1H NMR (400 MHz, acetone) δ ppm 8.43-8.54 (m, 1H) 8.07-8.15 (m, 1H) 7.96 (dt, J = 6.7, 1.9 Hz, 1H) 7.81 (d, J = 8.6 Hz, 1H) 7.60-7.73 (m, 1H) 7.34-7.49 (m, 2H) 4.71 (d, J = 5.9 Hz, 2H) 4.24 (t, J = 5.9 Hz, 1H) 2.36 (s, 3H) |
| 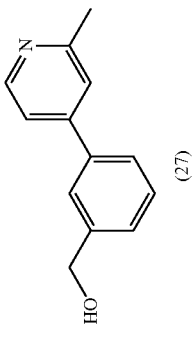 (27) | $C_{13}H_{13}NO$ | 200.1070 | | 200.1087 | | 0.998/B | 1H NMR (400 MHz, acetone) δ ppm 8.50 (d, J = 5.9 Hz, 1H) 7.75 (s, 1H) 7.58-7.67 (m, 1H) 7.52 (s, 1H) 7.40-7.49 (m, 3H) 4.73 (d, J = 5.9 Hz, 2H) 4.32 (t, J = 5.7 Hz, 1H) 2.55 (s, 3H) |

-continued

| Structure (Employed in preparation of compound as indicated) | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| (26) 2-cyanopyridin-3-yl with 3-(hydroxymethyl)phenyl | C13H10N2O | 211.0866 | | 211.0881 | | 1.391/B | 1H NMR (400 MHz, acetone) δ ppm 8.75 (dd, J = 4.7, 1.6 Hz, 1H) 8.02-8.14 (m, 1H) 7.80 (dd, J = 8.6, 4.7 Hz, 1H) 7.61-7.67 (m, 1H) 7.51-7.58 (m, 3H) 4.75 (d, J = 5.9 Hz, 2H) 4.38 (t, J = 5.9 Hz, 1H) |
| (29) 4'-cyano-3-(hydroxymethyl)biphenyl | C14H11NO | 210.0913 | | 210.0925 | | 1.741/B | 1H NMR (400 MHz, acetone) δ ppm 7.84-7.92 (m, 4H) 7.72-7.76 (m, 1H) 7.62 (dt, J = 7.0, 2.0 Hz, 1H) 7.43-7.51 (m, 2H) 4.73 (d, J = 5.9 Hz, 2H) 4.30 (t, J = 5.9 Hz, 1H) |
| (30) 4'-cyano-3'-fluoro-3-(hydroxymethyl)biphenyl | C14H10FNO | 228.0929 | | 228.0819 | | 1.800/B | 1H NMR (400 MHz, acetone) δ ppm 7.89-7.96 (m, 1H) 7.71-7.80 (m, 3H) 7.66 (td, J = 3.5, 1.6 Hz, 1H) 7.46-7.52 (m, 2H) 4.74 (d, J = 5.9 Hz, 2H) 4.32 (t, J = 5.7 Hz, 1H) |
| (28) 6-nitropyridin-3-yl with 3-(hydroxymethyl)phenyl | C12H10N2O3 | 231.0764 | | 231.0767 | | 1.507/B | 1H NMR (400 MHz, acetone) δ ppm 8.94 (dd, J = 2.3, 0.8 Hz, 1H) 8.49 (dd, J = 8.4, 2.5 Hz, 1H) 8.39 (dd, J = 8.6, 0.8 Hz, 1H) 7.82-7.85 (m, 1H) 7.70-7.76 (m, 1H) 7.52-7.58 (m, 2H) 4.76 (d, J = 5.4 Hz, 2H) 4.36 (t, J = 5.7 Hz, 1H) |

-continued

| Structure (Employed in preparation of compound as indicated) | Formula | Calc. [M + H]⁺ m/z | Calc. [M + H]⁺ – H₂O m/z | LCMS [M + H]⁺ m/z | LCMS [M + H]⁺ – H₂O m/z | HPLC Retention Time (Min)/ Method | NMR |
|---|---|---|---|---|---|---|---|
| (31) | C₁₅H₁₄O₃ | 243.1027 | | 243.1013 | | 1.854/B | ¹H NMR (400 MHz, acetone) δ ppm 7.58 (dt, J = 2.4, 0.9 Hz, 1H) 7.43-7.47 (m, 1H) 7.37 (t, J = 7.6 Hz, 1H) 7.28-7.32 (m, 1H) 7.11-7.14 (m, 2H) 6.89-6.92 (m, 1H) 4.69 (d, J = 5.9 Hz, 2H) 4.30 (s, 4H) 4.20 (t, J = 5.9 Hz, 1H) |
| (32) | C₁₃H₁₂FNO | 218.0976 | | | 218.1007 | 1.604/B | ¹H NMR (400 MHz, acetone) δ ppm 8.07 (s, 1H) 7.93 (dt, J = 6.4, 2.3 Hz, 1H) 7.80 (dd, J = 8.6, 3.5 Hz, 1H) 7.57 (t, J = 8.8 Hz, 1H) 7.37-7.46 (m, 2H) 4.72 (d, J = 5.8 Hz, 2H) 4.25 (t, J = 5.9 Hz, 1H) 2.54 (d, J = 3.1 Hz, 3H) |
| (33) | C₁₂H₉F₂NO | 222.0725 | | | 222.0747 | 1.672/B | ¹H NMR (400 MHz, acetone) δ ppm 8.51-8.56 (m, 1H) 7.93-7.98 (m, 1H) 7.81 (ddt, J = 5.2, 3.7, 2.0, 2.0 Hz, 1H) 7.68-7.77 (m, 1H) 7.43-7.50 (m, 2H) 4.73 (d, J = 5.8 Hz, 2H) 4.30 (t, J = 5.9 Hz, 1H) |
| (37) | C₁₄H₁₆N₂O₂ | 205.0772 | | 205.0873 | | 1.837/B | ¹H NMR (400 MHz, acetone) δ ppm 8.81 (s, 2 H) 7.65 (s, 1H) 7.51-7.58 (m, 1H) 7.46 (t, J = 7.5 Hz, 1H) 7.39-7.43 (m, 1H) 4.71 (d, J = 5.9 Hz, 2H) 4.33 (t, J = 6.7 Hz, 2H) 4.27 (t, J = 6.1 Hz, 1H) 1.81 (sxt, J = 7.1 Hz, 2H) 1.02 (t, J = 7.4 Hz, 3H) |

-continued

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 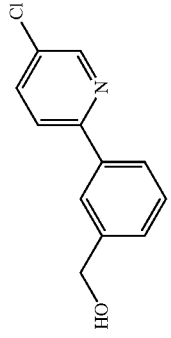 (36) | $C_{12}H_{10}ClNO$ | 220.0524 | | 220.0545 | | 1.759/B | $^1$H NMR (400 MHz, acetone) δ ppm 8.65 (d, J = 2.3 Hz, 1 H) 8.12 (s, 1H) 7.94-8.01 (m, 2H) 7.89-7.94 (m, 1H) 7.42-7.49 (m, 2H) 4.69-4.76 (m, 2H) 4.28 (t, J = 5.9 Hz, 1H) |
| 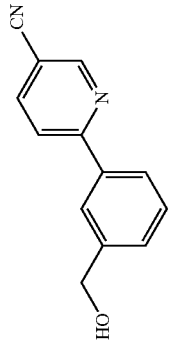 (35) | $C_{13}H_{10}N_2O$ | 211.0866 | | 211.0875 | | 1.515/B | $^1$H NMR (400 MHz, acetone) δ ppm 9.03 (dd, J = 2.2, 1.0 Hz, 1H) 8.26-8.31 (m, 1H) 8.20-8.24 (m, 1H) 8.17 (dd, J = 8.4, 1.0 Hz, 1H) 8.04-8.10 (m, 1H) 7.47-7.56 (m, 2H) 4.72-4.78 (m, 2H) 4.34 (t, J = 5.9 Hz, 1H) |
| 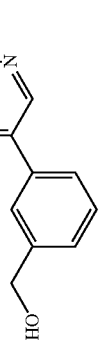 (34) | $C_{13}H_{13}NO_2$ | 216.1019 | | 216.1052 | | 1.628/B | $^1$H NMR (400 MHz, CDCl3) δ ppm 8.40 (d, J = 2.7 Hz, 1H), 7.81 (dd, J = 8.4, 2.2 Hz, 1H), 7.55 (s, 1H), 7.42-7.51 (m, 2H), 7.37 (d, J = 2.7 Hz, 1H), 6.83 (d, J = 8.6 Hz, 1H), 4.79 (d, J = 5.9 Hz, 2H), 4.00 (s, 3H), 1.70 (t, J = 5.9 Hz, 1H) |
| 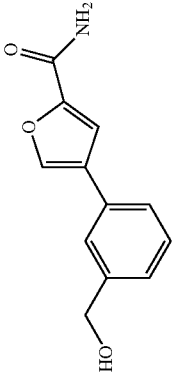 (41) | $C_{12}H_{11}NO_3$ | 218.0812 | | 218.0830 | | 1.299/B | $^1$H NMR (400 MHz, DMSO-d6) δ ppm 8.31 (s, 1H) 7.82 (br. s., 1H) 7.53-7.60 (m, 2H) 7.50 (d, J = 7.8 Hz, 1H) 7.43 (br. s., 1H) 7.37 (t, J = 7.8 Hz, 1H) 7.25 (d, J = 7.4 Hz, 1H) 5.22 (br. s., 1H) 4.53 (s, 2H) |

| Structure (Employed in preparation of compound as indicated) | Formula | Calc. [M + H]+ m/z | Calc. [M + H]+ − H₂O m/z | LCMS [M + H]+ m/z | LCMS [M + H]+ − H₂O m/z | HPLC Retention Time (Min)/ Method | NMR |
|---|---|---|---|---|---|---|---|
| 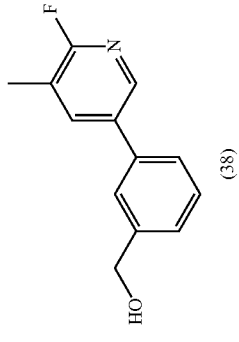 (38) | C₁₃H₁₂FNO | 218.0976 | | 218.1002 | | 1.725/B | ¹H NMR (400 MHz, acetone) δ ppm 8.25-8.31 (m, 1H) 8.01-8.09 (m, 1H) 7.66 (s, 1H) 7.55 (dt, J = 7.3, 1.6 Hz, 1H) 7.45 (t, J = 7.3 Hz, 1H) 7.40-7.43 (m, 1H) 4.72 (d, J = 5.9 Hz, 2H) 4.27 (t, J = 5.9 Hz, 1H) 2.32-2.38 (m, 3H) |
| 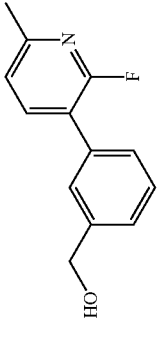 (39) | C₁₃H₁₂FNO | 218.0976 | | 218.1005 | | 1.654/B | ¹H NMR (400 MHz, acetone) δ ppm 7.93 (dd, J = 10.6, 7.4 Hz, 1H) 7.56-7.62 (m, 1H) 7.38-7.51 (m, 3H) 7.25-7.31 (m, 1H) 4.71 (d, J = 5.9 Hz, 2H) 4.28 (t, J = 5.7 Hz, 1H) 2.49 (s, 3H) |
| 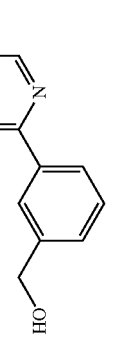 (40) | C₁₃H₁₃NO₂ | 216.1019 | | 216.1059 | | 1.099/B | ¹H NMR (400 MHz, acetone) δ ppm 8.34-8.38 (m, 1H) 8.04-8.08 (m, 1H) 7.91 (dt, J = 7.1, 1.7 Hz, 1H) 7.84-7.88 (m, 1H) 7.33-7.46 (m, 3H) 4.71 (d, J = 5.9 Hz, 2H) 4.21 (t, J = 5.9 Hz, 1H) 3.93 (s, 3H) |
| 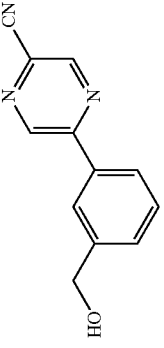 (42) | C₁₂H₉N₃O | 212.0817 | | | | 1.546/B | ¹H NMR (400 MHz, acetone) δ ppm 9.40 (s, 1H) 9.16 (s, 1H) 8.25-8.30 (m, 1H) 8.14 (dt, J = 7.4, 1.8 Hz, 1H) 7.53-7.63 (m, 2H) 4.77 (d, J = 6.3 Hz, 2H) 4.43 (t, J = 5.9 Hz, 1H) |

-continued

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 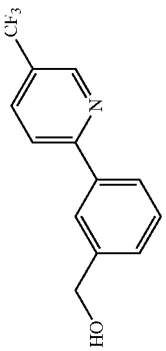 (43) | $C_{13}H_{10}F_3NO$ | 254.0787 | | 254.0802 | | 1.857/B | 1H NMR (400 MHz, acetone) δ ppm 8.97-9.03 (m, 1H) 8.15-8.25 (m, 3H) 8.05-8.10 (m, 1H) 7.46-7.54 (m, 2H) 4.75 (d, J = 5.9 Hz, 2H) 4.35 (t, J = 5.9 Hz, 1H) |
| 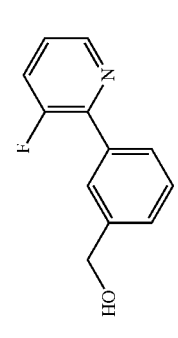 (44) | $C_{12}H_{10}FNO$ | 204.0819 | | 204.0834 | | 1.447/B | 1H NMR (400 MHz, acetone) δ ppm 8.51-8.57 (m, 1H) 7.99-8.04 (m, 1H) 7.87 (ddt, J = 5.3, 3.6, 2.0, 2.0 Hz, 1H) 7.71 (ddd, J = 11.6, 8.3, 1.5 Hz, 1H) 7.41-7.49 (m, 3H) 4.73 (d, J = 5.9 Hz, 2H) 4.32 (t, J = 5.9 Hz, 1H) |
| 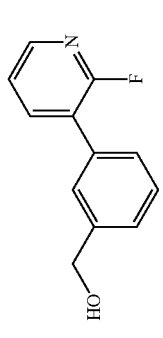 (46) | $C_{13}H_{10}N_2O$ | 211.0883 | | 211.0886 | | 1.363/B | 1H NMR (400 MHz, acetone) δ ppm 8.89 (d, J = 0.8 Hz, 1H) 8.82 (d, J = 5.1 Hz, 1H) 7.86 (dd, J = 4.9, 1.0 Hz, 1H) 7.64-7.67 (m, 1H) 7.53-7.58 (m, 3H) 4.76 (d, J = 5.9 Hz, 2H) 4.37 (t, J = 5.9 Hz, 1H) |
| 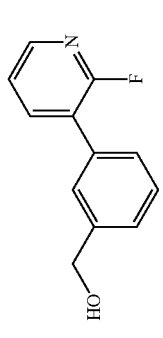 (45) | $C_{12}H_{10}FNO$ | 204.0819 | | 204.0833 | | 1.497/B | 1H NMR (400 MHz, acetone) δ ppm 8.22 (dt, J = 4.6, 1.8 Hz, 1H) 8.06 (ddd, J = 10.2, 7.4, 2.0 Hz, 1H) 7.60-7.64 (m, 1H) 7.41-7.53 (m, 4H) 4.72 (d, J = 5.5 Hz, 2H) 4.30 (t, J = 5.9 Hz, 1H) |

| Structure (Employed in preparation of compound as indicated) | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| 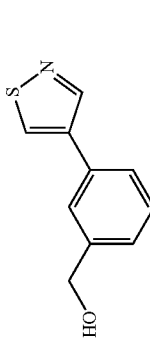 (48) | $C_{10}H_9NOS$ | 192.0478 | | 192.0488 | | 1.445/B | 1H NMR (400 MHz, acetone) δ ppm 9.17 (s, 1H) 8.94 (s, 1H) 7.74-7.79 (m, 1H) 7.62-7.67 (m, 1H) 7.42 (t, J = 7.5 Hz, 1H) 7.35-7.39 (m, 1H) 4.70 (d, J = 5.9 Hz, 2H) 4.26 (t, J = 5.9 Hz, 1H) |
| 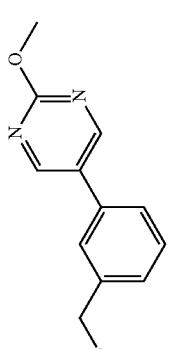 (47) | $C_{12}H_{12}N_2O_2$ | 217.0972 | | 217.0977 | | 1.477/B | 1H NMR (400 MHz, acetone) δ ppm 8.84 (s, 2H) 7.65-7.69 (m, 1H) 7.53-7.59 (m, 1H) 7.45-7.50 (m, 1H) 7.41-7.45 (m, 1H) 4.72 (d, J = 5.9 Hz, 2H) 4.29 (t, J = 5.9 Hz, 1H) 4.00 (s, 3H) |
| 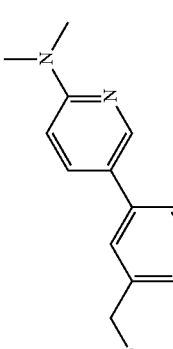 (49) | $C_{14}H_{16}N_2O$ | 229.1335 | | 229.1350 | | 1.122/B | 1H NMR (400 MHz, acetone) δ ppm 8.42 (dd, J = 2.3, 0.8 Hz, 1H) 7.79 (dd, J = 9.0, 2.8 Hz, 1H) 7.58 (dt, J = 2.1, 1.1 Hz, 1H) 7.43-7.49 (m, 1H) 7.37 (t, J = 7.6 Hz, 1H) 7.26-7.32 (m, 1H) 6.70 (dd, J = 9.0, 0.8 Hz, 1H) 4.68 (d, J = 6.2 Hz, 2H) 4.19 (t, J = 5.9 Hz, 1H) 3.11 (s, 6H) |
| 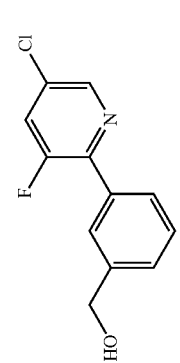 (50) | $C_{12}H_9ClFNO$ | 238.0429 | | 238.0452 | | 1.821/B | 1H NMR (400 MHz, acetone) δ ppm 8.57 (dd, J = 2.0, 1.2 Hz, 1H) 7.98-8.02 (m, 1H) 7.92 (dd, J = 11.0, 2.0 Hz, 1H) 7.81-7.87 (m, 1H) 7.46-7.52 (m, 2H) 4.71-4.76 (m, 2H) 4.32 (t, J = 5.9 Hz, 1H) |

-continued

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 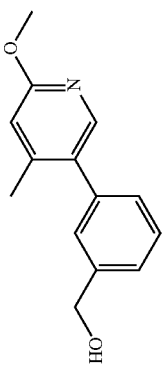 (51) | $C_{14}H_{15}NO_2$ | 230.1176 | | 230.1207 | | 1.487/B | $^1$H NMR (400 MHz, acetone) δ ppm 7.94 (s, 1H) 7.32-7.45 (m, 3H) 7.19-7.24 (m, 1H) 6.69 (quin, J = 0.8 Hz, 1H) 4.70 (d, J = 6.3 Hz, 2H) 4.24 (t, J = 5.9 Hz, 1H) 3.90 (s, 3H) 2.23 (d, J = 0.8 Hz, 3H) |
| 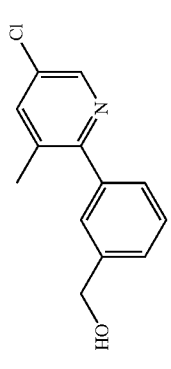 (52) | $C_{13}H_{12}ClNO$ | 234.068 | | 234.0713 | | 1.665/B | $^1$H NMR (400 MHz, acetone) δ ppm 8.45-8.48 (m, 1H) 7.78 (dq, J = 2.4, 0.8 Hz, 1H) 7.54-7.57 (m, 1H) 7.43 (d, J = 1.6 Hz, 3H) 4.71 (d, J = 5.9 Hz, 2H) 4.26 (t, J = 5.9 Hz, 1H) 2.38 (s, 3H) |
| 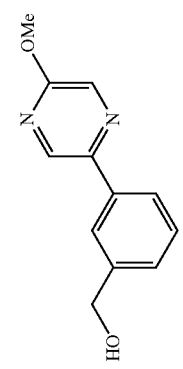 (53) | $C_{12}H_{12}N_2O_2$ | 217.0972 | | 217.0991 | | 1.647/B | $^1$H NMR (400 MHz, acetone) δ ppm 8.69 (d, J = 1.2 Hz, 1H) 8.29 (d, J = 1.6 Hz, 1H) 8.03-8.07 (m, 1H) 7.90 (dt, J = 7.3, 1.8 Hz, 1H) 7.39-7.48 (m, 2H) 4.72 (d, J = 6.3 Hz, 2H) 4.25 (t, J = 5.9 Hz, 2H) 4.00 (s, 3H) |
| 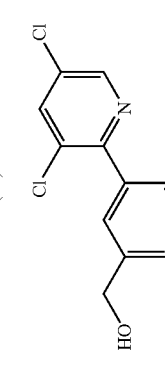 (54) | $C_{12}H_9Cl_2NO$ | 254.1034 | | | 254.0157 | 1.872/B | $^1$H NMR (400 MHz, acetone) δ ppm 8.63 (d, J = 2.3 Hz, 1H) 8.09-8.13 (m, 1H) 7.70-7.75 (m, 1H) 7.58-7.63 (m, 1H) 7.41-7.50 (m, 2H) 4.72 (d, J = 5.9 Hz, 2H) 4.28 (t, J = 5.9 Hz, 1H) |

-continued

| Structure (Employed in preparation of compound as indicated) | Formula | Calc. [M + H]+ m/z | Calc. [M + H]+ − H2O m/z | LCMS [M + H]+ m/z | LCMS [M + H]+ − H2O m/z | HPLC Retention Time (Min)/ Method | NMR |
|---|---|---|---|---|---|---|---|
| (55) 2-fluoro-4-[3-(hydroxymethyl)phenyl]pyridine | C12H10FNO | 204.0819 | | | 204.0838 | 1.534/B | 1H NMR (400 MHz, acetone) δ ppm 8.25-8.31 (m, 1H) 7.79-7.83 (m, 1H) 7.66-7.73 (m, 1H) 7.60-7.66 (m, 1H) 7.47-7.55 (m, 2H) 7.34-7.38 (m, 1H) 4.71-4.76 (m, 2H) 4.32 (t, J = 5.9 Hz, 1H) |
| (56) 2-chloro-5-[3-(hydroxymethyl)phenyl]pyridine | C12H10ClNO | 220.0524 | | | 220.0545 | 1.658/B | 1H NMR (400 MHz, acetone) δ ppm 8.68 (dd, J = 2.7, 0.8 Hz, 1H) 8.10 (dd, J = 8.4, 2.5 Hz, 1H) 7.68-7.72 (m, 1H) 7.57-7.60 (m, 1H) 7.54 (dd, J = 8.2, 0.8 Hz, 1H) 7.43-7.50 (m, 2H) 4.73 (d, J = 6.3 Hz, 2H) 4.29 (t, J = 5.7 Hz, 1H) |
| (57) {5-[3-(hydroxymethyl)phenyl]pyridin-2-yl}(morpholin-4-yl)methanone | C17H18N2O3 | 299.1390 | | | 299.1421 | 1.365/B | 1H NMR (400 MHz, acetone) δ ppm 8.86 (dd, J = 2.3, 1.2 Hz, 1H) 8.17 (dd, J = 8.2, 2.3 Hz, 1H) 7.72-7.77 (m, 2H) 7.63 (dt, J = 7.0, 1.8 Hz, 1H) 7.43-7.53 (m, 2H) 4.74 (d, J = 6.3 Hz, 2H) 4.30 (t, J = 5.9 Hz, 1H) 3.73 (s, 4 H) 3.60-3.71 (m, 4H) |

| Structure (Employed in preparation of compound as indicated) | Formula | Calc. [M + H]+ m/z | Calc. [M + H]+ – H2O m/z | LCMS [M + H]+ m/z | LCMS [M + H]+ – H2O m/z | HPLC Retention Time (Min)/ Method | NMR |
|---|---|---|---|---|---|---|---|
| 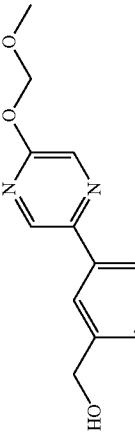 (58) | $C_{13}H_{14}N_2O_3$ | 247.1077 | | 247.1095 | | 1.300/B | 1H NMR (400 MHz, acetone) δ ppm 8.13 (d, J = 1.2 Hz, 1H) 8.06 (d, J = 1.2 Hz, 1H) 7.87-7.91 (m, 1H) 7.73-7.79 (m, 1H) 7.39 (t, J = 7.6 Hz, 1H) 7.29-7.35 (m, 1H) 5.37 (s, 2H) 4.69 (d, J = 6.3 Hz, 2H) 4.24 (t, J = 5.7 Hz, 1H) 3.42 (s, 3H) |
| 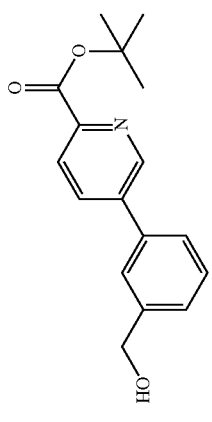 (60) | $C_{17}H_{19}NO_3$ | 286.14 | | 230.2 [M + H]+ – tBu | | 1.612/B | 1H NMR (400 MHz, acetone) δ ppm 8.96 (dd, J = 2.3, 0.8 Hz, 1H) 8.19 (dd, J = 8.2, 2.3 Hz, 1H) 8.11 (dd, J = 8.2, 0.8 Hz, 1H) 7.74-7.79 (m, 1H) 7.65 (dt, J = 7.2, 1.7 Hz, 1H) 7.45-7.55 (m, 2H) 4.72-4.77 (m, 2H) 4.32 (t, J = 5.9 Hz, 1H) 1.62 (s, 9H) |
| 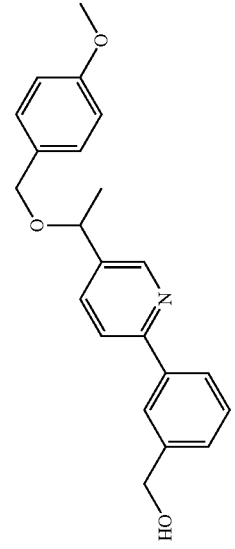 (61) | $C_{22}H_{23}NO_3$ | 350.18 | | 350.2 | | 1.784/B | 1H NMR (400 MHz, acetone) δ ppm 8.62-8.68 (m, 1H) 8.12-8.18 (m, 1H) 7.97-8.03 (m, 1H) 7.94 (dd, J = 8.2, 0.8 Hz, 1H) 7.81-7.90 (m, 1H) 7.39-7.48 (m, 2H) 7.22-7.31 (m, 2H) 6.86-6.94 (m, 2H) 4.71-4.76 (m, 2H) 4.66 (q, J = 6.3 Hz, 1H) 4.34-4.44 (m, 2H) 4.26 (t, J = 5.9 Hz, 1H) 3.79 (s, 3H) 1.49 (d, J = 6.7 Hz, 3H) |

Examples 4 to 61

The following additional Examples have been prepared, isolated and characterized using the method disclosed in Examples 1 to 3 employing the appropriate benzylic alcohol set out hereinbefore.

| Ex. | Structure | Formula | Calc. [M + H]+ m/z | HPLC Retention Time (Min)/ Method | LCMS [M + H]+ m/z | NMR |
|---|---|---|---|---|---|---|
| 4 | 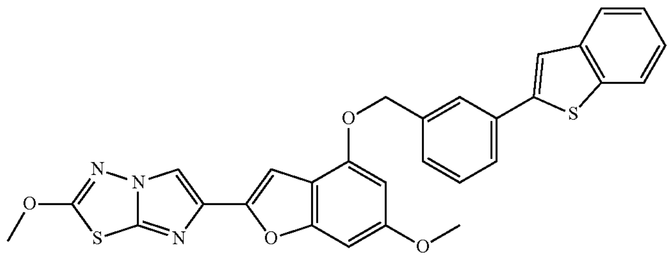 [SMILES: COc1cc(OCc2cccc(-c3cc4ccccc4s3)c2)c2cc(-c3cn4nc(OC)sc4n3)oc2c1] | C29H21N3O4S | 540.1055 | 2.688/B | 540.1046 | 1H NMR (400 MHz, DMSO-d6) δ ppm 8.34-8.43 (m, 1H) 7.99 (d, J = 7.4 Hz, 1H) 7.92 (s, 2H) 7.83-7.90 (m, 1 H) 7.73-7.83 (m, 1H) 7.54 (d, J = 4.3 Hz, 2H) 7.39 (quint, J = 7.3, 7.3, 7.3, 7.3, 1.4, 1.4 Hz, 2H) 7.03 (s, 1H) 6.80-6.91 (m, 1H) 6.49-6.64 (m, 1H) 5.35 (s, 2H) 4.21 (s, 3H) 3.80 (s, 3H) |
| 5 | 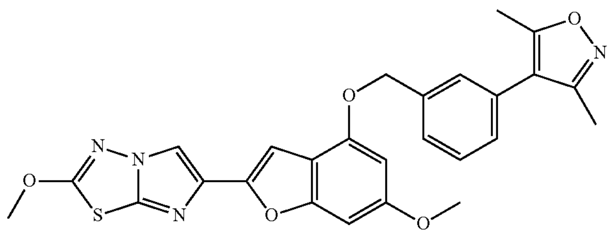 [SMILES: COc1cc(OCc2cccc(-c3c(C)noc3C)c2)c2cc(-c3cn4nc(OC)sc4n3)oc2c1] | C26H12N4O2S3 | 503.1384 | 2.396/B | 503.1399 | 1H NMR (400 MHz, DMSO-d6) δ ppm 8.38 (s, 1H) 7.47-7.57 (m, 3H) 7.36 (ddd, J = 5.2, 3.6, 1.8 Hz, 1H) 6.98 (d, J = 0.8 Hz, 1H) 6.79-6.88 (m, 1H) 6.56 (d, J = 2.0 Hz, 1H) 5.32 (s, 2H) 4.20 (s, 3H) 3.79 (s, 3H) 2.39 (s, 3H) 2.22 (s, 3H) |
| 6 | 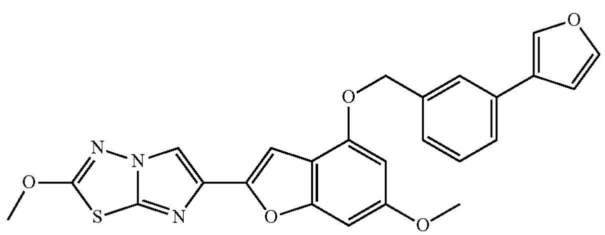 | C25H20N3O5S | 474.1118 | 2.411/B | 474.113 | 1H NMR (400 MHz, DMSO-d6) δ ppm 8.38 (s, 1H) 8.17-8.27 (m, 1H) 7.70-7.81 (m, 2H) 7.60 (d, J = 7.0 Hz, 1H) 7.33-7.48 (m, 2H) 6.92-7.04 (m, 2H) 6.83 (s, 1 H) 6.56 (s, 1H) 5.27 (s, 2H) 4.21 (s, 3H) 3.80 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 7 | 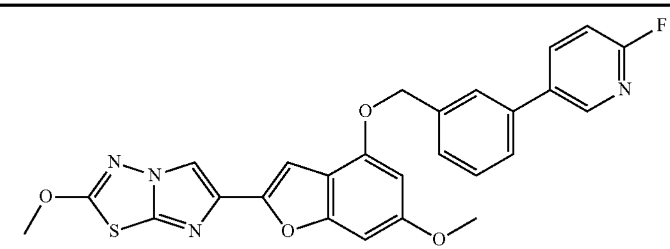 | $C_{26}H_{19}FN_4O_4S$ | 503.1184 | 2.400/B | 503.1205 | 1H NMR (400 MHz, DMSO-$d_6$) δ ppm 8.58 (d, J = 2.7 Hz, 1H) 8.38 (s, 1H) 8.32 (td, J = 8.2, 2.7 Hz, 1H) 7.81-7.93 (m, 1H) 7.71 (dt, J = 6.9, 2.1 Hz, 1H) 7.49-7.63 (m, 2H) 7.31 (dd, J = 8.6, 3.5 Hz, 1H) 7.01 (d, J = 0.8 Hz, 1H) 6.84 (dd, J = 2.0, 0.8 Hz, 1H) 6.57 (d, J = 2.0 Hz, 1H) 5.33 (s, 2H) 4.20 (s, 3H) 3.80 (s, 1H) |
| 8 | 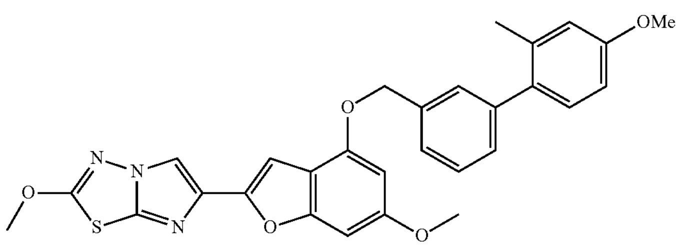 [SMILES: COc1ccc(-c2cccc(COc3cc(OC)cc4oc(-c5cn6nc(OC)sc6n5)cc34)c2)c(C)c1] | $C_{29}H_{25}N_3O_5S$ | 528.1588 | 2.573/B | 528.1607 | 1H NMR (400 MHz, DMSO-$d_6$) δ ppm 8.38 (s, 1H) 7.45-7.49 (m, 2H) 7.42 (s, 1H) 7.27 (ddd, J = 5.3, 3.5, 1.8 Hz, 1H) 7.14 (d, J = 8.6 Hz, 1H) 6.96 (d, J = 0.8 Hz, 1H) 6.88 (d, J = 2.7 Hz, 1H) 6.80-6.86 (m, 2H) 6.55 (d, J = 2.0 Hz, 1H) 5.31 (s, 2H) 4.20 (s, 3H) 3.79 (s, 3H) 3.77 (s, 3H) 2.20 (s, 3H) |
| 9 | 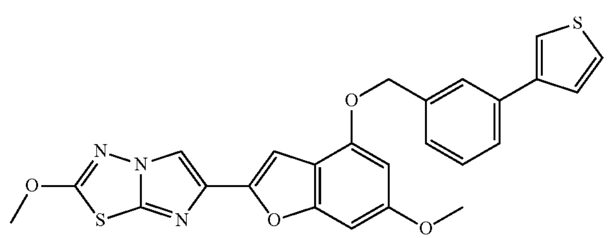 [SMILES: COc1cc(OCc2cccc(-c3ccsc3)c2)c2cc(-c3cn4nc(OC)sc4n3)oc2c1] | $C_{25}H_{19}N_3O_4S_2$ | 490.089 | 2.505/B | 490.0888 | 1H NMR (400 MHz, DMSO-$d_6$) δ ppm 8.38 (s, 1H) 7.89-7.95 (m, 1H) 7.85 (s, 1H) 7.70 (dt, J = 6.5, 2.1 Hz, 1H) 7.66 (ddd, J = 5.0, 3.0, 1.0 Hz, 1H) 7.58 (dt, J = 5.1, 1.2 Hz, 1H) 7.37-7.51 (m, 2H) 7.00 (s, 1H) 6.83 (s, 1H) 6.56 (d, J = 0.8 Hz, 1H) 5.29 (s, 2H) 4.20 (s, 3H) 3.79 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 10 | 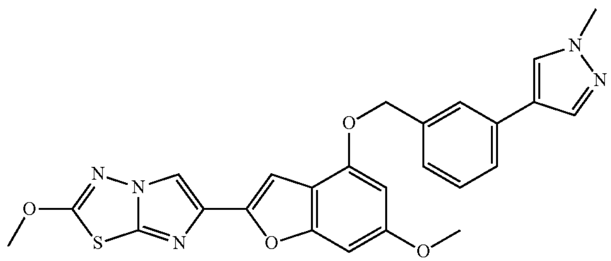 [SMILES: COc1cc(OCc2cccc(-c3cnn(C)c3)c2)c2cc(-c3cn4nc(OC)sc4n3)oc2c1] | $C_{25}H_{21}N_5O_4S$ | 488.1387 | 2.344/B | 488.1388 | 1H NMR (400 MHz, DMSO-d6) δ ppm 8.38 (s, 1H) 8.16 (s, 1H) 7.87 (s, 1H) 7.69 (s, 1H) 7.54 (d, J = 7.4 Hz, 1H) 7.39 (t, J = 7.6 Hz, 1H) 7.28-7.35 (m, 1H) 7.00 (s, 1H) 6.83 (s, 1H) 6.55 (d, J = 2.0 Hz, 1H) 5.25 (s, 2H) 4.20 (s, 3H) 3.86 (s, 3H) 3.79 (s, 3H) |
| 11 | 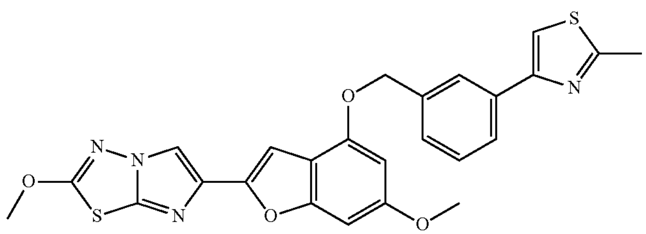 | $C_{25}H_{20}N_4O_4S_2$ | 505.0999 | 2.411/B | 505.0996 | 1H NMR (400 MHz, DMSO-d6) δ ppm 8.38 (s, 1H) 8.09 (s, 1H) 7.97 (s, 1H) 7.91 (t, J = 4.5 Hz, 1H) 7.48 (d, J = 5.1 Hz, 2H) 7.00 (s, 1H) 6.83 (s, 1H) 6.56 (s, 1H) 5.31 (s, 2H) 4.20 (s, 3H) 3.80 (s, 3H) 2.72 (s, 3H) |
| 12 | 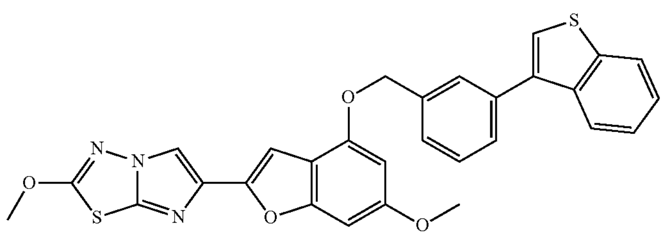 [SMILES: COc1cc(OCc2cccc(-c3csc4ccccc34)c2)c2cc(-c3cn4nc(OC)sc4n3)oc2c1] | $C_{29}H_{21}N_3O_4S_2$ | 540.1046 | 2.652/B | 540.1073 | 1H NMR (400 MHz, DMSO-d6) δ ppm 8.38 (s, 1H) 8.02-8.14 (m, 1H) 7.87 (s, 1H) 7.81-7.86 (m, 1H) 7.74 (s, 1H) 7.53-7.63 (m, 3H) 7.35-7.48 (m, 2H) 7.00 (s, 1H) 6.84 (d, J = 0.8 Hz, 1H) 6.58 (d, J = 1.6 Hz, 1H) 5.38 (s, 2H) 4.20 (s, 3H) 3.80 (s, 3H) |
| 13 | 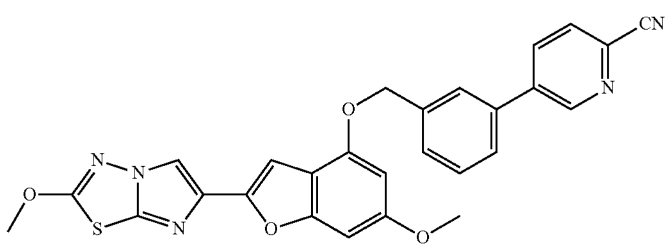 [SMILES: COc1cc(OCc2cccc(-c3ccc(C#N)nc3)c2)c2cc(-c3cn4nc(OC)sc4n3)oc2c1] | $C_{27}H_{19}N_5O_4S$ | 510.1231 | 2.364/B | 510.1108 | 1H NMR (400 MHz, acetone) ppm 9.11 (dd, J = 2.3, 0.8 Hz, 1H) 8.37 (dd, J = 8.3, 2.4 Hz, 1H) 8.10 (s, 1H) 8.01-8.09 (m, 2H) 7.81 (dt, J = 7.8, 1.4 Hz, 1H) 7.69-7.76 (m, 1H) 7.64 (t, J = 7.5 Hz, 1H) 7.05 (d, J = 0.8 Hz, 1H) 6.77 (dd, J = 2.0, 0.8 Hz, 1H) 6.56 (d, J = 2.0 Hz, 1H) 5.40 (s, 2H) 4.26 (s, 3H) 3.85 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 14 | (5-fluoropyridin-2-yl)phenyl-methoxy-benzofuran-imidazo-thiadiazole-OMe | $C_{26}H_{19}FN_4O_4S$ | 503.1184 | 2.431/B | 503.1222 | 1H NMR (400 MHz, DMSO-$d_6$) δ ppm 8.67 (d, J = 3.1 Hz, 1H) 8.38 (s, 1H) 8.20 (s, 1H) 8.08 (dd, J = 8.6, 4.3 Hz, 1H) 8.02 (d, J = 7.4 Hz, 1H) 7.84 (td, J = 8.8, 3.1 Hz, 1H) 7.56 (td, J = 14.9, 7.4 Hz, 2H) 7.00 (s, 1H) 6.83 (s, 1H) 6.56 (s, 1H) 5.34 (1H) |
| 15 | (pyridin-3-yl)phenyl-methoxy-benzofuran-imidazo-thiadiazole-OMe | $C_{26}H_{20}N_4O_4S$ | 485.1278 | 2.149/B | 485.1338 | 1H NMR (400 MHz, DMSO-$d_6$) δ ppm 9.01-9.10 (m, 1H) 8.66-8.78 (m, 1H) 8.42 (dd, J = 6.7, 3.9 Hz, 1 H) 8.38 (s, 1H) 7.94 (s, 1H) 7.68-7.81 (m, 2H) 7.52-7.67 (m, 2H) 7.01 (s, 1H) 6.84 (s, 1H) 6.58 (s, 1H) 5.35 (s, 2H) 4.20 (s, 3H) 3.80 (s, 3H) |
| 16 | (4-trifluoromethylphenyl)phenyl-methoxy-benzofuran-imidazo-thiadiazole-OMe | $C_{28}H_{20}F_3N_3O_4S$ | 552.1199 | 2.584/B | 552.1246 | 1H NMR (400 MHz, DMSO-$d_6$) δ ppm 8.38 (s, 1H) 7.93 (d, J = 7.8 Hz, 2H) 7.88 (s, 1H) 7.84 (d, J = 7.6 Hz, 2H) 7.73 (d, J = 6.7 Hz, 1H) 7.50-7.64 (m, 2H) 7.00 (s, 1H) 6.84 (d, J = 0.8 Hz, 1H) 6.57 (d, J = 1.2 Hz, 1H) 5.35 (s, 2H) 4.20 (s, 3H) 3.80 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 17 | 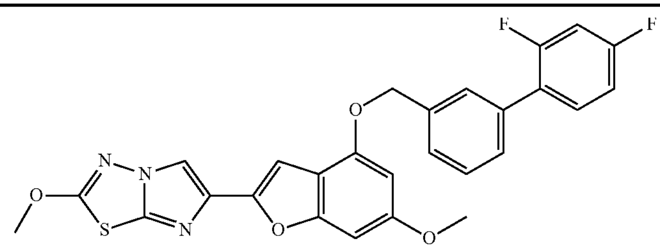 | C27H19F2N3O4S | 520.1137 | 2.540/B | 520.1128 | 1H NMR (400 MHz, DMSO-d6) δ ppm 8.38 (s, 1H) 7.46-7.69 (m, 5H) 7.33-7.44 (m, 1H) 7.15-7.28 (m, 1H) 6.98 (s, 1H) 6.84 (s, 1H) 6.56 (s, 1H) 5.32 (s, 2H) 4.20 (s, 3H) 3.80 (s, 3H) |
| 18 | 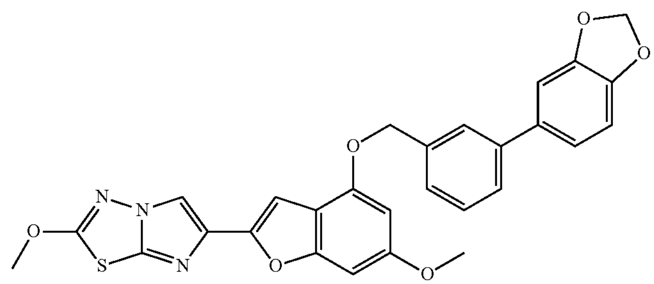 [SMILES: COc1cc(OCc2cccc(-c3ccc4c(c3)OCO4)c2)c2cc(-c3cn4nc(OC)sc4n3)oc2c1] | C28H21N3O6S | 528.1224 | 2.538/B | 528.1232 | 1H NMR (400 MHz, DMSO-d6) δ ppm 8.38 (s, 1H) 7.73 (s, 1H) 7.51-7.63 (m, 1H) 7.46 (d, J = 3.9 Hz, 2H) 7.26 (s, 1H) 7.11-7.21 (m, 1H) 6.95-7.04 (m, 2H) 6.83 (s, 1H) 6.56 (s, 1H) 6.06 (s, 2H) 5.30 (s, 2H) 4.20 (s, 3H) 3.79 (s, 3H) |
| 19 | 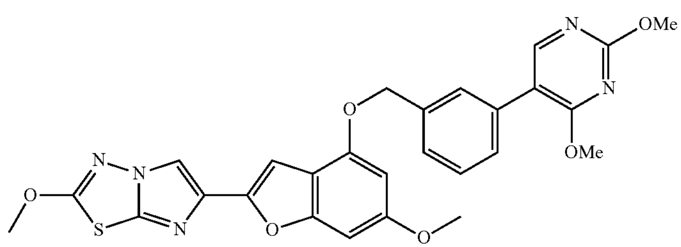 [SMILES: COc1cc(OCc2cccc(-c3cnc(OC)nc3OC)c2)c2cc(-c3cn4nc(OC)sc4n3)oc2c1] | C27H23N5O6S | 546.1442 | 2.395/B | 546.1466 | 1H NMR (400 MHz, DMSO-d6) δ ppm 8.39 (s, 1H) 8.37 (s, 1H) 7.67 (s, 1H) 7.40-7.57 (m, 3H) 6.99 (s, 1H) 6.83 (s, 1H) 6.56 (s, 1H) 5.30 (s, 2H) 4.20 (s, 3H) 3.94 (s, 3H) 3.93 (s, 3H) 3.79 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 20 | 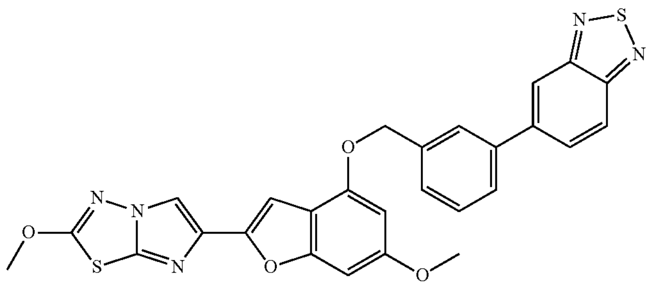 [SMILES: COc1cc(OCc2cccc(-c3ccc4nsnc4c3)c2)c2cc(-c3cn4nc(OC)sc4n3)oc2c1] | C27H19N5O4S2 | 542.0951 | 2.605/B | 542.0929 | 1H NMR (400 MHz, DMSO-d6) δ ppm 8.39 (dd, J = 1.8, 1.0 Hz, 1H) 8.37 (s, 1H) 8.20 (dd, J = 9.4, 0.8 Hz, 1H) 8.12 (dd, J = 9.2, 1.8 Hz, 1H) 8.03 (s, 1H) 7.87 (dt, J = 7.0, 2.0 Hz, 1H) 7.52-7.68 (m, 2H) 7.02 (d, J = 0.8 Hz, 1H) 6.84 (dd, J = 2.0, 0.8 Hz, 1H) 6.59 (d, J = 2.0 Hz, 1H) 5.37 (s, 2H) 4.20 (s, 3H) 3.80 (s, 3H) |
| 21 | 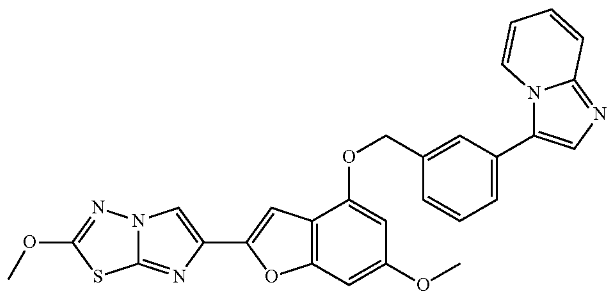 [SMILES: COc1cc(OCc2cccc(-c3cnc4ccccn34)c2)c2cc(-c3cn4nc(OC)sc4n3)oc2c1] | C28H21N5O4S | 524.1387 | 2.032/B | 524.1393 | 1H NMR (400 MHz, DMSO-d6) δ ppm 8.78 (dd, J = 6.8, 1.0 Hz, 1H) 8.39-8.45 (m, 1H) 8.37 (s, 1H) 8.03 (d, J = 9.0 Hz, 1H) 7.95 (t, J = 8.0 Hz, 1H) 7.88 (s, 1H) 7.64-7.79 (m, 3H) 7.45 (td, J = 7.1, 1.0 Hz, 1H) 7.01 (s, 1H) 6.83-6.89 (m, 1H) 6.58 (d, J = 2.0 Hz, 1H) 5.39 (s, 2H) 4.20 (s, 3H) 3.80 (s, 3H) |
| 22 | 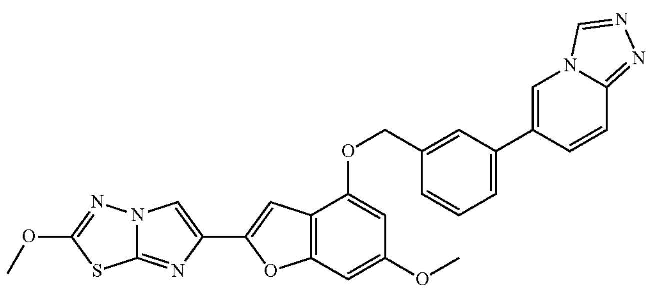 [SMILES: COc1cc(OCc2cccc(-c3ccc4nncn4c3)c2)c2cc(-c3cn4nc(OC)sc4n3)oc2c1] | C27H20N6O4S | 525.1340 | 2.217/B | 525.1351 | 1H NMR (400 MHz, DMSO-d6) δ ppm 9.32 (s, 1H) 8.96-9.05 (m, 1H) 8.32-8.43 (m, 1H) 7.79-8.00 (m, 3H) 7.67-7.79 (m, 1H) 7.50-7.65 (m, 2H) 7.02 (s, 1H) 6.84 (s, 1H) 6.58 (s, 1H) 5.34 (s, 2H) 4.20 (s, 3H) 3.80 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 23 | 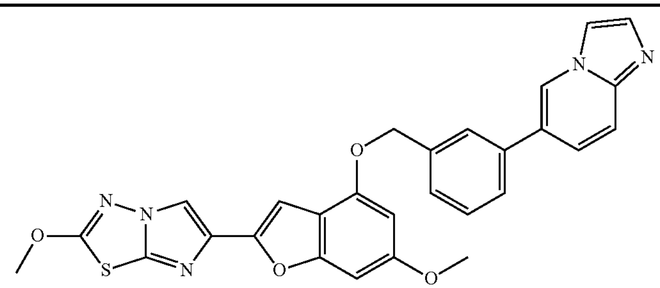 | C28H21N5O4S | 524.1387 | 2.069/B | 524.1411 | 1H NMR (400 MHz, DMSO-d6) δ ppm 9.32 (dd, J = 1.8, 1.0 Hz, 1H) 8.38 (s, 1H) 8.26-8.34 (m, 2H) 8.21 (d, J = 2.3 Hz, 1H) 8.06 (d, J = 9.4 Hz, 1H) 7.94 (s, 1H) 7.78 (dt, J = 6.5, 2.2 Hz, 1H) 7.50-7.70 (m, 3H) 7.01 (d, J = 0.8 Hz, 1H) 6.85 (dd, J = 1.8, 1.0 Hz, 1H) 6.58 (d, J = 1.6 Hz, 1H) 5.36 (s, 2H) 4.20 (s, 3H) 3.80 (s, 3H) |
| 24 | 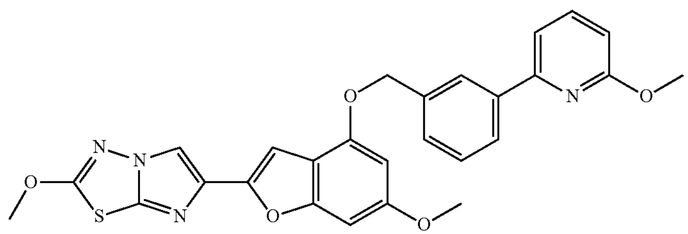 | C27H22N4O5S | 515.1384 | 2.548/B | 515.1382 | 1H NMR (400 MHz, DMSO-d6) δ ppm 8.38 (s, 1H) 8.21-8.30 (m, 1H) 8.06 (dt, J = 7.4, 1.6 Hz, 1H) 7.79 (t, J = 7.8 Hz, 1H) 7.48-7.62 (m, 3H) 7.00 (s, 1H) 6.83 (s, 1H) 6.79 (d, J = 8.2 Hz, 1H) 6.58 (d, J = 2.0 Hz, 1H) 5.36 (s, 2H) 4.20 (s, 3H) 3.94 (s, 3H) 3.79 (s, 3H) |
| 25 | 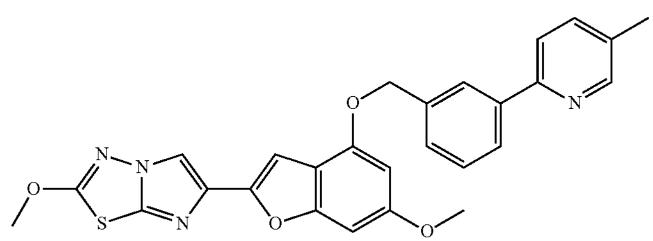 | C27H22N4O4S | 499.1435 | 2.138/B | 499.1456 | 1H NMR (400 MHz, DMSO-d6) δ ppm 8.46-8.56 (m, 1H) 8.38 (s, 1H) 8.21 (t, J = 1.6 Hz, 1H) 8.02 (dt, J = 7.4, 1.6 Hz, 1H) 7.89 (d, J = 8.2 Hz, 1H) 7.71 (ddd, J = 8.2, 2.4, 0.8 Hz, 1H) 7.45 |

| Ex. | Structure | Formula | Calc. [M + H]⁺ m/z | HPLC Retention Time (Min)/ Method | LCMS [M + H]⁺ m/z | NMR |
|---|---|---|---|---|---|---|
| 26 | 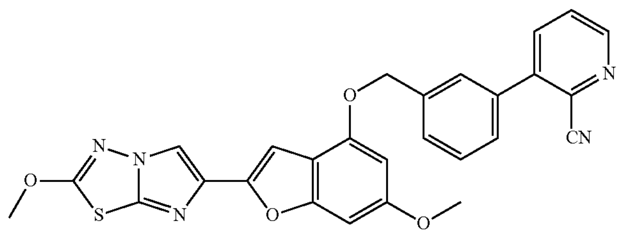 [SMILES: COc1cc(OCc2cccc(-c3cccnc3C#N)c2)c2cc(-c3cn4nc(OC)sc4n3)oc2c1] | $C_{27}H_{19}N_5O_4S$ | 510.1231 | 2.285/B | 510.1244 | ¹H NMR (400 MHz, DMSO-d₆) δ ppm 8.79 (d, J = 4.7 Hz, 1H) 8.37 (s, 1H) 8.16 (dt, J = 8.0, 1.3 Hz, 1H) 7.85 (dd, J = 8.0, 4.9 Hz, 1H) 7.82 (s, 1H) 7.59-7.72 (m, 3H) 7.03 (s, 1H) 6.84 (s, 1H) 6.59 (s, 1H) 5.34 (s, 2H) 4.21 (s, 3H) 3.81 (s, 3H) |
| 27 | 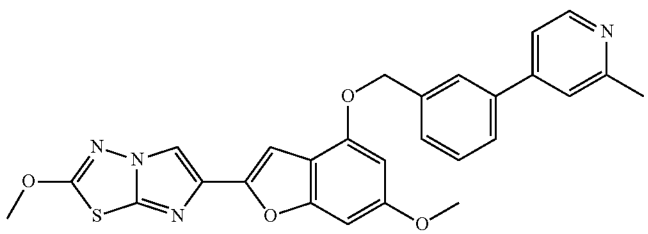 | $C_{27}H_{22}N_4O_4S$ | 499.1435 | 2.058/B | 499.1453 | ¹H NMR (400 MHz, DMSO-d₆) δ ppm 8.51 (d, J = 5.1 Hz, 1H) 8.37 (s, 1H) 7.92 (s, 1H) 7.76 (d, J = 7.8 Hz, 1H) 7.46-7.68 (m, 4H) 7.00 (s, 1H) 6.83 (s, 1H) 6.57 (s, 1H) 5.34 (s, 2H) 4.20 (s, 3H) 3.79 (s, 3H) 2.53 (s, 3H) |
| 28 | 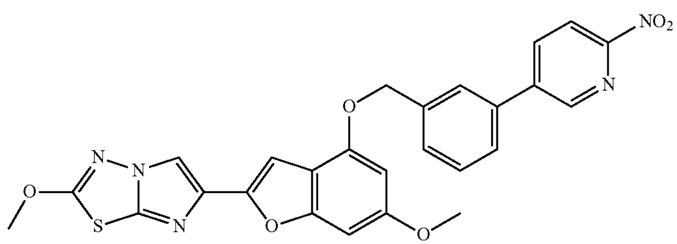 [SMILES: COc1cc(OCc2cccc(-c3ccc([N+](=O)[O-])nc3)c2)c2cc(-c3cn4nc(OC)sc4n3)oc2c1] | $C_{26}H_{19}N_5O_6S$ | 530.1140 | 2.355/B | 530.1129 | ¹H NMR (400 MHz, DMSO-d₆) δ ppm 9.02-9.07 (m, 1H) 8.53-8.59 (m, 1H) 8.42 (d, J = 8.2 Hz, 1H) 8.38 (s, 1H) 8.03 (s, 1H) 7.87 (d, J = 7.4 Hz, 1H) 7.59-7.71 (m, 2H) 7.02 (s, 1H) 6.84 (s, 1H) 6.58 (s, 1H) 5.36 (s, 2H) 4.21 (s, 3H) 3.80 (s, 3H) |
| 29 | 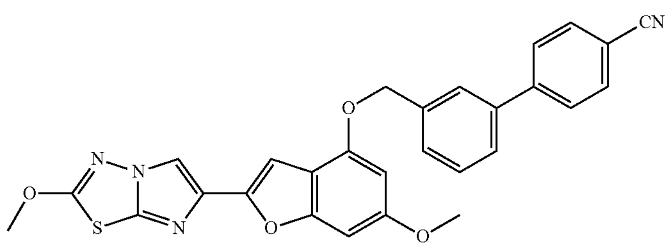 | $C_{28}H_{20}N_4O_4S$ | 509.1278 | 2.433/B | 509.1289 | ¹H NMR (400 MHz, DMSO-d₆) δ ppm 8.38 (s, 1H) 7.86-7.98 (m, 5H) 7.74 (d, J = 7.0 Hz, 1H) 7.52-7.63 (m, 2H) 7.00 (s, 1H) 6.84 (s, 1H) 6.57 (s, 1H) 5.34 (s, 2H) 4.20 (s, 3H) 3.79 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 30 | (structure with CN, F biphenyl, methoxy benzofuran, imidazothiazole-OMe) | C₂₈H₁₉FN₄O₄S | 527.1184 | 2.446/B | 527.1194 | ¹H NMR (400 MHz, DMSO-d₆) δ ppm 8.37 (s, 1H) 8.00-8.07 (m, 1H) 7.90-7.98 (m, 2H) 7.79 (dd, J = 8.2, 1.2 Hz, 2H) 7.54-7.66 (m, 2H) 7.01 (s, 1H) 6.84 (s, 1H) 6.57 (d, J = 1.6 Hz, 1H) 5.33 (s, 2H) 4.20 (s, 3H) 3.80 (s, 3H) |
| 31 | (structure with benzodioxine, methoxy benzofuran, imidazothiazole-OMe) | C₂₉H₂₃N₃O₆S | 543.1380 | 2.534/B | 543.1380 | ¹H NMR (400 MHz, DMSO-d₆) δ ppm 8.38 (s, 1H) 7.72 (s, 1H) 7.53-7.59 (m, 1H) 7.42-7.47 (m, 2H) 7.12-7.18 (m, 2H) 6.99 (s, 1H) 6.94 (d, J = 8.2 Hz, 1H) 6.81-6.84 (m, 1H) 6.55 (d, J = 1.2 Hz, 1H) 5.30 (s, 2H) 4.28 (s, 4H) 4.20 (s, 3H) 3.79 (s, 3H) |
| 32 | (structure with F-methylpyridine, methoxy benzofuran, imidazothiazole-OMe) | C₂₇H₂₁FN₄O₄S | 517.1340 | 2.467/B | 517.1355 | ¹H NMR (400 MHz, DMSO-d₆) δ ppm 8.38 (s, 1H) 8.18 (s, 1H) 8.00 (d, J = 7.4 Hz, 1H) 7.88 (dd, J = 7.8, 3.5 Hz, 1H) 7.73 (t, J = 9.0 Hz, 1H) 7.49-7.60 (m, 2H) 7.00 (s, 1H) 6.84 (s, 1H) 6.57 (s, 1H) 5.34 (s, 2H) 4.21 (s, 3H) 3.80 (s, 3H) 2.53 (d, J = 2.3 Hz, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 33 | 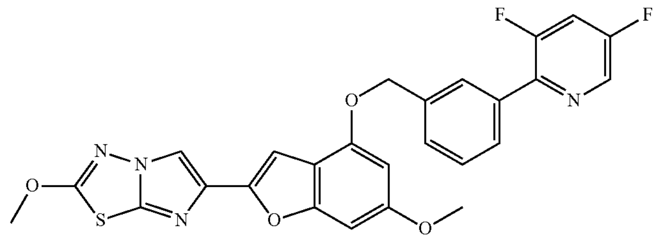 | C26H18F2N4O4S | 521.1090 | 2.454/B | 521.1101 | 1H NMR (400 MHz, DMSO-d6) d ppm 8.64-8.68 (m, 1H) 8.38 (s, 1H) 8.09 (ddd, J = 11.3, 9.0, 2.3 Hz, 1H) 8.00-8.03 (m, 1H) 7.82-7.87 (m, 1H) 7.63 (dt, J = 7.7, 1.4 Hz, 1H) 7.58 (t, J = 7.6 Hz, 1H) 6.98 (d, J = 0.8 Hz, 1H) 6.83 (dd, J = 1.6, 0.8 Hz, 1H) 6.56 (d, J = 2.0 Hz, 1H) 5.35 (s, 2H) 4.20 (s, 3H) 3.79 (s, 3H) |
| 34 | 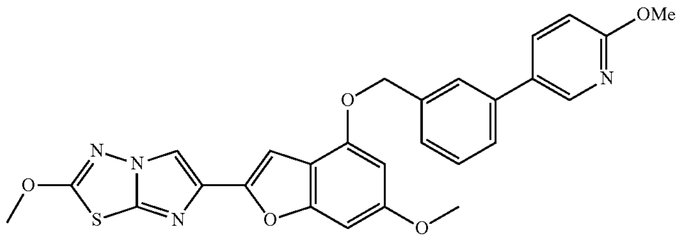 [SMILES: COc1cc(OCc2cccc(-c3ccc(OC)nc3)c2)c2cc(-c3cn4nc(OC)sc4n3)oc2c1] | C27H22N4O5S | 515.1384 | 2.482/B | 515.1386 | 1H NMR (400 MHz, DMSO-d6) δ ppm 8.50 (d, J = 2.1 Hz, 1H) 8.38 (s, 1H) 8.04 (dd, J = 8.6, 2.7 Hz, 1H) 7.79 (s, 1H) 7.60-7.68 (m, 1H) 7.48-7.55 (m, 2H) 7.00 (s, 1H) 6.93 (d, J = 8.6 Hz, 1H) 6.81-6.85 (m, 1H) 6.57 (d, J = 1.2 Hz, 1H) 5.32 (s, 2H) 4.20 (s, 3H) 3.90 (s, 3H) 3.79 (s, 3H) |
| 35 | 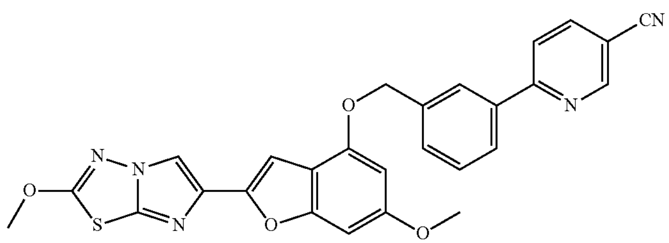 [SMILES: COc1cc(OCc2cccc(-c3ccc(C#N)cn3)c2)c2cc(-c3cn4nc(OC)sc4n3)oc2c1] | C27H19N5O4S | 510.1231 | 2.399/B | 510.1229 | 1H NMR (400 MHz, DMSO-d6) ppm δ 9.09-9.16 (m, 1H) 8.39-8.44 (m, 1H) 8.38 (s, 1H) 8.34 (s, 1H) 8.21-8.27 (m, 1H) 8.15 (d, J = 8.2 Hz, 1H) 7.68 (d, J = 7.4 Hz, 1H) 7.60 (t, J = 7.6 Hz, 1H) 7.00 (s, 1H) 6.84 (s, 1H) 6.57 (s, 1H) 5.36 (s, 2H) 4.20 (s, 3H) 3.79 (s, 3H) |
| 36 | 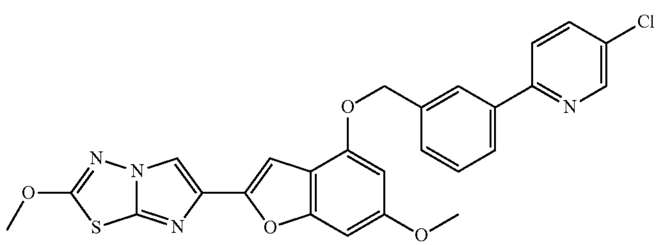 [SMILES: COc1cc(OCc2cccc(-c3ccc(Cl)cn3)c2)c2cc(-c3cn4nc(OC)sc4n3)oc2c1] | C26H19ClN4O4S | 519.0888 | 2.529/B | 519.0887 | 1H NMR (400 MHz, DMSO-d6) δ ppm 8.70-8.75 (m, 1H) 8.38 (s, 1H) 8.22-8.26 (m, 1H) 8.00-8.08 (m, 3H) 7.58-7.64 (m, 1H) 7.55 (t, J = 7.7 Hz, 1H) 7.00 (s, 1H) 6.81-6.85 (m, 1H) 6.56 (d, J = 1.6 Hz, 1H) 5.35 (s, 2H) 4.20 (s, 3H) 3.79 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 37 | 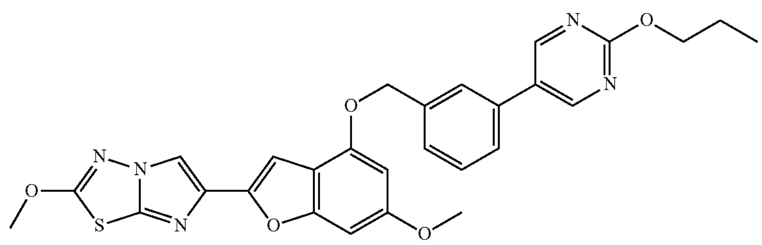 [SMILES: CCCOc1ncc(-c2cccc(COc3cc(OC)cc4oc(-c5cn6nc(OC)sc6n5)cc34)c2)cn1] | C28H25N5O5S | 544.1649 | 2.511/B | 544.1651 | 1H NMR (400 MHz, DMSO-d6) δ ppm 8.95 (s, 2 H) 8.38 (s, 1H) 7.88 (s, 1H) 7.67-7.76 (m, 1H) 7.51-7.61 (m, 2H) 7.02 (s, 1H) 6.84 (s, 1H) 6.54-6.61 (m, 1H) 5.32 (s, 2H) 4.32 (t, J = 6.7 Hz, 2H) 4.20 (s, 3H) 3.80 (s, 3H) 1.78 (sxt, J = 7.0 Hz, 2H) 0.99 (t, J = 7.4 Hz, 3H) |
| 38 | 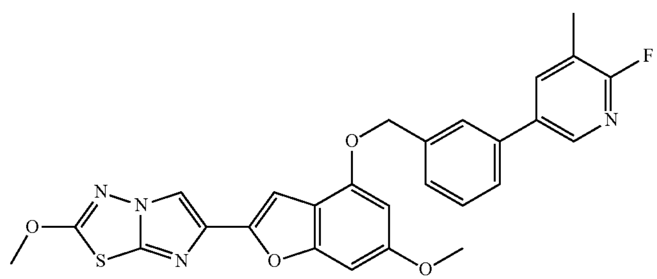 [SMILES: COc1cc(OCc2cccc(-c3cnc(F)c(C)c3)c2)c2cc(-c3cn4nc(OC)sc4n3)oc2c1] | C27H21FN4O4S | 517.134 | 2.453/B | 517.1355 | 1H NMR (400 MHz, DMSO-d6) δ ppm 8.37 (s, 2H) 8.19 (d, J = 9.8 Hz, 1H) 7.85 (s, 1H) 7.66-7.73 (m, 1H) 7.50-7.60 (m, 2H) 7.01 (s, 1H) 6.84 (s, 1H) 6.54-6.59 (m, 1H) 5.32 (s, 2H) 4.20 (s, 3H) 3.80 (s, 3H) 2.32 (s, 3H) |
| 39 | 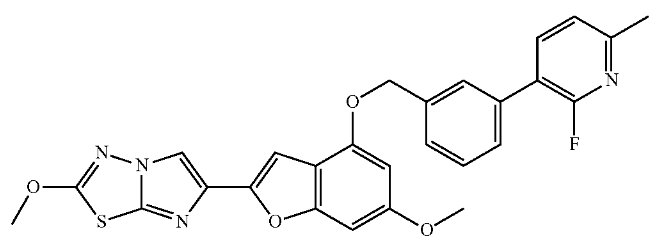 | C27H21FN4O4S | 517.134 | 2.413/B | 517.1358 | 1H NMR (400 MHz, DMSO-d6) δ ppm 8.37 (s, 1H) 8.03 (dd, J = 10.4, 7.6 Hz, 1H) 7.74 (s, 1H) 7.50-7.61 (m, 3H) 7.34 (d, J = 7.4 Hz, 1H) 6.99 (s, 1H) 6.84 (s, 1H) 6.57 (s, 1H) 5.32 (s, 2H) 4.21 (s, 3H) 3.80 (s, 3H) 2.48 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 40 | 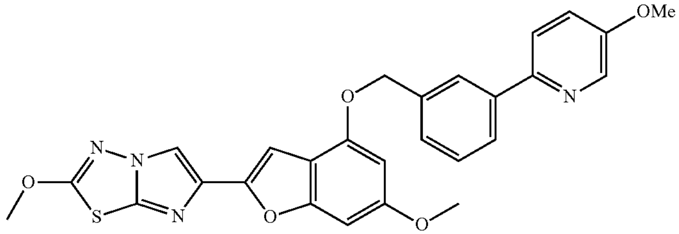 | C27H22N4O5S | 515.1384 | 2.245/B | 515.1412 | 1H NMR (400 MHz, DMSO-d6) δ ppm 8.36-8.41 (m, 2H) 8.17 (s, 1H) 7.92-8.01 (m, 2H) 7.46-7.55 (m, 3H) 6.99 (s, 1H) 6.83 (s, 1H) 6.56 (s, 1H) 5.33 (s, 2H) 4.20 (s, 3H) 3.88 (s, 3H) 3.79 (s, 3H) |
| 41 | 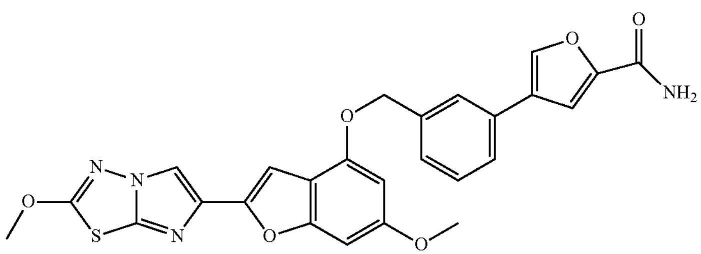 [SMILES: COc1cc(OCc2cccc(-c3coc(C(N)=O)c3)c2)c2cc(-c3cn4nc(OC)sc4n3)oc2c1] | C26H20N4O6S | 517.1176 | 2.233/B | 517.1206 | 1H NMR (400 MHz, DMSO-d6) δ ppm 8.38 (s, 1H) 8.36-8.37 (m, 1H) 7.84 (br. s., 1H) 7.79 (s, 1H) 7.63 (dt, J = 6.4, 2.1 Hz, 1H) 7.58 (d, J = 1.2 Hz, 1H) 7.41-7.50 (m, 3H) 7.01 (d, J = 0.8 Hz, 1H) 6.84 (dd, J = 2.0, 0.8 Hz, 1H) 6.56 (d, J = 2.0 Hz, 1H) 5.27 (s, 2H) 4.20 (s, 3H) 3.80 (s, 3H) |
| 42 | 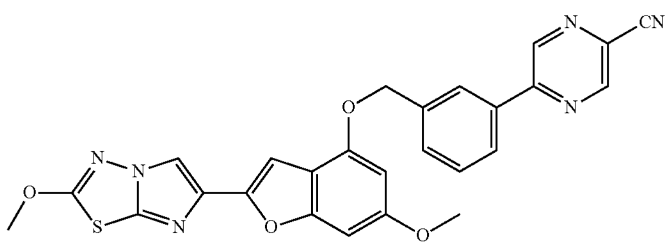 [SMILES: COc1cc(OCc2cccc(-c3cnc(C#N)cn3)c2)c2cc(-c3cn4nc(OC)sc4n3)oc2c1] | C26H18N6O4S | 511.1183 | 2.380/B | 511.1215 | 1H NMR (400 MHz, DMSO-d6) δ ppm 9.52 (d, J = 1.6 Hz, 1H) 9.29 (d, J = 1.6 Hz, 1H) 8.34-8.45 (m, 2H) 8.23 (d, J = 7.8 Hz, 1H) 7.75 (d, J = 7.8 Hz, 1H) 7.65 (t, J = 7.6 Hz, 1H) 7.01 (s, 1H) 6.84 (d, J = 0.8 Hz, 1H) 6.57 (d, J = 1.6 Hz, 1H) 5.38 (s, 2H) 4.20 (s, 3H) 3.80 (s, 3H) |
| 43 | 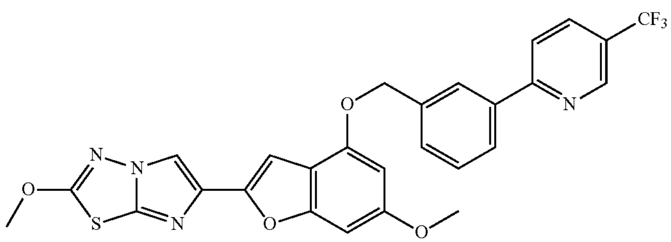 | C27H19F3N4O4S | 553.1152 | 2.500/B | 553.1183 | 1H NMR (400 MHz, DMSO-d6) δ ppm 9.07 (dd, J = 1.6, 0.8 Hz, 1H) 8.38 (s, 1H) 8.29-8.35 (m, 2H) 8.21-8.27 (m, 1H) 8.14 (dt, J = 7.8, 1.6 Hz, 1H) 7.68 (dt, J = 7.5, 1.5 Hz, 1H) 7.60 (t, J = 7.6 Hz, 1H) 7.01 (d, J = 0.8 Hz, 1H) 6.84 (dd, J = 2.0, 0.8 Hz, 1H) 6.57 (d, J = 2.0 Hz, 1H) 5.37 (s, 2H) 4.20 (s, 3H) 3.80 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 44 | 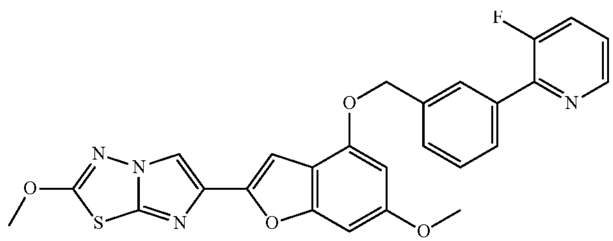 [SMILES: COc1cc(OCc2cccc(-c3ncccc3F)c2)c2cc(-c3cn4nc(OC)sc4n3)oc2c1] | $C_{26}H_{19}FN_4O_4S$ | 503.1184 | 2.371/B | 503.1214 | $^1$H NMR (400 MHz, DMSO-d$_6$) δ ppm 8.55-8.59 (m, 1H) 8.38 (s, 1H) 8.07 (d, J = 1.6 Hz, 1H) 7.82-7.92 (m, 2H) 7.63 (dt, J = 7.7, 1.4 Hz, 1H) 7.58 (t, J = 7.6 Hz, 1H) 7.47-7.54 (m, 1H) 6.98 (d, J = 0.8 Hz, 1H) 6.83 (dd, J = 2.0, 0.8 Hz, 1H) 6.57 (d, J = 2.0 Hz, 1H) 5.36 (s, 2H) 4.20 (s, 3H) 3.80 (s, 3H) |
| 45 | 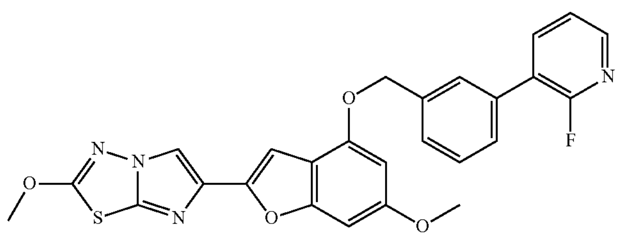 [SMILES: COc1cc(OCc2cccc(-c3cccnc3F)c2)c2cc(-c3cn4nc(OC)sc4n3)oc2c1] | $C_{26}H_{19}FN_4O_4S$ | 503.1184 | 2.358/B | 503.1258 | $^1$H NMR (400 MHz, DMSO-d$_6$) δ ppm 8.38 (s, 1H) 8.24-8.28 (m, 1 H) 8.11-8.19 (m, 1H) 7.77 (d, J = 1.2 Hz, 1H) 7.54-7.63 (m, 3H) 7.50 (ddd, J = 7.3, 5.0, 2.2 Hz, 1H) 6.99 (d, J = 0.8 Hz, 1H) 6.84 (dd, J = 2.0, 0.8 Hz, 1H) 6.57 (d, J = 2.0 Hz, 1H) 5.33 (s, 2H) 4.20 (s, 3H) 3.80 (s, 3H) |
| 46 | 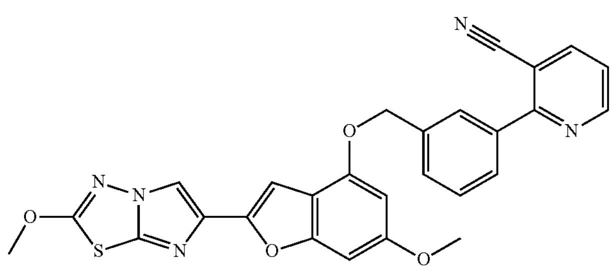 [SMILES: COc1cc(OCc2cccc(-c3ncccc3C#N)c2)c2cc(-c3cn4nc(OC)sc4n3)oc2c1] | $C_{27}H_{19}N_5O_4S$ | 510.1231 | 2.288 | 510.1248 | $^1$H NMR (400 MHz, DMSO-d$_6$) δ ppm 8.95 (s, 1H) 8.85 (d, J = 5.1 Hz, 1H) 8.37 (s, 1 H) 8.01 (d, J = 5.1 Hz, 1H) 7.82-7.86 (m, 1H) 7.61-7.72 (m, 3H) 7.03 (s, 1H) 6.82-6.86 (m, 1H) 6.59 (d, J = 1.6 Hz, 1H) 5.34 (s, 2 H) 4.20 (s, 3H) 3.81 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 47 | 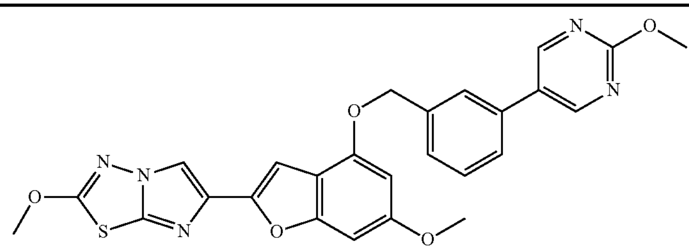 | $C_{26}H_{21}N_5O_5S$ | 516.1336 | 2.361/B | 516.1367 | 1H NMR (400 MHz, DMSO-d6) δ ppm 8.96 (s, 2H) 8.37 (s, 1H) 7.88 (s, 1H) 7.69-7.74 (m, 1H) 7.52-7.59 (m, 2H) 7.02 (d, J = 0.8 Hz, 1H) 6.84 (dd, J = 2.0, 0.8 Hz, 1H) 6.57 (d, J = 1.6 Hz, 1H) 5.32 (s, 2H) 4.20 (s, 3H) 3.98 (s, 3H) 3.80 (s, 3H) |
| 48 | 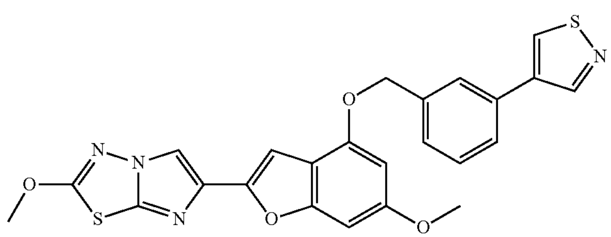 [SMILES: COc1cc(OCc2cccc(-c3cnsc3)c2)c2cc(-c3cn4nc(OC)sc4n3)oc2c1] | $C_{24}H_{18}N_4O_4S_2$ | 491.0842 | 2.363/B | 491.0867 | 1H NMR (400 MHz, DMSO-d6) δ ppm 9.40 (s, 1H) 9.08 (s, 1H) 8.38 (s, 1H) 7.95 (s, 1H) 7.76-7.82 (m, 1H) 7.48-7.54 (m, 2H) 7.01 (d, J = 0.8 Hz, 1H) 6.84 (dd, J = 1.8, 1.0 Hz, 1H) 6.57 (d, J = 2.0 Hz, 1H) 5.30 (s, 2H) 4.20 (s, 3H) 3.80 (s, 3H) |
| 49 | 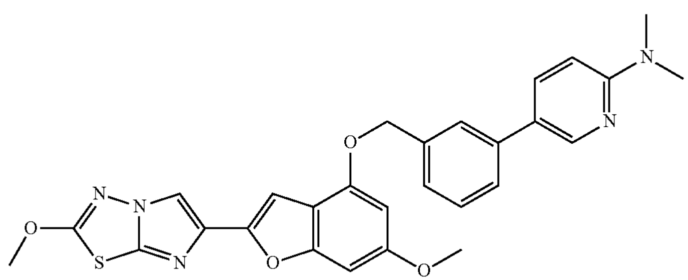 | $C_{28}H_{25}N_5O_4S$ | 528.1700 | 2.094/B | 528.1727 | 1H NMR (400 MHz, DMSO-d6) δ ppm 8.38 (s, 1H) 8.32 (s, 1H) 8.13 (br. s, 1H) 7.79 (s, 1H) 7.61-7.68 (m, 1H) 7.51 (d, J = 5.5 Hz, 2H) 7.08 (br. s, 1H) 7.00 (d, J = 0.8 Hz, 1H) 6.84 (dd, J = 2.0, 0.8 Hz, 1H) 6.56 (d, J = 2.0 Hz, 1H) 5.32 (s, 2H) 4.20 (s, 3H) 3.80 (s, 3H) 3.17 (s, 6H) |

| Ex. | Structure | Formula | Calc. [M + H]+ m/z | HPLC Retention Time (Min)/ Method | LCMS [M + H]+ m/z | NMR |
|---|---|---|---|---|---|---|
| 50 | 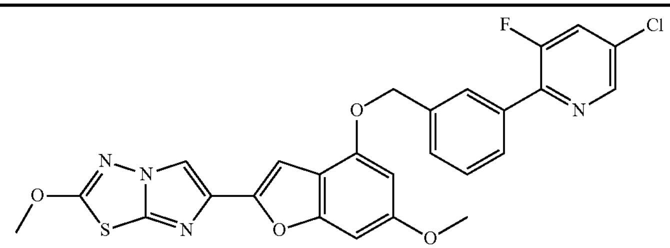 | C26H18ClFN4O4S | 537.0794 | 2.534/B | 537.0818 | 1H NMR (400 MHz, DMSO-d6) δ ppm 8.66 (dd, J = 2.2, 1.4 Hz, 1H) 8.38 (s, 1H) 8.23 (dd, J = 11.2, 2.2 Hz, 1H) 8.05 (d, J = 1.2 Hz, 1H) 7.88 (dq, J = 7.7, 1.6 Hz, 1H) 7.65 (dt, J = 7.5, 1.5 Hz, 1H) 7.59 (t, J = 7.8 Hz, 1H) 6.98 (d, J = 0.8 Hz, 1H) 6.83 (dd, J = 1.8, 1.0 Hz, 1H) 6.56 (d, J = 1.6 Hz, 1H) 5.36 (s, 2H) 4.20 (s, 3H) 3.79 (s, 3H) |
| 51 | 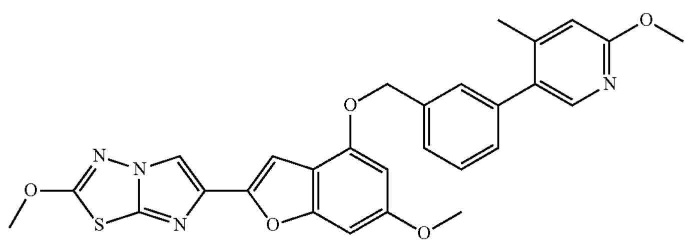 | C28H24N4O5S | 529.157 | 2.419/B | 529.154 | 1H NMR (400 MHz, DMSO-d6) δ ppm 8.37 (s, 1H) 7.99 (s, 1H) 7.46-7.55 (m, 3H) 7.33 (dt, J = 6.7, 1.9 Hz, 1H) 6.97 (d, J = 0.8 Hz, 1H) 6.83 (dd, J = 1.8, 1.0 Hz, 1H) 6.78 (d, J = 0.8 Hz, 1H) 6.56 (d, J = 2.0 Hz, 1H) 5.32 (s, 2H) 4.20 (s, 3H) 3.86 (s, 3H) 3.79 (s, 3H) 2.20 (d, J = 0.8 Hz, 3 H) |
| 52 | 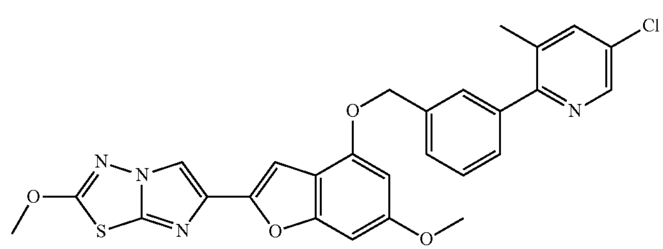 [SMILES: COc1cc(OCc2cccc(-c3ncc(Cl)cc3C)c2)c2cc(-c3cn4nc(OC)sc4n3)oc2c1] | C27H21ClN4O4S | 533.1045 | 2.434/B | 533.1073 | 1H NMR (400 MHz, DMSO-d6) δ ppm 8.52-8.55 (m, 1H) 8.37 (s, 1H) 7.90-7.94 (m, 1H) 7.67 (s, 1H) 7.58 (qd, J = 4.2, 1.5 Hz, 1H) 7.50-7.54 (m, 2H) 6.97 (d, J = 0.8 Hz, 1H) 6.83 (dd, J = 1.8, 1.0 Hz, 1H) 6.56 (d, J = 2.0 Hz, 1H) 5.33 (s, 2H) 4.20 (s, 3H) 3.79 (s, 3H) 2.33 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 53 | 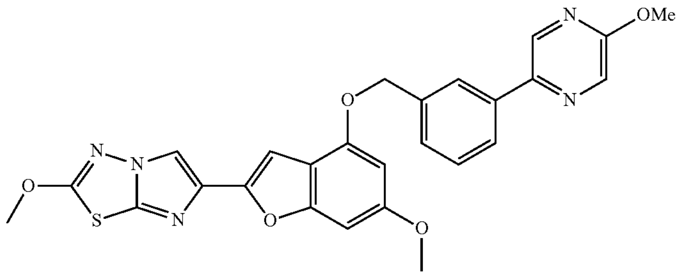 [SMILES: COc1cc(OCc2cccc(-c3cnc(OC)cn3)c2)c2cc(-c3cn4nc(OC)sc4n3)oc2c1] | C26H21N5O5S | 516.1336 | 2.449/BS | 516.1359 | 1H NMR (400 MHz, DMSO-d6) δ ppm 8.83 (d, J = 1.6 Hz, 1H) 8.41 (d, J = 1.6 Hz, 1H) 8.38 (s, 1H) 8.16-8.19 (m, 1H) 8.00 (dt, J = 7.1, 1.9 Hz, 1H) 7.51-7.60 (m, 2H) 7.00 (d, J = 0.8 Hz, 1H) 6.83 (dd, J = 1.8, 1.0 Hz, 1H) 6.56 (d, J = 2.0 Hz, 1H) 5.34 (s, 2H) 4.20 (s, 3H) 3.97 (s, 3H) 3.80 (s, 3H) |
| 54 | 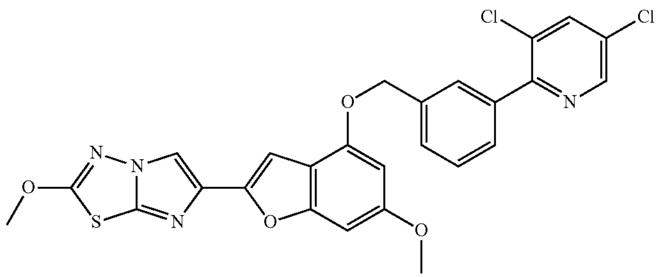 [SMILES: COc1cc(OCc2cccc(-c3ncc(Cl)cc3Cl)c2)c2cc(-c3cn4nc(OC)sc4n3)oc2c1] | C26H18Cl2N4O4S | 553.0449 | 2.526/B | 553.052 | 1H NMR (400 MHz, DMSO-d6) δ ppm 8.73 (d, J = 2.0 Hz, 1H) 8.35-8.39 (m, 2H) 7.82 (t, J = 1.6 Hz, 1H) 7.66 (dt, J = 7.7, 1.6 Hz, 1H) 7.63 (dt, J = 7.8, 1.5 Hz, 1H) 7.55 (t, J = 7.6 Hz, 1H) 6.98 (d, J = 0.8 Hz, 1H) 6.83 (dd, J = 1.8, 1.0 Hz, 1H) 6.56 (d, J = 1.6 Hz, 1H) 5.35 (s, 2H) 4.20 (s, 3H) 3.79 (s, 3H) |
| 55 | 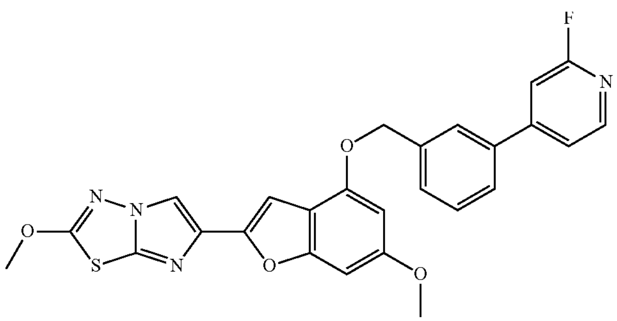 [SMILES: COc1cc(OCc2cccc(-c3ccnc(F)c3)c2)c2cc(-c3cn4nc(OC)sc4n3)oc2c1] | C26H19FN4O4S | 503.1184 | 2.375/B | 503.121 | 1H NMR (400 MHz, DMSO-d6) δ ppm 8.38 (s, 1H) 8.33 (d, J = 5.1 Hz, 1H) 8.01 (t, J = 1.6 Hz, 1H) 7.85 (dt, J = 7.8, 1.6 Hz, 1H) 7.73 (dt, J = 5.2, 1.7 Hz, 1H) 7.63-7.69 (m, 1H) 7.54-7.63 (m, 2H) 7.01 (s, 1H) 6.82-6.86 (m, 1H) 6.57 (d, J = 2.0 Hz, 1H) 5.34 (s, 2 H) 4.20 (s, 3H) 3.80 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 56 | 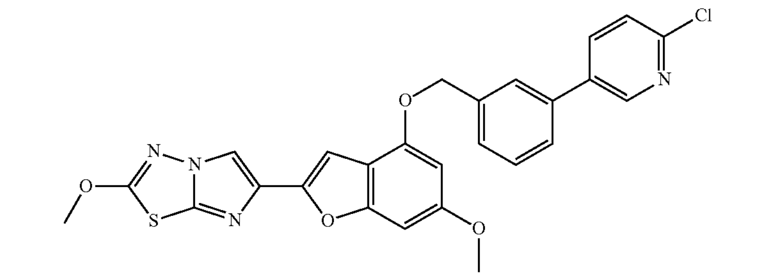 [SMILES: COc1cc(OCc2cccc(-c3ccc(Cl)nc3)c2)c2cc(-c3cn4nc(OC)sc4n3)oc2c1] | $C_{26}H_{19}ClN_4O_4S$ | 519.0888 | 2.415/B | 519.0913 | 1H NMR (400 MHz, DMSO-$d_6$) δ ppm 8.77 (dd, J = 2.7, 0.8 Hz, 1H) 8.37 (s, 1H) 8.19 (dd, J = 8.4, 2.5 Hz, 1H) 7.89 (t, J = 1.8 Hz, 1H) 7.73 (dt, J = 7.2, 1.7 Hz, 1H) 7.52-7.65 (m, 3H) 7.01 (d, J = 0.8 Hz, 1H) 6.84 (dd, J = 2.0, 0.8 Hz, 1H) 6.57 (d, J = 2.0 Hz, 1H) 5.33 (s, 2H) 4.20 (s, 3H) 3.80 (s, 3 H) |
| 57 | 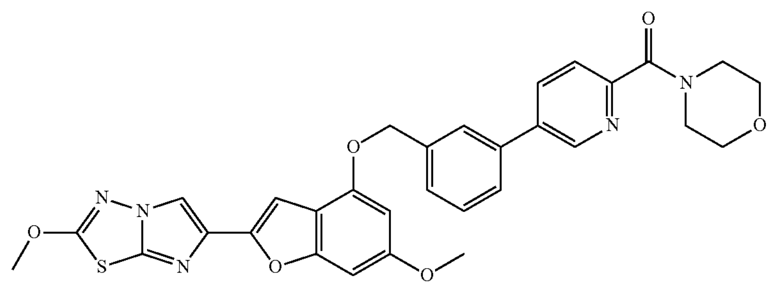 [SMILES: COc1cc(OCc2cccc(-c3ccc(C(=O)N4CCOCC4)nc3)c2)c2cc(-c3cn4nc(OC)sc4n3)oc2c1] | $C_{31}H_{27}N_5O_6S$ | 598.1775 | 2.267/B | 598.1884 | 1H NMR (400 MHz, DMSO-$d_6$) δ ppm 8.93 (dd, J = 2.3, 0.8 Hz, 1 H) 8.38 (s, 1 H) 8.25 (dd, J = 8.2, 2.3 Hz, 1 H) 7.92 (t, J = 1.8 Hz, 1 H) 7.77 (dt, J = 7.1, 1.9 Hz, 1 H) 7.72 (dd, J = 8.2, 0.8 Hz, 1 H) 7.53-7.64 (m, 2 H) 7.01 (d, J = 0.8 Hz, 1 H) 6.84 (dd, J = 1.8, 1.0 Hz, 1 H) 6.57 (d, J = 2.0 Hz, 1 H) 5.34 (s, 2H) 4.20 (s, 3H) 3.80 (s, 3H) 3.68 (s, 4H) 3.48-3.61 (m, 4H) |
| 58 | 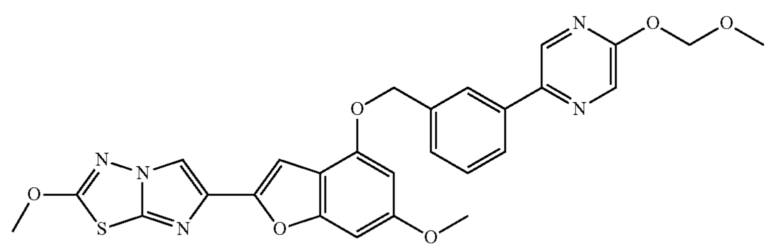 | $C_{27}H_{23}N_5O_6S$ | 546.1442 | 2.305/B | 546.1478 | 1H NMR (400 MHz, DMSO-$d_6$) δ ppm 8.38 (s, 1H) 8.33 (s, 1H) 8.22 (d, J = 0.8 Hz, 1H) 8.03 (s, 1 H) 7.81-7.87 (m, 1H) 7.46-7.53 (m, 2H) 6.99 (s, 1H) 6.81-6.85 (m, 1H) 6.55 (d, J = 2.0 Hz, 1H) 5.30 (s, 2H) 5.30 (s, 2H) 4.20 (s, 3H) 3.79 (s, 3H) 3.35 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 59 | 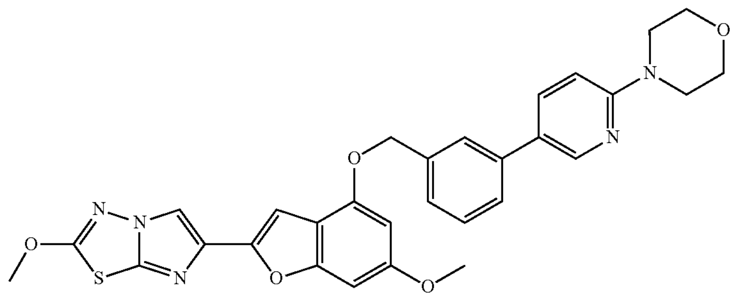 [SMILES: COc1cc(OCc2cccc(-c3ccc(N4CCOCC4)nc3)c2)c2cc(-c3cn4nc(OC)sc4n3)oc2c1] | $C_{30}H_{27}N_5O_5S$ | 570.1806 | | 570.1861 | $^1$H NMR (400 MHz, DMSO-$d_6$) δ ppm 8.49 (d, J = 2.3 Hz, 1H) 8.38 (s, 1H) 7.90 (dd, J = 8.8, 2.5 Hz, 1H) 7.73-7.78 (m, 1H) 7.61 (dt, J = 7.2, 1.7 Hz, 1H) 7.41-7.51 (m, 2H) 6.98-7.01 (m, 1H) 6.94 (d, J = 9.0 Hz, 1H) 6.83 (dd, J = 1.8, 1.0 Hz, 1H) 6.56 (d, J = 2.0 Hz, 1H) 5.30 (s, 2H) 4.20 (s, 3H) 3.79 (s, 3H) 3.68-3.75 (m, 4H) 3.46-3.54 (m, 4H) |
| 60 | 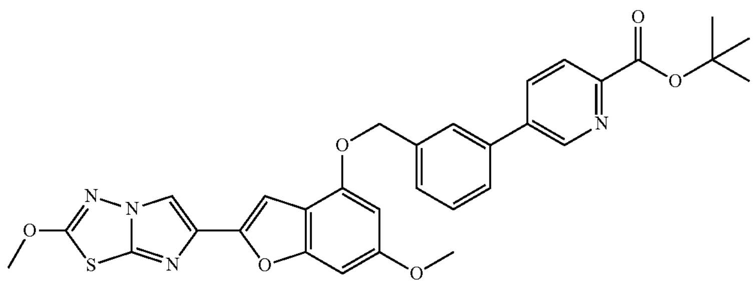 [SMILES: COc1cc(OCc2cccc(-c3ccc(C(=O)OC(C)(C)C)nc3)c2)c2cc(-c3cn4nc(OC)sc4n3)oc2c1] | $C_{31}H_{28}N_4O_6S$ | 585.1802 | 2.510/B | 585.1849 | $^1$H NMR (400 MHz, DMSO-$d_6$) δ ppm 9.01-9.07 (m, 1H) 8.38 (s, 1H) 8.28 (dd, J = 8.2, 2.3 Hz, 1H) 8.05-8.10 (m, 1H) 7.91-7.97 (m, 1H) 7.79 (dt, J = 7.2, 1.9 Hz, 1H) 7.56-7.66 (m, 2H) 6.99-7.03 (m, 1H) 6.84 (dd, J = 1.8, 1.0 Hz, 1H) 6.58 (d, J = 1.6 Hz, 1H) 5.35 (s, 2H) 4.20 (s, 3H) 3.80 (s, 3H) 1.58 (s, 9H) |
| 61 | 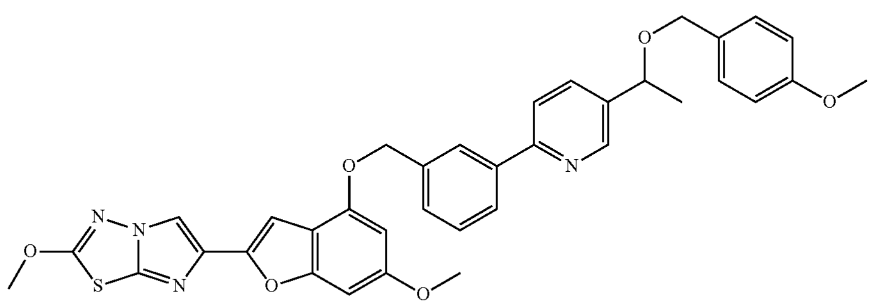 | $C_{36}H_{32}N_4O_6S$ | 649.2115 | 2.413/B | 649.2145 | $^1$H NMR (400 MHz, DMSO-$d_6$) δ ppm 8.65 (d, J = 2.0 Hz, 1H) 8.38 (s, 1H) 8.25 (t, J = 2.0 Hz, 1H) 8.06 (dt, J = 7.7, 1.6 Hz, 1H) 8.00 (dd, J = 8.2, 0.8 Hz, 1H) 7.87 (dd, J = 8.4, 2.2 Hz, 1H) 7.51-7.61 (m, 2H) 7.21-7.26 (m, 2H) 7.00 (d, J = 0.8 Hz, 1H) 6.87-6.92 (m, 2H) 6.83 (dd, J = 2.0, 0.8 Hz, 1H) 6.57 (d, J = 2.0 Hz, 1H) 5.35 (s, 2H) 4.64 (q, J = 6.3 Hz, 1H) 4.32 (s, 2H) 4.20 (s, 3H) 3.79 (s, 3H) 3.74 (s, 3H) 1.44 (d, J = 6.3 Hz, 3H) |

Example 62

6-(4-((3-Fluoro-5-(5-methoxypyridin-2-yl)benzyl)oxy)-6-methoxybenzofuran-2-yl)-2-methoxyimidazo[2,1-b][1,3,4]thiadiazole

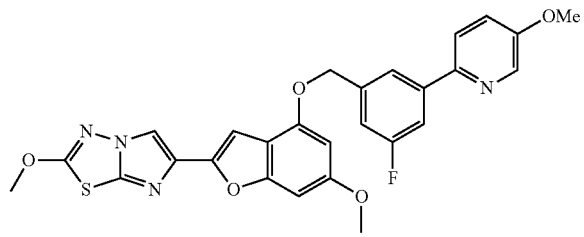 [SMILES: COc1ccc(-c2cc(F)cc(COc3cc(OC)cc4oc(-c5cn6nc(OC)sc6n5)cc34)c2)nc1]

62A. 3-Fluoro-5-(5-methoxypyridin-2-yl)benzoic acid

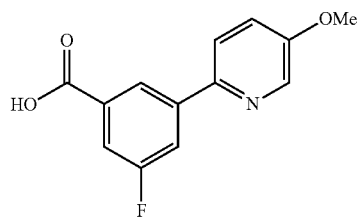 [SMILES: COc1ccc(-c2cc(F)cc(C(=O)O)c2)nc1]

In a 4 mL vial, palladium acetate (4.9 mg, 0.022 mmol), triphenylphosphine (12.1 mg, 0.046 mmol), 2M aqueous solution of sodium carbonate (0.96 ml, 1.920 mmol) and water (0.3 ml, 16.65 mmol) were successively added to a mixture of 2-bromo-5-methoxypyridine (0.1 ml, 0.814 mmol) and 3-carboxy-5-fluorophenylboronic acid (148 mg, 0.805 mmol) in 1-propanol (1.5 ml, 19.97 mmol) under nitrogen. The mixture was stirred at 95° C. overnight. The mixture was quenched with 1N HCl and the product was extracted three times with AcOEt. The aqueous phase was neutralized to pH 7 with NaOH 10% and extracted twice with AcOEt. The combined organic layers were washed once with water, once with brine, dried over anh. Na$_2$SO$_4$ and concentrated. The white solid in suspension in aqueous phase was filtrated and the two products were mixed together to give the title material as a white solid used as is. LC (Method B): 1.747 min. $^1$H NMR (400 MHz, acetone) δ ppm 8.54-8.58 (m, 1H) 8.41 (dd, J=3.1, 0.8 Hz, 1H) 8.07 (ddd, J=10.3, 2.7, 1.7 Hz, 1H) 8.03 (dd, J=9.0, 0.8 Hz, 1H) 7.69 (ddd, J=9.0, 2.6, 1.4 Hz, 1H) 7.50 (dd, J=8.8, 2.9 Hz, 1H) 3.96 (s, 3H).

62B. (3-Fluoro-5-(5-methoxypyridin-2-yl)phenyl)methanol

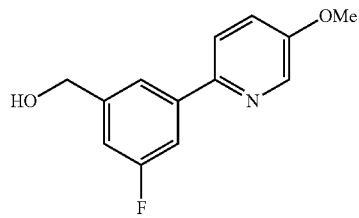 [SMILES: COc1ccc(-c2cc(F)cc(CO)c2)nc1]

At 0° C. under nitrogen, lithium aluminum hydride (115 mg, 3.03 mmol) was added portionwise over 10 min. to 3-fluoro-5-(5-methoxypyridin-2-yl)benzoic acid (Example 62A, 150 mg, 0.607 mmol) in THF (6 ml, 73.2 mmol) and the mixture was stirred for 24 h at room temperature. The reaction was quenched with water (1.5 mL) and stirred for 30 min. at room temperature. It was filtrated on CELITE®, washed with AcOEt and concentrated. The residue was purified on ISCO using a REDISEP® Gold 24 g column (Hex/EtOAc). The crude product was adsorbed on SiO$_2$. The fractions were collected and concentrated to give the title material as a yellow oil (96 mgs, 96%). LC (Method B): 1.346 min. MS(ESI) calcd for C$_{13}$H$_{13}$FNO$_2$ [M+H]$^+$ m/z 234.0925. found 234.0962. $^1$H NMR (400 MHz, acetone) δ ppm 8.35-8.39 (m, 1H) 7.91 (dd, J=8.6, 0.8 Hz, 1H) 7.85-7.89 (m, 1H) 7.63-7.70 (m, 1H) 7.45 (dd, J=8.6, 3.1 Hz, 1H) 7.10-7.16 (m, 1H) 4.73 (d, J=5.9 Hz, 2H) 4.40 (t, J=5.9 Hz, 1H) 3.94 (s, 3H).

Example 62

6-(4-((3-Fluoro-5-(5-methoxypyridin-2-yl)benzyl)oxy)-6-methoxybenzofuran-2-yl)-2-methoxyimidazo[2,1-b][1,3,4]thiadiazole

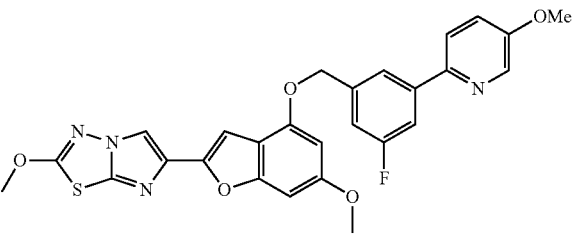 [SMILES: COc1ccc(-c2cc(F)cc(COc3cc(OC)cc4oc(-c5cn6nc(OC)sc6n5)cc34)c2)nc1]

In a 10 mL round-bottomed flask, a mixture of 6-methoxy-2-(2-methoxyimidazo[2,1-b][1,3,4]thiadiazol-6-yl)benzofuran-4-ol (Example 1G, 51 mg, 0.161 mmol), (3-fluoro-5-(5-methoxypyridin-2-yl)phenyl)methanol (Example 62B, 96 mg, 0.412 mmol) and triphenylphosphine (106 mg, 0.404 mmol) was dried under high vacuum for 10 min. THF (1.5 mL) was added and the mixture was sonificated for 15 min. Diisopropyl azodicarboxylate (0.08 ml, 0.411 mmol) in THF (1.0 mL) was added portionwise over 15 min. and the yellow solution was sonicated 30 min. and stirred 1 h 30 at room temperature. The mixture was diluted in CH$_2$Cl$_2$, washed once with sat. NaHCO$_3$, once with brine, dried over anh. Na$_2$SO$_4$ and concentrated. The residue was purified on ISCO using a REDISEP® Gold 12 g column (CH$_2$Cl$_2$/EtOAc). The crude product was adsorbed on SiO$_2$.

The fractions were concentrated, triturated once in ACN and lyophilized in ACN/water to give the title material as a beige solid (58 mgs, 68%). LC (Method B): 2.376 min. MS(ESI) calcd for $C_{27}H_{22}FN_4O_5S$ [M+H]$^+$ m/z 533.1328. found 533.1318. $^1$H NMR (400 MHz, DMSO-d$_6$) δ ppm 8.40 (d, J=3.1 Hz, 1H) 8.39 (s, 1H) 8.04 (t, J=1.6 Hz, 1H) 8.01 (d, J=8.6 Hz, 1H) 7.77-7.83 (m, 1H) 7.51 (dd, J=8.9, 3.0 Hz, 1H) 7.32-7.38 (m, 1H) 7.02-7.05 (m, 1H) 6.83-6.87 (m, 1H) 6.55 (d, J=1.6 Hz, 1H) 5.35 (s, 2H) 4.21 (s, 3H) 3.89 (s, 3H) 3.80 (s, 3H).

The following benzylic alcohols were prepared according to the procedure described in Example 62A and 62B using 3-carboxy-5-fluorophenylboronic acid or (3-fluoro-5-(methoxycarbonyl)phenyl)boronic acid and the corresponding bromides.

dropwise and then the cooling bath was removed and the mixture was stirred at room temperature for 1 h. The vessel was then sealed and the mixture was heated at 90-95° C. (oil bath temperature) for 5 h. The resulting turbid mixture was concentrated under reduced pressure and the concentrate was poured into ice water (150 mL). This mixture was basified to ca. pH 9 using 40% aqueous NaOH and the resulting slurry was filtered and the residue was washed with water, then with ether and finally with hexanes. The residue was dried in vacuo to give the title compound (4.31 g, 64%) as a white solid which was used as such in the next step. LC (Method A): 1.045 min. LCMS: Anal. Calcd. for $C_4H_5F_2N_3S$: 165.02. found: 166.04 (M+1)$^+$. $^1$H NMR (600 MHz, DMSO-d$_6$) δ 7.69 (s, 2H), 2.06 (t, J=19.0 Hz, 3H).

| Structure (Employed in preparation of compound as indicated) | Formula | Calc. [M + H]$^+$ m/z | LCMS [M + H]$^+$ m/z | HPLC Retention Time (Min)/ Method | NMR |
|---|---|---|---|---|---|
| 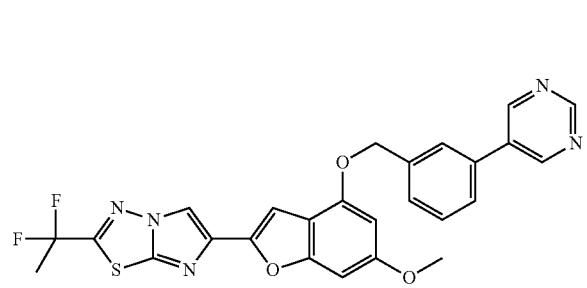 [SMILES: COc1cc(OCc2cccc(-c3cncnc3)c2)c2cc(-c3cn4nc(C(C)(F)F)sc4n3)oc2c1] (70) | $C_{12}H_8F_3NO$ | 240.06 | 240.0 | 1.760/B | $^1$H NMR (400 MHz, acetone): δ ppm 8.56 (d, J = 2.7 Hz, 1H) 7.74-7.82 (m, 2H) 7.53-7.59 (m, 1H) 7.22-7.28 (m, 1H) 4.76 (d, J = 5.9 Hz, 2H) 4.48 (t, J = 5.9 Hz, 1H) |

Example 63

2-(1,1-Difluoroethyl)-6-(6-methoxy-4-((3-(pyrimidin-5-yl)benzyl)oxy)benzofuran-2-yl)imidazo[2,1-b][1,3,4]thiadiazole

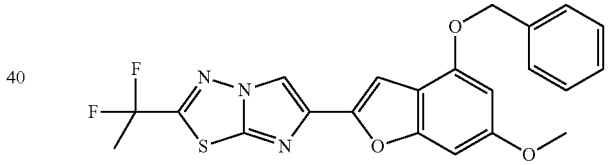

63A. 5-(1,1-Difluoroethyl)-1,3,4-thiadiazol-2-amine

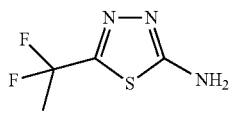

General Method: A modification of a literature procedure was used (cf. He, J. et al., *Chinese Chemical Letters*, 19:1281 (2008)). Thus, to an ice-cold suspension of thiosemicarbazide (4.97 g, 54.5 mmol) in dioxane (45 mL) was slowly added a solution of the 2,2-difluoropropanoic acid (4.50 g, 40.9 mmol) in dioxane (5 mL). To the resulting thick off-white slurry was added POCl$_3$ (4.99 mL, 54.5 mmol)

63B. 6-(4-(Benzyloxy)-6-methoxybenzofuran-2-yl)-2-(1,1-difluoroethyl)imidazo[2,1-b][1,3,4]thiadiazole The reaction was split in two 20 mL vials. 1-(4-(Benzyloxy)-6-methoxybenzofuran-2-yl)-2-bromoethanone (Example 1D, 775 mg, 2.065 mmol) and 5-(1,1-difluoroethyl)-1,3,4-thiadiazol-2-amine (Example 63A, 450 mg, 2.72 mmol) were suspended in 2-propanol (24 ml, 312 mmol) and heated at 80° C. for 17 h. After 5 min., the solution became homogeneous and a precipitate was present after stirring overnight. The cooled mixtures were then transferred into two 20 mL microwaves vials and then heated for 30 min at 150° C. The mixtures were combined, diluted in CH$_2$Cl$_2$ (200 mL) and washed once with sat. NaHCO$_3$, once with brine, dried over anh. Na$_2$SO$_4$ and concentrated. The residue was purified on ISCO using a REDISEP® Gold 24 g column (CH$_2$Cl$_2$/EtOAc). The orange solid obtained was triturated twice in MeOH to give the title material (539 mg, 59%) as a light yellow solid. LC (Method B): 2.457 min. MS(ESI) calcd for $C_{22}H_{18}F_2N_3O_3S$ [M+H]$^+$ m/z 442.1031. found 442.1064. $^1$H NMR (400 MHz, DMSO-d$_6$) ppm 8.72 (s, 1H) 7.48-7.56 (m, 2H) 7.42 (tt, J=7.4, 1.6 Hz, 2H) 7.35 (tt, J=7.4, 1.8 Hz, 1H) 7.12 (d, J=0.8 Hz, 1H) 6.85 (dd, J=2.0, 0.8 Hz, 1H) 6.55 (d, J=2.0 Hz, 1H) 5.27 (s, 2H) 3.80 (s, 3H) 2.24 (t, J=19.4 Hz, 3H).

63C. 2-(2-(1,1-Difluoroethyl)imidazo[2,1-b][1,3,4]thiadiazol-6-yl)-6-methoxybenzofuran-4-ol

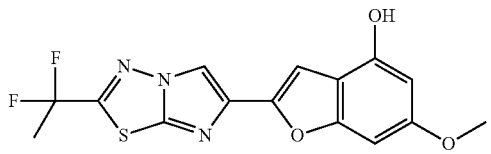 [SMILES: COc1cc(O)c2cc(-c3cn4nc(C(C)(F)F)sc4n3)oc2c1]

A mixture of 6-(4-(benzyloxy)-6-methoxybenzofuran-2-yl)-2-(1,1-difluoroethyl)imidazo[2,1-b][1,3,4]thiadiazole (Example 63B, 0.534 g, 1.210 mmol) and pentamethylbenzene (1.264 g, 8.53 mmol) in dichloromethane (80 ml, 1243 mmol) was cooled to −78° C. under nitrogen atmosphere and then treated immediately (to avoid crystallization) with boron trichloride 1.0M in dichloromethane (3.2 ml, 3.20 mmol) added dropwise over 3 min. The resulting mixture was stirred at −78° C. for 1 h. Boron trichloride (1.0M in DCM, 1.0 ml, 1.00 mmol) was added again and the mixture was stirred for an extra 1.5 hrs. The reaction mixture was then quenched by addition of a solution of sodium bicarbonate (2.4 g) in water (40 mL) added in one portion. The cooling bath was removed and the resulting mixture was stirred at room temperature for 1 h. The resulting solid was filtered, washed successively with water (20 mL) and dichloromethane (20 mL). The filter cake was soaked with anh. ethanol and sucked dry. The white solid obtained was dried under vacuum on $P_2O_5$ over week-end to give the title material (312 mg, 73%). LC (Method B): 2.134 min. MS(ESI) calcd for $C_{15}H_{12}F_2N_3O_3S$ [M+H]$^+$ m/z 352.0562. found 352.0579. $^1$H NMR (400 MHz, DMSO-$d_6$) ppm 10.09 (s, 1H) 8.67 (s, 1H) 7.13 (s, 1H) 6.68 (dd, J=2.0, 0.8 Hz, 1H) 6.27 (d, J=2.0 Hz, 1H) 3.76 (s, 3H) 2.24 (t, J=19.4 Hz, 3H).

Example 63

2-(1,1-Difluoroethyl)-6-(6-methoxy-4-((3-(pyrimidin-5-yl)benzyl)oxy)benzofuran-2-yl)imidazo[2,1-b][1,3,4]thiadiazole

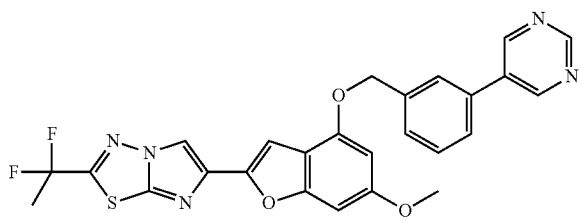 [SMILES: COc1cc(OCc2cccc(-c3cncnc3)c2)c2cc(-c3cn4nc(C(C)(F)F)sc4n3)oc2c1]

In a 10 mL round-bottomed flask, benzene was added to 2-(2-(1,1-difluoroethyl)imidazo[2,1-b][1,3,4]thiadiazol-6-yl)-6-methoxybenzofuran-4-ol (Example 63C, 26 mg, 0.074 mmol) and the mixture was sonificated 30 sec. and concentrated in vacuo to remove traces of water in the starting material. Triphenylphosphine (49 mg, 0.187 mmol) and (3-(pyrimidin-5-yl)phenyl)methanol (43 mg, 0.231 mmol) were added and the mixture was dried under high vacuum for 10 min. THF (1.2 mL) was added and the mixture was sonificated for 5 min. Diisopropylazodicarboxylate (0.035 ml, 0.180 mmol) in THF (0.8 mL) was added dropwise over 5 min. and the yellow solution was stirred over weekend at room temperature. The reaction mixture was diluted in $CH_2Cl_2$, washed once with sat. NaHCO$_3$, once with brine, dried over anh. Na$_2$SO$_4$ and concentrated. The residue was purified on ISCO using a REDISEP® Gold 12 g column ($CH_2Cl_2$/EtOAc). The crude product was adsorbed on SiO$_2$. The fractions were collected, concentrated in vacuo and lyophilized in ACN/water to give the title material as a white solid. LC (Method B): 2.426 min. MS(ESI) calcd for $C_{26}H_{20}F_2N_5O_3S$ [M+H]$^+$ m/z 520.1249. found 520.1248. $^1$H NMR (400 MHz, DMSO-$d_6$) ppm 9.21 (s, 1H) 9.18 (s, 2H) 8.71 (s, 1H) 7.98 (s, 1H) 7.81 (d, J=7.0 Hz, 1H) 7.51-7.71 (m, 2H) 7.17 (s, 1H) 6.80-6.93 (m, 1H) 6.60 (d, J=1.6 Hz, 1H) 5.35 (s, 2H) 3.81 (s, 3H) 2.23 (t, J=19.4 Hz, 3H).

Example 64

(S)-2-(1-Fluoroethyl)-6-(6-methoxy-4-((3-(pyrimidin-5-yl)benzyl)oxy)benzofuran-2-yl)imidazo[2,1-b][1,3,4]thiadiazole

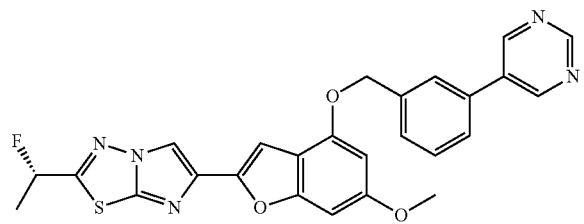 [SMILES: COc1cc(OCc2cccc(-c3cncnc3)c2)c2cc(-c3cn4nc([C@H](C)F)sc4n3)oc2c1]

64A. (S)-5-(1-Fluoroethyl)-1,3,4-thiadiazol-2-amine

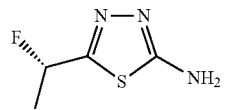

A 350 mL sealable pressure vessel was charged with thiosemicarbazide (11.17 g, 122.5 mmol) and dry dioxane (100 mL), and the mixture was cooled at 0° C. under an N$_2$ atmosphere. To this rapidly stirring mixture was slowly added a solution of (S)-2-fluoropropanoic acid (9.40 g, 102.1 mmol, from Fritz-Langhals, E., *Tetrahedron Asymmetry*, 981 (1994)) in dioxane (10 mL). To the resulting mixture was added POCl$_3$ (11.22 mL, 122.5 mmol) dropwise, then the cooling bath was removed and the thick white slurry was stirred at room temperature for 1 h. The vessel was then sealed and the mixture was heated at 90-95° C. (oil bath temperature) for 5 h. The cooled mixture was stirred at room temperature for 14 h (Note: this was for convenience only and is optional) and then the supernatant (two-phase mixture) was decanted and concentrated under reduced pressure. The lower phase was slowly poured into ice water (250 mL) and then the concentrate was also added. This mixture was rapidly stirred until it was essentially a homogeneous (turbid) solution, and then it was basified to pH 9-9.5 using 40% aqueous NaOH. The resulting slurry was filtered and the filter-cake was washed with water (Note: LC of this beige solid showed that it contained only a trace of the desired product, so it was not further investigated). The combined filtrate was then extracted with EtOAc (×3) and the organic phase was dried (Na$_2$SO$_4$) and evaporated to give a cream solid (10.58 g, 70%) which was the essentially pure product according to LC and LCMS. This material was used as such without further purification. An analytical sample was purified by flash chromatography [Isco/0-20% (MeOH—NH$_4$OH, 9:1)-DCM] to give a white solid. LC (Method B): 0.608 min. MS(ESI) calcd. for C$_4$H$_6$FN$_3$S m/z: 147.03. found: 148.05 [M+H]$^+$. $^1$H NMR (600 MHz, DMSO-d$_6$) δ 7.38 (s, 2H), 5.82 (dq, J=6.4, 48.0 Hz, 1H), 1.65 (dd, J=6.4, 24.0 Hz, 3H). Chiral LC: S:R=95:5.

64B. (S)-6-(4-(Benzyloxy)-6-methoxybenzofuran-2-yl)-2-(1-fluoroethyl)imidazo[2,1-b][1,3,4]thiadiazole

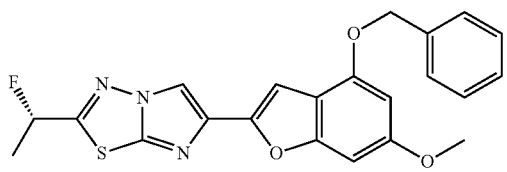 [SMILES: COc1cc(OCc2ccccc2)c2cc(-c3cn4nc([C@H](C)F)sc4n3)oc2c1]

In a 20 mL vial, 1-(4-(benzyloxy)-6-methoxybenzofuran-2-yl)-2-bromoethanone (Example 1D, 407 mg, 1.085 mmol) and (S)-5-(1-fluoroethyl)-1,3,4-thiadiazol-2-amine (202 mg, 1.373 mmol) were suspended in 2-propanol (10 ml, 130 mmol) and heated at 80° C. for 18 h. After 5 min. the solution became homogeneous. A precipitate was present after ON stirring. The cooled mixtures were transferred into 20 mL microwaves vials and then heated 30 min at 150° C. The mixtures were combined, diluted in CH$_2$Cl$_2$ (200 mL) and washed once with sat. NaHCO$_3$, once with brine, dried over anh. Na$_2$SO$_4$ and concentrated. The residue was purified on ISCO using a REDISEP® Gold 40 g column (CH$_2$Cl$_2$/EtOAc). The crude product was adsorbed on SiO$_2$. Fractions were collected and the orange solid obtained was triturated twice in ACN to give the title material a light yellow solid. LC (Method B): 2.403 min. MS(ESI) calcd. for C$_{22}$H$_{19}$FN$_3$O$_3$S [M+H]$^+$ m/z: 424.1126. found: 424.1146. $^1$H NMR (400 MHz, DMSO-d$_6$) δ ppm 8.61 (s, 1H) 7.51 (d, J=7.4 Hz, 2H) 7.42 (t, J=7.6 Hz, 2H) 7.35 (t, J=7.0 Hz, 1H) 7.08 (s, 1H) 6.83-6.85 (m, 1H) 6.54 (d, J=1.2 Hz, 1H) 6.16 (dq, J=47.1, 6.4 Hz, 1H) 5.26 (s, 2H) 3.80 (s, 3H) 1.79 (dd, J=24.5, 6.8 Hz, 3H).

64C. (S)-2-(2-(1-Fluoroethyl)imidazo[2,1-b][1,3,4]thiadiazol-6-yl)-6-methoxybenzofuran-4-ol

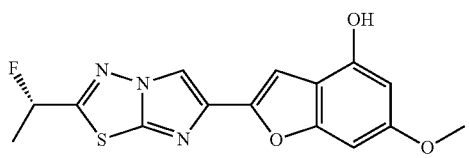 [SMILES: COc1cc(O)c2cc(-c3cn4nc([C@H](C)F)sc4n3)oc2c1]

A mixture of (S)-6-(4-(benzyloxy)-6-methoxybenzofuran-2-yl)-2-(1-fluoroethyl)imidazo[2,1-b][1,3,4]thiadiazole (Example 64B, 0.152 g, 0.359 mmol) and pentamethylbenzene (0.374 g, 2.52 mmol) in dichloromethane (24 ml, 373 mmol) was cooled to -78° C. under nitrogen atmosphere and then treated immediately (to avoid crystallization) with boron trichloride 1.0M in dichloromethane (1 ml, 1.000 mmol) added dropwise over 3 min. The resulting mixture was stirred at -78° C. for 1 h. The reaction mixture was quenched by addition of a solution of sodium bicarbonate (0.71 g) in water (12 mL) added in one portion. The cooling bath was removed and the resulting mixture was stirred at room temperature for 1 h. The solid formed was filtered, washed successively with water (8 mL) and dichloromethane (8 mL). The filter cake was soaked with anh. ethanol and suck dried. The white solid obtained was dried under vacuum on P$_2$O$_5$ for 36 h. LC (Method B): 2.038 min. MS(ESI) calcd. for C$_{15}$H$_{13}$FN$_3$O$_3$S [M+H]$^+$ m/z: 334.0656. found: 334.0680. $^1$H NMR (400 MHz, DMSO-d$_6$) δ ppm 10.06 (s, 1H) 8.56 (s, 1H) 7.09 (s, 1H) 6.67 (s, 1H) 6.26-6.28 (m, 1H) 6.16 (dq, J=46.9, 6.4 Hz, 1H) 3.76 (s, 3H) 1.80 (dd, J=24.7, 6.3 Hz, 3H).

Example 64

(S)-2-(1-Fluoroethyl)-6-(6-methoxy-4-((3-(pyrimidin-5-yl)benzyl)oxy)benzofuran-2-yl)imidazo[2,1-b][1,3,4]thiadiazole

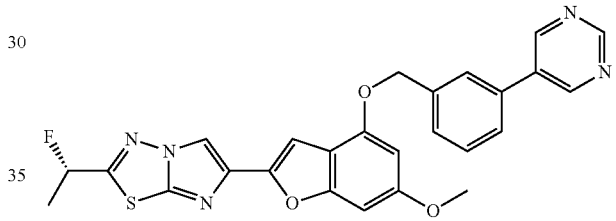

In a 10 mL round-bottomed flask, benzene was added to (S)-2-(2-(1-fluoroethyl)imidazo[2,1-b][1,3,4]thiadiazol-6-yl)-6-methoxybenzofuran-4-ol (Example 64C, 17 mg, 0.051 mmol) and the mixture was sonificated during 30 sec. and concentrated in vacuo to remove traces of water in the starting material. Triphenylphosphine (30 mg, 0.114 mmol) and (3-(pyrimidin-5-yl)phenyl)methanol (33 mg, 0.177 mmol) were added and the mixture was dried on high vacuum for 10 min. THF (1.0 mL) was added and the mixture was stirred until complete dissolution. Diisopropylazodicarboxylate (0.025 ml, 0.129 mmol) in THF (0.5 mL) was added dropwise on 5 min. and the yellow solution was stirred overnight at room temperature. The reaction mixture was diluted in CH$_2$Cl$_2$, washed once with sat. NaHCO$_3$, once with brine, dried over anh. Na$_2$SO$_4$ and concentrated. The residue was purified on ISCO using a REDISEP® Gold 12 g column (CH$_2$Cl$_2$/EtOAc). The crude product was adsorbed on SiO$_2$ and the fractions were collected, concentrated in vacuo, triturated once with ACN and lyophilized in ACN/water to give the title material as a light yellow solid. LC (Method B): 2.331 min. MS(ESI) calcd. for C$_{26}$H$_{21}$FN$_5$O$_3$S [M+H]$^+$ m/z: 502.1344. found: 502.1353.

Example 65

6-(4-((5-(Furan-3-yl)pyridin-3-yl)methoxy)-6-methoxybenzofuran-2-yl)-2-methoxyimidazo[2,1-b][1,3,4]thiadiazole

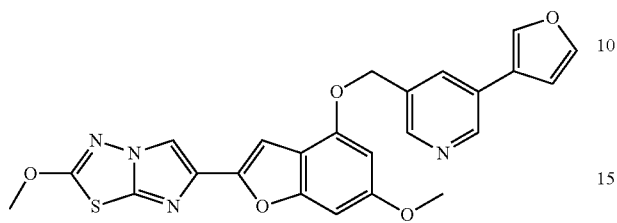

65A. (5-Bromopyridin-3-yl)methanol

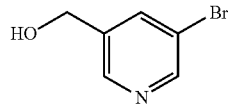

To a cold solution of ethyl 5-bromonicotinate (1.003 g, 4.36 mmol) in methanol (15 ml, 371 mmol) was added sodium borohydride (0.652 g, 17.23 mmol) portionwise on 10 min. The reaction was stirred for 30 min. at 0° C. The reaction was quenched with water and extracted three times with CH$_2$Cl$_2$. The combined organic layers were dried on anh. Na$_2$SO$_4$ and concentrated. The residue was purified on ISCO using a 80 g SILICYCLE® column (Hex/EtOAc) and afforded the title material (0.477 g, 54%) as a clear oil. LC (Method B): 0.756 min. MS(ESI) calcd. for C$_6$H$_7$BrNO [M+H]$^+$ m/z: 187.97. found: 190.0, 191.0. $^1$H NMR (400 MHz, acetone) δ ppm 8.50-8.58 (m, 2H) 7.93-7.98 (m, 1H) 4.67-4.74 (m, 2H) 4.48-4.56 (m, 1H).

65B. (5-(Furan-3-yl)pyridin-3-yl)methanol

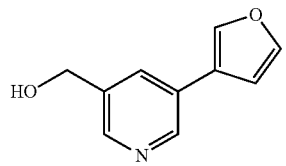 [SMILES: OCc1cncc(-c2ccoc2)c1]

In a 2 mL vial, palladium acetate (5.5 mg, 0.024 mmol), triphenylphosphine (13.2 mg, 0.050 mmol), 2M aqueous solution of sodium carbonate (0.63 ml, 1.260 mmol) and water (0.35 ml, 19.43 mmol) were successively added to a mixture of furan-3-ylboronic acid (Example 65A, 112 mg, 1.001 mmol) and (5-bromopyridin-3-yl)methanol (170 mg, 0.904 mmol) in 1-propanol (1.75 ml, 23.30 mmol) under nitrogen. The mixture was stirred at 95° C. for 30 min. and the reaction was stirred at room temperature overnight. The mixture was quenched with water and the product was extracted three times with AcOEt. The combined organic layers were washed once with sat. NaHCO$_3$, once with brine, dried over anh. Na$_2$SO$_4$ and concentrated. The residue was purified on silica gel using a REDISEP® Gold 24 g column (Hex/EtOAc). The title material was obtained (149 mgs, 94%) after concentration of the fractions as a light yellow oil. LC (Method B): 0.702 min. MS(ESI) calcd. for C$_{10}$H$_{10}$NO$_2$ [M+H]$^+$ m/z: 176.07. found: 176.2. $^1$H NMR (400 MHz, acetone) δ ppm 8.73 (d, J=2.0 Hz, 1H) 8.46 (d, J=2.0 Hz, 1H) 8.11-8.17 (m, 1H) 7.90-7.95 (m, 1H) 7.67-7.72 (m, 1H) 6.97 (dd, J=2.0, 0.8 Hz, 1H) 4.71 (d, J=6.3 Hz, 2H) 4.38 (t, J=5.7 Hz, 1H).

Example 65

6-(4-((5-(Furan-3-yl)pyridin-3-yl)methoxy)-6-methoxybenzofuran-2-yl)-2-methoxyimidazo[2,1-b][1,3,4]thiadiazole

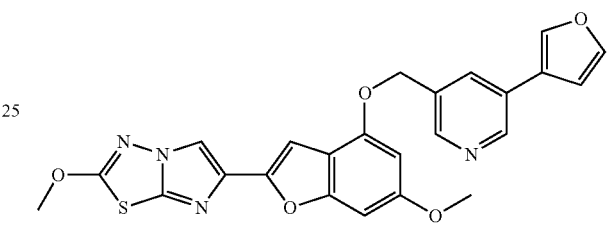

In a 10 mL round-bottomed flask, a mixture of 6-methoxy-2-(2-methoxyimidazo[2,1-b][1,3,4]thiadiazol-6-yl)benzofuran-4-ol (Example 1G, 45 mg, 0.142 mmol) and triphenylphosphine (100 mg, 0.381 mmol) was dried on high vacuum for 10 min. THF (1.0 mL) was added and the mixture was sonificated for 10 min. A mixture of (5-(furan-3-yl)pyridin-3-yl)methanol (Example 65B, 61 mg, 0.348 mmol) and diisopropyl azodicarboxylate (0.08 ml, 0.411 mmol) in THF (1.5 mL) was added portionwise on 10 min. and the yellow solution was sonicated for 20 min. and stirred for 2 h at room temperature. The mixture was diluted in CH$_2$Cl$_2$, washed once with sat. NaHCO$_3$, once with brine, dried over anh. Na$_2$SO$_4$ and concentrated. The residue was purified on ISCO using a REDISEP® Gold 12 g column (CH$_2$Cl$_2$/EtOAc). The fractions were concentrated, triturated twice in ACN to give an impure beige solid. The residue was purified for a second time on ISCO using a REDISEP® Gold 12 g column (CH$_2$Cl$_2$/EtOAc). The fractions were concentrated, triturated in ACN and lyophilized in ACN/water to give the title material (12 mgs, 18%) as a white solid. LC (Method B): 2.096 min. MS(ESI) calcd. for C$_{24}$H$_{19}$N$_4$O$_5$S [M+H]$^+$ m/z: 475.1071. found: 475.1224. $^1$H NMR (400 MHz, DMSO-d$_6$) δ ppm: 8.88 (d, J=2.3 Hz, 1H) 8.61 (d, J=2.0 Hz, 1H) 8.38 (s, 1H) 8.36-8.37 (m, 1H) 8.16 (t, J=2.2 Hz, 1H) 7.82 (t, J=1.8 Hz, 1H) 7.10 (dd, J=2.0, 0.8 Hz, 1H) 7.02 (d, J=0.8 Hz, 1H) 6.86 (dd, J=1.8, 1.0 Hz, 1H) 6.60 (d, J=2.0 Hz, 1H) 5.32 (s, 2H) 4.20 (s, 3H) 3.81 (s, 3H).

The following benzylic alcohols were prepared according to the procedure described in Example 65A and 65B using (5-bromopyridin-3-yl)methanol and the corresponding boronic acids and were employed in preparation compounds of the Examples as indicated.

| Structure (Employed in preparation of Example compound as indicated) | Formula | Calc. [M + H]+ m/z | LCMS [M + H]+ m/z | HPLC Retention Time (Min)/ Method | NMR |
|---|---|---|---|---|---|
| 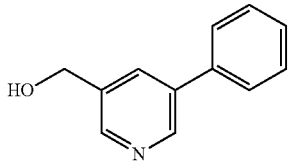 [SMILES: OCc1cncc(-c2ccccc2)c1] (72) | C₁₂H₁₁NO | 186.09 | 186.2 | 0.990/B | ¹H NMR (400 MHz, acetone) δ ppm 8.75 (d, J = 2.3 Hz, 1H) 8.56 (d, J = 2.3 Hz, 1H) 7.96-8.02 (m, 1H) 7.68-7.74 (m, 2H) 7.47-7.55 (m, 2H) 7.39-7.46 (m, 1H) 4.76 (d, J = 5.9 Hz, 2H) 4.42 (t, J = 5.9 Hz, 1H) |
| 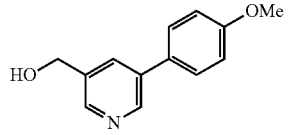 [SMILES: COc1ccc(-c2cncc(CO)c2)cc1] (73) | C₁₃H₁₄NO₂ | 216.10 | 216.2 | 1.101/B | ¹H NMR (400 MHz, acetone) δ ppm 8.71 (d, J = 2.3 Hz, 1H) 8.50 (d, J = 2.0 Hz, 1H) 7.92-7.96 (m, 1H) 7.61-7.68 (m, 2H) 7.04-7.10 (m, 2H) 4.74 (d, J = 6.3 Hz, 2H) 4.39 (t, J = 5.7 Hz, 1H) 3.86 (s, 3H) |
| 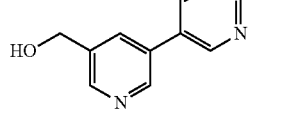 (74) | C₁₁H₉ClN₂O | 221.05 | 221.0 | 0.910/B | ¹H NMR (400 MHz, acetone) δ ppm 8.81 (d, J = 2.3 Hz, 1H) 8.72-8.78 (m, 1H) 8.64 (d, J = 2.0 Hz, 1H) 8.18 (dd, J = 8.2, 2.4 Hz, 1H) 8.05-8.09 (m, 1H) 7.60 (dd, J =8.2, 0.8 Hz, 1H) 4.75-4.80 (m, 2H) 4.48 (t, J = 5.7 Hz, 1H) |
| 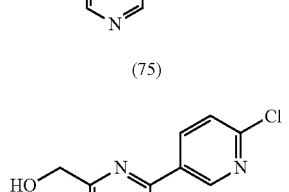 (75) | C₁₁H₁₁N₃O₂ | 218.09 | 218.2 | 0.752/B | ¹H NMR (400 MHz, acetone) δ ppm 8.91 (s, H) 8.79 (d, J = 2.3 Hz, 1H) 8.60-8.64 (m, 1H) 8.02-8.07 (m, 1H) 4.75-4.79 (m, 2H) 4.47 (t, J = 5.9 Hz, 1H) 4.02 (s, 3H) |
| 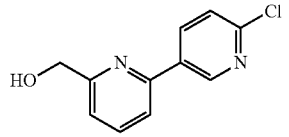 [SMILES: OCc1cccc(-c2ccc(Cl)nc2)n1] (76) | C₁₁H₉ClN₂O | 221.05 | 221.0 | 1.455/B | ¹H NMR (400 MHz, acetone) δ ppm 9.11 (dd, J = 2.3, 0.8 Hz, 1H) 8.53 (dd, J = 8.4, 2.5 Hz, 1H) 7.87-7.98 (m, 2H) 7.50-7.61 (m, 2H) 4.78 (d, J = 5.9 Hz, 2H) 4.53 (t, J = 5.9 Hz, 1H) |
| 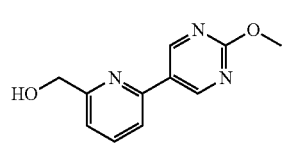 [SMILES: COc1ncc(-c2cccc(CO)n2)cn1] (77) | C₁₁H₁₁N₃O₂ | 218.09 | 218.2 | 1.243/B | ¹H NMR (400 MHz, acetone) δ ppm 9.24 (s, 2H) 7.91 (t, J = 7.6 Hz, 1H) 7.82-7.87 (m, 1H) 7.48-7.54 (m, 1H) 4.77 (d, J = 5.9 Hz, 2H) 4.52 (t, J = 5.7 Hz, 1H) 4.02 (s, 3H) |
| 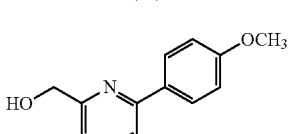 (78) | C₁₃H₁₃NO₂ | 216.10 | 216.2 | 1.214/B | ¹H NMR (400 MHz, acetone) δ ppm 8.06-8.12 (m, 2H) 7.81 (t, J = 7.6 Hz, 1H) 7.69-7.76 (m, 1H) 7.33-7.40 (m, 1H) 6.99-7.06 (m, 2H) 4.74 (d, J = 5.9 Hz, 2H) 4.46 (t, J = 5.5 Hz, 1H) 3.86 (s, 3H) |

Example 66

6-(4-((3-(6-Chloropyridin-3-yl)-5-methoxybenzyl)oxy)-6-methoxybenzofuran-2-yl)-2-methoxyimidazo[2,1b][1,3,4]thiadiazole

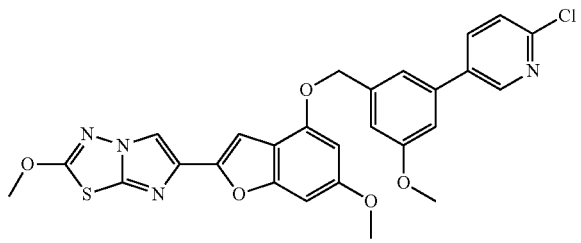 [SMILES: COc1cc(COc2cc(OC)cc3oc(-c4cn5nc(OC)sc5n4)cc23)cc(-c2ccc(Cl)nc2)c1]

66A. (3-Bromo-5-methoxyphenyl)methanol

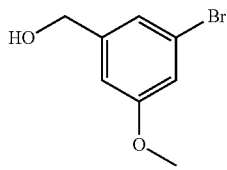

Boron methyl sulfide complex (1.4 ml, 14.00 mmol) was added dropwise to a solution of 3-bromo-5-methoxybenzoic acid (0.866 g, 3.75 mmol) in THF (20 ml, 244 mmol) under nitrogen at room temperature. The resulting mixture was stirred at 65° C. for 5 h. At 0° C., water was added dropwise and the reaction mixture was concentrated in vacuo. The residue was diluted in AcOEt and washed successively with 1N NaOH, 1N HCl, sat. NaHCO$_3$ and brine, dried over anh. Na$_2$SO$_4$ and concentrated. The residue was purified on ISCO using a REDISEP® Gold 24 g column (Hex/EtOAc). The title material (0.746 g, 92%) was obtained as a white solid after concentration of the fractions. LC (Method B): 1.749 min. $^1$H NMR (400 MHz, acetone) δ ppm 7.11 (dq, J=2.1, 0.9 Hz, 1H) 6.97 (t, J=2.2 Hz, 1H) 6.93 (dq, J=2.3, 1.1 Hz, 1H) 4.57-4.63 (m, 2H) 4.33 (t, J=5.9 Hz, 1H) 3.81 (s, 3H).

66B. (3-(6-Chloropyridin-3-yl)-5-methoxyphenyl)methanol

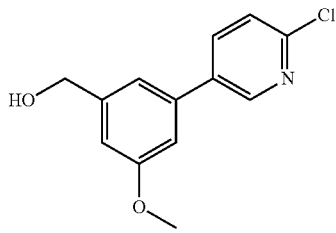 [SMILES: COc1cc(CO)cc(-c2ccc(Cl)nc2)c1]

In a 4 mL vial, palladium(II) acetate (0.0051 g, 0.023 mmol), triphenylphosphine (0.012 g, 0.046 mmol), 2M sodium carbonate (0.62 ml, 1.240 mmol) and water (0.3 ml, 16.65 mmol) were successively added to a mixture of (3-bromo-5-methoxyphenyl)methanol (Example 66A, 0.191 g, 0.880 mmol) and 6-chloropyridin-3-yl)boronic acid (0.151 g, 0.960 mmol) in 1-propanol (1.5 ml, 19.97 mmol) under nitrogen. The mixture was stirred at 85° C. for 30 min. and was quenched with water. The product was extracted three times with AcOEt and the combined organic layers were washed once with sat. NaHCO$_3$, once with brine, dried over anh. Na$_2$SO$_4$ and concentrated. The residue was purified on ISCO using a 40 g SILICYCLE® column (Hex/EtOAc) to afford the desired compound (0.055 g, 25%) as a colorless oil. LC (Method B): 1.797 min. MS(ESI) calcd. for C$_{13}$H$_{13}$ClNO$_2$ [M+H]$^+$ m/z: 250.06. found: 250.0. $^1$H NMR (400 MHz, acetone) δ ppm 8.68 (dd, J=2.7, 0.8 Hz, 1H) 8.10 (dd, J=8.2, 2.7 Hz, 1H) 7.53 (dd, J=8.2, 0.8 Hz, 1H) 7.24-7.28 (m, 1H) 7.13 (t, J=2.0 Hz, 1H) 7.04 (dd, J=2.2, 1.0 Hz, 1H) 4.70 (d, J=5.9 Hz, 2H) 4.29 (t, J=5.9 Hz, 1H) 3.88 (s, 3H).

Example 66

6-(4-((3-(6-Chloropyridin-3-yl)-5-methoxybenzyl)oxy)-6-methoxybenzofuran-2-yl)-2-methoxyimidazo[2,1b][1,3,4]thiadiazole

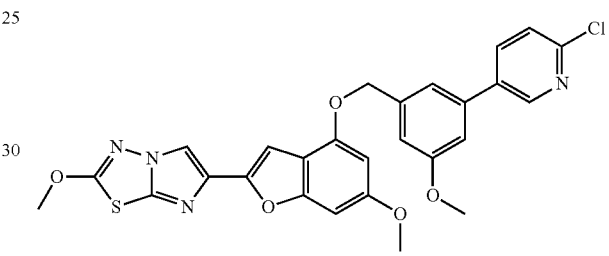

In a 20 mL vial, a mixture of 6-methoxy-2-(2-methoxy-imidazo[2,1-b][1,3,4]thiadiazol-6-yl)benzofuran-4-ol (Example 1G, 0.044 g, 0.139 mmol) and (3-(6-chloropyridin-3-yl)-5-methoxyphenyl)methanol (Example 66A, 0.055 g, 0.220 mmol) was dried 5 min. on high vacuum. Tri-n-butylphosphine (0.085 ml, 0.345 mmol) and THF (3 mL) were added and the mixture was sonificated for 10 min under nitrogen. A solution of 1,1'-(azodicarbonyl)dipiperidine (0.088 g, 0.349 mmol) in THF (1.5 mL) was added dropwise for 10 min. and the heterogeneous mixture was stirred for 3 h at room temperature. The mixture was diluted in CH$_2$Cl$_2$, washed once with sat. NaHCO$_3$, once with brine, dried over anh. Na$_2$SO$_4$ and concentrated. The residue was purified on ISCO using a REDISEP® Gold 24 g column (CH$_2$Cl$_2$/EtOAc). The fractions were combined and concentrated to give a residue which was purified again on ISCO using a REDISEP® Gold 24 g column (CH$_2$Cl$_2$/EtOAc). The desired product (0.056 g, 74%) was obtained as an off-white solid after concentration of the fractions and lyophilization in CAN/water. LC (Method B): 2.518 min. MS(ESI) calcd. for C$_{27}$H$_{22}$ClN$_4$O$_5$S [M+H]$^+$ m/z: 549.0994. found: 549.1006 $^1$H NMR (400 MHz, DMSO-d$_6$) δ ppm 8.74-8.79 (m, 1H) 8.38 (s, 1H) 8.20 (dd, J=8.6, 2.7 Hz, 1H) 7.62 (d, J=7.8 Hz, 1H) 7.45 (t, J=1.4 Hz, 1H) 7.27 (t, J=2.0 Hz, 1H) 7.13-7.18 (m, 1H) 6.99-7.03 (m, 1H) 6.81-6.86 (m, 1H) 6.56 (d, J=1.6 Hz, 1H) 5.29 (s, 2H) 4.20 (s, 3H) 3.86 (s, 3H) 3.80 (s, 3H).

The following benzylic alcohol was prepared according to the procedure described in Example 66A and 66B using (3-bromo-5-methoxyphenyl)methanol and the corresponding boronic acid and used in preparing the compound of Example 71.

| Structure | Formula | Calc. [M + H]+ m/z | LCMS [M + H]+ m/z | HPLC Retention Time (Min)/ Method | NMR |
|---|---|---|---|---|---|
| (71) | C13H14N2O3 | 247.11 | 247.2 | 1.637/B | 1H NMR (400 MHz, acetone) δ ppm 8.83 (s, 2H) 7.23 (s, 1H) 7.11 (t, J = 2.2 Hz, 1H) 7.00-7.05 (m, 1H) 4.69 (d, J = 6.3 Hz, 2H) 4.28 (t, J = 5.9 Hz, 1H) 4.00 (s, 3 H) 3.88 (s, 3H) |

Examples 67 to 80

The following additional Examples have been prepared, isolated and characterized using the method disclosed above.

| Ex. | Structure | Formula | Calc. [M + H]+ m/z | HPLC Retention Time (Min)/ Method | LCMS [M + H]+ m/z | NMR |
|---|---|---|---|---|---|---|
| 67 | 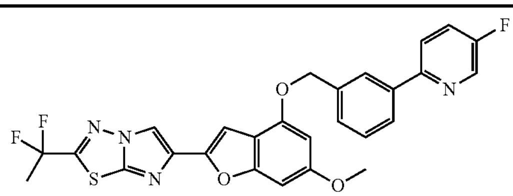 | C27H19F3N4O3S | 537.1203 | 2.478/B | 537.1111 | 1H NMR (400 MHz, DMSO-d6) δ ppm 8.72 (s, 1H) 8.68 (d, J = 2.7 Hz, 1H) 8.21 (s, 1H) 8.09 (dd, J = 8.8, 3.7 Hz, 1H) 8.03 (dd, J = 7.8, 1.2 Hz, 1H) 7.85 (td, J = 8.7, 2.9 Hz, 1H) 7.47-7.65 (m, 2H) 7.14 (s, 1H) 6.86 (s, 1H) 6.59 (s, 1H) 5.36 (s, 2H) 3.81 (s, 3H) 2.24 (t, J = 19.2 Hz, 3H) |
| 68 | 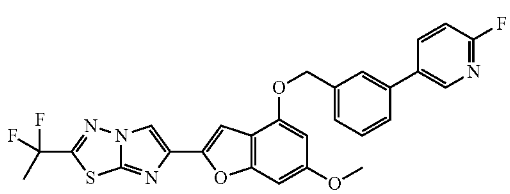 [SMILES: COc1cc(OCc2cccc(-c3ccc(F)nc3)c2)c2cc(-c3cn4nc(C(C)(F)F)sc4n3)oc2c1] | C27H19F3N4O3S | 537.1203 | 2.465/B | 537.1065 | 1H NMR (400 MHz, DMSO-d6) δ ppm 8.71 (s, 1H) 8.58 (d, J = 2.7 Hz, 1H) 8.32 (td, J = 8.2, 2.7 Hz, 1H) 7.87 (s, 1H) 7.71 (dt, J = 7.0, 2.0 Hz, 1H) 7.47-7.65 (m, 2H) 7.31 (dd, J = 8.6, 2.7 Hz, 1H) 7.15 (s, 1H) 6.87 (d, J = 0.8 Hz, 1H) 6.59 (d, J = 1.6 Hz, 1H) 5.34 (s, 2H) 3.81 (s, 3H) 2.23 (t, J = 19.4 Hz, 3 H) |
| 69 | 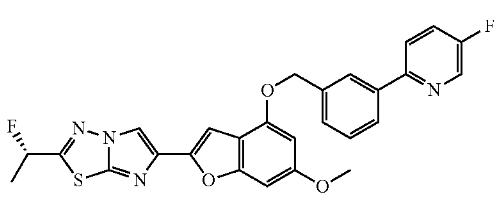 [SMILES: COc1cc(OCc2cccc(-c3ccc(F)cn3)c2)c2cc(-c3cn4nc([C@H](C)F)sc4n3)oc2c1] | C27H20F2N4O3S | 519.1297 | 2.430/B | 519.1308 | 1H NMR (400 MHz, DMSO-d6) δ ppm 8.67 (d, J = 3.1 Hz, 1H) 8.61 (s, 1H) 8.21 (s, 1H) 8.08 (dd, J = 8.8, 4.5 Hz, 1H) 8.02 (d, J = 7.4 Hz, 1H) 7.85 |

| Ex. | Structure | Formula | Calc. [M + H]+ m/z | HPLC Retention Time (Min)/ Method | LCMS [M + H]+ m/z | NMR |
|---|---|---|---|---|---|---|
| | | | | | | (td, J = 8.7, 2.9 Hz, 1H) 7.51-7.63 (m, 2H) 7.10 (s, 1H) 6.80-6.90 (m, 1H) 6.58 (d, J = 1.6 Hz, 1H) 6.17 (dq, J = 46.7, 6.5 Hz, 1H) 5.35 (s, 2H) 3.80 (s, 3H) 1.79 (dd, J = 24.6, 6.3 Hz, 3H) |
| 70 | 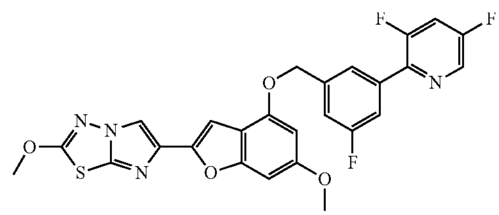 [SMILES: COc1cc(OCc2cc(F)cc(-c3ncc(F)cc3F)c2)c2cc(-c3cn4nc(OC)sc4n3)oc2c1] | $C_{26}H_{17}F_3N_4O_4S$ | 539.0995 | 2.481/B | 539.1022 | 1H NMR (400 MHz, DMSO-$d_6$) δ ppm 8.67 (d, J = 2.3 Hz, 1H) 8.38 (s, 1H) 8.13 (ddd, J = 11.3, 9.0, 2.3 Hz, 1H) 7.87-7.91 (m, 1H) 7.61-7.68 (m, 1H) 7.46-7.53 (m, 1H) 7.02 (d, J = 0.8 Hz, 1H) 6.85 (dd, J = 1.8, 1.0 Hz, 1H) 6.55 (d, J = 2.0 Hz, 1H) 5.38 (s, 2H) 4.21 (s, 3H) 3.80 (s, 3H) |
| 71 | 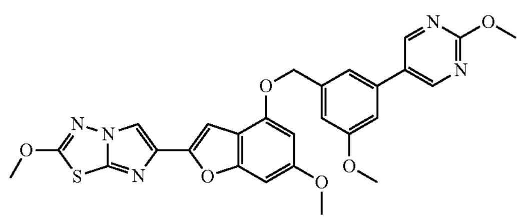 | $C_{27}H_{23}N_5O_6S$ | 546.1442 | 2.439/B | 546.1461 | 1H NMR (400 MHz, DMSO-$d_6$) δ ppm 8.97 (s, 2H) 8.38 (s, 1H) 7.42-7.47 (m, 1H) 7.27 (t, J = 2.0 Hz, 1H) 7.10-7.15 (m, 1H) 7.02 (s, 1H) 6.84 (dd, J = 1.8, 0.6 Hz, 1H) 6.56 (d, J = 2.0 Hz, 1H) 5.28 (s, 2H) 4.20 (s, 3H) 3.97 (s, 3H) 3.85 (s, 3H) 3.80 (s, 3H) |
| 72 | 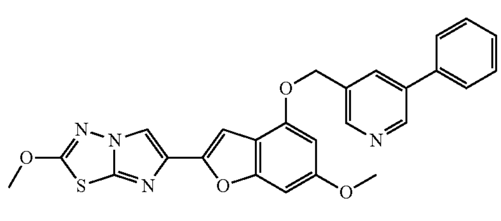 [SMILES: COc1cc(OCc2cncc(-c3ccccc3)c2)c2cc(-c3cn4nc(OC)sc4n3)oc2c1] | $C_{26}H_{20}N_4O_4S$ | 485.1278 | 2.205/B | 485.1312 | 1H NMR (400 MHz, DMSO-$d_6$) δ ppm 8.89 (d, J = 2.3 Hz, 1H) 8.73 (d, J = 2.3 Hz, 1H) 8.38 (s, 1H) 8.21 (t, J = 2.2 Hz, 1H) 7.74-7.80 (m, 2H) 7.49-7.57 (m, 2H) 7.40-7.49 (m, 1H) 7.02 (d, J = 0.8 Hz, 1H) 6.86 (dd, J = 2.0, 0.8 Hz, 1H) 6.61 (d, J = 2.0 Hz, 1H) 5.38 (s, 2H) 4.20 (s, 3H) 3.81 (s, 3H) |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| 73 | 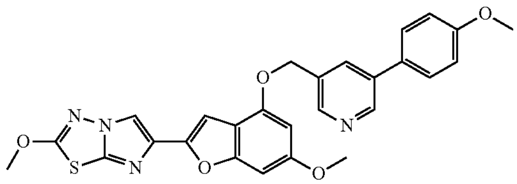 | C27H22N4O5S | 515.1384 | 2.185/B | 515.1422 | 1H NMR (400 MHz, DMSO-d6) δ ppm 8.84 (d, J = 2.0 Hz, 1H) 8.66 (d, J = 2.0 Hz, 1H) 8.38 (s, 1H) 8.15 (t, J = 2.2 Hz, 1H) 7.67-7.75 (m, 2H) 7.04-7.11 (m, 2H) 7.01 (d, J = 0.8 Hz, 1H) 6.85 (dd, J = 2.0, 0.8 Hz, 1H) 6.61 (d, J = 2.0 Hz, 1H) 5.36 (s, 2H) 4.20 (s, 3H) 3.81 (s, 3H) 3.81 (s, 3H) |
| 74 | 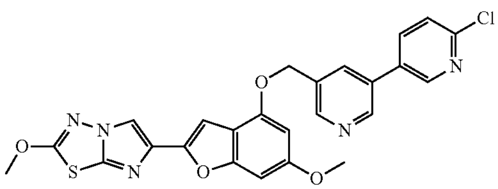 [SMILES: COc1cc(OCc2cncc(-c3ccc(Cl)nc3)c2)c2cc(-c3cn4nc(OC)sc4n3)oc2c1] | C25H18ClN5O4S | 520.0841 | 2.212/B | 520.0884 | 1H NMR (400 MHz, DMSO-d6) δ ppm 8.96 (d, J = 2.3 Hz, 1H) 8.83-8.87 (m, 1H) 8.80 (d, J = 2.0 Hz, 1H) 8.37 (s, 1H) 8.33 (t, J = 2.2 Hz, 1H) 8.29 (dd, J = 8.4, 2.5 Hz, 1H) 7.65-7.71 (m, 1H) 7.04 (d, J = 0.8 Hz, 1H) 6.86 (dd, J = 1.8, 1.0 Hz, 1H) 6.62 (d, J = 2.0 Hz, 1H) 5.38 (s, 2H) 4.20 (s, 3H) 3.81 (s, 3H) |
| 75 | 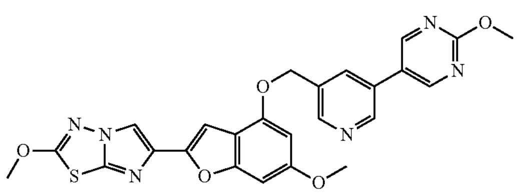 | C25H20N6O5S | 517.1289 | 2.132/B | 517.1333 | 1H NMR (400 MHz, DMSO-d6) δ ppm 9.05 (s, 2H) 8.95 (d, J = 2.3 Hz, 1H) 8.77 (d, J = 2.0 Hz, 1H) 8.37 (s, 1H) 8.32 (t, J = 2.2 Hz, 1H) 7.05 (d, J = 0.8 Hz, 1H) 6.86 (dd, J = 1.8, 1.0 Hz, 1H) 6.62 (d, J = 2.0 Hz, 1H) 5.36 (s, 2H) 4.20 (s, 3H) 3.99 (s, 3H) 3.81 (s, 3H) |
| 76 | 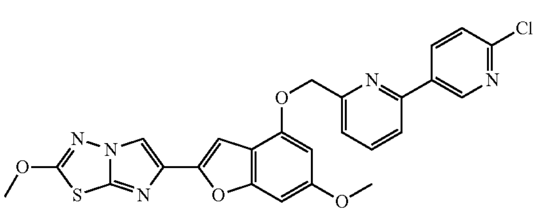 [SMILES: COc1cc(OCc2cccc(-c3ccc(Cl)nc3)n2)c2cc(-c3cn4nc(OC)sc4n3)oc2c1] | C25H18ClN5O4S | 520.0841 | 2.439/B | 520.0871 | 1H NMR (400 MHz, DMSO-d6) δ ppm 9.10-9.16 (m, 1H) 8.54 (dd, J = 8.4, 2.5 Hz, 1H) 8.39 (s, 1H) 7.97-8.10 (m, 2H) 7.63-7.71 (m, 2H) 7.07 (d, J = 0.8 Hz, 1H) 6.85 (dd, J = 1.8, 1.0 Hz, 1H) 6.57 (d, J = 2.0 Hz, 1H) 5.42 (s, 2H) 4.21 (s, 3H) 3.79 (s, 3H) |

| Ex. | Structure | Formula | Calc. [M + H]+ m/z | HPLC Retention Time (Min)/ Method | LCMS [M + H]+ m/z | NMR |
|---|---|---|---|---|---|---|
| 77 | 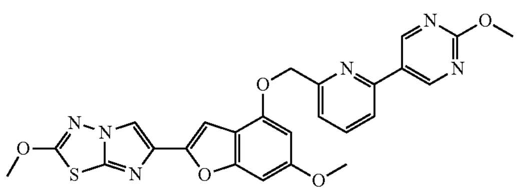 | C25H20N6O5S | 517.1289 | 2.383/B | 517.1389 | 1H NMR (400 MHz, DMSO-d6) δ ppm 9.27 (s, 2H) 8.39 (s, 1H) 7.94-8.05 (m, 2H) 7.62 (dd, J = 5.7, 2.9 Hz, 1H) 7.07 (d, J = 0.8 Hz, 1H) 6.85 (dd, J = 1.8, 1.0 Hz, 1H) 6.57 (d, J = 2.0 Hz, 1H) 5.41 (s, 2H) 4.21 (s, 3H) 4.00 (s, 3H) 3.79 (s, 3H) |
| 78 | 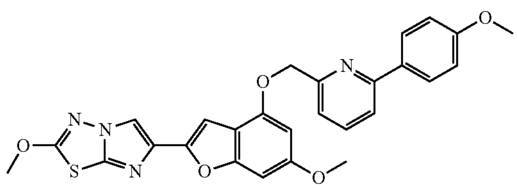 | C27H22N4O5S | 515.1384 | 2.413/B | 515.1427 | 1H NMR (400 MHz, DMSO-d6) δ ppm 8.39 (s, 1H) 8.04-8.12 (m, 2H) 7.82-7.94 (m, 2H) 7.49 (dd, J = 7.2, 1.4 Hz, 1H) 7.02-7.09 (m, 3H) 6.84 (dd, J = 1.6, 0.8 Hz, 1H) 6.57 (d, J = 2.0 Hz, 1H) 5.38 (s, 2H) 4.21 (s, 3H) 3.82 (s, 3H) 3.78 (s, 3H) |
| 80 | 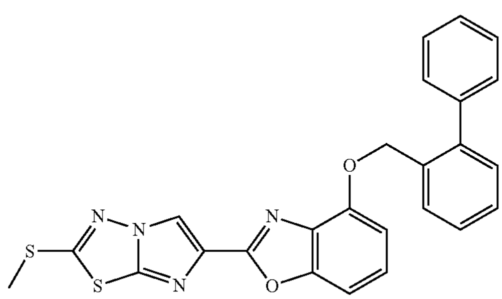 [SMILES: CSc1nn2cc(-c3nc4c(OCc5ccccc5-c5ccccc5)cccc4o3)nc2s1] | C25H18N4O2S2 | 471.0944 | 2.453/A | 471.0954 | 1H NMR (600 MHz, DMSO-d6) δ ppm 9.02 (s, 1H), 7.69 (dd, J1 = 1.8 Hz, J2 = 7.0 Hz, 1H), 7.51-7.46 (m, 4H), 7.39 (t, J = 7.6 Hz, 3H), 7.36-7.33 (m, 2H), 7.26 (t, J = 8.2 Hz, 1H), 6.85 (d, J = 8.2 Hz, 1H), 5.19 (s, 2H), 2.81 (s, 3H) |

Example 81

4-((3-(Furan-3-yl)benzyl)oxy)-2-(2-methoxyimidazo [2,1-b][1,3,4]thiadiazol-6-yl)benzo[d]oxazole

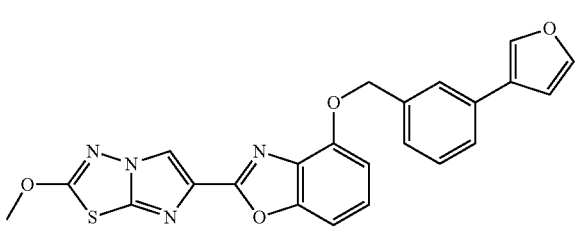 [SMILES: COc1nn2cc(-c3nc4c(OCc5cccc(-c6ccoc6)c5)cccc4o3)nc2s1]

81A. Ethyl 2-(methylthio)imidazo[2,1-b][1,3,4]thiadiazole-6-carboxylate

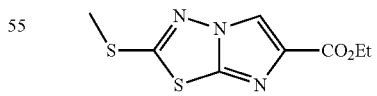

A mixture of 2-amino-5-methylthio-1,3,4-thiadiazole (25 g, 0.17 mol), ethyl 3-bromopyruvate (23.7 mL, 0.189 mol) and ethanol (125 mL) in a 350 mL sealable vessel was heated at 150° C. (oil bath temperature) for 20 min. The cooled mixture was concentrated to dryness and the residue was partitioned with ethyl acetate-saturated NaHCO3. The organic phase was washed (brine), dried (MgSO4), filtered and concentrated to dryness. The residue was taken up in a minimum volume of dichloromethane and the resulting slurry was filtered and the filter-cake was washed with a little dichloromethane. The solid was dried in vacuo to give recovered amino-5-methylthio-1,3,4-thiadiazole (3.72 g, 15%). The filtrate was concentrated to dryness and the residue was crystallized from a minimum volume of hot ethanol to give the title compound as a beige crystalline solid (10.8 g, 0.044 mol, 26%). LC (Method E): 1.267 min. $^1$H NMR (600 MHz, DMSO-$d_6$) δ ppm 8.76 (s, 1H), 4.27 (q, J=7.2 Hz, 2H), 2.78 (s, 3H), 1.28 (t, J=7.2 Hz, 3H).

81B. 2-(Methylthio)imidazo[2,1-b][1,3,4]thiadiazole-6-carboxylic acid

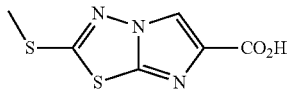

To a stirred solution of ethyl 2-(methylthio)imidazo[2,1-b][1,3,4]thiadiazole-6-carboxylate (Example 81A, 0.106 g, 0.434 mmol) in THF (4 mL) was added NaOTMS (0.608 mL, 0.608 mmol). The reaction mixture was stirred at rt for 18 hours then acidified to pH=3 with AcOH. The reaction mixture was concentrated to dryness and triturated with H$_2$O (sonicated for 1 minute). The resulting light yellow precipitate was filtered off and washed with Et$_2$O to afford the title material (58 mg, 0.27 mmol, 62%). LC (Method E): 0.912 min; LCMS: Anal. Calcd. for C$_6$H$_5$N$_3$O$_2$S$_2$: 214.98. found: 215.99 (M+1)$^+$. $^1$H NMR (600 MHz, DMSO-$d_6$) δ ppm 12.69 (b.s, 1H), 8.66 (s, 1H), 2.79 (s, 3H).

81C. 2-(Methylthio)imidazo[2,1-b][1,3,4]thiadiazole-6-carbonyl chloride

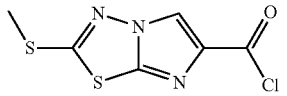

To a stirred suspension of 2-(methylthio)imidazo[2,1-b][1,3,4]thiadiazole-6-carboxylic acid (Example 81B, 15 g, 0.070 mol) in DCM (350 mL) was added oxalyl chloride (29.5 mL, 0.348 mol) followed by DMF (1 drop). Gas evolution was observed and the reaction mixture stirred at ambient temperature for 3.5 hours. The suspension was then concentrated to dryness to give a light-yellow solid and used as such by assuming a quantitative yield. LC (Method D): 1.686 min; $^1$H NMR (600 MHz, DMSO-$d_6$) δ ppm 8.68 (s, 1H) 2.78 (s, 3H).

81D. N-(2,6-Dihydroxyphenyl)-2-(methylthio)imidazo[2,1-b][1,3,4]thiadiazole-6-carboxamide

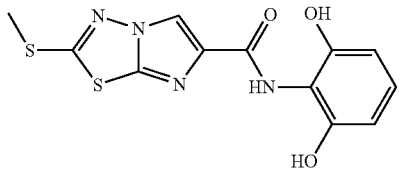 [SMILES: CSc1nn2cc(C(=O)Nc3c(O)cccc3O)nc2s1]

To a stirred suspension of 2-amino-1,3-benzenediol (4.28 g, 34.2 mmol) and 2-(methylthio)imidazo[2,1-b][1,3,4]thiadiazole-6-carbonyl chloride (Example 81C, 8 g, 34.2 mmol) in DMF (160 mL) was added triethylamine (9.53 mL, 68.4 mmol) at 0° C. The ice bath was allowed to discharge while the reaction mixture continued to stir overnight. The reaction mixture was then concentrated to dryness and triturated with methanol to afford the title material (4.61 g, 14.3 mmol, 42%). LC (Method D): 1.949 min. $^1$H NMR (600 MHz, DMSO-$d_6$) δ ppm 9.89 (s, 1H), 8.91 (s, 1H), 8.75 (s, 1H), 8.57 (s, 1H), 7.14 (d, J=8.2 Hz, 1H), 6.83 (d, J=7.9 Hz, 1H), 6.77 (d, J=8.2 Hz, 1H), 2.75 (s, 3H).

81 E. 2-(2-(Methylthio)imidazo[2,1-b][1,3,4]thiadiazol-6-yl)benzo[d]oxazol-4-ol

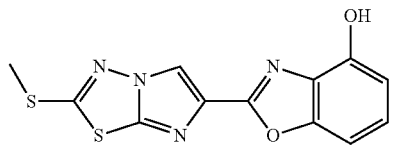 [SMILES: CSc1nn2cc(-c3nc4c(O)cccc4o3)nc2s1]

N-(2,6-Dihydroxyphenyl)-2-(methylthio)imidazo[2,1-b][1,3,4]thiadiazole-6-carboxamide (Example 81D, 3×1.5 g, 13.95 mmol) was placed in a microwavable vial with TFA (5 mL) and acetic acid (5 mL). The reaction was heated at 200° C. for 10 minutes. All 3 reaction mixtures were combined and concentrated to near dryness. The residue was triturated with methanol and the solid material was filtered off. The solid was then dissolved in hot DMF and the insoluble material was filtered off. The filtrate was concentrated to dryness and triturated with water and saturated sodium bicarbonate. The resulting solid was filtered off and dried under reduced pressure to give the title material as an off-white solid (1.28 g, 4.19 mmol, 30%). LC (Method D): 1.937. MS(ESI) calcd. for C$_{12}$H$_9$N$_4$O$_2$S$_2$ [M+H]$^+$ m/z: 305.01. found: 305.04. $^1$H NMR (600 MHz, DMSO-$d_6$) δ ppm 10.39 (s, 1H), 9.95 (s, 1H), 7.20-7.14 (m, 2H), 6.76 (dd, J$_1$=0.6 Hz, J$_2$=7.8 Hz, 1H), 2.81 (s, 3H).

81F. 2-(2-(Methylsulfonyl)imidazo[2,1-b][1,3,4]thiadiazol-6-yl)benzo[d]oxazol-4-ol

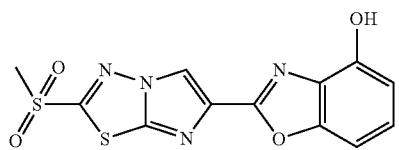 [SMILES: CS(=O)(=O)c1nn2cc(-c3nc4c(O)cccc4o3)nc2s1]

To a stirred solution of 2-(2-(methylthio)imidazo[2,1-b][1,3,4]thiadiazol-6-yl)benzo[d]oxazol-4-ol (Example 81E, 610 mg, 2.004 mmol) in TFA (10 ml, 130 mmol) was added trifluoroperacetic acid (1.002 ml, 4.01 mmol). The resulting brown solution was stirred at r.t. for 3 hours then stored in freezer overnight (~16 hours). Trifluoroperacetic acid (0.5 ml) was added again and the mixture continued to stir for 2 hours then concentrated to dryness. The mixture was triturated with MeOH and filtered off to provide the title material as a brownish solid (600 mg, 1.784 mmol, 89% yield) which was used as such for the next reaction.

81G. 2-(2-Methoxyimidazo[2,1-b][1,3,4]thiadiazol-6-yl)benzo[d]oxazol-4-ol

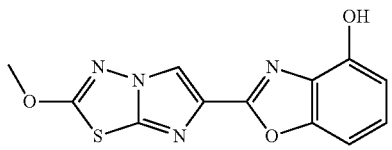

To a stirred solution of 2-(2-(methylsulfonyl)imidazo[2,1-b][1,3,4]thiadiazol-6-yl)benzo[d]oxazol-4-ol (Example 81F, 600 mg, 1.784 mmol) in methanol (10 ml, 247 mmol) was added sodium methoxide (385 mg, 1.784 mmol). The resulting brown solution was stirred at r.t. for 1 hour after which it was deemed incomplete by HPLC. Sodium methoxide (385 mg, 1.784 mmol) was added again and the reaction was stirred for 1 more hour. The reaction was then quenched with sat. NH$_4$Cl and the insoluble material was filtered off. The insoluble material was suspended in DCM and adsorbed onto silica gel. The residue was purified on ISCO using a REDISEP® Gold 24 g column (CH$_2$Cl$_2$/EtOAc) to give the desired product as a light pink solid (136 mg, 0.472 mmol, 26.4% yield). The column was then flushed with 10% 9:1 MeOH:NH$_4$OH in DCM which forced more compound to come off the column. Those fractions were concentrated to yield the desired product as a tan solid (85 mg, 0.295 mmol, 16.53% yield). LC (Method B): 1.816. MS(ESI) calcd. for C$_{12}$H$_9$N$_4$O$_3$S [M+H]$^+$ m/z: 289.039. found: 289.0384. $^1$H NMR (400 MHz, DMSO-d$_6$) δ ppm 10.36 (s, 1H), 8.85 (s, 1H), 7.19-7.13 (m, 2H), 6.76 (m, 1H), 4.23 (s, 3H).

Example 81

4-((3-(Furan-3-yl)benzyl)oxy)-2-(2-methoxyimidazo[2,1-b][1,3,4]thiadiazol-6-yl)benzo[d]oxazole

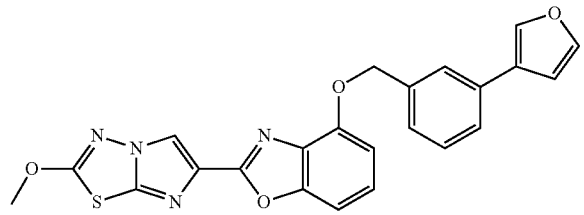 [SMILES: COc1nn2cc(-c3nc4c(OCc5cccc(-c6ccoc6)c5)cccc4o3)nc2s1]

A flame-dried 10 ml round bottom flask containing 2-(2-methoxyimidazo[2,1-b][1,3,4]thiadiazol-6-yl)benzo[d]oxazol-4-ol (Example 81G, 44 mg, 0.153 mmol), (3-(furan-3-yl)phenyl)methanol (80 mg, 0.458 mmol) and triphenylphoshine (120 mg, 0.458 mmol) was dried under reduced pressure for 30 minutes then charged with THF (4 ml) under a N$_2$ atmosphere. The stirred mixture was then charged with a solution of diisopropylazodicarboxylate (0.089 ml, 0.458 mmol) in THF (1 ml) over 30 minutes. The heterogeneous reaction mixture was stirred at ambient temperature for 2.5 hours after which it became homogeneous for about 10 minutes followed by the appearance of a ppt. The reaction mixture was diluted with DCM, washed with sat. NaHCO$_3$ then brine. The organic phase was dried (MgSO$_4$), filtered and concentrated to dryness. The residue was adsorbed onto silica and purified by combiflash using a 25 g column and a gradient of 0 to 15% Et$_2$O in DCM to give a white solid which was triturated with MeOH. The solid was filtered off and the resulting white solid was rinsed with MeOH then ether. The solid material was dissolved in DMF and purified by prep HPLC in TFA buffered in CH$_3$CN/water. Fractions containing the desired product were concentrated to dryness, suspended in acetonitrile/water, frozen and lyophilized to give the title material as an amorphous white solid (15.2 mg, 0.034 mmol, 22.41% yield). LC (Method B): 2.322. MS(ESI) calcd. for C$_{23}$H$_{17}$N$_4$O$_4$S [M+H]$^+$ m/z: 445.0965. found: 445.0968. $^1$H NMR (400 MHz, DMSO-d$_6$) δ ppm 8.92 (s, 1H), 8.22 (t, J=1.4 Hz, 1H), 7.79 (br. S, 1H), 7.75 (t, J=1.8 Hz, 1H), 7.62 (m, 1H), 7.46-7.41 (m, 2H), 7.35-7.30 (m, 2H), 7.07 (dd, J=2.2, 6.8 Hz, 1H), 6.99 (dd, J=0.8, 2.0 Hz, 1H), 5.38 (s, 2H), 4.22 (s, 3H).

Example 82

2-(6-Methoxy-4-((3-(2-methoxypyrimidin-5-yl)benzyl)oxy)benzofuran-2-yl)-6-methylimidazo[1,2-b]pyridazine

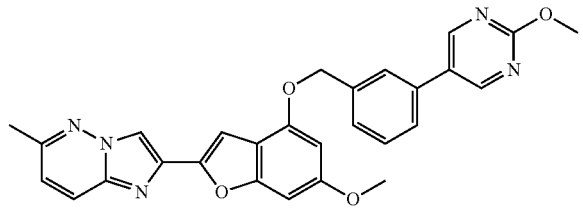

82A: 2-(4-(Benzyloxy)-6-methoxybenzofuran-2-yl)-6-methylimidazo[1,2-b]pyridazine

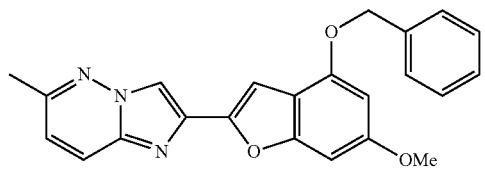 [SMILES: COc1cc(OCc2ccccc2)c2cc(-c3cn4nc(C)ccc4n3)oc2c1]

A mixture of 6-methylpyridazin-3-amine (1.52 g, 13.93 mmol), 1-(4-(benzyloxy)-6-methoxybenzofuran-2-yl)-2-bromoethanone (Example 1D, 5.00 g, 13.33 mmol) and 2-propanol (110 mL) in a 150 mL pressure flask was heated at 65° C. The mixture was almost homogeneous after 30 min of heating and precipitated again after 40 min. The mixture was heated for a total of 48 h. The cooled reaction mixture was diluted with dichloromethane (600 mL), washed with saturated aqueous sodium bicarbonate and brine and dried over anhydrous magnesium sulfate. Evaporation gave an orange brown solid which was chromatographed on silica gel (4×9 cm, elution with 0-5% ethyl acetate-DCM) to give the product (3.64 g) as an orange-brown solid. The solid was boiled with ethyl acetate (30 mL, partially soluble) and allowed to stand at room temperature for 2 h. The crystals were collected by filtration and dried overnight in vacuo to give the title material (3.440 g, 67%) as pale yellow-brown needles. LC (Method A): 2.279 min. HRMS(ESI) calcd for C$_{23}$H$_{20}$N$_3$O$_3$ [M+H]$^+$ m/z 386.1505. found 386.1532. $^1$H NMR (CDCl$_3$, 400 MHz): δ ppm 2.59 (s, 3H), 3.86 (s, 3H), 5.21 (s, 2H), 6.43 (d, J=1.96 Hz, 1H), 6.75 (br d, 1H), 6.94 (d, J=9.39 Hz, 1H), 7.31-7.38 (m, 2H), 7.38-7.45 (m, 2H), 7.50 (br d, J=7.43 Hz, 2H), 7.82 (d, J=9.39 Hz, 1H), 8.19 (s, 1H).

82B: 6-Methoxy-2-(6-methylimidazo[1,2-b]pyridazin-2-yl)benzofuran-4-ol

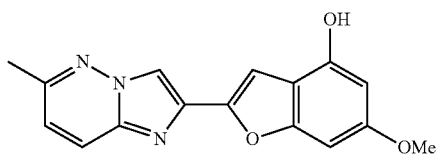 [SMILES: COc1cc(O)c2cc(-c3cn4nc(C)ccc4n3)oc2c1]

A solution of 2-(4-(benzyloxy)-6-methoxybenzofuran-2-yl)-6-methylimidazo[1,2-b]pyridazine (1.00 g, 2.59 mmol), in a mixture of dichloromethane (420 mL) and methanol (150 mL) in a 1 L flask, was hydrogenated over 10% palladium on carbon (0.30 g) under 1 atm of hydrogen for 6 h. The reaction mixture was then maintained under vacuum for 2 min and finally was flushed with nitrogen. The catalyst was filtered and washed with warm dichloromethane-methanol (8:2, 100 mL) and the combined filtrate was concentrated under reduced pressure. The yellow residue was boiled with 1,2-dichloroethane (30 mL) and allowed to stand at room temperature for 18 h. The solid was filtered (contains methanol by NMR) and dried in vacuo at 120° C. for 12 h to give the title material (0.760 g, 99%) as a yellow solid. LC (Method A): 1.844 min. $^1$H NMR (DMSO-d$_6$, 400 MHz): δ ppm 2.54 (s, 3H), 3.77 (s, 3H), 6.28 (d, J=1.96 Hz, 1H), 6.70 (dd, J=1.96, 1.17 Hz, 1H), 7.20 (d, J=9.39 Hz, 1H), 7.24 (d, J=0.78 Hz, 1H), 8.03 (d, J=9.78 Hz, 1H), 8.50 (s, 1H), 10.10 (br s, 1H).

Example 82

2-(6-Methoxy-4-((3-(2-methoxypyrimidin-5-yl)benzyl)oxy)benzofuran-2-yl)-6-methylimidazo[1,2-b]pyridazine

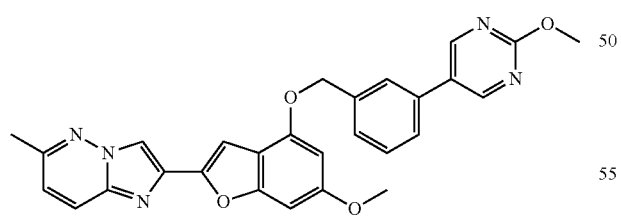

In a 10 mL round-bottomed flask, a mixture of 6-methoxy-2-(6-methylimidazo[1,2-b]pyridazin-2-yl)benzofuran-4-ol (0.050 g, 0.169 mmol), (3-(2-methoxypyrimidin-5-yl)phenyl)methanol (0.099 g, 0.458 mmol) and triphenylphosphine (0.120 g, 0.458 mmol) was dried under high vacuum for 10 min. Dry THF (1.5 mL) was then added and the mixture was sonicated for 15 min. Diisopropyl azodicarboxylate (0.090 mL, 0.463 mmol) in THF (1 mL) was added dropwise on 15 min, then the yellow solution was sonicated for 30 min and finally it was stirred at room temperature for 1.5 h. The reaction mixture was diluted with CH$_2$Cl$_2$, washed with saturated aqueous NaHCO$_3$ and brine, dried over anhydrous Na$_2$SO$_4$ and concentrated. The obtained residue was purified on the ISCO using a 12 g SILICYCLE® column (elution with CH$_2$Cl$_2$-EtOAc) to give the title compound (0.040 g, 48%) as pale yellow solid, after trituration with acetonitrile and lyophilization from acetonitrile-water. LC (Method B): 2.319 min. HRMS(ESI): calcd for C$_{28}$H$_{24}$N$_5$O$_4$ [M+H]$^+$ m/z 494.1828. found 494.1860. $^1$H NMR (400 MHz, DMSO-d$_6$): δ ppm 8.94-8.99 (m, 2H) 8.55 (s, 1H) 8.01 (d, J=9.4 Hz, 1H) 7.90 (s, 1H) 7.69-7.75 (m, 1H) 7.52-7.61 (m, 2H) 7.30 (s, 1H) 7.19 (d, J=9.4 Hz, 1H) 6.87-6.90 (m, 1H) 6.57-6.63 (m, 1H) 5.34 (s, 2H) 3.97 (s, 3H) 3.82 (s, 3H) 2.53 (s, 3H).

Example 83

6-(4-((3-Fluoro-5-(2-methoxypyrimidin-5-yl)benzyl)oxy)-6-methoxybenzofuran-2-yl)-2-methoxyimidazo[2,1-b][1,3,4]thiadiazole

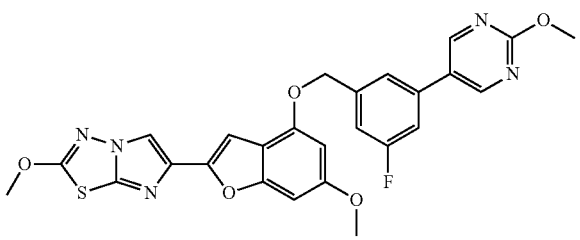

83A: (3-Fluoro-5-(methoxycarbonyl)phenyl)boronic acid

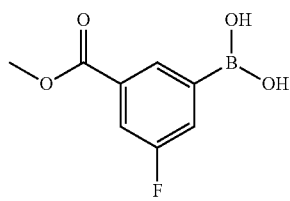

To a 50 mL round-bottomed flask fitted with a reflux condenser and charged with 3-carboxy-5-fluorophenylboronic acid (0.53 g, 2.88 mmol) in methanol (16 mL) was added a 6 M aqueous solution of sulfuric acid (0.33 mL, 1.98 mmol) and the mixture was heated to reflux overnight. The cooled mixture was diluted with water and the product was extracted with diethyl ether (×3). The combined organic extract was concentrated to give the title material (0.535 g, 94%) as white solid. LC (Method B): 1.596 min. LCMS (APCI): calcd for C$_8$H$_7$BFO$_4$ [M−H]$^−$ m/z 197.043. found 197.2. $^1$H NMR (400 MHz, acetone-d$_6$): δ ppm 8.34 (s, 1H) 7.80 (ddd, J=9.2, 2.7, 1.0 Hz, 1H) 7.72 (ddd, J=9.4, 2.7, 1.6 Hz, 1H) 7.56 (s, 2H) 3.91 (s, 3H).

83B: Methyl and n-propyl 3-fluoro-5-(2-methoxypyrimidin-5-yl)benzoate

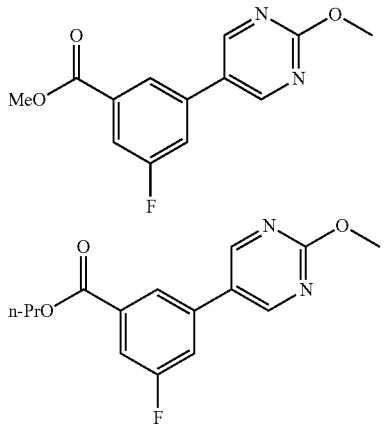

In a 20 mL vial, palladium(II) acetate (0.0084 g, 0.037 mmol), triphenylphosphine (0.018 g, 0.068 mmol), 2 M aqueous sodium carbonate (0.90 mL, 1.80 mmol) and water (0.6 mL, 33.3 mmol) were successively added to a mixture of 5-bromo-2-methoxypyrimidine (0.246 g, 1.302 mmol) and (3-fluoro-5-(methoxycarbonyl)phenyl)boronic acid (0.278 g, 1.404 mmol) in 1-propanol (2.8 mL) under nitrogen. The mixture was stirred at 95° C. for 1 h and kept overnight at room temperature. The mixture was then quenched with water and the product was extracted with EtOAc (×3). The combined organic extract was washed once with saturated aqueous NaHCO$_3$, once with brine, dried over anhydrous Na$_2$SO$_4$ and concentrated. The residue was purified on the ISCO using a REDISEP® Gold 40 g column (elution with hexanes-EtOAc) to give methyl 3-fluoro-5-(2-methoxypyrimidin-5-yl)benzoate (0.236 g, 69%) as a white solid. LC (Method B): 1.856 min. LCMS (APCI): calcd for C$_{13}$H$_{12}$FN$_2$O$_3$ [M+H]$^+$ m/z 263.083. found 263.1. $^1$H NMR (400 MHz, acetone-d$_6$): δ ppm 8.96 (s, 2H) 8.13 (t, J=1.4 Hz, 1H) 7.82 (ddd, J=9.6, 2.5, 1.8 Hz, 1H) 7.73 (ddd, J=9.0, 2.5, 1.4 Hz, 1H) 4.03 (s, 3H) 3.94 (s, 3H). Further elution afforded n-propyl 3-fluoro-5-(2-methoxypyrimidin-5-yl)benzoate (0.026 g, 6.9%) as a white solid. LC (Method B): 2.119 min. LCMS (APCI): calcd for C$_{15}$H$_{16}$FN$_2$O$_3$ [M+H]$^+$ m/z 291.114. found 291.2. $^1$H NMR (400 MHz, acetone-d$_6$): δ ppm 8.96 (s, 2H) 8.14 (t, J=1.6 Hz, 1H) 7.81 (ddd, J=9.6, 2.6, 1.6 Hz, 1H) 7.75 (ddd, J=9.0, 2.6, 1.4 Hz, 1H) 4.32 (t, J=6.5 Hz, 2H) 4.02 (s, 3H) 1.82 (sext, J=7.1 Hz, 2H) 1.04 (t, J=7.4 Hz, 3H).

83C: (3-Fluoro-5-(2-methoxypyrimidin-5-yl)phenyl)methanol

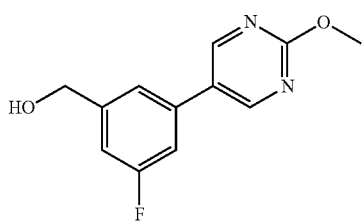 [SMILES: COc1ncc(-c2cc(F)cc(CO)c2)cn1]

In a 25 mL round-bottomed flask under nitrogen, lithium aluminum hydride (0.075 g, 1.976 mmol) was added portionwise over 10 min to a solution of methyl 3-fluoro-5-(2-methoxypyrimidin-5-yl)benzoate (0.235 g, 0.896 mmol) and propyl 3-fluoro-5-(2-methoxypyrimidin-5-yl)benzoate (0.025 g, 0.086 mmol) in dry THF (10 mL) at 0° C. The mixture was stirred 5 h at room temperature and then it was quenched by the addition of 0.08 mL of water, followed by 0.08 mL of 15% aqueous NaOH and finally 0.24 mL of water. The mixture was stirred for 30 min at room temperature and then anhydrous Na$_2$SO$_4$ was added and stirring was continued for 30 min at room temperature. The resulting mixture was filtered, the filter-cake was washed with EtOAc and the filtrate was concentrated. The residue was purified on the ISCO using a 40 g SILICYCLE® column (elution with hexanes-EtOAc) to give the title material (0.048 g, 21%) as a white solid. LC (Method B): 1.557 min. LCMS (APCI): calcd for C$_{12}$H$_{12}$FN$_2$O$_2$ [M+H]$^+$ m/z 235.088. found 235.2. $^1$H NMR (400 MHz, acetone-d$_6$): δ ppm 8.88 (s, 2H) 7.49-7.53 (m, 1H) 7.34-7.41 (m, 1H) 7.17-7.25 (m, 1H) 4.74 (d, J=5.9 Hz, 2H) 4.45 (t, J=5.9 Hz, 1H) 4.01 (s, 3H).

Example 83

6-(4-((3-Fluoro-5-(2-methoxypyrimidin-5-yl)benzyl)oxy)-6-methoxybenzofuran-2-yl)-2-methoxyimidazo[2,1-b][1,3,4]thiadiazole

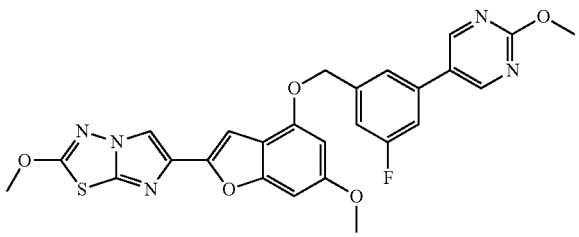

In a 20 mL vial, a mixture of 6-methoxy-2-(2-methoxyimidazo[2,1-b][1,3,4]thiadiazol-6-yl)benzofuran-4-ol (Example 1G, 0.040 g, 0.126 mmol) and (3-fluoro-5-(2-methoxypyrimidin-5-yl)phenyl)methanol (0.048 g, 0.205 mmol) was dried for 5 min under high vacuum. Under a nitrogen atmosphere, tri-n-butylphosphine (0.080 mL, 0.324 mmol) and THF (2 mL) were added and the mixture was sonicated for 10 min. A solution of 1,1'-(azodicarbonyl)dipiperidine (0.081 g, 0.321 mmol) in THF (1 mL) was then added dropwise on 10 min, the mixture was sonicated for 30 min and then stirred for 1 h at room temperature. The resulting mixture was diluted with CH$_2$Cl$_2$ and washed once with saturated aqueous NaHCO$_3$, once with brine, dried on anhydrous Na$_2$SO$_4$ and concentrated. The residue was purified on the ISCO using a REDISEP® Gold 12 g column (elution with CH$_2$Cl$_2$-EtOAc) to give the title compound (0.048 g, 71%) as a white solid, after trituration with acetonitrile and lyophilization from acetonitrile/water. LC (Method B): 2.394 min. HRMS(ESI): calcd for C$_{26}$H$_{21}$FN$_5$O$_5$S [M+H]$^+$ m/z 534.1247. found 534.1259. $^1$H NMR (400 MHz, DMSO-d$_6$): δ ppm 9.01 (s, 2H) 8.38 (s, 1H) 7.76 (t, J=1.6 Hz, 1H) 7.61-7.68 (m, 1H) 7.37-7.43 (m, 1H) 7.06 (d, J=0.8 Hz, 1H) 6.85 (dd, J=1.6, 0.8 Hz, 1H) 6.56 (d, J=2.0 Hz, 1H) 5.33 (s, 2H) 4.20 (s, 3H) 3.98 (s, 3H) 3.80 (s, 3H).

Example 84

5-(3-(((6-Methoxy-2-(2-methoxyimidazo[2,1-b][1,3,4]thiadiazol-6-yl)benzofuran-4-yl)oxy)methyl)phenyl)picolinic acid

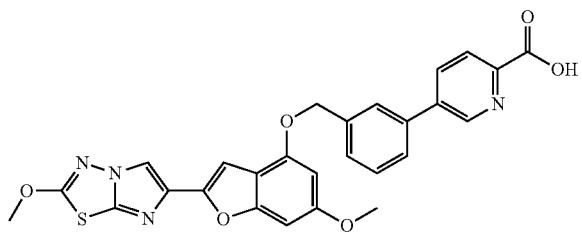 [SMILES: COc1cc(OCc2cccc(-c3ccc(C(=O)O)nc3)c2)c2cc(-c3cn4nc(OC)sc4n3)oc2c1]

In a 10 mL round-bottomed flask, tert-butyl 5-(3-(((6-methoxy-2-(2-methoxyimidazo[2,1-b][1,3,4]thiadiazol-6-yl)benzofuran-4-yl)oxy)methyl)phenyl)picolinate (Example 60, 0.023 g, 0.039 mmol) was stirred in dichloromethane (0.5 mL) and trifluoroacetic acid (0.5 mL) for 5 h at room temperature. Toluene was then added and the mixture was concentrated under reduced pressure. This afforded the title compound (TFA salt, 0.025 g, 91%) as a white solid, after lyophilization from acetonitrile-water. LC (Method B): 2.313 min. LCMS (APCI): calcd for $C_{27}H_{21}N_4O_6S$ [M+H]$^+$ m/z 529.118. found 529.2. $^1$H NMR (400 MHz, DMSO-d$_6$): δ ppm 9.05 (dd, J=2.3, 0.8 Hz, 1H) 8.38 (s, 1H) 8.30 (dd, J=7.8, 2.3 Hz, 1H) 8.14 (dd, J=8.2, 0.8 Hz, 1H) 7.96 (t, J=1.8 Hz, 1H) 7.80 (dt, J=7.3, 1.6 Hz, 1H) 7.56-7.67 (m, 2H) 7.02 (d, J=0.8 Hz, 1H) 6.84 (dd, J=2.0, 0.8 Hz, 1H) 6.58 (d, J=2.0 Hz, 1H) 5.35 (s, 2H) 4.20 (s, 3H) 3.80 (s, 3H).

Example 85

5-(3-(((6-Methoxy-2-(2-methoxyimidazo[2,1-b][1,3,4]thiadiazol-6-yl)benzofuran-4-yl)oxy)methyl)phenyl)-N-(2-methoxyethyl)-N-methylpicolinamide In a 10 mL round-bottomed flask under nitrogen, DIEA (0.025 mL, 0.143 mmol) was added to a stirred solution of 5-(3-(((6-methoxy-2-(2-methoxyimidazo[2,1-b][1,3,4]thiadiazol-6-yl)benzofuran-4-yl)oxy)methyl)phenyl)picolinic acid, TFA salt (0.025 g, 0.039 mmol) and 2-methoxy-N-methylethanamine (0.005 mL, 0.047 mmol) in DMF (0.5 mL) and the solution was stirred at room temperature for 5 min. HATU (0.016 g, 0.042 mmol) was then added and the reaction was stirred at room temperature for 45 min. The reaction mixture was then quenched with a few drops of acetic acid, the sample was diluted with DMSO and the solution was purified using preparative HPLC (Method X: ZORBAX® SB-C18 column 21.2×100 mm, eluted with MeOH-water-0.1% TFA. Gradient: Isocratic 50% for 3 min, then gradient to 100% MeOH over 8 min). The product-containing fractions were evaporated and the title compound (0.014 g, 60%) was obtained as yellowish solid after lyophilization of the residue from acetonitrile-water. LC (Method B): 2.347 min. HRMS(ESI): calcd for $C_{31}H_{30}N_5O_6S$ [M+H]$^+$ m/z 600.1917. found 600.1948. $^1$H NMR (400 MHz, acetone-d$_6$): δ ppm 8.91 (dd, J=8.8, 1.8 Hz, 1H) 8.21 (dt, J=8.2, 2.3 Hz, 1H) 8.10 (s, 1H) 7.97 (t, J=1.8 Hz, 1H) 7.73-7.78 (m, 1H) 7.64-7.73 (m, 2H) 7.57-7.63 (m, 1H) 7.06 (s, 1H) 6.77 (dd, J=2.0, 0.8 Hz, 1H) 6.56 (d, J=1.6 Hz, 1H) 5.39 (s, 2H) 4.26 (s, 3H) 3.85 (s, 3H) 3.54-3.74 (m, 4H) 3.09-3.37 (m, 6H).

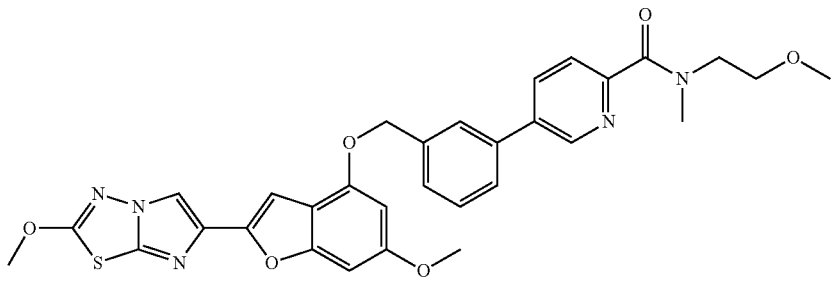

Example 86

2-Methoxy-6-(6-methoxy-4-((3-(5-(1-((tetrahydro-2H-pyran-2-yl)oxy)ethyl)pyridin-2-yl)benzyl)oxy)benzofuran-2-yl)imidazo[2,1-b][1,3,4]thiadiazole In a 20 mL vial under nitrogen, p-toluenesulfonic acid monohydrate (0.007 g, 0.037 mmol) was added to a solution of 1-(6-bromopyridin-3-yl)ethanol (0.259 g, 1.282 mmol) and 3,4-dihydro-2H-pyran (0.58 mL, 6.36 mmol) in dichloromethane (5 mL) and the mixture was stirred for 1 h at room temperature. The mixture was then diluted with

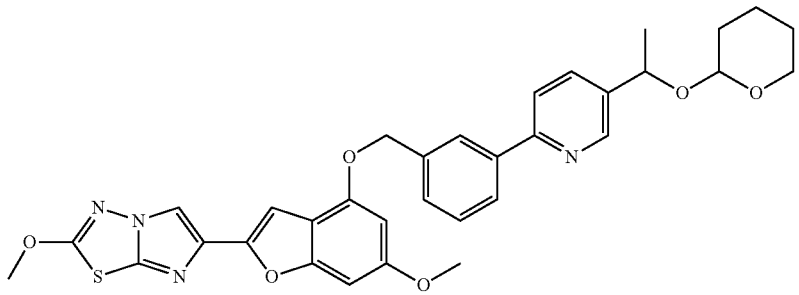 [SMILES: COc1cc(OCc2cccc(-c3ccc(C(C)OC4CCCCO4)cn3)c2)c2cc(-c3cn4nc(OC)sc4n3)oc2c1]

86A. 1-(6-Bromopyridin-3-yl)ethanol

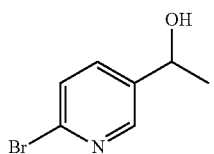

dichloromethane, the organic layer was separated, washed once with saturated aqueous NaHCO$_3$, once with brine, dried over anhydrous Na$_2$SO$_4$ and concentrated. The obtained residue was purified on the ISCO using a REDISEP® Gold 24 g column (elution with hexanes-EtOAc) to give the title material (0.355 g, 97%) as colorless oil which was a mixture of diastereomers. LC (Method B): 2.014 min. LCMS (APCI): calcd for C$_{12}$H$_{17}$BrNO$_2$ [M+H]$^+$ m/z 286.044. found 286.0. $^1$H NMR (400 MHz, acetone-d$_6$): δ ppm 8.41-7.55 (3H) 4.93-3.31 (4H) 1.85-1.48 (6H) 1.46-1.42 (3H).

In a 50 ml, round-bottomed flask under nitrogen, sodium borohydride (0.390 g, 10.31 mmol) was added portionwise on 5 min to a solution of 5-acetyl-2-bromopyridine (0.515 g, 2.57 mmol) in 2-propanol (10 mL) and water (4 mL) and the mixture was stirred at room temperature for 30 min. The mixture was then concentrated in vacuo and water was added to the concentrate. The mixture was extracted with ethyl acetate (×3) and the combined organic extract was dried over anhydrous Na$_2$SO$_4$ and concentrated. The obtained residue was purified on the ISCO using a 25 g SILICYCLE® column (elution with hexanes-EtOAc) to give the title material (0.470 g, 90%) as colorless oil. LC (Method B): 1.233 min. LCMS (APCI): calcd for C$_7$H$_9$BrNO [M+H]$^+$ m/z 201.986. found 202.0. $^1$H NMR (400 MHz, acetone-d$_6$): δ ppm 8.38 (d, J=2.7 Hz, 1H) 7.71-7.77 (m, 1H) 7.54 (d, J=8.2 Hz, 1H) 4.92 (q, J=6.7 Hz, 1H) 1.43 (d, J=6.7 Hz, 3H).

86C. (3-(5-(1-((Tetrahydro-2H-pyran-2-yl)oxy)ethyl)pyridin-2-yl)phenyl)methanol

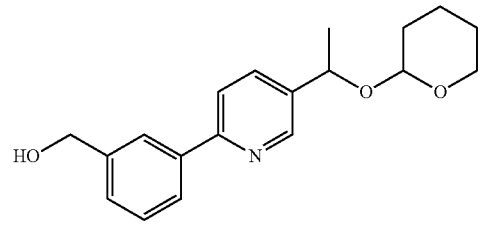

In a 20 mL vial, palladium(II) acetate (0.007 g, 0.030 mmol), triphenylphosphine (0.016 g, 0.059 mmol), aqueous sodium carbonate (2 M, 0.86 mL, 1.72 mmol) and water (0.4 mL, 22.2 mmol) were successively added to a mixture of 2-bromo-5-(1-((tetrahydro-2H-pyran-2-yl)oxy)ethyl)pyridine (0.353 g, 1.234 mmol) and (3-(hydroxymethyl)phenyl)boronic acid (0.207 g, 1.362 mmol) in 1-propanol (2.1 mL) under nitrogen. The mixture was stirred at 95° C. for 1 h and then the cooled mixture was quenched with water and the product was extracted with EtOAc (×3). The combined organic extract was washed once with saturated aqueous NaHCO$_3$, once with brine, dried over anhydrous Na$_2$SO$_4$ and concentrated. The residue was purified on the ISCO using a REDISEP® Gold 40 g column (elution with hexanes-EtOAc) to give the title material (0.288 g, 75%) as a colorless oil which was a mixture of diastereomers. LC (Method B): 1.603 min, 1.673 min. LCMS (APCI): calcd for

86B. 2-Bromo-5-(1-((tetrahydro-2H-pyran-2-yl)oxy)ethyl)pyridine

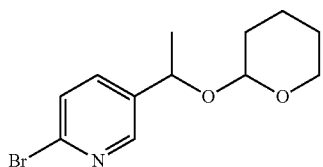 [SMILES: CC(OC1CCCCO1)c1ccc(Br)nc1]

$C_{19}H_{24}NO_3$ [M+H]$^+$ m/z 314.175. found 314.2. $^1$H NMR (400 MHz, acetone-d$_6$): δ ppm 8.70-740 (m, 7H) 4.98-3.33 (m, 7H) 1.90-1.47 (m, 9H).

Example 86

2-Methoxy-6-(6-methoxy-4-((3-(5-(1-((tetrahydro-2H-pyran-2-yl)oxy)ethyl)pyridin-2-yl)benzyl)oxy)benzofuran-2-yl)imidazo[2,1-b][1,3,4]thiadiazole

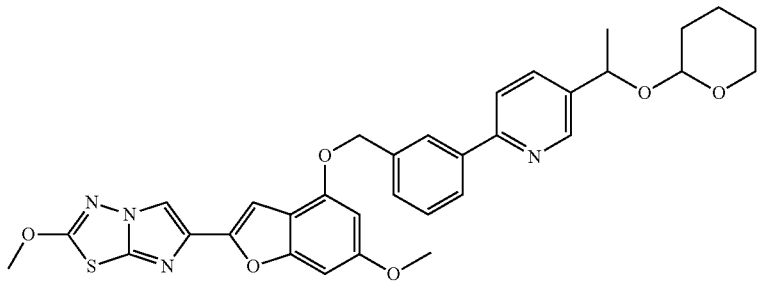 [SMILES: COc1cc(OCc2cccc(-c3ccc(C(C)OC4CCCCO4)cn3)c2)c2cc(-c3cn4nc(OC)sc4n3)oc2c1]

In a 35 mL round-bottomed flask, a mixture of 6-methoxy-2-(2-methoxyimidazo[2,1-b][1,3,4]thiadiazol-6-yl)benzofuran-4-ol (Example 1G, 0.199 g, 0.627 mmol) and (3-(5-(1-((tetrahydro-2H-pyran-2-yl)oxy)ethyl)pyridin-2-yl)phenyl)methanol (0.288 g, 0.919 mmol) was dried under high vacuum for 15 min and then the flask was flushed with nitrogen. Under a nitrogen atmosphere, tri-n-butylphosphine (0.38 mL, 1.540 mmol) and dry THF (10 mL) were then added. A solution of 1,1'-(azodicarbonyl)dipiperidine (0.394 g, 1.562 mmol) in THF (6 mL) was then added dropwise over 10 min and the mixture was stirred at room temperature for 3 h. The reaction mixture was subsequently diluted with CH$_2$Cl$_2$ and washed once with saturated aqueous NaHCO$_3$, once with brine, dried over anhydrous Na$_2$SO$_4$ and concentrated. The obtained residue was purified on the ISCO using a 80 g SILICYCLE® column (elution with CH$_2$Cl$_2$-EtOAc) to give the title material (0.273 g, 71%) as a beige solid which was a mixture of diastereomers. LC (Method B): 2.361 min, 2.410 min. LCMS (APCI): calcd for $C_{33}H_{33}N_4O_6S$ [M+H]$^+$ m/z 613.212. found 613.2. $^1$H NMR (400 MHz, DMSO-d$_6$): δ ppm 8.68-6.56 (m, 11H) 5.35 (m, 3H) 4.94-3.43 (m, 4H) 4.20 (s, 3H) 3.79 (s, 3H) 1.75-1.43 (m, 9H).

Example 87

1-(6-(3-(((6-Methoxy-2-(2-methoxyimidazo[2,1-b][1,3,4]thiadiazol-6-yl)benzofuran-4-yl)oxy)methyl)phenyl)pyridin-3-yl)ethanol

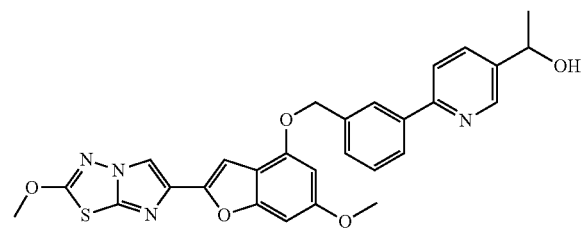 [SMILES: COc1cc(OCc2cccc(-c3ccc(C(C)O)cn3)c2)c2cc(-c3cn4nc(OC)sc4n3)oc2c1]

In a 20 mL vial, 2-methoxy-6-(6-methoxy-4-((3-(5-(1-((tetrahydro-2H-pyran-2-yl)oxy)ethyl)pyridin-2-yl)benzyl)oxy)benzofuran-2-yl)imidazo[2,1-b][1,3,4]thiadiazole (0.100 g, 0.163 mmol) was stirred overnight at 45° C. in 5.6 mL of a 4:2:1 mixture of acetic acid-THF-water. The cooled mixture was diluted with ethyl acetate, washed twice with saturated aqueous NaHCO$_3$, once with brine, dried over anhydrous Na$_2$SO$_4$ and concentrated. The obtained residue was purified on the ISCO using a REDISEP® Gold 12 g column (elution with CH$_2$Cl$_2$-EtOAc) to give the title material (0.097 g, 88%) as white solid after lyophilization from acetonitrile-water. LC (Method B): 2.157 min. HRMS(ESI): calcd for $C_{28}H_{25}N_4O_5S$ [M+H]$^+$ m/z 529.1546. found 529.1581. $^1$H NMR (400 MHz, DMSO-d$_6$): δ ppm 8.64 (d, J=2.3 Hz, 1H) 8.38 (s, 1H) 8.20-8.25 (m, 1H) 8.03 (dt, J=7.4, 1.6 Hz, 1H) 7.94 (d, J=8.2 Hz, 1H) 7.84 (dd, J=8.4, 2.2 Hz, 1H) 7.49-7.60 (m, 2H) 7.00 (s, 1H) 6.80-6.87 (m, 1H) 6.57 (d, J=1.6 Hz, 1H) 5.31-5.39 (m, 3H) 4.83 (dq, J=6.5, 4.5 Hz, 1H) 4.20 (s, 3H) 3.79 (s, 3H) 1.39 (d, J=6.3 Hz, 3H).

Preparation of Benzylic Alcohols

The following additional benzylic alcohols were prepared according to the procedures described in Example 86 using (3-(hydroxymethyl)phenyl)boronic acid and the corresponding bromides or chlorides and were employed in preparing compounds of the Examples as indicated.

| Structure (Employed in preparation of Example compound as indicated) | Formula | Calc. [M + H]⁺ m/z | Calc. [M]⁻-C₅H₉O m/z | LCMS [M + H]⁺ m/z | LCMS [M]⁻-C₅H₉O m/z | HPLC Retention Time (Min)/ Method | NMR |
|---|---|---|---|---|---|---|---|
| (Ex. 88) | C₁₈H₂₀O₃ | | 199.077 | | 199.0 | 2.149/B | ¹H NMR (400 MHz, acetone-d₆): δ ppm 7.60-7.63 (m, 1H) 7.55-7.60 (m, 2H) 7.48 (dt, J = 7.8, 1.6 Hz, 1H) 7.38 (t, J = 7.6 Hz, 1H) 7.29-7.33 (m, 1H) 7.10-7.16 (m, 2H) 5.50 (t, J = 3.3 Hz, 1H) 4.69 (d, J = 5.8 Hz, 2H) 4.20 (t, J = 5.7 Hz, 1H) 3.87 (ddd, J = 11.3, 9.2, 3.3 Hz, 1H) 3.59 (dtd, J = 11.4, 4.3, 4.3, 1.2 Hz, 2H) 1.93-2.03 (m, 1H) 1.77-1.92 (m, 2H) 1.53-1.73 (m, 3H). |
| (Ex. 89) | C₁₇H₁₉NO₃ | 286.144 | | 286.0 | | 1.658/B | ¹H NMR (400 MHz, acetone-d₆): δ ppm 8.39-8.46 (m, 1H) 8.06 (s, 1H) 7.91 (dt, J = 7.4, 1.6 Hz, 1H) 7.82-7.88 (m, 1H) 7.53 (dd, J = 8.6, 2.7 Hz, 1H) 7.32-7.44 (m, 2H) 5.58 (t, J = 3.1 Hz, 1H) 4.71 (d, J = 6.2 Hz, 2 H) 4.22 (t, J = 5.9 Hz, 1H) 3.86 (ddd, J = 11.2, 9.5, 3.1 Hz, 1H) 3.57-3.67 (m, 1H) 1.81-2.03 (m, 3H) 1.55-1.76 (m, 3H). |

Examples 88 to 91

The following additional Examples have been prepared, isolated and characterized using the methods disclosed in Examples 86 and 87 employing the appropriate benzylic alcohol set out hereinbefore.

| Ex. | Structure | Formula | Calc. [M + H]⁺ m/z | HPLC Retention Time (Min)/ Method | LCMS [M + H]⁺ m/z | NMR |
|---|---|---|---|---|---|---|
| 88 | 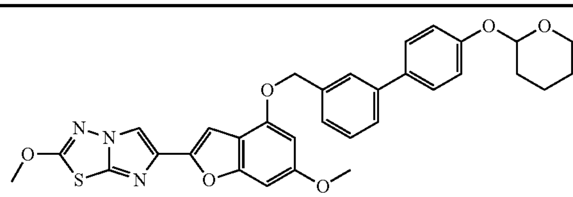 | C₃₂H₂₉N₃O₆S | 584.1855 | 2.663/B | 584.1863 | ¹H NMR (400 MHz, DMSO-d₆): δ ppm 8.38 (s, 1H) 7.74 (s, 1H) 7.56-7.65 (m, 3H) 7.42-7.52 (m, 2H) 7.08-7.16 (m, 2H) 6.99 (s, 1H) 6.81-6.85 (m, 1H) 6.56 (d, J = 2.0 Hz, 1H) 5.52 (t, J = 3.3 Hz, 1H) 5.31 (s, 2H) 4.20 (s, 3H) 3.72-3.82 (m, 4H) 3.52-3.61 (m, |

| Ex. | Structure | Formula | Calc. [M + H]+ m/z | HPLC Retention Time (Min)/ Method | LCMS [M + H]+ m/z | NMR |
|---|---|---|---|---|---|---|
| | | | | | | 1H) 1.69-1.96 (m, 3H) 1.48-1.69 (m, 3H). |
| 89 | 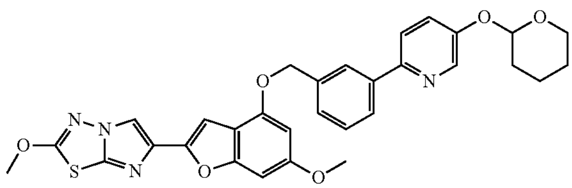 [SMILES: COc1cc(OCc2cccc(-c3ccc(OC4CCCCO4)cn3)c2)c2cc(-c3cn4nc(OC)sc4n3)oc2c1] | C₃₁H₂₈N₄O₆S | 585.1808 | 2.396/B | 585.1821 | ¹H NMR (400 MHz, DMSO-d6): δ ppm 8.43 (d, J = 2.3 Hz, 1H) 8.38 (s, 1H) 8.17 (s, 1H) 7.98 (dt, J = 6.8, 2.1 Hz, 1H) 7.93 (d, J = 9.0 Hz, 1H) 7.56 (dd, J = 8.8, 2.9 Hz, 1H) 7.47-7.54 (m, 2H) 7.00 (d, J = 0.8 Hz, 1H) 6.83 (dd, J = 2.0, 0.8 Hz, 1H) 6.56 (d, J = 1.6 Hz, 1H) 5.63 (t, J = 3.1 Hz, 1H) 5.33 (s, 2H) 4.20 (s, 3H) 3.79 (s, 3H) 3.73-3.78 (m, 1H) 3.55-3.63 (m, 1H) 1.72-1.97 (m, 3H) 1.48-1.71 (m, 3H). |
| 90 | 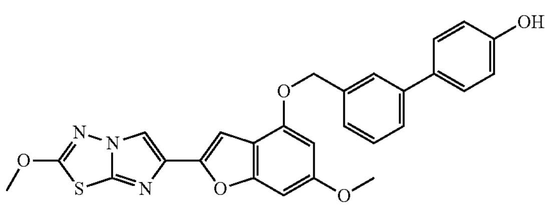 [SMILES: COc1cc(OCc2cccc(-c3ccc(O)cc3)c2)c2cc(-c3cn4nc(OC)sc4n3)oc2c1] | C₂₇H₂₁N₃O₅S | 500.1275 | 2.388/B | 500.1292 | ¹H NMR (400 MHz, DMSO-d₆): δ ppm 9.56 (s, 1H) 8.38 (s, 1H) 7.70 (s, 1H) 7.55 (dt, J = 7.3, 1.6 Hz, 1H) 7.48-7.52 (m, 2H) 7.39-7.47 (m, 2H) 6.99 (s, 1H) 6.83-6.88 (m, 2H) 6.82-6.83 (m, 1H) 6.56 (d, J = 2.0 Hz, 1H) 5.30 (s, 2 H) 4.20 (s, 3H) 3.79 (s, 3H). |
| 91 | 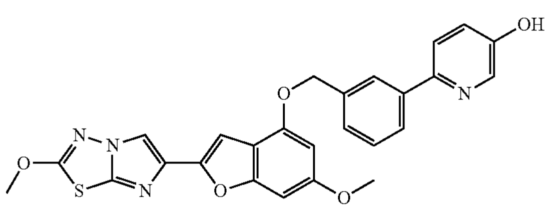 [SMILES: COc1cc(OCc2cccc(-c3ccc(O)cn3)c2)c2cc(-c3cn4nc(OC)sc4n3)oc2c1] | C₂₆H₂₀N₄O₅S | 501.1227 | 2.155/B | 501.1258 | ¹H NMR (400 MHz, DMSO-d₆): δ ppm 10.09 (br s, 1H) 8.38 (s, 1H) 8.22 (d, J = 2.3 Hz, 1H) 8.12 (s, 1H) 7.93 (ddd, J = 5.6, 3.4, 2.0 Hz, 1H) 7.82 (d, J = 8.6 Hz, 1H) 7.45-7.51 (m, 2H) 7.25 (dd, J = 8.6, 2.7 Hz, 1H) 6.99 (d, J = 0.8 Hz, 1H) 6.83 (dd, J = 1.8, 1.0 Hz, 1H) 6.55 (d, J = 2.0 Hz, 1H) 5.32 (s, |

| Ex. | Structure | Formula | Calc. [M + H]+ m/z | HPLC Retention Time (Min)/ Method | LCMS [M + H]+ m/z | NMR |
|---|---|---|---|---|---|---|
| | | | | | | 2H) 4.20 (s, 3H) 3.79 (s, 3H). |

Example 92

2-Methoxy-6-(6-methoxy-4-((3-(tetrahydro-2H-pyran-4-yl)benzyl)oxy)benzofuran-2-yl)imidazo[2,1-b][1,3,4]thiadiazole

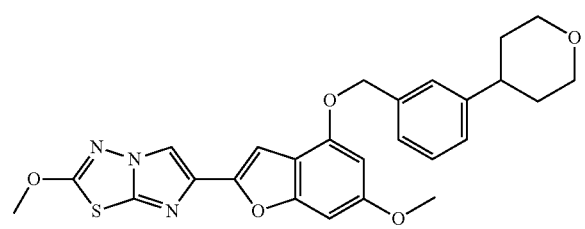 [SMILES: COc1cc(OCc2cccc(C3CCOCC3)c2)c2cc(-c3cn4nc(OC)sc4n3)oc2c1]

92A.
(3-(3,6-Dihydro-2H-pyran-4-yl)phenyl)methanol

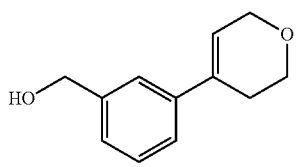 [SMILES: OCc1cccc(C2=CCOCC2)c1]

In a 50 mL round-bottomed flask under nitrogen, a solution of n-butyllithium (1.45 M in hexanes, 1.90 mL, 2.76 mmol) was added dropwise to a solution of diisopropylamine (0.39 mL, 2.74 mmol) in THF (5 mL) at 0° C. and the resulting mixture was stirred for 15 min. The reaction mixture was then cooled to −78° C. and a solution of dihydro-2H-pyran-4(3H)-one (0.23 mL, 2.481 mmol) in THF (7.5 mL) was slowly added and the mixture was at −78° C. for another 2 h. To this mixture was added a solution of 2-(N,N-bis(trifluoromethylsulfonyl)amino)-5-chloropyridine (1.082 g, 2.76 mmol) in THF (5 ml) over 15 min and the mixture was then allowed to warm to 0° C. and stirred for 3 h. The reaction was then quenched with water (15 mL) and the mixture was extracted with Et₂O (×3). The combined organic extract was washed successively with 15% aqueous NaOH and brine and then it was dried over anhydrous Na₂SO₄, filtered and concentrated. The crude product was chromatographed on a silica gel column (22 mm×80 mm) which was eluted with 0 to 20% EtOAc in hexanes. This afforded 3,6-dihydro-2H-pyran-4-yl trifluoromethanesulfonate (0.307 g, 53%) as a colorless oil which was used as such in the following step. $^1$H NMR (400 MHz, acetone-$d_6$): δ ppm 6.01 (tt, J=2.8, 1.5 Hz, 1H) 4.25 (q, J=3.0 Hz, 2H) 3.88 (t, J=5.5 Hz, 2H) 2.48 (ttd, J=5.5, 2.8, 1.4 Hz, 2H). In a 25 mL round-bottomed flask, the obtained 3,6-dihydro-2H-pyran-4-yl trifluoromethanesulfonate (0.307 g, 1.322 mmol) and potassium fluoride (0.270 g, 4.65 mmol) were added to a solution of (3-(hydroxymethyl)phenyl)boronic acid (0.250 g, 1.645 mmol) in THF (7.5 ml) and the flask was evacuated and purged with nitrogen three times. Bis(diphenylphosphino)ferrocene-palladium(II) dichloride dichloromethane complex (0.024 g, 0.029 mmol) was then added in one portion and the mixture was stirred at room temperature for 66 h. The resulting mixture was diluted with ethyl acetate, filtered through CELITE® and concentrated. The residue was purified on the ISCO using a REDISEP® Gold 24 g column (elution with hexanes-EtOAc) to give the title compound (0.131 g, 52%) as yellowish oil. LC (Method B): 1.614 min LCMS (APCI): calcd for $C_{12}H_{13}O$ [M+H]+—H₂O m/z 173.096. found 173.2. $^1$H NMR (400 MHz, acetone-$d_6$): δ ppm 7.46 (s, 1H) 7.22-7.36 (m, 3H) 6.21 (tt, J=3.0, 1.5 Hz, 1H) 4.64 (d, J=5.9 Hz, 2H) 4.24 (q, J=3.0 Hz, 2H) 4.17 (t, J=5.7 Hz, 1H) 3.86 (t, J=5.5 Hz, 2H) 2.49 (ttd, J=5.4, 2.8, 1.6 Hz, 2H).

92B.
(3-(Tetrahydro-2H-pyran-4-yl)phenyl)methanol

In a 25 mL round-bottomed flask, a mixture of (3-(3,6-dihydro-2H-pyran-4-yl)phenyl)methanol (0.101 g, 0.531 mmol) and 5% palladium on carbon (0.033 g, 0.016 mmol) in ethanol (10 mL) was hydrogenated (1 atm H₂) for 45 min. The mixture was filtered through CELITE®, the filter-cake was rinsed with ethyl acetate and the filtrate was concentrated. The residue was purified on the ISCO using a REDISEP® Gold 12 g column (elution with hexanes-EtOAc) to give the title compound (0.070 g, 69%) as a yellowish oil. LC (Method B): 2.157 min HRMS(ESI): calcd for $C_{28}H_{25}N_4O_5S$ [M+H]+ m/z 529.1546. found 529.1581. $^1$H NMR (400 MHz, acetone-$d_6$): δ ppm 7.22-7.30 (m, 2H) 7.16-7.21 (m, 1H) 7.13 (dt, J=7.5, 1.3 Hz, 1H) 4.62 (d, J=5.9 Hz, 2H) 4.11 (t, J=5.9 Hz, 1H) 3.97 (dt, J=11.3, 3.1 Hz, 2H) 3.42-3.52 (m, 2H) 2.75-2.78 (m, 1H) 1.69-1.77 (m, 4H).

Example 92

2-Methoxy-6-(6-methoxy-4-((3-(tetrahydro-2H-pyran-4-yl)benzyl)oxy)benzofuran-2-yl)imidazo[2,1-b][1,3,4]thiadiazole

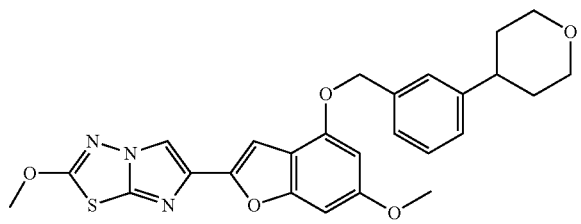 [SMILES: COc1cc(OCc2cccc(C3CCOCC3)c2)c2cc(-c3cn4nc(OC)sc4n3)oc2c1]

In a 35 mL round-bottomed flask under nitrogen, a solution of 1,1'-(azodicarbonyl)dipiperidine (0.141 g, 0.559 mmol) in THF (2.5 mL) was added dropwise over 10 min to a mixture of 6-methoxy-2-(2-methoxyimidazo[2,1-b][1,3,4]thiadiazol-6-yl)benzofuran-4-ol (Example 1G, 0.073 g, 0.230 mmol), (3-(tetrahydro-2H-pyran-4-yl)phenyl)methanol (0.070 g, 0.364 mmol) and tri-n-butylphosphine (0.145 mL, 0.588 mmol) in dry THF (3 mL) and the mixture was stirred at room temperature for 3 h. The reaction mixture was then diluted with $CH_2Cl_2$, washed once with saturated aqueous $NaHCO_3$, once with brine, dried on anhydrous $Na_2SO_4$ and concentrated. The residue was purified on the ISCO using a REDISEP® Gold 24 g column (elution with $CH_2Cl_2$-EtOAc) to give the title compound (0.066 g, 58%) as white solid, after lyophilization from acetonitrile-water. LC (Method B): 2.436 min HRMS(ESI): calcd for $C_{26}H_{26}N_3O_5S$ $[M+H]^+$ m/z 492.1593. found 492.1633. $^1$H NMR (400 MHz, DMSO-$d_6$): δ ppm 8.38 (s, 1H) 7.40 (s, 1H) 7.32-7.38 (m, 2H), 7.22-7.27 (m, 1H) 6.97 (s, 1H) 6.80-6.85 (m, 1H) 6.54 (d, J=2.0 Hz, 1H) 5.22 (s, 2H) 4.20 (s, 3H) 3.90-3.99 (m, 2H) 3.79 (s, 3H) 3.38-3.49 (m, 2H) 2.80 (tt, J=10.6, 5.3 Hz, 1H) 1.60-1.76 (m, 4H).

Preparation of Alcohols

The following additional alcohols were prepared according to the procedures described in Example 92.

| Structure (Employed in preparation of compound as indicated) | Formula | Calc. [M + H]$^+$ —H$_2$O m/z | LCMS [M + H]$^+$ —H$_2$O m/z | HPLC Retention Time (Min)/ Method | NMR |
|---|---|---|---|---|---|
| (94) | $C_{13}H_{16}O$ | 171.1168 | 171.2 | 2.132/B | $^1$H NMR (400 MHz, acetone-$d_6$): δ ppm 7.40 (s, 1 H) 7.24-7.29 (m, 2H) 7.17-7.24 (m, 1H) 6.12 (tt, J = 4.1, 1.7 Hz, 1H) 4.62 (d, J = 6.3 Hz, 2H) 4.11 (t, J = 5.9 Hz, 1H) 2.36-2.44 (m, 2H) 2.15-2.23 (m, 2H) 1.72-1.81 (m, 2H) 1.60-1.69 (m, 2H). |
| (95) | $C_{13}H_{18}O$ | 173.1325 | 173.2 | | $^1$H NMR (400 MHz, acetone-$d_6$): δ ppm 7.19-7.26 (m, 2H) 7.12-7.17 (m, 1H) 7.09 (dt, J = 7.4, 1.6 Hz, 1H) 4.60 (d, J = 5.9 Hz, 1H) 4.07 (t, J = 5.7 Hz, 1H) 2.43-2.57 (m, 1H) 1.78-1.87 (m, 4H) 1.69-1.78 (m, 1H) 1.34-1.54 (m, 4H) 1.23-1.34 (m, 1H). |

Examples 93 to 95

The following additional Examples have been prepared, isolated and characterized using the method disclosed in Examples 92 employing the appropriate alcohol set out hereinbefore.

| Ex. | Structure | Formula | Calc. [M + H]+ m/z | HPLC Retention Time (Min)/ Method | LCMS [M + H]+ m/z | NMR |
|---|---|---|---|---|---|---|
| 93 | 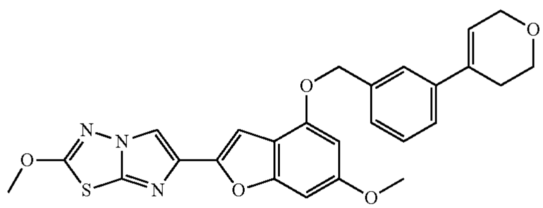 [SMILES: COc1cc(OCc2cccc(C3=CCOCC3)c2)c2cc(-c3cn4nc(OC)sc4n3)oc2c1] | $C_{26}H_{23}N_3O_5S$ | 490.1437 | 2.449/B | 490.1453 | $^1$H NMR (400 MHz, DMSO-$d_6$) δ ppm 8.38 (s, 1 H) 7.58 (s, 1 H) 7.35-7.46 (m, 3 H) 6.98 (d, J = 0.8 Hz, 1 H) 6.83 (dd, J = 1.8, 1.0 Hz, 1 H) 6.53 (d, J = 2.0 Hz, 1 H) 6.25-6.32 (m, 1 H) 5.25 (s, 2 H) 4.23 (q, J = 2.7 Hz, 2 H) 4.20 (s, 3 H) 3.83 (t, J = 5.5 Hz, 2 H) 3.79 (s, 3 H) 2.43-2.48 (m, 2 H) |
| 94 | 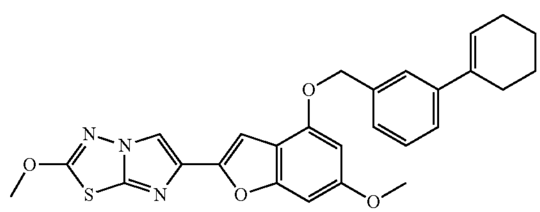 [SMILES: COc1cc(OCc2cccc(C3=CCCCC3)c2)c2cc(-c3cn4nc(OC)sc4n3)oc2c1] | $C_{27}H_{25}N_3O_4S$ | 488.1644 | 2.726/B | 488.1651 | $^1$H NMR (400 MHz, DMSO-$d_6$) δ ppm 8.38 (s, 1H) 7.52 (s, 1H) 7.33-7.40 (m, 3H) 6.97 (s, 1H) 6.80-6.85 (m, 1H) 6.53 (d, J = 1.6 Hz, 1H) 6.18 (tt, J = 3.8, 2.1 Hz, 1H) 5.24 (s, 2H) 4.20 (s, 3H) 3.79 (s, 3H) 2.34-2.43 (m, 2H) 2.13-2.23 (m, 2H) 1.67-1.79 (m, 2H) 1.55-1.66 (m, 2H). |
| 95 | 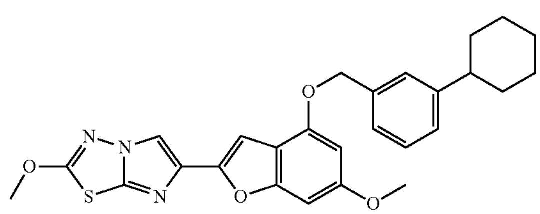 [SMILES: COc1cc(OCc2cccc(C3CCCCC3)c2)c2cc(-c3cn4nc(OC)sc4n3)oc2c1] | $C_{27}H_{27}N_3O_4S$ | 490.1801 | 2.751/B | 490.1809 | $^1$H NMR (400 MHz, DMSO-$d_6$): δ ppm 8.38 (s, 1H) 7.28-7.38 (m, 3H) 7.20 (dt, J = 6.0, 2.1 Hz, 1H) 6.93-6.98 (m, 1H) 6.80-6.85 (m, 1H) 6.53 (d, J = 2.0 Hz, 1H) 5.21 (s, 2H) 4.20 (s, 3H) 3.79 (s, 3H) 2.52-2.56 (m, 1H) 1.79 (d, J = 8.6 Hz, 4H) 1.64-1.74 (m, 1H) 1.30-1.49 (m, 4H) 1.14-1.30 (m, 1H). |

Example 96

4-(6-(((6-Methoxy-2-(2-methoxyimidazo[2,1-b][1,3,4]thiadiazol-6-yl)benzofuran-4-yl)oxy)methyl)pyridin-2-yl)-N,N-dimethylbenzamide

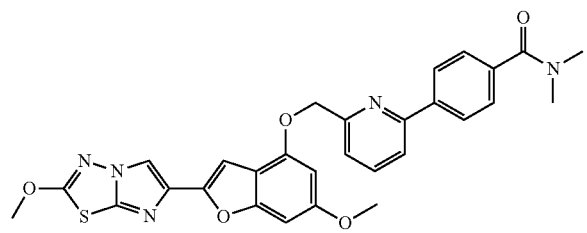

96A. 2-Bromo-6-(((tert-butyldimethylsilyl)oxy)methyl)pyridine

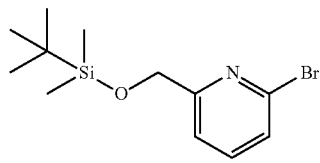 [SMILES: CC(C)(C)[Si](C)(C)OCc1cccc(Br)n1]

In a 25 mL round-bottomed flask under nitrogen, tert-butylchlorodimethylsilane (1.54 g, 10.22 mmol) was added to a solution of (6-bromopyridin-2-yl)methanol (1.27 g, 6.75 mmol) and imidazole (0.545 g, 8.01 mmol) in DMF (8 mL) and the mixture was stirred at room temperature for 1.5 h. The mixture was then diluted with water and the product was extracted with ethyl acetate (×3). The combined organic extract was washed once with water, once with brine, dried over anhydrous $Na_2SO_4$ and concentrated. The obtained residue was purified on the ISCO using a SILICYCLE® 80 g column (elution with hexanes-EtOAc) to give the title material (1.97 g, 96%) as colorless liquid. LC (Method B): 2.422 min. LCMS (APCI): calcd for $C_{12}H_{21}BrNOSi$ $[M+H]^+$ m/z 302.057. found 302.0. $^1H$ NMR (400 MHz, MeOH-$d_4$): δ 7.71 (t, J=7.83 Hz, 1H), 7.51 (dd, J=0.78, 7.83 Hz, 1H), 7.46 (dd, J=0.78, 7.83 Hz, 1H), 4.76 (s, 2H), 0.97 (s, 9H), 0.14 (s, 6H).

96B. 4-(6-(((tert-Butyldimethylsilyl)oxy)methyl)pyridin-2-yl)-N,N-dimethylbenzamide

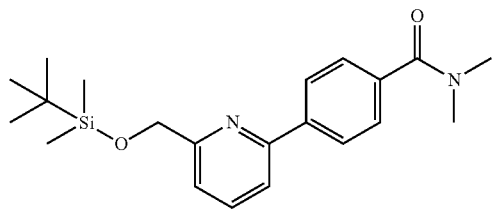 [SMILES: CN(C)C(=O)c1ccc(-c2cccc(CO[Si](C)(C)C(C)(C)C)n2)cc1]

In a 75 mL pressure vessel, a solution of 2-bromo-6-(((tert-butyldimethylsilyl)oxy)-methyl)pyridine (0.197 g, 0.652 mmol), (4-(dimethylcarbamoyl)phenyl)boronic acid (0.197 g, 1.021 mmol) and Pd(dppf)Cl$_2$·CH$_2$Cl$_2$ (0.032 g, 0.039 mmol) in a mixture of toluene (6 mL) and ethanol (2 mL) was purged with a stream of nitrogen bubbles for 15 min. To this mixture was added aqueous sodium carbonate (2 M, 0.41 mL, 0.82 mmol) and the mixture was heated at 95° C. overnight. The cooled mixture was diluted with water and the product was extracted with ethyl acetate (×3). The combined organic extract was washed once with saturated aqueous NaHCO$_3$, once with brine, dried over anhydrous Na$_2$SO$_4$ and concentrated. The obtained residue was purified on the ISCO using an Innoflash 25 g column (elution with CH$_2$Cl$_2$-EtOAc) to give the title material (0.214 g, 89%) as yellow oil. LC (Method B): 2.330 min LCMS (APCI): calcd for $C_{21}H_{31}N_2O_2Si$ $[M+H]^+$ m/z 371.215. found 371.2. $^1H$ NMR (400 MHz, MeOH-$d_4$): δ 8.09 (d, J=7.83 Hz, 2H), 7.91 (t, J=7.83 Hz, 1H), 7.77 (d, J=7.83 Hz, 1H), 7.49-7.58 (m, 3H), 4.89 (s, 2H), 3.13 (s, 3H), 3.05 (s, 3H), 0.99 (s, 9H), 0.17 (s, 6H).

96C. 4-(6-(Hydroxymethyl)pyridin-2-yl)-N,N-dimethylbenzamide

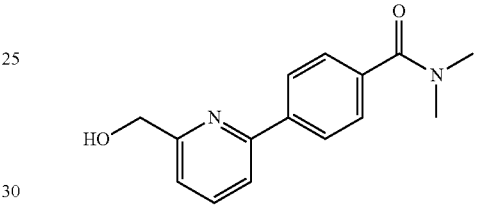

In a 25 mL round-bottomed flask, a solution of 4-(6-(((tert-butyldimethylsilyl)oxy)-methyl)pyridin-2-yl)-N,N-dimethylbenzamide (0.214 g, 0.578 mmol) and triethylamine trihydrofluoride (0.45 mL, 2.76 mmol) in dry THF (8 mL) was stirred at room temperature under nitrogen for 19 h. The reaction was then quenched by the addition of 5 mL of methanol and the mixture was concentrated. The concentrate was diluted with ethyl acetate and the solution was washed once with saturated aqueous NaHCO$_3$, once with brine, dried on anhydrous Na$_2$SO$_4$ and concentrated. The obtained residue was purified on the ISCO using an Innoflash 12 g column (elution with CH$_2$Cl$_2$-EtOAc) to give the title compound (0.121 g, 82%) as white solid. LC (Method B): 1.110 min LCMS (APCI): calcd for $C_{15}H_{17}N_2O_2$ $[M+H]^+$ m/z 257.129. found 257.2. $^1H$ NMR (400 MHz, DMSO-$d_6$): δ 8.39 (s, 1H), 8.15-8.21 (m, 2H), 7.96-8.02 (m, 2H), 7.57-7.64 (m, 1H), 7.50-7.57 (m, 2H), 7.07 (s, 1H), 6.85 (dd, J=0.98, 1.76 Hz, 1H), 6.58 (d, J=1.96 Hz, 1H), 5.42 (s, 2H), 4.21 (s, 3H), 3.79 (s, 3H), 3.01 (br s, 3H), 2.95 (br s, 3H).

Example 96

4-(6-(((6-Methoxy-2-(2-methoxyimidazo[2,1-b][1,3,4]thiadiazol-6-yl)benzofuran-4-yl)oxy)methyl)pyridin-2-yl)-N,N-dimethylbenzamide

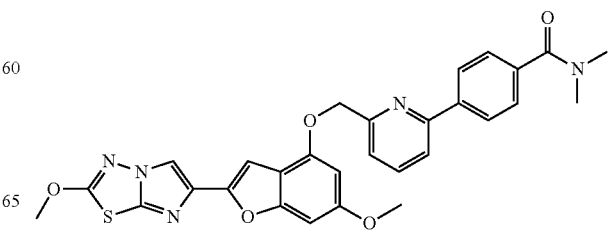

In a 25 mL round-bottomed flask, a mixture of 6-methoxy-2-(2-methoxyimidazo[2,1-b][1,3,4]thiadiazol-6-yl)benzofuran-4-ol (Example 1G, 0.050 g, 0.158 mmol), 4-(6-(hydroxymethyl)pyridin-2-yl)-N,N-dimethylbenzamide (0.051 g, 0.199 mmol) and tri-n-butylphosphine (0.12 mL, 0.486 mmol) was kept under high vacuum for 10 min, back-filled with nitrogen and suspended in dry THF (1.5 mL). A solution of 1,1'-(azodicarbonyl)dipiperidine (0.095 g, 0.377 mmol) in THF (1.5 mL) was then added dropwise on 10 min and the mixture was stirred at room temperature for 4.5 h. The reaction mixture was then diluted with $CH_2Cl_2$ and washed once with saturated aqueous $NaHCO_3$, once with brine, dried on anhydrous $Na_2SO_4$ and concentrated. The residue was purified on the ISCO using a REDISEP® Gold 24 g column (elution with $CH_2Cl_2$-EtOAc) to give the title compound (0.068 g, 78%) as a white solid, after lyophilization from acetonitrile-water. LC (Method B): 2.237 min. HRMS(ESI): calcd for $C_{29}H_{26}N_5O_5S$ $[M+H]^+$ m/z 556.1655. found 556.1649. $^1H$ NMR (400 MHz, DMSO-$d_6$): δ 8.39 (s, 1H), 8.15-8.21 (m, 2H), 7.96-8.02 (m, 2H), 7.57-7.64 (m, 1H), 7.50-7.57 (m, 2H), 7.07 (s, 1H), 6.85 (dd, J=0.98, 1.76 Hz, 1H), 6.58 (d, J=1.96 Hz, 1H), 5.42 (s, 2H), 4.21 (s, 3H), 3.79 (s, 3H), 3.01 (br s, 3H), 2.95 (br s, 3H).

Example 97

6-(4-((2-(2-Fluoropyridin-4-yl)pyrimidin-4-yl)methoxy)-6-methoxybenzofuran-2-yl)-2-methoxy-imidazo[2,1-b][1,3,4]thiadiazole

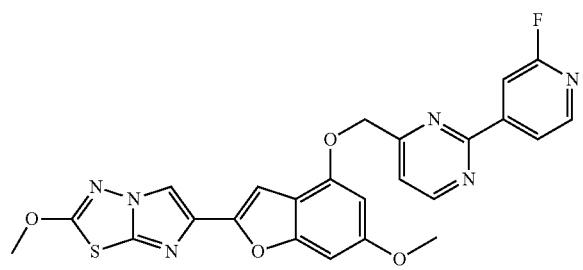 [SMILES: COc1cc(OCc2ccnc(-c3ccnc(F)c3)n2)c2cc(-c3cn4nc(OC)sc4n3)oc2c1]

97A. Methyl 2-(2-fluoropyridin-4-yl)pyrimidine-4-carboxylate

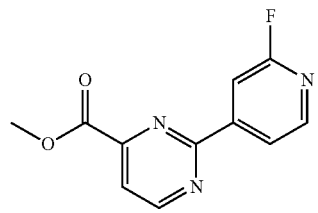 [SMILES: COC(=O)c1ccnc(-c2ccnc(F)c2)n1]

In a 15 mL pressure vessel, a solution of methyl 2-chloropyrimidine-4-carboxylate (0.048 g, 0.278 mmol), (2-fluoropyridin-4-yl)boronic acid (0.060 g, 0.426 mmol) and Pd(dppf)Cl$_2$.DCM (0.013 g, 0.016 mmol) in a mixture of toluene (4 mL) and ethanol (3 mL) was degassed under high vacuum and back-filled with nitrogen three times. An aqueous solution of sodium carbonate (2 M, 0.18 mL, 0.360 mmol) was then added and the mixture was heated at 105° C. overnight. The cooled mixture was diluted with water and the resulting mixture was washed with ethyl acetate (×3). The aqueous layer was separated, acidified to pH 1 with 1 M hydrochloric acid and extracted with ethyl acetate (×1) and then dichloromethane (×2). The combined organic extract was washed once with brine, dried over anhydrous $Na_2SO_4$ and concentrated. The crude residue was taken up in THF (3 mL) and treated with a solution of diazomethane (0.77 M in $Et_2O$, 1 mL, 0.77 mmol) and the mixture was stirred at room temperature for 64 h. The volatiles were then removed in vacuo and the residue was purified on the ISCO using a REDISEP® 4 g column (elution with hexanes-EtOAc) to give the title compound (0.020 g, 31%) as a white solid. LC (Method B): 1.691 min. LCMS (APCI): calcd for $C_{11}H_9FN_3O_2$ $[M+H]^+$ m/z 234.067. found 234.2. $^1H$ NMR (400 MHz, MeOH-$d_4$): δ 9.20 (d, J=4.70 Hz, 1H), 8.33-8.41 (m, 2H), 8.10 (s, 1H), 8.08 (d, J=4.70 Hz, 1H), 4.06 (s, 3H).

97B. (2-(2-Fluoropyridin-4-yl)pyrimidin-4-yl)methanol

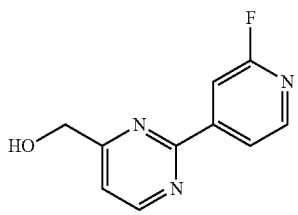 [SMILES: OCc1ccnc(-c2ccnc(F)c2)n1]

In a 25 mL round-bottomed flask under nitrogen at 0° C., sodium borohydride (0.007 g, 0.185 mmol) and methanol (0.01 mL, 0.25 mmol) were added to a solution of methyl 2-(2-fluoropyridin-4-yl)pyrimidine-4-carboxylate (0.020 g, 0.086 mmol) in THF (2 mL) and the mixture was then stirred at room temperature for 18 h. The mixture was re-cooled in an ice bath and quenched by the dropwise addition of saturated aqueous $NH_4Cl$. The product was extracted with ethyl acetate (×3) and the combined organic extract was washed once with brine, dried over anhydrous $Na_2SO_4$ and concentrated. The crude residue was purified on the ISCO using a REDISEP® 4 g column (elution with hexanes-EtOAc) to give the title compound (0.012 g, 65%) as a white solid. LC (Method B): 1.406 min. LCMS (APCI): calcd for $C_{10}H_9FN_3O$ $[M+H]^+$ m/z 206.072. found 206.2. $^1H$ NMR (400 MHz, MeOH-$d_4$): δ 8.92 (d, J=5.09 Hz, 1H), 8.35 (d, J=5.48 Hz, 1H), 8.29 (td, J=1.47, 5.28 Hz, 1H), 8.01 (s, 1H), 7.64 (d, J=5.09 Hz, 1H), 4.79 (s, 2H).

Example 97

6-(4-((2-(2-fluoropyridin-4-yl)pyrimidin-4-yl)methoxy)-6-methoxybenzofuran-2-yl)-2-methoxy-imidazo[2,1-b][1,3,4]thiadiazole

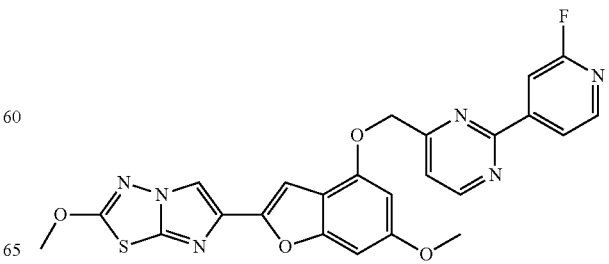

In a 25 mL round-bottomed flask, a mixture of 6-methoxy-2-(2-methoxyimidazo[2,1-b][1,3,4]thiadiazol-6-yl)benzofuran-4-ol (Example 1G, 0.014 g, 0.044 mmol), (2-(2-fluoropyridin-4-yl)pyrimidin-4-yl)methanol (0.011 g, 0.054 mmol) and tri-n-butylphosphine (0.040 mL, 0.162 mmol) was kept under high vacuum for 10 min, then the flask was back-filled with nitrogen and dry THF (1 mL) was added. A solution of 1,1'-(azodicarbonyl)dipiperidine (0.035 g, 0.139 mmol) in dry THF (1 mL) was then added dropwise on 10 min and the mixture was stirred at room temperature for 17 h. The reaction mixture was then diluted with $CH_2Cl_2$ and the mixture was washed once with saturated aqueous $NaHCO_3$, once with brine, dried over anhydrous $Na_2SO_4$ and concentrated. The residue was purified twice on the ISCO using a REDISEP® Gold 12 g column (elution with $CH_2Cl_2$-EtOAc, then with hexanes-EtOAc) to give the title compound (0.0057 g, 26%) as a white solid, after lyophilization from acetonitrile-water. LC (Method B): 2.507 min. HRMS(ESI): calcd for $C_{24}H_{18}FN_6O_4S$ $[M+H]^+$ m/z 505.1094. found 505.1092. $^1H$ NMR (400 MHz, DMSO-$d_6$): δ 9.07 (d, J=5.09 Hz, 1H), 8.47 (d, J=5.09 Hz, 1H), 8.40 (s, 1H), 8.24 (td, J=1.66, 5.28 Hz, 1H), 7.94 (s, 1H), 7.85 (d, J=5.09 Hz, 1H), 7.16 (s, 1H), 6.88 (s, 1H), 6.58 (d, J=1.57 Hz, 1H), 5.50 (s, 2H), 4.21 (s, 3H), 3.80 (s, 3H).

Preparation of Alcohols

The following additional intermediate alcohols were prepared according to the procedures described in Example 97.

| Structure (Employed in preparation of Example as indicated) | Formula | Calc. $[M + H]^+$ m/z | LCMS $[M + H]^+$ m/z | HPLC Retention Time (Min)/ Method | NMR |
|---|---|---|---|---|---|
| (Ex. 98) | C14H15N3O2 | 258.1237 | 258.2 | 1.362/B | |
| (Ex. 99) | C12H9N3O | 212.0818 | 212.2 | 1.581/B | $^1H$ NMR (400 MHz, MeOH-$d_4$): δ 8.86 (d, J = 5.48 Hz, 1H), 8.78 (s, 1H), 8.74 (d, J = 7.83 Hz, 1H), 7.86 (d, J = 7.83 Hz, 1H), 7.69 (t, J = 7.83 Hz, 1H), 7.56 (d, J = 5.09 Hz, 1H), 4.78 (s, 2H). |
| (Ex. 100) | C12H12N2O2 | 217.0972 | 217.2 | 1.595/B | $^1H$ NMR (400 MHz, MeOH-$d_4$): δ 8.74 (d, J = 5.09 Hz, 1H), 8.31-8.38 (m, 2H), 7.42 (d, J = 5.09 Hz, 1H), 6.98-7.05 (m, 2H), 4.72 (s, 2H), 3.87 (s, 3H). |

Examples 98 to 100

The following additional Examples have been prepared, isolated and characterized according to the method disclosed in Example 97.

| Ex. | Structure | Formula | Calc. [M + H]+ m/z | HPLC Retention Time (Min)/ Method | LCMS [M + H]+ m/z | NMR |
|---|---|---|---|---|---|---|
| 98 | 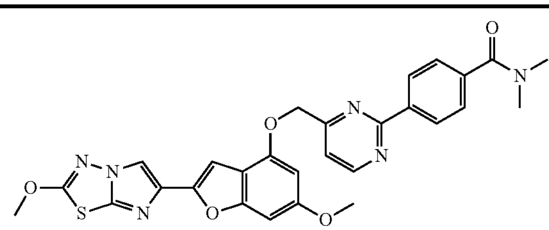 | C28H24N6O5S | 557.1607 | 2.337/B | 557.1598 | 1H NMR (400 MHz, DMSO-d6): δ 8.98 (d, J = 5.09 Hz, 1H), 8.43-8.49 (m, 2H), 8.40 (s, 1H), 7.69 (d, J = 5.09 Hz, 1H), 7.54-7.60 (m, 2H), 7.15 (s, 1H), 6.85-6.89 (m, 1H), 6.57 (d, J = 1.96 Hz, 1H), 5.46 (s, 2H), 4.21 (s, 3H), 3.79 (s, 3H), 3.01 (br s, 3H), 2.94 (br s, 3H). |
| 99 | 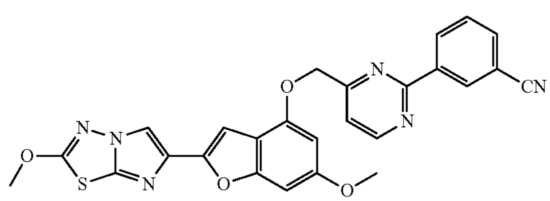 [SMILES: COc1cc(OCc2ccnc(-c3cccc(C#N)c3)n2)c2cc(-c3cn4nc(OC)sc4n3)oc2c1] | C26H18N6O4S | 511.1189 | 2.517/B | 511.1163 | 1H NMR (400 MHz, DMSO-d6): δ 9.00 (d, J = 5.09 Hz, 1H), 8.67-8.73 (m, 2H), 8.39 (s, 1H), 8.03 (d, J = 7.43 Hz, 1H), 7.78 (t, J = 8.02 Hz, 1H), 7.74 (d, J = 5.09 Hz, 1H), 7.15 (s, 1H), 6.87 (s, 1H), 6.57 (s, 1H), 5.48 (s, 2H), 4.21 (s, 3H), 3.79 (s, 3H). |
| 100 | 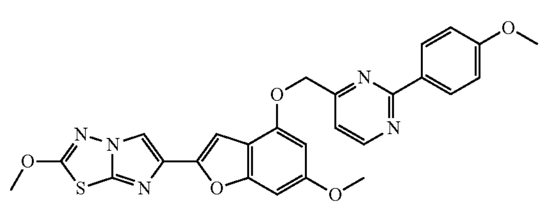 | C26H21N5O5S | 516.1342 | 2.550/B | 516.1316 | 1H NMR (400 MHz, DMSO-d6): δ 8.88 (d, J = 5.09 Hz, 1H), 8.34-8.41 (m, 3H), 7.56 (d, J = 5.09 Hz, 1H), 7.13 (s, 1H), 7.0-7.11 (m, 2H), 6.87 (s, 1H), 6.56 (s, 1H), 5.42 (s, 2H), 4.21 (s, 3H), 3.84 (s, 3H), 3.79 (s, 3H). |

Example 101

2-Methoxy-6-(6-methoxy-4-((2-phenylpyrimidin-4-yl)methoxy)benzofuran-2-yl)imidazo[2,1-b][1,3,4]thiadiazole

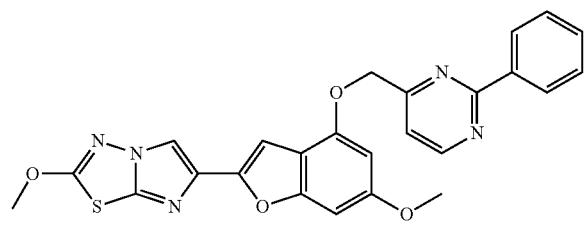 [SMILES: COc1cc(OCc2ccnc(-c3ccccc3)n2)c2cc(-c3cn4nc(OC)sc4n3)oc2c1]

101A. Ethyl 2-phenylpyrimidine-4-carboxylate

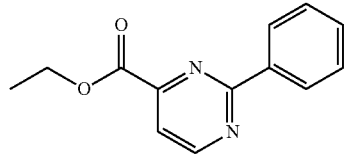 [SMILES: CCOC(=O)c1ccnc(-c2ccccc2)n1]

To an ice-cold solution of benzimidamide hydrochloride (0.156 g, 0.996 mmol) in ethanol (5 mL) was added dropwise a solution of lithium 2-methylpropan-2-olate (1 M in THF, 1 mL, 1.00 mmol). The mixture was stirred for 5 min and then (E)-ethyl 4-ethoxy-2-oxobut-3-enoate (0.223 g, 1.295 mmol) was added. The mixture was then heated at 140° C. (microwave) for 20 min. The resulting dark mixture was concentrated on the rotary evaporator and the residue was partitioned between ethyl acetate (40 mL) and brine (20 mL). The aqueous layer was separated and re-extracted with ethyl acetate (2×20 mL) and the combined organic extract was washed with brine, dried (MgSO$_4$) and evaporated. The obtained residue was purified on the ISCO using a REDISEP® Gold 12 g column (elution with hexanes-EtOAc) to give the title compound (0.048 g, 21%) as a solid. LC (Method F): 2.099 min. LCMS (APCI): calcd for C$_{13}$H$_{13}$N$_2$O$_2$ [M+H]$^+$ m/z 229.097. found 229.2. $^1$H NMR (400 MHz, CDCl$_3$): δ 9.03 (d, J=5.1 Hz, 1H), 8.54 (dd, J=6.7, 3.1 Hz, 2H), 7.85 (d, J=5.1 Hz, 1H), 7.47-7.57 (m, 3H), 4.53 (d, J=7.0 Hz, 2H), 1.49 (t, J=7.0 Hz, 3H).

101B: (2-Phenylpyrimidin-4-yl)methanol

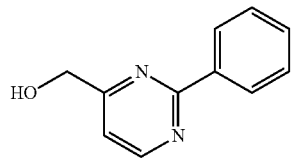 [SMILES: OCc1ccnc(-c2ccccc2)n1]

An ice-cold solution of ethyl 2-phenylpyrimidine-4-carboxylate (0.048 g, 0.210 mmol) in THF (3 mL) under nitrogen was treated with NaBH$_4$ (0.032 g, 0.841 mmol) and methanol (0.051 mL, 1.262 mmol). The mixture was stirred at 0° C. for 12 h, after which the mixture was allowed to stir at room temperature for 18 h. The resulting turbid solution was re-cooled in an ice bath and quenched with saturated aqueous NH$_4$Cl (10 mL) and diluted with ethyl acetate (40 mL). The aqueous layer was separated and re-extracted with ethyl acetate (2×20 mL). The combined organic extract was washed with saturated aqueous sodium bicarbonate (2×20 mL) and brine (20 mL) and then dried over anhydrous magnesium sulfate. Evaporation of the solvent gave an oily residue that was purified on the ISCO using a REDISEP® Gold 4 g column (elution with hexanes-EtOAc) to give the title compound (0.034 g, 87%) as an oil. LC (Method F): 1.688 min. LCMS (APCI): calcd for C$_{11}$H$_{11}$N$_2$O [M+H]$^+$ m/z 187.087. found 187.2. $^1$H NMR (400 MHz, CDCl$_3$): δ 8.77 (d, J=5.1 Hz, 1H), 8.42-8.54 (m, 2H), 7.48-7.56 (m, 3H), 7.18 (d, J=5.1 Hz, 1H), 4.79-4.87 (m, 2H), 3.62 (t, J=5.1 Hz, 1H).

Example 101

2-Methoxy-6-(6-methoxy-4-((2-phenylpyrimidin-4-yl)methoxy)benzofuran-2-yl)imidazo[2,1-b][1,3,4]thiadiazole

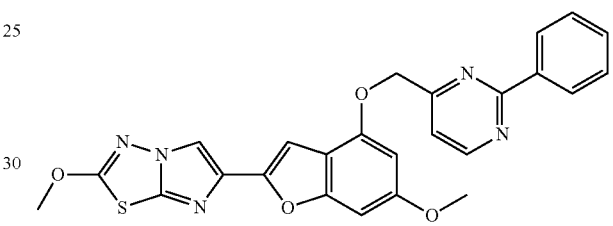

A mixture of 6-methoxy-2-(2-methoxyimidazo[2,1-b][1,3,4]thiadiazol-6-yl)benzofuran-4-ol (0.050 g, 0.158 mmol) and tri-n-butylphosphine (0.194 mL, 0.788 mmol) was pumped under high vacuum for 20 min. To this mixture was then added, at room temperature under nitrogen, a solution of (2-phenylpyrimidin-4-yl)methanol (0.0323 g, 0.173 mmol) in THF (4 mL), followed by the dropwise addition of a solution of 1,1'-(azodicarbonyl)dipiperidine (0.099 g, 0.394 mmol) in THF (3 mL) over 20 min. The mixture was stirred at room temperature for an additional 3 h and then it was diluted with dichloromethane (75 mL), washed twice with saturated aqueous NaHCO$_3$ (20 mL), water (20 mL) and brine (20 mL), and finally dried (MgSO$_4$). Evaporation of the solvent gave a semi-solid that was purified on the ISCO using a REDISEP® Gold 12 g column (elution with hexanes-EtOAc) to give the slightly impure product. This material was repurified on the ISCO using a REDISEP® Gold 12 g column (elution with dichloromethane-EtOAc) and the obtained material was further triturated with acetonitrile (1 mL) and the resulting solid was lyophilized from acetonitrile-water to give the title compound (0.046 g, 60.1%) as a solid. LC (Method F): 2.692 min. HRMS(ESI): calcd for C$_{25}$H$_{20}$N$_5$O$_4$S [M+H]$^+$ m/z 486.1236. found 486.1217. $^1$H NMR (400 MHz, CDCl$_3$): δ 8.95 (d, J=5.1 Hz, 1H), 8.41-8.46 (m, 2H), 8.40 (s, 1H), 7.65 (d, J=5.1 Hz, 1H), 7.50-7.59 (m, 3H), 7.11-7.17 (m, 1H), 6.87 (d, J=0.8 Hz, 1H), 6.57 (d, J=1.6 Hz, 1H), 5.45 (s, 2H), 4.21 (s, 3H), 3.79 (s, 3H).

Preparation of Alcohols

The following additional intermediate alcohols were prepared according to the procedures described in Example 101.

| Structure (Employed in preparation of Example as indicated) | Formula | Calc. [M + H]+ m/z | LCMS [M + H]+ m/z | HPLC Retention Time (Min)/ Method | NMR |
|---|---|---|---|---|---|
| 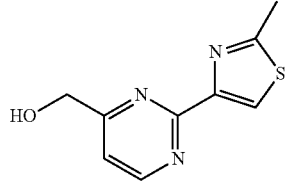<br>(Ex. 102) | C₉H₉N₃OS | 208.0539 | 208.0 |  | ¹H NMR (400 MHz, CDCl₃): δ 8.81 (d, J = 5.1 Hz, 1H), 8.22 (s, 1H), 7.25 (s, 1H), 4.85 (d, J = 5.5 Hz, 2H), 3.22 (t, J = 5.3 Hz, 1H), 2.85 (s, 3H). |
| 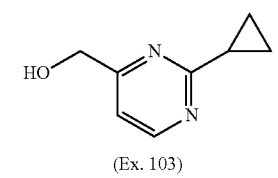 [SMILES: OCc1ccnc(C2CC2)n1]<br>(Ex. 103) | C₈H₁₀N₂O | 151.0866 | 151.2 | 0.889/F | ¹H NMR (400 MHz, CDCl₃): δ 8.51 (d, J = 5.1 Hz, 1H), 6.97-7.03 (m, 1 H), 4.69 (d, J = 5.1 Hz, 2H), 3.55 (t, J = 5.1 Hz, 1H), 2.27 (tt, J = 7.9, 4.8 Hz, 1H), 1.14-1.21 (m, 2H), 1.07-1.14 (m, 2H). |
| 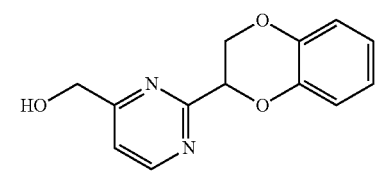<br>(Ex. 104) | C₁₃H₁₂N₂O₃ | 245.0921 | 245.2 | 1.739/F | ¹H NMR (400 MHz, CDCl₃): δ 8.77 (d, J = 5.1 Hz, 1 H), 7.32 (d, J = 5.1 Hz, 1 H), 7.05-7.12 (m, 1 H), 6.83-6.96 (m, 3 H), 5.43 (dd, J = 6.8, 2.5 Hz, 1 H), 4.80 (d, J = 5.1 Hz, 2 H), 4.63 (dd, J = 11.3, 2.3 Hz, 1 H), 4.48 (dd, J = 11.3, 7.0 Hz, 1 H), 3.08 (t, J = 5.3 Hz, 1 H). |
| 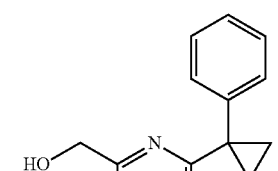<br>(Ex. 105) | C₁₄H₁₄N₂O | 227.1179 | 227.2 | 1.794/F | ¹H NMR (400 MHz, CDCl₃): δ 8.51 (d, J = 5.1 Hz, 1H), 7.40-7.47 (m, 2H), 7.33-7.40 (m, 2H), 7.28-7.33 (m, 1H), 6.93 (d, J = 5.1 Hz, 1H), 4.63 (d, J = 4.7 Hz, 2H), 3.59 (t, J = 4.9 Hz, 1H), 1.73-1.81 (m, 2H), 1.46 (q, J = 3.8 Hz, 2H). |

Examples 102 to 105

The following additional Examples have been prepared, isolated and characterized according to the method disclosed in Example 101.

| Ex. | Structure | Formula | Calc. [M + H]+ m/z | HPLC Retention Time (Min)/ Method | LCMS [M + H]+ m/z | NMR |
|---|---|---|---|---|---|---|
| 102 | 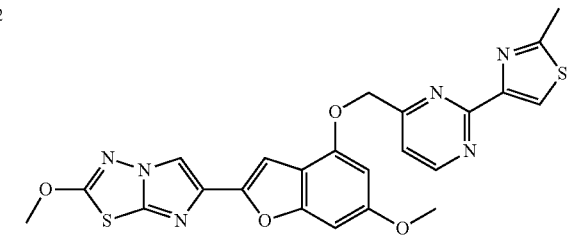 | C₂₃H₁₈N₆O₄S₂ | 507.0904 | 2.637/F | 507.0892 | ¹H NMR (400 MHz, DMSO-d₆): δ 8.90 (d, J = 5.1 Hz, 1H), 8.40 (s, 1H), 8.37 (s, 1H), 7.64 (d, J = 5.1 Hz, 1H), 7.14 (s, 1H), 6.87 (d, J = 0.8 Hz, 1H), 6.55 (d, J = 2.0 Hz, 1H), 5.41 (s, 2H), 4.21 (s, 3H), 3.80 (s, 3H), 2.75 (s, |

-continued

| Ex. | Structure | Formula | Calc. [M + H]+ m/z | HPLC Retention Time (Min)/ Method | LCMS [M + H]+ m/z | NMR |
|---|---|---|---|---|---|---|
| | | | | | | 3H). |
| 103 | 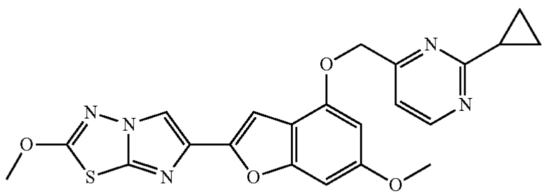 [SMILES: COc1cc(OCc2ccnc(C3CC3)n2)c2cc(-c3cn4nc(OC)sc4n3)oc2c1] | C22H19N5O4S | 450.1231 | 450.1218 | 2.585/F | 1H NMR (400 MHz, DMSO-d6): δ 8.66 (d, J = 5.1 Hz, 1H), 8.39 (s, 1H), 7.44 (d, J = 5.1 Hz, 1H), 7.09 (s, 1H), 6.85 (dd, J = 1.8, 1.0 Hz, 1H), 6.48 (d, J = 2.0 Hz, 1H), 5.27 (s, 2H), 4.21 (s, 3H), 3.79 (s, 3H), 2.15-2.26 (m, 1H), 0.95-1.11 (m, 4H). |
| 104 | 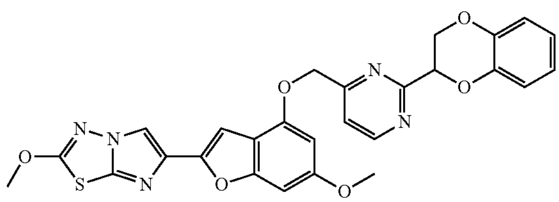 [SMILES: COc1cc(OCc2ccnc(C3COc4ccccc4O3)n2)c2cc(-c3cn4nc(OC)sc4n3)oc2c1] | C27H21N5O6S | 544.1285 | 544.1312 | 2.643/F | 1H NMR (400 MHz, DMSO-d6): δ 8.90 (d, J = 5.5 Hz, 1H), 8.39 (s, 1H), 7.75 (d, J = 5.1 Hz, 1H), 7.12 (s, 1H), 6.99 (dd, J = 7.8, 2.0 Hz, 1H), 6.80-6.94 (m, 4H), 6.53 (d, J = 2.0 Hz, 1H), 5.46 (dd, J = 6.7, 2.3 Hz, 1H), 5.39 (d, J = 2.7 Hz, 2H), 4.62 (dd, J = 11.5, 2.5 Hz, 1H), 4.44 (dd, J = 11.7, 6.7 Hz, 1H), 4.21 (s, 3H), 3.79 (s, 3H). |
| 105 | 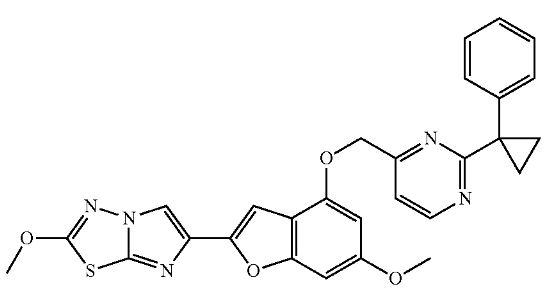 [SMILES: COc1cc(OCc2ccnc(C3(c4ccccc4)CC3)n2)c2cc(-c3cn4nc(OC)sc4n3)oc2c1] | C28H23N5O4S | 526.1544 | 526.1684 | 2.665/F | 1H NMR (400 MHz, DMSO-d6): δ 8.63 (d, J = 5.1 Hz, 1H), 8.39 (s, 1H), 7.44 (d, J = 5.1 Hz, 1H), 7.27-7.39 (m, 4H), 7.19-7.27 (m, 1H), 7.07 (s, 1H), 6.79-6.88 (m, 1H), 6.47 (d, J = 2.0 Hz, 1H), 5.23 (s, 2H), 4.21 (s, 3H), 3.79 (s, 3H), 1.64 (q, J = 3.4 Hz, 2H), 1.30-1.39 (m, 2H). |

Example 106

(2-(3-(((6-Methoxy-2-(2-methoxyimidazo[2,1-b][1,3,4]thiadiazol-6-yl)benzofuran-4-yl)oxy)methyl)phenyl)-5-methylthiazol-4-yl)methanol

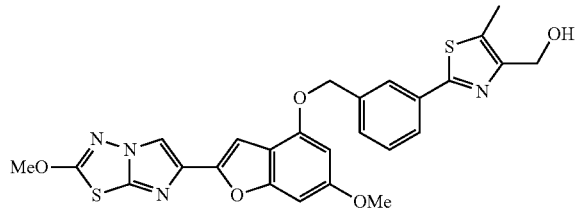 [SMILES: COc1cc(OCc2cccc(-c3nc(CO)c(C)s3)c2)c2cc(-c3cn4nc(OC)sc4n3)oc2c1]

106A. (2-Bromo-5-methylthiazol-4-yl)methanol

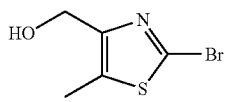

A solution of methyl 2-bromo-5-methylthiazole-4-carboxylate (1.00 g, 4.24 mmol) in tetrahydrofuran (20 mL) was cooled to 0° C. under nitrogen and treated with methanol (0.343 mL, 8.47 mmol) followed by lithium borohydride (0.185 g, 8.47 mmol), both added all at once. After 30 min, the cooling bath was removed and the resulting yellow solution was stirred at room temperature for 1.5 h. The reaction mixture was re-cooled at 0° C., quenched with acetic acid (6 drops) and water (1 mL) and vigorously stirred for 10 min. The resulting mixture was then diluted with dichloromethane (200 mL), washed with saturated aqueous sodium bicarbonate and brine, and dried over anhydrous magnesium sulfate. Concentration under reduced pressure afforded the title compound (0.83 g, 94%) as a white solid which was used as such in the next step. HRMS(ESI): Calcd for $C_5H_7BrNOS$ [M+H]$^+$ m/z 207.9426. found 207.9424. $^1$H NMR (CDCl$_3$, 400 MHz): δ 4.63 (s, 2H), 2.42 (s, 3H), 2.30 (br s, 1H).

106B. 2-Bromo-4-((((tert-butyldimethylsilyl)oxy)methyl)-5-methylthiazole

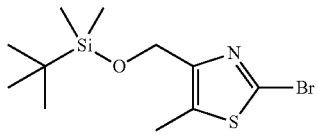 [SMILES: Cc1sc(Br)nc1CO[Si](C)(C)C(C)(C)C]

In a 250 mL round-bottomed flask, a solution of crude (2-bromo-5-methylthiazol-4-yl)methanol (0.825 g, 3.96 mmol) in DMF (10 mL) was maintained under vacuum (2 mbar) for 10 min. The flask was then flushed with nitrogen and charged with imidazole (0.540 g, 7.93 mmol), followed by TBS-Cl (0.896 g, 5.95 mmol), both added in one portion. The resulting clear solution was stirred at 23° C. for 18 h before the DMF was evaporated under reduced pressure and the residue was partitioned with ethyl acetate-saturated aqueous sodium bicarbonate. The organic phase was separated, washed with brine, dried over anhydrous magnesium sulfate and concentrated in vacuo. The resulting oil was chromatographed on silica gel (3×12 cm, elution with toluene) to give the title compound (1.05 g, 82%) as a clear oil. LCMS (APCI): calcd for $C_{11}H_{21}BrNOSSi$ [M+H]$^+$ m/z 322.03. found 322.0. $^1$H NMR (CDCl$_3$, 400 MHz): δ ppm 4.64 (s, 2H), 2.34 (s, 3H), 0.81 (s, 9H), 0.00 (s, 6H).

106C. (3-(4-4(tert-Butyldimethylsilyl)oxy)methyl)-5-methylthiazol-2-yl)phenyl)methanol

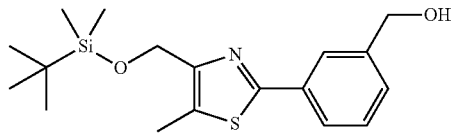 [SMILES: Cc1sc(-c2cccc(CO)c2)nc1CO[Si](C)(C)C(C)(C)C]

In a 75 mL glass pressure vial, a mixture of 2-bromo-4-(((tert-butyldimethylsilyl)oxy)-methyl)-5-methylthiazole (0.400 g, 1.241 mmol), (3-(hydroxymethyl)phenyl)boronic acid (0.283 g, 1.861 mmol) in toluene (14 mL) and EtOH (4 mL) was treated with 2 M Na$_2$CO$_3$ (0.745 mL, 1.489 mmol) and the resulting heterogeneous mixture was flushed with nitrogen for 10 min. Then Pd(dppf)Cl$_2$.DCM (0.061 g, 0.074 mmol) was added and the sealed vial was heated at 95° C. for 3 h. The cooled reaction mixture was partitioned between ethyl acetate (200 mL) and saturated aqueous sodium bicarbonate (25 mL). The organic phase was separated, washed with brine, dried over anhydrous magnesium sulfate and concentrated in vacuo. The brown syrup obtained was chromatographed on silica gel (gradient elution with toluene-ethyl acetate, 9:1 to 7:3) to give 0.365 g (84%) of the title compound as a white solid. LC (Method B): 2.375 min. $^1$H NMR (400 MHz, CDCl$_3$): δ ppm 7.89 (br s, 1H), 7.78-7.82 (m 1H), 7.37-7.45 (m, 2H), 4.85 (s, 2H), 4.76 (d, J=6.2 Hz, 2H), 2.53 (s, 3H), 1.73 (t, J=6.2 Hz, 1H), 0.94 (s, 9H), 0.13 (s, 6H).

106D. 6-(4-((3-(4-(((tert-Butyldimethylsilyl)oxy)methyl)-5-methylthiazol-2-yl)benzyl)oxy)-6-methoxybenzofuran-2-yl)-2-methoxyimidazo[2,1-b][1,3,4]thiadiazole

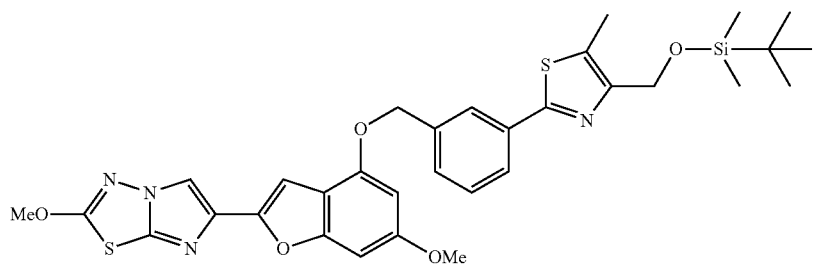 [SMILES: COc1cc(OCc2cccc(-c3nc(CO[Si](C)(C)C(C)(C)C)c(C)s3)c2)c2cc(-c3cn4nc(OC)sc4n3)oc2c1]

A mixture of 6-methoxy-2-(2-methoxyimidazo[2,1-b][1,3,4]thiadiazol-6-yl)benzofuran-4-ol (Example 1G, 0.070 g, 0.221 mmol) and (3-(4-(((tert-butyldimethylsilyl)oxy)methyl)-5-methylthiazol-2-yl)phenyl)methanol (0.081 g, 0.232 mmol) in a 50 mL round-bottomed flask fitted with an addition funnel was maintained under vacuum for 5 min. The flask was then flushed with nitrogen and charged with dry tetrahydrofuran (8 mL) and tri-n-butylphosphine (0.110 mL, 0.441 mmol), added in one portion. To this heterogeneous mixture was added a solution of (E)-diazene-1,2-diylbis(piperidin-1-ylmethanone) (0.067 g, 0.265 mmol) in tetrahydrofuran (3 mL), drop-wise over 1 h. After stirring at room temperature for another 4 h, the reaction mixture was partitioned between ethyl acetate (200 mL) and saturated aqueous sodium bicarbonate (20 mL). The organic phase was washed with brine, dried over anhydrous magnesium sulfate and concentrated in vacuo to give a glassy light yellow residue. This residue was chromatographed on silica gel (elution with toluene-ethyl acetate, 95:5 to 9:1) to give 0.116 g (66%) of the title compound as a white solid. LC (Method B): 2.829 min. $^1$H NMR (400 MHz, CDCl$_3$): δ ppm 7.97 (s, 1H), 7.85 (s, 1H), 7.84 (d, J=7.5 Hz, 1H), 7.53 (d, J=7.5 Hz, 1H), 7.44 (t, J=7.5 Hz, 1H), 7.11 (s, 1H), 6.71 (br s, 1H), 6.41 (d, J=1.6 Hz, 1H), 5.23 (s, 2H), 4.86 (s, 2H), 4.21 (s, 3H), 3.85 (s, 3H), 2.53 (s, 3H), 0.93 (s, 9H), 0.13 (s, 6H).

Example 106

(2-(3-((((6-Methoxy-2-(2-methoxyimidazo[2,1-b][1,3,4]thiadiazol-6-yl)benzofuran-4-yl)oxy)methyl)phenyl)-5-methylthiazol-4-yl)methanol

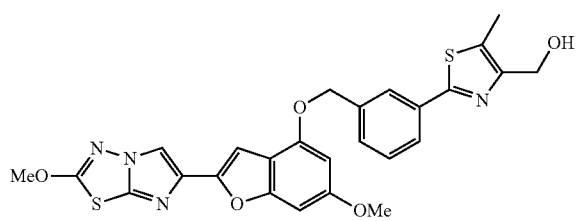 [SMILES: COc1cc(OCc2cccc(-c3nc(CO)c(C)s3)c2)c2cc(-c3cn4nc(OC)sc4n3)oc2c1]

In a 100 mL round-bottomed flask, a solution of 6-(4-((3-(4-(((tert-butyldimethylsilyl)oxy)methyl)-5-methylthiazol-2-yl)benzyl)oxy)-6-methoxybenzofuran-2-yl)-2-methoxyimidazo[2,1-b][1,3,4]thiadiazole (0.090 g, 0.139 mmol) in tetrahydrofuran (3 mL) was treated with triethylamine trihydrofluoride (0.11 mL, 0.69 mmol), added all at once, and the resulting clear solution was stirred at 23° C. for 18 h. The reaction was then quenched with saturated aqueous sodium bicarbonate (20 mL) and dichloromethane (100 mL) and the mixture was stirred for 30 min. The aqueous phase was separated and back-extracted with dichloromethane (2×30 mL) and the combined organic phase was washed with brine, dried over anhydrous magnesium sulfate and concentrated in vacuo to give a white solid. This material was crystallized from acetonitrile to give 0.069 g (93%) of the title compound as a white solid. LC (Method B): 2.456 min. HRMS(ESI): Calcd for C$_{26}$H$_{23}$N$_4$O$_5$S$_2$ [M+H]$^+$ m/z 535.1104. found 535.1114. $^1$H NMR (400 MHZ, DMSO-d$_6$): δ ppm 8.40 (s, 1H), 8.02 (s, 1H), 7.84 (br d, J=7.8 Hz, 1H), 7.58 (br d, J=7.8 Hz, 1H), 7.54 (t, J=7.8 Hz, 1H), 7.02 (br d, 1H), 6.84-6.87 (m, 1H), 6.57 (d, J=2.0 Hz, 1H), 5.36 (s, 2H), 5.13 (t, J=4.8 Hz, 1H), 4.55 (d, J=4.8 Hz, 2H), 4.22 (s, 3H), 3.81 (s, 3H), 2.50 (s, 3H).

Example 107

6-(6-Chloro-4-((3-(2-methoxypyrimidin-5-yl)benzyl)oxy)benzofuran-2-yl)-2-methoxyimidazo[2,1-b][1,3,4]thiadiazole

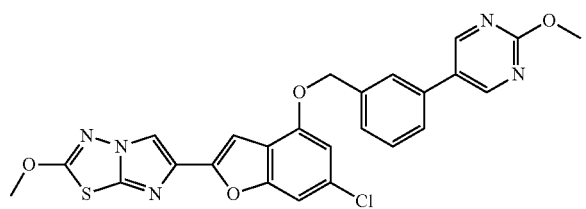

107A. 4-Chloro-2,6-dimethoxybenzaldehyde

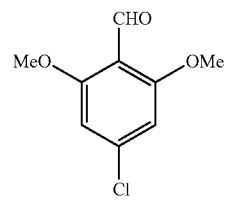 [SMILES: COc1cc(Cl)cc(OC)c1C=O]

A solution of 1-chloro-3,5-dimethoxybenzene (5 g, 29.0 mmol) and TMEDA (4.37 mL, 29.0 mmol) in diethyl ether (100 mL, 962 mmol) at −78° C. under N$_2$ atmosphere was charged with BuLi (19.91 mL, 31.9 mmol) dropwise over a period of 30 minutes using a syringe pump. After stirring for 4 hours at −78° C., DMF was added and the reaction mixture continued to stir for 1.5 hours after which 1N HCl (~30 mL) was added (all at −78° C.). The reaction mixture was warmed to room temperature and extracted withy ethyl acetate. The organic phase was dried (MgSO$_4$), filtered and concentrated to dryness. The residue was purified by ISCO using hexanes/EtOAc as eluent. Fractions containing the desired product were concentrated to dryness to give the title material (1.97 g, 9.82 mmol, 33.9% yield) as a light yellow solid. LC (Method B): 1.924 min. LCMS (APCI): calcd for C$_9$H$_{10}$ClO$_3$ [M+H]$^+$ m/z 201.03. found 201.0. $^1$H NMR (CDCl$_3$, 400 MHz): δ ppm 10.28 (s, 1H), 6.87 (s, 2H), 3.86 (s, 6H).

107B. 4-Chloro-2-hydroxy-6-methoxybenzaldehyde

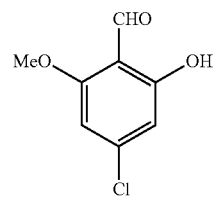 [SMILES: COc1cc(Cl)cc(O)c1C=O]

A stirred solution of 4-chloro-2,6-dimethoxybenzaldehyde (1.95 g, 9.72 mmol) in DCM (20 mL, 311 mmol) at -78° C. was slowly added boron tribromide (9.72 mL, 9.72 mmol). The reaction mixture was stirred at -78° C. for 10 minutes then warmed to r.t. and stirred for 1 hour while monitoring reaction progress by LCMS. Once all s.m. had been consumed, the reaction was quenched with water and extracted with DCM. The organic phase was washed with brine, dried (MgSO$_4$), filtered and concentrated to dryness to give the title material (1.79 g, 9.59 mmol, 99% yield) as a purple solid. LC (Method B): 2.199 min. LCMS (APCI): calcd for C$_8$H$_8$ClO$_3$ [M+H]$^+$ m/z 187.02. found 187.0. $^1$H NMR (CDCl$_3$, 400 MHz) δ ppm: 11.89 (s, 1H), 10.20 (s, 1H), 6.75 (t, J=2.0 Hz, 1H), 6.66 (m, 1H), 3.91 (s, 1H).

107C.
1-(6-Chloro-4-methoxybenzofuran-2-yl)ethanone

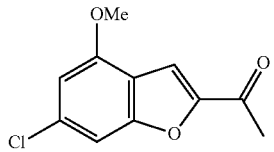

A stirred solution of 4-chloro-2-hydroxy-6-methoxybenzaldehyde (1.79 g, 9.59 mmol) in N,N-dimethylformamide (15 mL, 9.59 mmol) was charged with cesium carbonate (3.75 g, 11.51 mmol) and 1-chloropropan-2-one (0.975 mL, 11.51 mmol). The reaction mixture was heated in a sealable vessel at 65° C. for 7 hours, was filtered over a Whatman filter paper to remove insolubles rinsing with DCM then washed with sat. NaHCO$_3$. The organic phase was dried (MgSO$_4$), filtered and concentrated to dryness. The residue was purified by ISCO using hexanes/EtOAc as eluent. Fractions containing the desired product were concentrated to give the title material (1.43 g, 6.37 mmol, 66% yield) as a light yellow solid. LC (Method A): 1.952 min. LCMS (APCI) calcd for C$_{11}$H$_{10}$ClO$_3$ [M+H]$^+$ m/z 225.03. found 225.0. $^1$H NMR (CDCl$_3$, 400 MHz) δ ppm: 7.94 (d, J=0.8 Hz, 1H), 7.49 (dd, J=0.8, 1.6 Hz, 1H), 6.97 (d, J=1.6 Hz, 1H), 3.97 (s, 3H).

107D.
1-(6-Chloro-4-hydroxybenzofuran-2-yl)ethanone

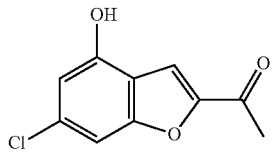

To a stirred solution of 1-(6-chloro-4-methoxybenzofuran-2-yl)ethanone (1.43 g, 6.37 mmol) in chlorobenzene (15 mL, 148 mmol) was added aluminum chloride (3.40 g, 25.5 mmol) in portions over a period of 10 minutes. The reaction vessel was then sealed and heated at 100° C. for 40 minutes, then cool to r.t. and poured onto crushed ice (rinsed stirring bar with EtOAc). This was stirred for 30 minutes, then extracted with ethyl acetate. The organic phase was dried (MgSO$_4$), filtered and concentrated to dryness. The residue was purified by ISCO using hexanes/EtOAc as eluent. Fractions containing the desired product were concentrated to give the title material (1.18 g, 5.60 mmol, 88% yield) as a light brown solid. LC (Method A): 1.783 min. LCMS (APCI): calcd for C$_{10}$H$_8$ClO$_3$ [M+H]$^+$ m/z 211.02. found 211.0. $^1$H NMR (CDCl$_3$, 400 MHz): δ ppm 11.01 (s, 1H), 7.89 (s, 1H), 6.72 (s, 1H), 2.52 (s, 3H).

107E.
1-(4-(Benzyloxy)-6-chlorobenzofuran-2-yl)ethanone

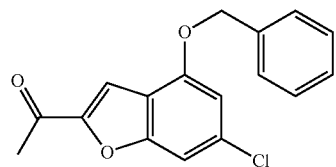 [SMILES: CC(=O)c1cc2c(OCc3ccccc3)cc(Cl)cc2o1]

A stirred solution of 1-(6-chloro-4-hydroxybenzofuran-2-yl)ethanone (1.18 g, 5.60 mmol) in dry DMF (10 mL, 129 mmol) at r.t. was charged with K$_2$CO$_3$ (0.774 g, 5.60 mmol) and DMF. The reaction mixture was stirred for 1.5 hours then partitioned between ethyl acetate and water. The organic phase was washed with brine, dried (MgSO$_4$), filtered and concentrated to dryness. The residue was purified by ISCO using hexanes/EtOAc as eluent. Fractions containing the desired product were concentrated to give the title material (1.57 g, 5.22 mmol, 93% yield) as an amber colored oil. LC (Method B): 2.420 min. LCMS (APCI): calcd for C$_{17}$H$_{14}$ClO$_3$ [M+H]$^+$ m/z 301.06. found 301.0. $^1$H NMR (CDCl$_3$, 400 MHz): δ ppm 8.00 (d, J=0.8 Hz, 1H), 7.53 (m, 3H), 7.44 (m, 2H), 7.38 (m, 1H), 7.10 (d, J=1.6 Hz, 1H), 5.53 (s, 2H), 2.54 (s, 3H).

107F. 1-(4-(Benzyloxy)-6-chlorobenzofuran-2-yl)-2-bromoethanone

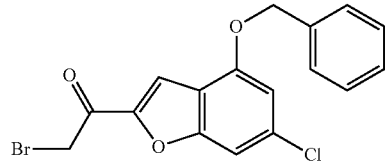 [SMILES: O=C(CBr)c1cc2c(OCc3ccccc3)cc(Cl)cc2o1]

A flame dried 200 ml round-bottom flask equipped with a stirring bar and under nitrogen atmosphere was charged with anhydrous THF (12 mL) followed by lithium bis(trimethylsilyl)amide (6.22 mL, 6.22 mmol). The mixture was cooled to -78° C. and treated with a solution of 1-(4-(benzyloxy)-6-chlorobenzofuran-2-yl)ethanone (1.56 g, 5.19 mmol) in THF (6 ml+2 ml washing) added dropwise over 10 minutes via a syringe pump. The resulting mixture was stirred at -78° C. for 45 minutes and was then charged with trimethylchlorosilane (0.769 mL, 6.02 mmol) added dropwise over 5 minutes by syringe pump then stirred for another 20 minutes. The cooling bath was removed and the mixture was allowed to warm to +10° C. for 30 minutes. The reaction mixture was quenched with a mixture of cold ethyl acetate (80 mL), sat. NaHCO$_3$ (12 mL) and ice. The organic phase was dried (MgSO$_4$), stirring for ~5 minutes to remove all traces of water), filtered and concentrated to dryness to give the silyl enol ether as a yellow oil which was co-evaporated with toluene (4 mL). The silyl enol ether was dissolved in dry THF (20 mL), cooled to -30° C. (employing a cooling bath made from 1:1 CaCl$_2$: water using dry ice, bath stabilizes around −30 to −45° C.) and treated with NaHCO₃ (~50 mgs) followed by N-bromosuccinimide (0.923 g, 5.19 mmol) added in small portions over 15 minutes. The reaction mixture was allowed to warm to 0° C. over 2 hours (monitored by LCMS) and then quenched by addition of ethyl acetate (100 mL) and sat. NaHCO₃. The organic phase was washed with brine, dried (MgSO₄) and evaporated to give an orange solid which was purified by ISCO using hexanes/EtOAc as eluent. Fractions containing the desired product were concentrated to give the title material 1.48 g, 3.51 mmol, 67.6% yield) as a yellow solid. LC (Method B): 2.528 min. LCMS (APCI): calcd for C₁₇H₁₃BrClO₃ [M+H]⁺ m/z 378.97. found 379.0.

107G. 6-(4-(Benzyloxy)-6-chlorobenzofuran-2-yl)-2-bromoimidazo[2,1-b][1,3,4]thiadiazole

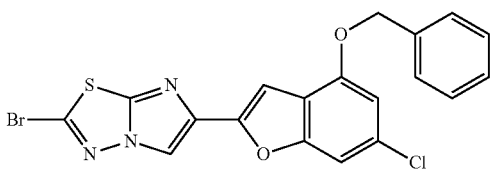 [SMILES: Clc1cc(OCc2ccccc2)c2cc(-c3cn4nc(Br)sc4n3)oc2c1]

A sealable vessel was charged with 1-(4-(benzyloxy)-6-chlorobenzofuran-2-yl)-2-bromoethanone (1.48 g, 3.51 mmol), 5-bromo-1,3,4-thiadiazol-2-amine (0.632 g, 3.51 mmol) and IPA (25 mL, 324 mmol). The reaction mixture was heated in an oil bath at 80° C. for 6 hours then heated in the microwave at 150° C. for 1 hour. The reaction mixture was allowed to stand for 1 hour and the insoluble material was filtered off and rinsed with MeOH to give the desired product as a brown solid (1.19 g, 2.58 mmol, 73.6% yield). LC (Method A): 2.549 min. LCMS (APCI): calcd for C₁₉H₁₂BrClN₃O₂S [M+H]⁺ m/z 459.95. found 460.0. ¹H NMR (CDCl₃, 400 MHz): δ ppm 8.74 (s, 1H), 7.55–7.50 (m, 2H), 7.45–7.34 (m, 4H), 7.17 (d, J=0.8 Hz, 1H), 7.02 (d, J=1.6 Hz, 1H), 5.32 (s, 2H).

107H. 6-(4-(Benzyloxy)-6-chlorobenzofuran-2-yl)-2-methoxyimidazo[2,1-b][1,3,4]thiadiazole

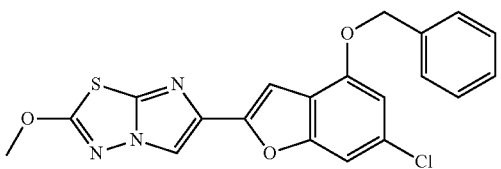 [SMILES: COc1nn2cc(-c3cc4c(OCc5ccccc5)cc(Cl)cc4o3)nc2s1]

To a stirred solution of 6-(4-(benzyloxy)-6-chlorobenzofuran-2-yl)-2-bromoimidazo[2,1-b][1,3,4]thiadiazole (1.18 g, 2.56 mmol) in DCM (40 mL, 622 mmol) and methanol (10 mL, 247 mmol) was added sodium methoxide (1.164 mL, 5.12 mmol). The reaction mixture was stirred at r.t. for 1 h 15 min while monitoring by TLC (7:3 hexanes: EtOAc). The reaction mixture was quenched with 1N HCl and extracted with DCM. The organic phase was washed with brine, dried (MgSO₄), filtered and concentrated to dryness. The residue was triturated with MeOH (sonication) and the solid material was filtered off, rinsed with MeOH and sucked dry to give the desired compound as a brown solid (859 mg, 2.086 mmol, 81% yield). LC (Method A): 2.478 min. LCMS (APCI): calcd for C₂₀H₁₅ClN₃O₃S [M+H]⁺ m/z 412.05. found 412.0. ¹H NMR (CDCl₃, 400 MHz) δ ppm: 8.50 (s, 1H), 7.52 (m, 2H), 7.43 (m, 2H), 7.36 (m, 2H), 7.09 (d, J=0.8 Hz, 1H), 7.00 (d, J=1.6 Hz, 1H), 5.31 (s, 2H), 4.21 (s, 3H).

107I. 6-Chloro-2-(2-methoxyimidazo[2,1-b][1,3,4]thiadiazol-6-yl)benzofuran-4-ol

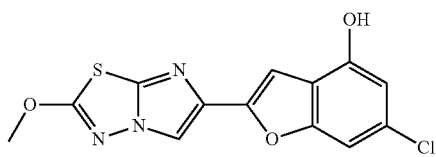 [SMILES: COc1nn2cc(-c3cc4c(O)cc(Cl)cc4o3)nc2s1]

A stirred solution of 6-(4-(benzyloxy)-6-chlorobenzofuran-2-yl)-2-methoxyimidazo[2,1-b][1,3,4]thiadiazole (0.85 g, 2.064 mmol) and pentamethylbenzene (2.142 g, 14.45 mmol) in DCM under N₂ atmosphere was cooled to −78° C. after which boron trichloride (5.16 mL, 5.16 mmol) was added dropwise over ~4 minutes. The reaction was monitored by TLC using 1:1 hexanes-EtOAc as eluent. The reaction mixture was stirred at −78° C. for 30 minutes after which a mixture of water (40 mL) and saturated NaHCO₃ (5 mL) was added (at −78° C.) and the mixture was stirred until ambient temperature was obtained (removed from cooling bath). The solid precipitate was filtered off and rinsed with diethyl ether then allowed to dry overnight to give the title material (441 mgs, 1.371 mmol, 66.4% yield) as a beige solid. The filtrate was extracted with DCM. The organic phase was washed with brine, dried (MgSO₄) and concentrated to dryness. The residue was purified by ISCO using DCM/EtOAc as eluent. Fractions containing the desired product were concentrated to give the title material (25 mgs, 0.078 mmol, 3.77% yield) as a beige solid. LC (Method A): 2.167 min. LCMS (APCI): calcd for C₁₃H₉ClN₃O₃S [M+H]⁺ m/z 322.00. found 322.0. ¹H NMR (CDCl₃, 400 MHz): δ ppm 10.50 (br s, 1H), 8.45 (s, 1H), 7.17 (dd, J=0.8, 1.6 Hz, 1H), 7.09 (d, J=0.8 Hz, 1H), 6.67 (d, J=2.0 Hz, 2H), 4.21 (s, 3H).

Example 107

6-(6-Chloro-4-((3-(2-methoxypyrimidin-5-yl)benzyl)oxy)benzofuran-2-yl)-2-methoxyimidazo[2,1-b][1,3,4]thiadiazole

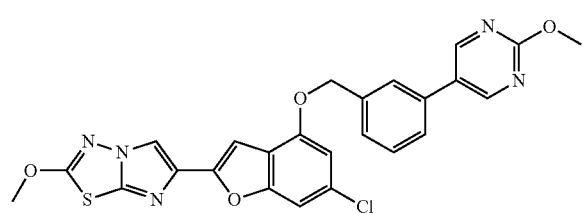

To a flame-dried 100 mL round-bottomed flask containing 6-chloro-2-(2-methoxyimidazo[2,1-b][1,3,4]thiadiazol-6-yl)benzofuran-4-ol (0.025 g, 0.078 mmol) and (3-(2-methoxypyrimidin-5-yl)phenyl)methanol (0.042 g, 0.194 mmol) in dry THF (4 mL) was added tri-n-butylphosphine (0.050 mL, 0.194 mmol). To this mixture was added a solution of ADDP (0.049 g, 0.194 mmol) in dry THF (1 mL)

dropwise over 30 min (via syringe pump). After stirring for 1.5 h at room temperature and then heating to reflux for 2 h, tri-n-butylphosphine (0.050 mL, 0.194 mmol) and ADDP (0.049 g, 0.194 mmol) were again added and heating at reflux was continued for 1.5 h. The cooled mixture was diluted with EtOAc, then washed with saturated aqueous NaHCO₃, water and brine. The organic phase was dried (MgSO₄), then concentrated to dryness and the residue was purified using the ISCO (gradient, 0 to 10% diethyl ether-DCM). Fractions containing the desired product were concentrated to give a beige solid which was further triturated with acetonitrile to give (after filtration and drying in vacuo) the title compound (0.026 g, 64.4%) as a white solid. LC (Method A): 2.476 min. HRMS(ESI): calcd for C₂₅H₁₉ClN₅O₄S [M+H]⁺ m/z 520.0846. found 520.0865. ¹H NMR (DMSO-d₆, 400 MHz): δ ppm 8.97 (s, 2H), 8.49 (s, 1H), 7.89 (br s, 1H), 7.73 (dt, J=2.3, 5.9 Hz, 1H), 7.59-7.54 (m, 2H), 7.39 (br s, 1H), 7.13 (d, J=0.8 Hz, 1H), 7.05 (dd, J=0.4, 1.6 Hz, 1H), 5.37 (s, 2H), 4.20 (s, 3H), 3.98 (s, 3H).

Example 108

6-(6-Chloro-4-((3-(5-methoxypyrazin-2-yl)benzyl) oxy)benzofuran-2-yl)-2-methoxyimidazo[2,1-b][1,3,4]thiadiazole

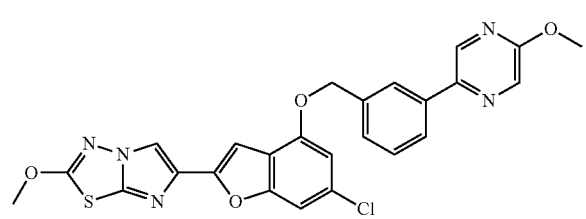

The title compound was prepared according to the method described in Example 107 above. LC (Method A): 2.601 min. HRMS(ESI): calcd for C₂₅H₁₈ClN₅O₄S [M+H]⁺ m/z 520.0841. found 520.0845. ¹H NMR (DMSO-d₆, 400 MHz): δ ppm 8.84 (d, J=1.2 Hz, 1H), 8.50 (s, 1H), 8.41 (d, J=1.6 Hz, 1H), 8.18 (m, 1H), 8.01 (dt, J=1.8, 7.4 Hz, 1H), 7.60-7.54 (m, 2H), 7.38 (dd, J=0.8, 1.6 Hz, 1H), 7.11 (d, J=0.8 Hz, 1H), 7.04 (d, J=1.6 Hz, 1H), 5.39 (s, 2H), 4.21 (s, 3H), 3.97 (s, 3H).

Example 109

4-(6-(((6-Methoxy-2-(2-methoxyimidazo[2,1-b][1,3,4]thiadiazol-6-yl)benzo-furan-4-yl)oxy)methyl)pyridin-2-yl)tetrahydro-2H-pyran-4-ol

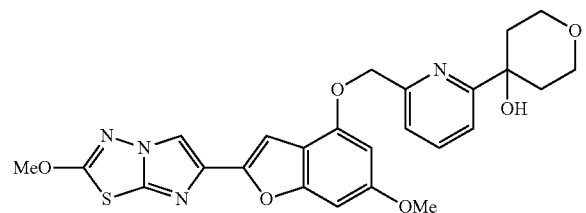

109A. 2-Bromo-6-(((tert-butyldimethylsilyl)oxy) methyl)pyridine

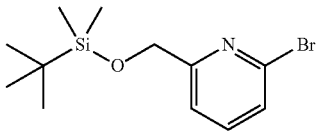 [SMILES: CC(C)(C)[Si](C)(C)OCc1cccc(Br)n1]

To a solution of (6-bromopyridin-2-yl)methanol (2.27 g, 12.07 mmol) and imidazole (2.466 g, 36.2 mmol) in DMF (50 mL) under N₂ was added tert-butyldimethylchlorosilane (2.002 g, 13.28 mmol) and the resulting mixture was stirred at room temperature under N₂ for 18 h. The solution was then concentrated under reduced pressure and the residual oil was partitioned with EtOAc—H₂O. The organic phase was separated, washed (H₂O, brine), dried (Na₂SO₄) and evaporated to give 2-bromo-6-(((tert-butyldimethylsilyl)-oxy)methyl)pyridine (3.65 g, 100%) as a nearly colorless oil which was used as such in the next step. LC (Method A): 2.446 min. LCMS (APCI): calcd for C₁₂H₂₁BrNOSi [M+H]⁺ m/z 302.058. found 302.1. ¹H NMR (400 MHz, CDCl₃): δ 7.45 (t, J=7.83 Hz, 1H), 7.36 (d, J=7.83 Hz, 1H), 7.22 (d, J=7.83 Hz, 1H), 4.69 (s, 2H), 0.84 (s, 9H), 0.00 (s, 6H).

109B. 4-(6-(((tert-Butyldimethylsilyl)oxy)methyl) pyridin-2-yl)tetrahydro-2H-pyran-4-ol

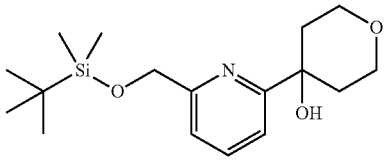 [SMILES: CC(C)(C)[Si](C)(C)OCc1cccc(C2(O)CCOCC2)n1]

A solution of 2-bromo-6-(((tert-butyldimethylsilyl)oxy) methyl)pyridine (1.209 g, 4.000 mmol) in dry THF (7 mL) was cooled at −78° C. under N₂ and then n-butyllithium (1.45 M in hexanes, 3.03 mL, 4.40 mmol) was added dropwise. The resulting mixture was stirred for 30 min to give a brown solution. To this mixture was slowly added a solution of dihydro-2H-pyran-4(3H)-one (0.443 mL, 4.80 mmol) in dry THF (2 mL) and the mixture was kept at −78° C. for 1 h to give a pale amber solution. The reaction was then quenched by the addition of saturated aqueous NH₄Cl (5 mL) and the mixture was partitioned with EtOAc-water. The organic phase was separated, the aqueous phase was back-extracted with EtOAc and the combined organic phase was washed (brine), dried (Na₂SO₄) and evaporated to give a pale yellow oil. Flash chromatography (Isco/0-40% EtOAc-hexane) afforded 4-(6-(((tert-butyldimethylsilyl) oxy)methyl)pyridin-2-yl)tetrahydro-2H-pyran-4-ol (0.728 g, 56.3%) as a colorless oil. LC (Method A): 2.084 min. HRMS(ESI): calcd for C₁₇H₃₀NO₃Si [M+H]⁺ m/z 324.1995. found 324.2076. ¹H NMR (400 MHz, DMSO-d₆): δ 7.72 (t, J=7.83 Hz, 1H), 7.45 (d, J=7.43 Hz, 1H), 7.19 (d, J=7.43 Hz, 1H), 5.14 (s, 1H), 4.64 (s, 2H), 3.68-3.59 (m, 4H), 2.07 (ddd, J=5.87, 11.74, 12.91 Hz, 2H), 1.32 (d, J=11.74 Hz, 1H), 0.82 (s, 9H), 0.00 (s, 6H).

109C. 4-(6-(Hydroxymethyl)pyridin-2-yl)tetrahydro-2H-pyran-4-ol

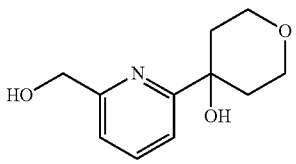 [SMILES: OCc1cccc(C2(O)CCOCC2)n1]

To a solution of 4-(6-(((tert-butyldimethylsilyl)oxy)methyl)pyridin-2-yl)tetrahydro-2H-pyran-4-ol (Example XB, 0.403 g, 1.246 mmol) in dry THF (10 mL) under $N_2$ was added triethylamine trihydrofluoride (1.014 mL, 6.23 mmol) dropwise and the mixture was stirred at room temperature for 16 h. The mixture was then diluted with DCM and the solution was washed (saturated aqueous $NaHCO_3$), dried ($Na_2SO_4$) and evaporated to give 4-(6-(hydroxymethyl)pyridin-2-yl)tetrahydro-2H-pyran-4-ol (0.199 g, 76%) as a colorless gum which solidified on standing. LC (Method A): 1.252 min. HRMS(ESI): calcd for $C_{11}H_{16}NO_3$ $[M+H]^+$ m/z 210.1130. found 210.1132. $^1$H NMR (400 MHz, DMSO-$d_6$): δ 7.75 (t, J=7.83 Hz, 1H), 7.48 (d, J=7.43 Hz, 1H), 7.29 (d, J=7.43 Hz, 1H), 5.32 (t, J=5.87 Hz, 1H), 5.20 (s, 1H), 4.51 (d, J=5.48 Hz, 2H), 3.75-3.66 (m, 4H), 2.13 (m, 2H), 1.38 (d, J=12.13 Hz, 2H).

Example 109

4-(6-(((6-Methoxy-2-(2-methoxyimidazo[2,1-b][1,3,4]thiadiazol-6-yl)benzofuran-4-yl)oxy)methyl)pyridin-2-yl)tetrahydro-2H-pyran-4-ol

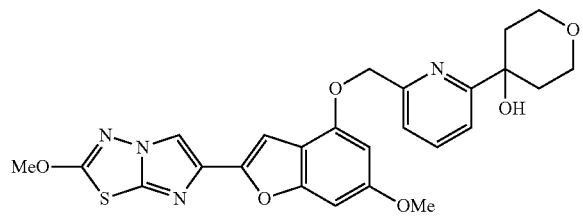

To a flame-dried flask was added 6-methoxy-2-(2-methoxyimidazo[2,1-b][1,3,4]thiadiazol-6-yl)benzofuran-4-ol (Example 1G, 0.052 g, 0.165 mmol) and 4-(6-(hydroxymethyl)pyridin-2-yl)tetrahydro-2H-pyran-4-ol (0.052 g, 0.248 mmol), then the flask was flushed with $N_2$ and dry THF (3 mL) was added. To the resulting suspension was added tri-n-butylphosphine (0.107 mL, 0.413 mmol) and then a solution of 1,1'-(azodicarbonyl)dipiperidine (0.105 g, 0.413 mmol) in dry THF (2 mL) was added dropwise (via syringe pump) over 30 min. The resulting mixture was stirred at room temperature for another 30 min and then it was diluted with EtOAc, washed (saturated aqueous $NaHCO_3$, $H_2O$, brine), dried ($Na_2SO_4$) and evaporated to give a pale yellow solid. This material was triturated with a minimum volume of DCM and the resulting suspension was filtered and the filter-cake was washed with DCM, then MeOH and finally DCM. The filter-cake was dried in vacuo to give pure 4-(6-(((6-methoxy-2-(2-methoxyimidazo[2,1-b][1,3,4]thiadiazol-6-yl)benzofuran-4-yl)oxy)-methyl)pyridin-2-yl)tetrahydro-2H-pyran-4-ol (0.055 g, 65.5%) as a cream solid. LC (Method A): 2.241 min. HRMS(ESI): calcd. for $C_{25}H_{25}N_4O_6S$ $[M+H]^+$ m/z 509.1495. found 509.1517. $^1$H NMR (400 MHz, DMSO-$d_6$): δ 8.35 (s, 1H), 7.83 (t, J=7.83 Hz, 1H), 7.60 (d, J=7.83 Hz, 1H), 7.43 (d, J=7.83 Hz, 1H), 6.99 (s, 1H), 6.79 (s, 1H), 6.51 (d, J=1.57 Hz, 1H), 5.28 (s, 2H), 5.26 (s, 1H), 4.17 (s, 3H), 3.76-3.69 (m, 4H), 3.75 (s, 3H), 2.19 (m, 2H), 1.43 (d, J=12.91 Hz, 2H).

Example 110

(S)-4-(6-(((2-(2-(1-Fluoroethyl)imidazo[2,1-b][1,3,4]thiadiazol-6-yl)-6-methoxybenzofuran-4-yl)oxy)methyl)pyridin-2-yl)tetrahydro-2H-pyran-4-ol

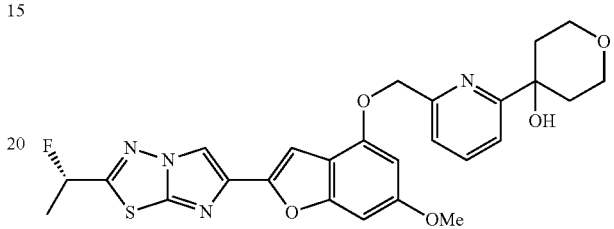

To a flame-dried flask was added (S)-2-(2-(1-fluoroethyl)imidazo[2,1-b][1,3,4]thiadiazol-6-yl)-6-methoxybenzofuran-4-ol (Example 64C, 0.045 g, 0.135 mmol) and 4-(6-(hydroxymethyl)pyridin-2-yl)tetrahydro-2H-pyran-4-ol (Example 109C, 0.034 g, 0.162 mmol), then the flask was flushed with $N_2$ and dry THF (3 mL) was added. To the resulting suspension was added tri-n-butylphosphine (0.088 mL, 0.337 mmol) and then a solution of 1,1'-(azodicarbonyl)dipiperidine (0.086 g, 0.337 mmol) in dry THF (2 mL) was added dropwise (via syringe pump) over 30 min. The resulting mixture was stirred at room temperature for another 1 h and then it was diluted with EtOAc, washed (saturated aqueous $NaHCO_3$, $H_2O$, brine), dried ($Na_2SO_4$) and evaporated to give a yellow gum. Flash chromatography (Isco/0-40% ether-DCM) gave (S)-4-(6-(((2-(2-(1-fluoroethyl)imidazo[2,1-b][1,3,4]thia-diazol-6-yl)-6-methoxybenzofuran-4-yl)oxy)-methyl)pyridin-2-yl)tetrahydro-2H-pyran-4-ol (0.060 g, 85%) as a cream solid. LC (Method A): 2.283 min. HRMS(ESI): calcd for $C_{26}H_{26}FN_4O_5S$ $[M+H]^+$ m/z 525.1608. found 525.1646. $^1$H NMR (400 MHz, DMSO-$d_6$): δ 8.58 (s, 1H), 7.83 (t, J=7.83 Hz, 1H), 7.60 (d, J=7.83 Hz, 1H), 7.44 (d, J=7.83 Hz, 1H), 7.10 (s, 1H), 6.81 (s, 1H), 6.52 (d, J=1.96 Hz, 1H), 6.13 (dq, J=6.26, 46.95 Hz, 1H), 5.29 (s, 2H), 5.23 (s, 1H), 3.76 (s, 3H), 3.71 (m, 4H), 3.75 (s, 3H), 2.20 (m, 2H), 1.76 (dd, J=6.26, 24.65 Hz, 3H), 1.43 (d, J=12.52 Hz, 2H).

Example 111

2-Methoxy-6-(6-methoxy-4-((6-(4-methoxytetrahydro-2H-pyran-4-yl)pyridin-2-yl)methoxy)benzofuran-2-yl)imidazo[2,1-b][1,3,4]thiadiazole

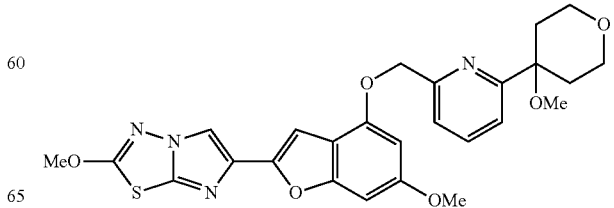

111A. 2-4(tert-Butyldimethylsilyl)oxy)methyl)-6-(4-methoxytetrahydro-2H-pyran-4-yl)pyridine

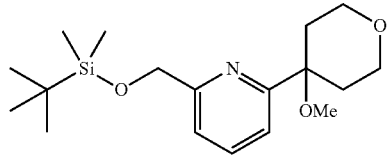

To a suspension of sodium hydride (0.047 g, 1.168 mmol) [Note: 60% NaH in oil was washed free of oil with hexane (×2) before dry THF was added to the reaction flask] in dry THF (1 mL) under $N_2$ was added a solution of 4-(6-(((tert-butyldimethylsilyl)oxy)methyl)pyridin-2-yl)tetrahydro-2H-pyran-4-ol (Example 109B, 0.189 g, 0.584 mmol) in dry THF (4 mL) and the mixture was stirred at room temperature for 30 min to give a light yellow turbid mixture, with no more gas evolution being observed. To the resulting mixture was added iodomethane (0.044 mL, 0.701 mmol) dropwise and stirring was continued at room temperature for 18 h. The reaction mixture was then quenched by the careful addition of saturated aqueous $NH_4Cl$ (5 mL) and the mixture was partitioned with EtOAc-water. The organic phase was separated, dried ($Na_2SO_4$) and evaporated to give a pale yellow gum. Flash chromatography (Isco/0-50% EtOAc-hexane) afforded 2-(((tert-butyldimethylsilyl)oxy)methyl)-6-(4-methoxytetrahydro-2H-pyran-4-yl)pyridine (0.175 g, 89%) as a colorless oil which was used as such in the next step. LC (Method A): 2.397 min. HRMS(ESI): calcd for $C_{18}H_{32}NO_3Si$ $[M+H]^+$ m/z 338.2151. found: 338.2205. $^1H$ NMR (400 MHz, DMSO-$d_6$): δ 7.76 (t, J=7.83 Hz, 1H), 7.29 (d, J=7.83 Hz, 1H), 7.25 (d, J=7.83 Hz, 1H), 4.65 (s, 2H), 3.57 (dd, J=2.74, 8.22 Hz, 4H), 2.85 (s, 3H), 2.05 (dt, J=8.22, 13.69 Hz, 4H), 1.79 (m, 2H), 0.82 (s, 9H), 0.00 (s, 6H).

111B. (6-(4-Methoxytetrahydro-2H-pyran-4-yl)pyridin-2-yl)methanol

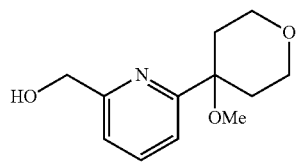 [SMILES: COC1(c2cccc(CO)n2)CCOCC1]

To a solution of 2-4(tert-butyldimethylsilyl)oxy)methyl)-6-(4-methoxytetrahydro-2H-pyran-4-yl)pyridine (0.171 g, 0.507 mmol) in dry THF (10 mL) under $N_2$ was added triethylamine trihydrofluoride (0.412 mL, 2.53 mmol) dropwise and the mixture was stirred at room temperature for 16 h. The mixture was then diluted with DCM and the solution was washed (saturated aqueous $NaHCO_3$), dried ($Na_2SO_4$) and evaporated to give (6-(4-methoxytetrahydro-2H-pyran-4-yl)pyridin-2-yl)methanol (0.112 g, 99%) as a colorless gum which crystallized on standing. This material was essentially pure and was used as such in the next step. LC (Method A): 0.869 min. HRMS(ESI): calcd for $C_{12}H_{16}NO_3$ $[M+H]^+$ m/z 224.1287. found 224.1304. $^1H$ NMR (400 MHz, DMSO-$d_6$): δ 7.79 (t, J=7.83 Hz, 1H), 7.34 (d, J=7.83 Hz, 1H), 7.32 (d, J=7.83 Hz, 1H), 5.33 (t, J=5.48 Hz, 1H), 4.52 (d, J=5.48 Hz, 2H), 3.64 (m, 4H), 2.93 (s, 3H), 2.05 (m, 2H), 1.79 (m, 2H).

Example 111

2-Methoxy-6-(6-methoxy-4-((6-(4-methoxytetrahydro-2H-pyran-4-yl)pyridin-2-yl)methoxy)benzofuran-2-yl)imidazo[2,1-b][1,3,4]thiadiazole

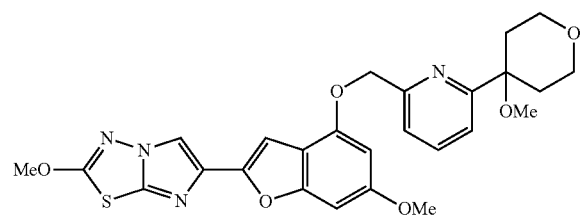 [SMILES: COc1cc(OCc2cccc(C3(OC)CCOCC3)n2)c2cc(-c3cn4nc(OC)sc4n3)oc2c1]

To a flame-dried flask was added 6-methoxy-2-(2-methoxyimidazo[2,1-b][1,3,4]thiadiazol-6-yl)benzofuran-4-ol (Example 1G, 0.048 g, 0.150 mmol) and (6-(4-methoxytetrahydro-2H-pyran-4-yl)pyridin-2-yl)methanol (0.042 g, 0.188 mmol), then the flask was flushed with $N_2$ and dry THF (2 mL) was added. To the resulting suspension was added tri-n-butylphosphine (0.097 mL, 0.375 mmol) and then a solution of 1,1'-(azodicarbonyl)dipiperidine (0.096 g, 0.375 mmol) in dry THF (2 mL) was added dropwise (via syringe pump) over 30 min. The resulting mixture was stirred at room temperature for 1 h to give a slurry which was diluted with EtOAc, washed (saturated aqueous $NaHCO_3$), dried ($Na_2SO_4$) and evaporated to give a solid residue. This material was taken up in DCM-MeOH and the solution was loaded on a silica gel pre-column, which was subsequently dried with a flow of air. Flash chromatography (Isco/0-30% ether-DCM) afforded 2-methoxy-6-(6-methoxy-4-((6-(4-methoxytetrahydro-2H-pyran-4-yl)pyridin-2-yl)methoxy)benzofuran-2-yl)imidazo[2,1-b][1,3,4]thiadiazole (0.077 g, 98%) as a pale yellow gum. This material was lyophilized from MeCN-water to give a white solid. LC (Method A): 2.376 min. HRMS(ESI): calcd for $C_{26}H_{27}N_4O_6S$ $[M+H]^+$ m/z 523.1651. found 523.1672. $^1H$ NMR (400 MHz, DMSO-$d_6$): δ 8.34 (s, 1H), 7.87 (t, J=7.43 Hz, 1H), 7.49 (d, J=7.43 Hz, 1H), 7.44 (d, J=7.83 Hz, 1H), 6.99 (s, 1H), 6.79 (s, 1H), 6.51 (d, J=1.96 Hz, 1H), 5.29 (s, 2H), 4.17 (s, 3H), 3.75 (s, 3H), 3.65 (dd, J=2.35, 7.83 Hz, 4H), 2.94 (s, 3H), 2.09 (dt, J=7.83, 14.09 Hz, 2H), 1.84 (d, J=12.91 Hz, 2H).

Example 112

(S)-2-(1-Fluoroethyl)-6-(6-methoxy-4-((6-(4-methoxytetrahydro-2H-pyran-4-yl)pyridin-2-yl)methoxy)benzofuran-2-yl)imidazo[2,1-b][1,3,4]thiadiazole

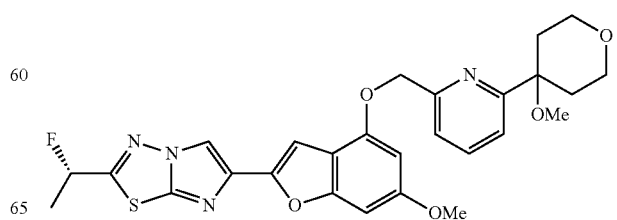

To a flame-dried flask was added (S)-2-(2-(1-fluoroethyl)imidazo[2,1-b][1,3,4]thiadiazol-6-yl)-6-methoxybenzofuran-4-ol (Example 64C, 0.050 g, 0.150 mmol) and (6-(4-methoxytetrahydro-2H-pyran-4-yl)pyridin-2-yl)methanol (Example 111 B, 0.042 g, 0.188 mmol), then the flask was flushed with $N_2$ and dry THF (2 mL) was added. To the resulting suspension was added tri-n-butylphosphine (0.097 mL, 0.375 mmol) and then a solution of 1,1'-(azodicarbonyl)dipiperidine (0.096 g, 0.375 mmol) in dry THF (2 mL) was added dropwise (via syringe pump) over 30 min. The resulting mixture was stirred at room temperature for another 30 min and then it was diluted with EtOAc, washed (saturated aqueous $NaHCO_3$, $H_2O$, brine), dried ($Na_2SO_4$) and evaporated to give a light yellow gum. Flash chromatography (Isco/0-30% ether-DCM) afforded (S)-2-(1-fluoroethyl)-6-(6-methoxy-4-((6-(4-methoxytetrahydro-2H-pyran-4-yl)pyridin-2-yl)methoxy)benzofuran-2-yl)imidazo-[2,1-b][1,3,4]thiadiazole (0.074 g, 92%) as pale yellow gum. This material was lyophilized from MeCN-water as an off-white solid. LC (Method A): 2.395 min. HRMS(ESI): calcd for $C_{27}H_{28}FN_4O_5S$ $[M+H]^+$ m/z 539.1764. found 539.1787. $^1$H NMR (400 MHz, DMSO-$d_6$): δ 8.55 (s, 1H), 7.84 (t, J=7.83 Hz, 1H), 7.47 (d, J=7.83 Hz, 1H), 7.41 (d, J=7.83 Hz, 1H), 7.07 (s, 1H), 6.78 (s, 1H), 6.49 (d, J=1.96 Hz, 1H), 6.10 (dq, J=6.65, 46.95 Hz, 1H), 5.27 (s, 2H), 3.72 (s, 3H), 3.62 (dd, J=2.74, 7.83 Hz, 4H), 2.91 (s, 3H), 2.06 (dt, J=7.43, 14.09 Hz, 2H), 1.81 (d, J=12.13 Hz, 2H), 1.73 (dd, J=6.65, 24.65 Hz, 3H).

Example 113

6-(4-((6-(4-Fluorotetrahydro-2H-pyran-4-yl)pyridin-2-yl)methoxy)-6-methoxybenzofuran-2-yl)-2-methoxyimidazo[2,1-b][1,3,4]thiadiazole

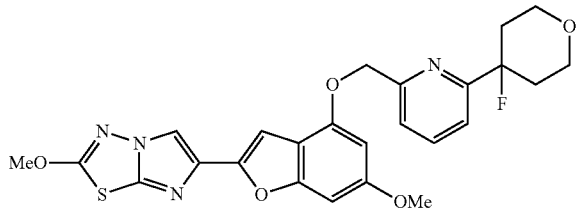 [SMILES: COc1cc(OCc2cccc(C3(F)CCOCC3)n2)c2cc(-c3cn4nc(OC)sc4n3)oc2c1]

To an ice-cold mixture of 4-(6-(((6-methoxy-2-(2-methoxyimidazo[2,1-b][1,3,4]thiadiazol-6-yl)benzofuran-4-yl)oxy)methyl)pyridin-2-yl)tetrahydro-2H-pyran-4-ol (Example 109, 0.015 g, 0.029 mmol) in DCM (2 mL) under $N_2$ was added DAST (4.87 μL, 0.037 mmol) dropwise and the resulting mixture was stirred at 0° C. for 1 h. Another aliquot of DAST (9.45 μl, 0.071 mmol) was added and stirring was continued at 0° C. for another 1 h. The cooling bath was removed and after 30 min another aliquot of DAST (9.45 μl, 0.071 mmol) was added and stirring was continued at room temperature for 1 h. The reaction mixture was then re-cooled at 0° C. and quenched by the dropwise addition of saturated aqueous $NaHCO_3$ (1 mL). The mixture was vigorously stirred at 0° C. for 5 min and then the cooling bath was removed, the mixture was diluted with DCM-saturated aqueous $NaHCO_3$ and stirring was continued until no more gas evolution was observed. The organic phase was then separated, dried ($Na_2SO_4$) and evaporated to give a pale yellow gum. Flash chromatography (Isco/0-100% EtOAc-hexane) afforded 6-(4-(((6-(4-fluorotetrahydro-2H-pyran-4-yl)pyridin-2-yl)methoxy)-6-methoxy-benzofuran-2-yl)-2-methoxyimidazo[2,1-b][1,3,4]thiadiazole (0.009 g, 59.8%) as a colorless gum which was lyophilized from MeCN-water to give a white solid. LC (Method A): 2.421 min. HRMS (ESI): calcd for $C_{25}H_{24}FN_4O_5S$ $[M+H]^+$ m/z 511.1451. found 511.1468. $^1$H NMR (400 MHz, DMSO-$d_6$): δ 8.32 (s, 1H), 7.89 (t, J=7.83 Hz, 1H), 7.52 (d, J=7.83 Hz, 1H), 7.49 (d, J=7.83 Hz, 1H), 6.97 (s, 1H), 6.77 (s, 1H), 6.48 (d, J=1.96 Hz, 1H), 5.27 (s, 2H), 4.14 (s, 3H), 3.81 (dd, J=5.89, 11.74 Hz, 2H), 3.72 (s, 3H), 3.63 (t, J=11.74 Hz, 2H), 2.32-2.14 (m, 2H), 1.78 (t, J=13.30 Hz, 2H).

Example 114

(S)-2-(1-Fluoroethyl)-6-(4-((6-(4-fluorotetrahydro-2H-pyran-4-yl)pyridin-2-yl)methoxy)-6-methoxy-benzo-furan-2-yl)imidazo[2,1-b][1,3,4]thiadiazole

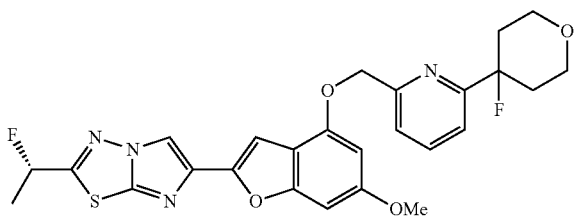 [SMILES: COc1cc(OCc2cccc(C3(F)CCOCC3)n2)c2cc(-c3cn4nc([C@H](C)F)sc4n3)oc2c1]

To an ice-cold mixture of (S)-4-(6-(((2-(2-(1-fluoroethyl)imidazo[2,1-b][1,3,4]thiadiazol-6-yl)-6-methoxybenzofuran-4-yl)oxy)methyl)pyridin-2-yl)tetrahydro-2H-pyran-4-ol (Example 110, 0.015 g, 0.029 mmol) in DCM (2 mL) under $N_2$ was added DAST (9.45 μL, 0.072 mmol) dropwise and the resulting mixture was stirred at 0° C. to room temperature for 1.5 h. Another aliquot of DAST (4.73 μL, 0.036 mmol) was then added and stirring was continued at room temperature for another 30 min. The reaction mixture was then re-cooled at 0° C. and quenched by the dropwise addition of saturated aqueous $NaHCO_3$ (1 mL). The mixture was vigorously stirred at 0° C. for 5 min, then the cooling bath was removed, the mixture was diluted with DCM, saturated aqueous $NaHCO_3$ was added and stirring was continued until no more gas evolution was observed. The organic phase was separated, dried ($Na_2SO_4$) and evaporated to give a pale yellow gum. Flash chromatography (Isco/0-100% EtOAc-hexane) gave (S)-2-(1-fluoroethyl)-6-(4-((6-(4-fluorotetrahydro-2H-pyran-4-yl)pyridin-2-yl)methoxy)-6-methoxy-benzofuran-2-yl)imidazo[2,1-b][1,3,4]thiadiazole (0.011 g, 73.0%) as an off-white solid. LC (Method A): 2.433 min. HRMS(ESI): calcd for $C_{26}H_{25}F_2N_4O_4S$ $[M+H]^+$ m/z 527.1565. found 527.1590. $^1$H NMR (400 MHz, DMSO-$d_6$): δ 8.55 (s, 1H), 7.89 (t, J=7.83 Hz, 1H), 7.53 (d, J=7.83 Hz, 1H), 7.48 (d, J=7.83 Hz, 1H), 7.08 (s, 1H), 6.79 (s, 1H), 6.50 (d, J=1.57 Hz, 1H), 6.10 (dq, J=6.26, 46.95 Hz, 1H), 5.28 (s, 2H), 3.81 (dd, J=6.26, 11.74 Hz, 2H), 3.73 (s, 3H), 3.63 (t, J=11.74 Hz, 2H), 2.33-2.15 (m, 2H), 1.78 (m, 2H), 1.73 (dd, J=6.26, 24.65 Hz, 3H).

BIOLOGY

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.,* 334(11):677-681 (1996); Blom, J. W. et al., *JAMA,* 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy,* 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, IAA, IA, IB, IC, ID, IE, IF, IG, IH, IJ, IK, IL, IM, IP or IQ, preferably, a compound selected from one of the examples, more preferably a compound selected from Examples 3 to 114, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-NH$_2$. As shown in Example B below, H-Ala-Phe(4-F)-Pro-Gly-Trp-Leu-Val-Lys-Asn-Gly-NH$_2$ was validated as a PAR4 agonist in the FLIPR assay. A side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays. Additionally, H-Ala-Phe(4-F)-Pro-Gly-Trp-Leu-Val-Lys-Asn-Gly-NH$_2$ has improved agonist activity as compared to AYPGKF with an EC$_{50}$ that is 10 fold lower than the EC$_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example C. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example D is an alpha-thrombin-induced platelet aggregation assay. Alpha-thrombin activates both PAR1 and PAR4. The ability of a selective PAR4 antagonist of the present invention, Example 13, to inhibit platelet aggregation was measured using a standard optical aggregometer. Inhibition of alpha-thrombin induced platelet aggregation by Example 13 is shown in FIGS. 1 and 2. The data shows that a PAR4 antagonist alone can effectively inhibit platelet aggregation. The extent of platelet inhibition by the PAR4 antagonist is at least comparable to what has been previously described for PAR1 antagonists.

Example E is a tissue factor-induced platelet aggregation assay. The conditions in this assay mimic the physiological events during thrombus formation. In this assay, platelet aggregation in human PRP was initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

FIGS. 1 and 2 show effective inhibition of tissue factor-induced platelet aggregation by the compound of Example 13 (a PAR4 antagonist of the present invention), as well as by trans-cinnamoyl-Phe(4-F)-Phe(4-guanidino)-Leu-Arg-Arg-NH$_2$ (a PAR1 antagonist). The PAR4 antagonist, like the PAR1 antagonist, is shown to effectively inhibit tissue factor induced platelet aggregation in this assay. This data demonstrates that the PAR4 antagonists of the present invention can effectively inhibit thrombin mediated platelet aggregation and can serve as antithrombotic agents. Thus, PAR4 antagonists represent a novel class of antithrombotic agents that prevent robust platelet activation by thrombin during thrombotic events.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example G describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

ASSAYS

Materials
1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay (EC$_{50}$ of 8 µM for H-Ala-Phe(4-F)-Pro-Gly-Trp-Leu-Val-Lys-Asn-Gly-NH$_2$ and 60 µM for AYPGKF) and in washed platelet aggregation assay (EC$_{50}$ of 0.9 µM for H-Ala-Phe(4-F)-Pro-Gly-Trp-Leu-Val-Lys-Asn-Gly-NH$_2$ and 12 µM for AYPGKF).

2) PAR4 Expressing Cells

HEK293 cells stably expressing PAR4 were generated by a standard method of transfection of human F2R23 cDNA expression vector or by RAGE technology from Athersys Inc. (Cleveland, Ohio) and selected based on PAR4 protein expression of mRNA expression. Those cells demonstrated functional responses to PAR4 agonist peptide-induced intracellular calcium elevation using FLIPR® (Fluorometric Imaging Plate Reader; Molecular Devices Corp.). These cells express endogenous PAR1 and can elicit calcium signal upon stimulation with PAR1 agonist peptide. Cells were grown in Dulbecco's Modified Eagle's Medium (DMEM) (Invitrogen, Carlsbad, Calif.), 10% FBS, 1% PSG, 3 µg/ml puromycin and 25 nM Methotrexate) at 37° C. with 5% CO$_2$.

3) Preparation of Platelet Rich Plasma (PRP)

Human blood was collected in 3.8% sodium citrate at a ratio of 1 ml per 9 ml blood. The platelet rich plasma was isolated by centrifugation at 170 g for 14 minutes.

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin. Platelets were resuspended at ~2.5×10$^8$/ml in Tyrode's Buffer (137 mM NaCl, 2 mM KCl, 1.0 mM MgCl$_2$, 1 mM CaCl$_2$, 5 mM glucose, 20 mM HEPES pH 7.4).

Example A

FLIPR Assay in PAR4-Expressing HEK293 Cells

The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$-induced intracellular calcium mobilization using FDSS6000 (Hamamatsu Photonics, Japan) by fluo-4. Counter screens for agonist activity and PAR1 antagonist activity were also performed. Briefly, HEK293 EBNA PAR4 clone 20664.1J cells were plated 24 hrs. prior to experiment in 384 well, Poly-D-Lysine coated, black, clear bottom plates (Greiner Bio-One, Monroe, N.C.). Cells were plated at 20,000 cells/well in 20 µl growth medium and incubated at 37° C. with 5% CO$_2$ overnight. At time of assay, media was replaced with 40 µl 1×Hank's Buffered Saline Solution (HBSS) (with 10 mM HEPES) and 20 µl test compound also diluted in 1×HBSS buffer was added at various concentrations and 0.67% DMSO final concentration on the FDSS for agonist measurement. The cells were then incubated for 30 minutes at room temperature followed by addition of 20 µl of agonist peptide for antagonist measurement on the FDSS. The agonist peptide H-Ala-Phe(4-F)-Pro-Gly-Trp-Leu-Val-Lys-Asn-Gly-NH$_2$ for PAR4 antagonist screen or SFFLRR for PAR1 counter screen were routinely tested to ensure a response at EC$_{50}$ in the assay (~2.5 µM for H-Ala-Phe(4-F)-Pro-Gly-Trp-Leu-Val-Lys-Asn-Gly-NH$_2$ and 600 nM for SFFLRR).

Example B

Validation of H-Ala-Phe(4-F)-Pro-Gly-Trp-Leu-Val-Lys-Asn-Gly-NH$_2$ as a PAR4 Agonist To validate H-Ala-Phe(4-F)-Pro-Gly-Trp-Leu-Val-Lys-Asn-Gly-NH$_2$ as a PAR4 agonist in the FLIPR assay, side-by-side comparison of the IC$_{50}$ values of ~180 compounds were performed using AYPGKF versus H-Ala-Phe(4-F)-Pro-Gly-Trp-Leu-Val-Lys-Asn-Gly-NH$_2$. The results demonstrated a strong correlation between the two assays (Spearman's rank correlation coefficient rho=0.7760, p<0.0001). The relevance of the FLIPR assay in the HEK293 cells was confirmed by a direct assay connectivity to the washed platelet assay. The IC$_{50}$ values of ~200 compounds from AYPGKF FLIPR assay was strongly correlated to that from AYPGKF washed platelet aggregation assay (Spearman's rank correlation coefficient rho=0.836, p<0.001). Similar results were obtained comparing FLIPR and washed platelet data using H-Ala-Phe(4-F)-Pro-Gly-Trp-Leu-Val-Lys-Asn-Gly-NH$_2$.

Example C

Gamma Thrombin Induced Platelet Aggregation Assays

The ability of the compounds of the current invention to inhibit platelet aggregation induced by gamma-thrombin was tested in a 96-well microplate aggregation assay format. Briefly, PRP or washed platelet suspension (100 µl) was pre-incubated for 5 minutes at room temperature with varying concentrations of compounds. Aggregation was initiated by ~10-50 nM gamma thrombin (Haematologic Technologies, Essex Junction, Vt.), which was titrated daily to achieve 80% platelet aggregation. Refludan at 1 U/mL (Berlex, Montville, N.J.) was added to the gamma thrombin sample to prevent PAR1 activation induced by residual alpha-thrombin contamination. The plate was then placed into a 37° C. Molecular Devices (Sunnyvale, Calif.) SPECTRAMAX® Plus Plate Reader. The plate was mixed for 10 seconds before the first read and 50 seconds between each read for up to 15 minutes at 405 nM. Data was collected with SOFTMAX® 4.71 software. The plate also included an untreated control sample which served as ODmax, while buffer containing no platelets was the ODmin. Platelet aggregation was determined by subtracting the ODmax from the ODmin for the 100% aggregation value. In experimental samples, the observed transmission was subtracted from the minimum value and then compared to the 100% aggregation value to determine the percentage aggregation. $IC_{50}$ values are determined using Excel Fit software.

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example D

Alpha-Thrombin Induced Platelet Aggregation Assays

The ability of a PAR4 antagonist (Example 13) compound to inhibit platelet aggregation induced by alpha-thrombin was tested using human washed platelets. Example 13 was pre-incubated with washed platelets for 20 min. Aggregation was initiated by addition of 1.5 nM alpha-thrombin (Haematologic Technologies, Essex Junction, Vt.) to 300 µl of washed platelets at stirring speed of 1000 rpm. Platelet aggregation was monitored using an Optical Aggregometer (Chrono-Log, Havertown, Pa.) and the area under the curve (AUC) at 6 min was measured. $IC_{50}$ was calculated using vehicle control as 0% inhibition. FIG. 1 shows % aggregation over time of human washed platelets induced by 1.5 nM alpha-thrombin employing the Example 13 compound in amounts of 0 nM, 3 nM, 100 nM and 300 nM. The $IC_{50}$ for the inhibition of platelet aggregation by Example 13 using 1.5 nM alpha-thrombin was calculated to be 11 nM (FIG. 2).

Example E

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of $CaCl_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 µg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example F

The following table sets out the results obtained employing various compounds of the invention tested in the FLIPR and platelet aggregation assay (PRP assay). As indicated above, the FLIPR assay, an in vitro assay, measures the PAR4 antagonist activity of compounds tested as described in Example A. The γ-thrombin induced platelet aggregation assay in PRP, measures the PAR4 antagonist activity of the compounds tested as described in Example C.

TABLE 1

| Example No. | PAR4 FLIPR Assay ($IC_{50}$, nM) |
|---|---|
| 1 | 1.06 |
| 2 | 4.35 |
| 3 | 3.08 |
| 4 | 9.35 |
| 5 | 2.36 |
| 6 | 1.86 |
| 7 | 1.29 |
| 8 | 1.69 |
| 9 | 1.26 |
| 10 | 3.55 |
| 11 | 3.66 |
| 12 | 3.76 |
| 13 | 1.74 |
| 14 | 1.53 |
| 15 | 6.40 |
| 16 | 67.00 |
| 17 | 3.78 |
| 18 | 3.50 |
| 19 | 2.42 |
| 20 | 8.54 |
| 21 | 7.34 |
| 22 | 23.56 |
| 24 | 6.31 |
| 25 | 2.04 |
| 27 | 4.29 |
| 32 | 0.57 |
| 33 | 0.67 |
| 34 | 0.48 |
| 35 | 0.49 |
| 36 | 0.38 |
| 37 | 0.36 |
| 38 | 0.68 |
| 39 | 0.53 |
| 40 | 0.47 |
| 41 | 8.68 |
| 42 | 1.05 |
| 43 | 0.60 |
| 44 | 1.21 |
| 45 | 1.03 |
| 46 | 1.64 |
| 47 | 0.69 |
| 48 | 1.03 |
| 49 | 2.02 |
| 50 | 1.88 |
| 51 | 1.19 |
| 52 | 0.56 |
| 53 | 1.48 |
| 54 | 1.47 |
| 55 | 0.69 |
| 56 | 0.74 |
| 57 | 1.66 |
| 58 | 1.22 |

TABLE 1-continued

| Example No. | PAR4 FLIPR Assay (IC$_{50}$, nM) |
|---|---|
| 59 | 4.81 |
| 60 | 4.18 |
| 61 | 1.00 |
| 62 | 0.84 |
| 63 | 4.04 |
| 65 | 1.08 |
| 66 | 0.57 |
| 67 | 4.54 |
| 68 | 3.37 |
| 70 | 1.48 |
| 71 | 0.50 |
| 72 | 7.19 |
| 73 | 2.18 |
| 74 | 1.57 |
| 75 | 2.14 |
| 76 | 6.66 |
| 77 | 2.18 |
| 78 | 0.95 |
| 80 | 3133 |
| 81 | 22.13 |
| 82 | 1.32 |
| 83 | 0.39 |
| 84 | 65.01 |
| 85 | 1.49 |
| 86 | 0.56 |
| 87 | 1.11 |
| 88 | 1.10 |
| 89 | 0.79 |
| 90 | 4.91 |
| 91 | 9.05 |
| 92 | 0.72 |
| 93 | 0.71 |
| 94 | 2.21 |
| 95 | 0.69 |
| 96 | 0.23 |
| 97 | 0.36 |
| 98 | 0.29 |
| 99 | 48.66 |
| 100 | 0.76 |
| 101 | 0.92 |
| 102 | 0.72 |
| 103 | 1.39 |
| 104 | 0.85 |
| 105 | 1.06 |
| 106 | 1.59 |
| 107 | 1.09 |
| 108 | 1.43 |
| 109 | 0.45 |
| 110 | 0.41 |
| 111 | 0.23 |
| 112 | 0.36 |
| 113 | 0.35 |
| 114 | 0.31 |

TABLE 2

| Example No. | PRP Assay (Gamma Thrombin IC$_{50}$, nM) |
|---|---|
| 2 | 4459.00 |
| 13 | 4.91 |
| 18 | 68.19 |
| 23 | 628.80 |
| 26 | 970.30 |
| 28 | 24.55 |
| 29 | 93.41 |
| 30 | 124.60 |
| 31 | 49.90 |
| 32 | 2773.00 |
| 40 | 2.86 |
| 48 | 65.88 |
| 53 | 3.63 |
| 59 | 2670.00 |
| 60 | 81.35 |
| 63 | 2426.00 |
| 64 | 489.70 |
| 68 | 2230.00 |
| 69 | 13.08 |
| 71 | 3.61 |
| 81 | 4996.00 |
| 93 | 105.10 |
| 97 | 2.97 |
| 98 | 1.67 |
| 100 | 1.80 |
| 110 | 87.64 |

Example G

Cynomolgus Monkey Electrolytic Injury-Induced Carotid Artery Thrombosis Model

Healthy cynomolgus monkeys are used in the study. These monkeys are retired from other pharmacokinetic and pharmacodynamic studies and have at least a 4-week washout period.

On the day of the study, compounds or vehicles are administered orally at 1 to 2 hours before the experiment. Monkeys are then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs.

The carotid arterial thrombosis model in monkeys is based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295:212-218 (2002).) Thrombosis is induced by electrical stimulation of the carotid artery for 5 min at 10 mA using an external stainless-steel bipolar electrode. Carotid blood flow is measured with an appropriately sized TRANSONIC® flow probe and a TRANSONIC® perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow has been maintained continuously for 90 min. In addition, thrombus from the injured artery is removed, blotted twice on a weighing paper to remove residual fluid, and weighed.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:
      Synthetic polypeptide

<400> SEQUENCE: 1

Ala Tyr Pro Gly Lys Phe
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic polypeptides
<220> FEATURE:
<221> NAME/KEY: MISC_FEATURE
<222> LOCATION: (2)..(2)
<223> OTHER INFORMATION: wherein this amino acid (the Phe amino acid
      in position 2) is fluorinated at the number 4 carbon of the side
      chain phenyl ring

<400> SEQUENCE: 2

Ala Phe Pro Gly Trp Leu Val Lys Asn Gly
1               5                   10

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence:  Synthetic
      polypeptide
<220> FEATURE:
<221> NAME/KEY: MISC_FEATURE
<222> LOCATION: (1)..(1)
<223> OTHER INFORMATION: wherein this amino acid is modified with a
      trans-cinnamoyl moiety and floronated at the number 4 carbon
<220> FEATURE:
<221> NAME/KEY: MISC_FEATURE
<222> LOCATION: (2)..(2)
<223> OTHER INFORMATION: wherein this amino acid is modified with a
      guanidino moiety at the 4 carbon

<400> SEQUENCE: 3

Phe Phe Leu Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:  Synthetic
      polypeptide

<400> SEQUENCE: 4

Ser Phe Phe Leu Arg Arg
1               5

What we claim is:
1. A compound of Formula I:

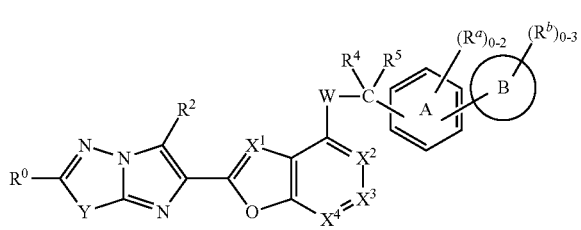

or a stereoisomer, tautomer, pharmaceutically acceptable salt, solvate or prodrug thereof, wherein:
W is O or S;
$R^0$ is $R^1$ or $R^{1a}$;
Y is S or —$CR^8$=$CR^9$—;
$R^1$ is independently selected from the group consisting of:
  halo,
  $C_1$-$C_4$ alkyl,
  $C_2$-$C_3$ alkenyl,
  $C_2$-$C_3$ alkynyl,
  $C_3$-$C_4$ cycloalkyl,
  $C_1$-$C_4$ alkoxy,
  $C_1$-$C_2$ alkoxy-$C_1$-$C_2$ alkyl,
  tetrahydrofuran-2-yl;
  $C_1$-$C_4$ alkylthio,
  $C_1$-$C_4$ alkylNH—,
  ($C_1$-$C_4$ alkyl)$_2$N—,
  halo-$C_1$-$C_2$-alkyl, which contains 1 to 5 halogens, where halo is F or Cl,
  halo-$C_3$-$C_4$ cycloalkyl,
  halo-$C_1$-$C_2$ alkoxy, and
  halo-$C_1$-$C_2$ alkylthio;
$R^{1a}$ is independently selected from the group consisting of:
  H,
  halo,
  $C_1$-$C_4$ alkyl,
  $C_2$-$C_3$ alkenyl,
  $C_2$-$C_3$ alkynyl,
  $C_3$-$C_4$ cycloalkyl,
  $C_1$-$C_4$ alkoxy,
  $C_1$-$C_2$ alkoxy-$C_1$-$C_2$ alkyl,
  tetrahydrofuran-2-yl;
  $C_1$-$C_4$ alkylthio,
  $C_1$-$C_4$ alkylNH—,
  ($C_1$-$C_4$ alkyl)$_2$N—,
  halo-$C_1$-$C_2$-alkyl, which contains 1 to 5 halogens, where halo is F or Cl,
  halo-$C_3$-$C_4$ cycloalkyl,
  halo-$C_1$-$C_2$ alkoxy, and
  halo-$C_1$-$C_2$ alkylthio;
$R^8$ and $R^9$ are independently selected from the group consisting of:
  H,
  halo,
  $C_1$-$C_4$ alkyl,
  $C_1$-$C_4$ alkoxy,
  halo-$C_1$-$C_2$ alkyl,
  halo-$C_1$-$C_2$ alkoxy,
  CN, and
  OH;
provided that at least one of $R^{1a}$, $R^8$ and $R^9$ is other than H;
$R^2$ is selected from the group consisting of:
  H,
  halo,
  $C_1$-$C_4$ alkyl,
  alkoxy, and
  cyano;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, which contains 1 to 5 halogens, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
$R^4$ and $R^5$ are independently selected from H, $C_1$-$C_6$ alkyl, halo-$C_1$-$C_3$ alkyl, hydroxy-$C_1$-$C_3$ alkyl, and $C_1$-$C_3$ alkoxy-$C_1$-$C_3$ alkyl; or $R^4$ and $R^5$ can be taken together with the carbon to which they are attached to form a $C_3$-$C_7$ cycloalkyl ring;

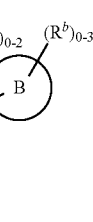

is phenyl or a 6-membered heteroaryl ring, at least one ring member of which is a nitrogen, which

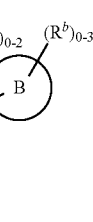

ring is substituted with 0 to 2 $R^a$ groups;
B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;
$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$- alkyl)-C$_1$-C$_4$-alkyl, di-C$_1$-C$_4$-alkylamino, C$_3$-C$_6$-cycloalkyl, phenyl, and C$_1$-C$_4$ alkylthio;

R$^b$, at each occurrence, is independently selected from the group consisting of H, halo, halo-C$_1$-C$_4$ alkoxy, OH, CN, NO$_2$, NR$^6$R$^7$, COOH, C$_1$-C$_4$ alkoxy, C$_1$-C$_4$ alkylthio, C$_1$-C$_4$ alkoxycarbonyl, (C=O)NR$^6$R$^7$, C$_1$-C$_4$ alkoxy-C$_1$-C$_4$ alkoxy, C$_1$-C$_4$ alkylsulfonyl, C$_1$-C$_4$ alkyl sulfinyl, S(=O)$_2$NR$^6$R$^7$, N(R$^{13}$)(C=O)NR$^6$R$^7$, N(R$^{13}$)(C=O)OR$^{14}$, N(R$^{13}$)(C=O)R$^{14}$, NR$^{13}$S(O) R$^{14}$, NR$^{13}$SO$_2$R$^{14}$, O(C=O)NR$^6$R$^7$, O(C=O)OR$^{14}$, O(C=O)R$^{14}$, (C=O)OR$^{14}$, C$_6$-C$_{10}$ aryl, 5-6-membered heteroaryl, 4- to 10-membered heterocyclyloxy and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, phenyl, C$_1$-C$_4$-alkoxyphenyl-C$_1$-C$_4$-alkoxy, 4- to 10-membered heterocyclyloxy and C$_1$-C$_4$ alkylthio;

R$^6$ and R$^7$ are independently, at each occurrence, selected from the group consisting of:
H,
C$_1$-C$_4$ alkyl,
halo-C$_1$-C$_4$-alkyl,
C$_1$-C$_4$ alkyleneoxy-C$_1$-C$_4$-alkylene,
C$_2$-C$_4$ alkenyl,
C$_2$-C$_4$ alkynyl,
—(CR$^{14}$R$^{14}$)$_n{^1}$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
—(CHR$^{13}$)$_n{^1}$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_n{^1}$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl,
—(CHR$^{13}$)$_n{^1}$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
C$_1$-C$_4$-alkylcarbonylamino-C$_1$-C$_4$-alkyl,
di-C$_1$-C$_4$-alkoxy-C$_1$-C$_4$-alkyl,
di-C$_1$-C$_4$-alkylaminophenyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl;
C$_1$-C$_4$-alkoxycarbonylamino-C$_1$-C$_4$-alkylcarbonyl,
di-C$_1$-C$_4$-alkylamino-C$_1$-C$_4$-alkylcarbonyl,
amino-C$_1$-C$_4$-alkylcarbonyl,
4- to 10-membered-heterocyclyl-carbonyl, and
alternatively, R$^6$ and R$^7$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;

R$^{13}$ is independently, at each occurrence, selected from the group consisting of H, C$_1$-C$_6$ alkyl and —(CH$_2$) phenyl;

R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino, (C$_6$-C$_{10}$ arylcarbonylamino), (a 5- to 10-membered heteroarylcarbonylamino) and —(CH$_2$)$_n{^1}$phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, R$^{10}$ is selected from the group consisting of C$_1$-C$_4$ alkyl, halo, C$_1$-C$_4$ alkoxy, and halo-C$_1$-C$_2$-alkyl, which contains 1 to 5 halogens, where halo is F or Cl;

n$^1$, at each occurrence, is selected from 0, 1, 2, 3, 4 or 5; and p, at each occurrence, is selected from 0, 1 and 2.

2. The compound as defined in claim 1, wherein the compound is a compound of formula IAA:

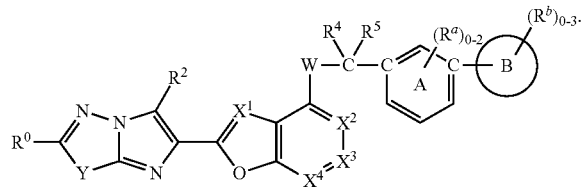

IAA

3. The compound of claim 2 wherein:
W is O;
R$^0$ is R$^1$ or R$^{1a}$;
Y is S or —CR$^8$=CR$^9$—;

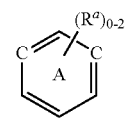

is phenyl or a 6-membered heteroaryl ring, at least one ring member of which is a nitrogen, which

ring is substituted with 0 to 2 R$^a$ groups;

 is attached at the meta position of and is selected from the group consisting of $C_6$-$C_{10}$ aryl ring, a 5- to 10-membered heteroaryl ring, a 4- to 10-membered heterocyclyl ring or a $C_3$-$C_6$-membered cycloalkyl ring, wherein each Ⓑ rings is substituted with 0 to 3 $R^b$ groups;

$R^1$ is selected from the group consisting of:
 halo,
 $C_1$-$C_4$ alkyl,
 $C_1$-$C_4$ alkoxy,
 halo-$C_1$-$C_2$-alkyl, which contains 1 to 5 halogens, where halo is F or Cl, and $C_1$-$C_4$ alkylthio;

$R^{1a}$ is selected from the group consisting of:
 H,
 halo,
 $C_1$-$C_4$ alkyl,
 $C_1$-$C_4$ alkoxy,
 halo-$C_1$-$C_2$-alkyl, which contains 1 to 5 halogens, and
 $C_1$-$C_4$ alkylthio;

$R^8$ and $R^9$ are independently selected from the group consisting of:
 H,
 $C_1$-$C_4$ alkyl,
 halo,
 $C_1$-$C_4$ alkoxy,
 $CF_3$,
 $CF_3O$,
 $CHF_2$, and
 OH;

provided that at least one of $R^{1a}$, $R^8$ and $R^9$ is other than H;

$R^2$ is selected from the group consisting of:
 H,
 halo,
 $C_1$-$C_4$ alkyl,
 $C_1$-$C_4$ alkoxy, and
 cyano;

$X^1$ is selected from the group consisting of CH, N or $CR^{10}$;

$X^2$, $X^3$ and $X^4$ are independently selected from $CR^3$ or N;

$R^3$ is selected from the group consisting of H, $C_1$-$C_4$ alkoxy, halo, $CF_3O$, $CHF_2O$, and halo-$C_1$-$C_2$-alkyl, which contains 1 to 5 halogens;

$R^4$ and $R^5$ are independently selected from H and $C_1$-$C_6$ alkyl, or $R^4$ and $R^5$ can be taken together with the carbon to which they are attached to form a $C_3$-$C_6$ cycloalkyl ring;

$R^a$ is, at each occurrence, independently selected from the group consisting of:
 H, halo, $OCF_3$, $NR^6R^7$, $OCHF_2$, halo-$C_1$-$C_2$-alkyl substituted with 1 to 5 fluorines, $CF_3$,
 $C_1$-$C_4$ alkyl,
 $C_1$-$C_4$ alkoxy,
 $C_1$-$C_4$ alkylthio,
 OH,
 CN,
 $NO_2$,
 COOH,
 $C_1$-$C_4$ alkoxycarbonyl,
 $C(=O)NR^6R^7$,
 $C_1$-$C_4$ alkylsulfonyl, and
 $S(=O)_2NR^6R^7$;

$R^b$ is, at each occurrence, independently selected from the group consisting of:
 H, halo, $OCF_3$, $NR^6R^7$, $OCHF_2$, halo-$C_1$-$C_2$-alkyl substituted with 1 to 5 fluorines, $CF_3$,
 $C_1$-$C_4$ alkyl,
 $C_1$-$C_4$ alkoxy,
 $C_1$-$C_4$ alkylthio,
 OH,
 CN,
 $NO_2$,
 COOH,
 $C_1$-$C_4$ alkoxycarbonyl,
 $C(=O)NR^6R^7$,
 $C_1$-$C_4$ alkylsulfonyl, and
 $S(=O)_2NR^6R^7$; or $R^6$ and $R^7$ are, independently, at each occurrence, selected from the group consisting of:
 H,
 $C_1$-$C_4$ alkyl, and
 —$(CH_2)_{n^1}$phenyl, alternatively, $R^6$ and $R^7$, when attached to the same nitrogen, combine to form a 4- to 6-membered heterocyclic ring containing carbon atoms and 1 to 2 additional heteroatoms selected from N, $NR^{13}$, O and $S(O)_p$;

$R^{13}$ is independently, at each occurrence, selected from the group consisting of H, alkyl and —$(CH_2)$phenyl;

$n^1$, at each occurrence, is selected from 0, 1, 2, 3, 4 and 5; and p, at each occurrence, is selected from 0, 1 and 2.

4. The compound of claim 3, wherein the compound is a compound of formula IA or IB:

IA

IB

5. The compound of claim 1 wherein:
 W is O or S;
 $R^0$ is $R^1$ or $R^{1a}$;
 Y is S or —$CR^8$=$CR^9$—;
 $R^1$ is independently selected from the group consisting of:
  halo,
  $C_1$-$C_4$ alkyl,
  $C_2$-$C_3$ alkenyl,
  $C_2$-$C_3$ alkynyl,
  $C_3$-$C_4$ cycloalkyl,
  $C_1$-$C_4$ alkoxy,
  $C_1$-$C_2$ alkoxy-$C_1$-$C_2$ alkyl,
  tetrahydrofuran-2-yl;

halo-$C_1$-$C_2$-alkyl, which contains 1 to 5 halogens, where halo is F or Cl,
halo-$C_3$-$C_4$ cycloalkyl, and
halo-$C_1$-$C_2$ alkoxy;

$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_2$ alkoxy-$C_1$-$C_2$ alkyl,
tetrahydrofuran-2-yl;
halo-$C_1$-$C_2$-alkyl, which contains 1 to 5 halogens, where halo is F or Cl,
halo-$C_3$-$C_4$ cycloalkyl, and
halo-$C_1$-$C_2$ alkoxy;

$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl,
halo-$C_1$-$C_2$ alkoxy, and
OH;

provided that at least one of $R^{1a}$, $R^8$ and $R^9$ is other than H;

$R^2$ is selected from the group consisting of:
H,
halo,
$C_1$-$C_4$ alkyl, and
$C_1$-$C_4$ alkoxy;

$X^1$ is selected from the group consisting of CH, N or $CR^{10}$;

$X^2$, $X^3$ and $X^4$ are independently selected from $CR^3$ or N;

$R^3$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, which contains 1 to 5 halogens, and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^4$ and $R^5$ are independently selected from H, $C_1$-$C_6$ alkyl, halo-$C_1$-$C_3$ alkyl, hydroxy-$C_1$-$C_3$ alkyl, and $C_1$-$C_3$ alkoxy-$C_1$-$C_3$ alkyl, or $R^4$ and $R^5$ can be taken together with the carbon to which they are attached to form a $C_3$-$C_7$ cycloalkyl ring;

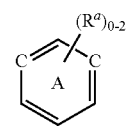

is phenyl or a 6-membered heteroaryl ring, at least one ring member of which is a nitrogen, which

ring is substituted with 0 to 2 $R^a$ groups;

B is selected from the group consisting of a $C_6$-$C_{10}$ aryl, a 5- to 10-membered heteroaryl, a 4-to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^6R^7$, $N(R^{13})$(C=O)$NR^6R^7$, $N(R^{13})$(C=O)$OR^{14}$, $N(R^{13})$(C=O)$R^{14}$, $NR^{13}$S(O)$R^{14}$, $NR^{13}SO_2R^{14}$, O(C=O)$NR^6R^7$, O(C=O)$OR^{14}$, O(C=O)$R^{14}$, (C=O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
$C_2$-$C_4$ alkynyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl, —(CHR$^{13}$)$_{n^1}$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
C$_1$-C$_4$-alkylcarbonylamino-C$_1$-C$_4$-alkyl,
di-C$_1$-C$_4$-alkoxy-C$_1$-C$_4$-alkyl,
di-C$_1$-C$_4$-alkylaminophenyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl; and
alternatively, R$^6$ and R$^7$, when attached to the same nitrogen, combine to form a 4- to 6-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-C$_1$-C$_4$-alkyl, C$_1$-C$_4$ alkyl and C$_1$-C$_4$ alkoxy, and 0 to 2 additional heteroatoms selected from N, NR$^{13}$, O and S(O)$_p$;
R$^{13}$ is independently, at each occurrence, selected from the group consisting of H, C$_1$-C$_6$ alkyl and —(CH$_2$)phenyl;
R$^{14}$ is independently, at each occurrence, selected from the group consisting of H, C$_1$-C$_6$ alkyl, halo-C$_1$-C$_4$-alkyl, C$_1$-C$_4$-alkoxycarbonylamino, (C$_6$-C$_{10}$ arylcarbonylamino), and —(CH$_2$)$_{n^1}$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
R$^{10}$ is selected from the group consisting of C$_1$-C$_4$ alkyl, halo, C$_1$-C$_4$ alkoxy, and halo-C$_1$-C$_2$-alkyl, which contains 1 to 5 halogens, where halo is F or Cl;
n$^1$, at each occurrence, is selected from 0, 1, 2, 3, 4 or 5; and
p, at each occurrence, is selected from 0, 1 and 2.

6. The compound of claim 1 wherein:
W is O or S;
R$^0$ is R$^1$ or R$^{1a}$;
Y is S or —CR$^8$=CR$^9$—;
R$^1$ is independently selected from the group consisting of:
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_2$ alkoxy-C$_1$-C$_2$ alkyl,
tetrahydrofuran-2-yl;
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;
R$^{1a}$ is independently selected from the group consisting of:
H,
halo,
C$_1$-C$_4$ alkyl,
C$_2$-C$_3$ alkenyl,
C$_2$-C$_3$ alkynyl,
C$_3$-C$_4$ cycloalkyl,
C$_1$-C$_4$ alkoxy,
C$_1$-C$_2$ alkoxy-C$_1$-C$_2$ alkyl,
tetrahydrofuran-2-yl;
C$_1$-C$_4$ alkylthio,
halo-C$_1$-C$_2$-alkyl, which contains 1 to 5 halogens, where halo is F or Cl,
halo-C$_3$-C$_4$ cycloalkyl,
halo-C$_1$-C$_2$ alkoxy, and
halo-C$_1$-C$_2$ alkylthio;
R$^8$ and R$^9$ are independently selected from the group consisting of:
H,
halo,
C$_1$-C$_4$ alkyl,
C$_1$-C$_4$ alkoxy,
halo-C$_1$-C$_2$ alkyl, and
halo-C$_1$-C$_2$ alkoxy;
provided that at least one of R$^{1a}$, R$^8$ and R$^9$ is other than H;
R$^2$ is selected from the group consisting of:
H,
halo,
C$_1$-C$_3$ alkyl, and
C$_1$-C$_2$ alkoxy;
X$^1$ is selected from the group consisting of CH, N or CR$^{10}$;
X$^2$, X$^3$ and X$^4$ are independently selected from CR$^3$ or N;
R$^3$ is selected from the group consisting of H, C$_1$-C$_4$ alkyl, C$_2$-C$_4$ alkenyl, C$_2$-C$_4$ alkynyl, C$_1$-C$_4$ alkoxy, C$_1$-C$_4$ alkylthio, halo, OH, CN, OCF$_3$, C$_1$-C$_2$-alkoxy-C$_1$-C$_2$-alkoxy, halo-C$_1$-C$_3$-alkyl, which contains 1 to 5 halogens, benzyloxy substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano, and —(CH$_2$)$_{n^1}$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano;
R$^4$ and R$^5$ are independently selected from H, C$_1$-C$_6$ alkyl, halo-C$_1$-C$_3$ alkyl, hydroxy-C$_1$-C$_3$ alkyl, and C$_1$-C$_3$ alkoxy-C$_1$-C$_3$ alkyl, or R$^4$ and R$^5$ can be taken together with the carbon to which they are attached to form a C$_3$-C$_7$ cycloalkyl ring;

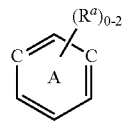

is phenyl or a 6-membered heteroaryl ring, at least one ring member of which is a nitrogen, which

ring is substituted with 0 to 2 R$^a$ groups;
B is selected from the group consisting of a C$_6$-C$_{10}$ aryl, a 5- to 10-membered heteroaryl, a 4-to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkyl aminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^6R^7$, $N(R^{13})$(C=O)$NR^6R^7$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^6R^7$, O(C=O)$OR^{14}$, O(C=O)$R^{14}$, (C=O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
$C_2$-$C_4$ alkynyl,
—($CR^{14}R^{14}$)phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —($CH_2$) phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —$(CH_2)_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, $R^{10}$ is selected from the group consisting of $C_1$-$C_4$ alkyl, halo, $C_1$-$C_4$ alkoxy, and halo-$C_1$-$C_2$-alkyl, which contains 1 to 5 halogens, where halo is F or Cl;

$n^1$, at each occurrence, is selected from 0, 1, 2, 3, 4 or 5; and p, at each occurrence, is selected from 0, 1 and 2.

7. The compound of claim 6 wherein:
W is O or S;
$R^o$ is $R^1$ or $R^{1a}$;
Y is S or —$CR^8$=$CR^9$—;
$R^1$ is independently selected from the group consisting of:
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;
$R^{1a}$ is independently selected from the group consisting of:
H,
halo,
$C_1$-$C_4$ alkyl,
$C_2$-$C_3$ alkenyl,
$C_2$-$C_3$ alkynyl,
$C_3$-$C_4$ cycloalkyl,
$C_1$-$C_4$ alkoxy,
$C_1$-$C_4$ alkylthio,
halo-$C_1$-$C_2$-alkyl, which contains 1 to 5 halogens, where halo is F or Cl,
halo-$C_3$-$C_4$ cycloalkyl,
halo-$C_1$-$C_2$ alkoxy, and
halo-$C_1$-$C_2$ alkylthio;

$R^8$ and $R^9$ are independently selected from the group consisting of:
H,
halo,
$C_1$-$C_4$ alkyl,
$C_1$-$C_4$ alkoxy,
halo-$C_1$-$C_2$ alkyl, and
halo-$C_1$-$C_2$ alkoxy;
provided that at least one of $R^{1a}$, $R^8$ and $R^9$ is other than H;
$R^2$ is selected from the group consisting of:
H,
fluoro,
chloro, and
$CH_3$;
$X^1$ is selected from the group consisting of CH, N or $CR^{10}$;
$X^2$, $X^3$ and $X^4$ are independently selected from $CR^3$ or N;
$R^3$ is selected from the group consisting of H, $C_1$-$C_3$ alkyl, $C_2$-$C_3$ alkenyl, $C_2$-$C_3$ alkynyl, $C_1$-$C_3$ alkoxy, $C_1$-$C_3$ alkylthio, halo, OH, CN, $OCF_3$, and halo-$C_1$-$C_3$-alkyl, which contains 1 to 5 halogens;
$R^4$ and $R^5$ are independently selected from H, $C_1$-$C_3$ alkyl, halo-$C_1$-$C_3$ alkyl, hydroxy-$C_1$-$C_3$ alkyl, and $C_1$-$C_3$ alkoxy-$C_1$-$C_3$ alkyl, or $R^4$ and $R^5$ can be taken together with the carbon to which they are attached to form a $C_3$-$C_7$ cycloalkyl ring;

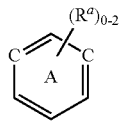

is phenyl or a 6-membered heteroaryl ring, at least one ring member of which is a nitrogen, which

ring is substituted with 0 to 2 $R^a$ groups;
B is selected from the group consisting of a $C_6$-$C_{10}$ aryl, a 5- to 10-membered heteroaryl, a 4-to 10-membered heterocyclyl containing carbon atoms and 1 to 4 additional heteroatoms selected from N, O, and S, and a $C_3$-$C_8$ cycloalkyl which may contain unsaturation, all of which are substituted by 0 to 3 $R^b$ groups;
$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, $C_3$-$C_6$-cycloalkyl, phenyl, and $C_1$-$C_4$ alkylthio;
$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, $(C=O)OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;
$R^6$ and $R^7$ are independently, at each occurrence, selected from the group consisting of:
H,
$C_1$-$C_4$ alkyl,
halo-$C_1$-$C_4$-alkyl,
$C_1$-$C_4$ alkyleneoxy-$C_1$-$C_4$-alkylene,
$C_2$-$C_4$ alkenyl,
—$(CR^{14}R^{14})_n^1$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
—$(CHR^{13})_n^1$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
—$(CHR^{13})_n^1$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
—$(CHR^{13})_n^1$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl,
phenylcarbonyl;
$C_1$-$C_4$-alkoxycarbonylamino-$C_1$-$C_4$-alkylcarbonyl,
di-$C_1$-$C_4$-alkylamino-$C_1$-$C_4$-alkylcarbonyl,
amino-$C_1$-$C_4$-alkylcarbonyl,
4- to 10-membered-heterocyclyl-carbonyl, and
alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;
$R^{13}$ is independently, at each occurrence, selected from the group consisting of H, $C_1$-$C_6$ alkyl and —$(CH_2)$ phenyl;
$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, $(C_6$-$C_{10}$ arylcarbonylamino) and —$(CH_2)_n^1$-phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-C$_1$-C$_4$-alkylamino, and cyano, R$^{10}$ is selected from the group consisting of C$_1$-C$_4$ alkyl, halo, and halo-C$_1$-C$_2$-alkyl, which contains 1 to 5 halogens, where halo is F or Cl;

n$^1$, at each occurrence, is selected from 0, 1, 2, 3 or 4; and p, at each occurrence, is selected from 0, 1 and 2.

8. The compound of claim 1 wherein:

W is O;

R$^0$ is R$^1$ or R$^{1a}$;

Y is S or —CR$^8$=CR$^9$—;

R$^1$ is independently selected from the group consisting of:
halo,
C$_1$-C$_2$ alkyl,
cyclopropyl,
C$_1$-C$_2$ alkoxy,
C$_1$-C$_2$ alkylthio,
halo-C$_1$-C$_2$-alkyl, which contains 1 to 5 halogens, where halo is F or Cl, and
halo-C$_3$-C$_4$ cycloalkyl;

R$^{1a}$ is independently selected from the group consisting of:
H,
halo,
C$_1$-C$_2$ alkyl,
cyclopropyl,
C$_1$-C$_2$ alkoxy,
C$_1$-C$_2$ alkylthio,
halo-C$_1$-C$_2$-alkyl, which contains 1 to 5 halogens, where halo is F or Cl, and
halo-C$_3$-C$_4$ cycloalkyl;

R$^8$ and R$^9$ are independently selected from the group consisting of:
H,
fluoro,
chloro,
C$_1$-C$_3$ alkyl,
C$_1$-C$_2$ alkoxy, and
halo-C$_1$-C$_2$ alkyl;

provided that at least one of R$^{1a}$, R$^8$ and R$^9$ is other than H;

R$^2$ is H;

X$^1$ is selected from the group consisting of CH or N;

X$^2$, X$^3$ and X$^4$ are independently selected from CR$^3$;

R$^3$ is selected from the group consisting of H, C$_1$-C$_3$ alkyl, C$_1$-C$_3$ alkoxy, fluoro, chloro, OCF$_3$, and halo-C$_1$-C$_2$-alkyl, which contains 1 to 5 halogens;

R$^4$ and R$^5$ are independently selected from H, C$_1$-C$_6$ alkyl, halo-C$_1$-C$_3$ alkyl, hydroxy-C$_1$-C$_3$ alkyl and C$_1$-C$_3$ alkoxy-C$_1$-C$_3$ alkyl;

is selected from the group consisting of phenyl, pyridyl, pyrazinyl, pyrimidinyl, pyridazinyl, and triazinyl;

B is selected from the group consisting of a C$_6$-C$_{10}$ aryl, a 5- to 10-membered heteroaryl, a 4-to 10-membered heterocyclyl containing carbon atoms and 1 to 2 additional heteroatoms selected from N, O, and S, and a C$_3$-C$_6$ cycloalkyl which may contain unsaturation, all of which are substituted by 0 to 3 R$^b$ groups;

R$^a$, at each occurrence, is independently selected from the group consisting of H, halo, halo-C$_1$-C$_4$ alkoxy, OH, CN, NO$_2$, NR$^6$R$^7$, COOH, C$_1$-C$_4$ alkoxy, C$_1$-C$_4$ alkylthio, C$_1$-C$_4$ alkoxycarbonyl, (C=O)NR$^6$R$^7$, C$_1$-C$_4$ alkoxy-C$_1$-C$_4$ alkoxy, C$_1$-C$_4$ alkylsulfonyl, C$_1$-C$_4$ alkylsulfinyl, S(=O)$_2$NR$^6$R$^7$, and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, phenyl, and C$_1$-C$_4$ alkylthio;

R$^b$, at each occurrence, is independently selected from the group consisting of H, halo, halo-C$_1$-C$_4$ alkoxy, OH, CN, NO$_2$, NR$^6$R$^7$, COOH, C$_1$-C$_4$ alkoxy, C$_1$-C$_4$ alkylthio, C$_1$-C$_4$ alkoxycarbonyl, (C=O)NR$^6$R$^7$, C$_1$-C$_4$ alkoxy-C$_1$-C$_4$ alkoxy, C$_1$-C$_4$ alkylsulfonyl, C$_1$-C$_4$ alkylsulfinyl, S(=O)$_2$NR$^6$R$^7$, N(R$^{13}$)(C=O)NR$^6$R$^7$, N(R$^{13}$)(C=O)OR$^{14}$, N(R$^{13}$)(C=O)R$^{14}$, NR$^{13}$S(O)R$^{14}$, NR$^{13}$SO$_2$R$^{14}$, O(C=O)NR$^6$R$^7$, O(C=O)OR$^{14}$, O(C=O)R$^{14}$, (C=O)OR$^{14}$, 5-6-membered heteroaryl, and C$_1$-C$_5$ alkyl substituted by 0 to 7 groups independently selected from halo, CF$_3$, OCF$_3$, OH, hydroxy-C$_1$-C$_4$-alkyl, C$_1$-C$_4$ alkoxy, C$_1$-C$_4$ alkoxy-C$_1$-C$_4$ alkoxy, di-C$_1$-C$_4$-alkylaminophenyl-C$_1$-C$_4$-alkyl, (di-C$_1$-C$_4$-alkoxy-C$_1$-C$_4$-alkyl)-C$_1$-C$_4$-alkyl, di-C$_1$-C$_4$-alkylamino, C$_3$-C$_6$-cycloalkyl, phenyl, and C$_1$-C$_4$ alkylthio;

R$^6$ and R$^7$ are independently, at each occurrence, selected from the group consisting of:
H,
C$_1$-C$_4$ alkyl,
halo-C$_1$-C$_4$-alkyl,
C$_2$-C$_4$ alkenyl,
—(CR$^{14}$R$^{14}$)$_n$$^1$-phenyl substituted by 0 to 3 groups independently selected from the group consisting of halo, C$_1$-C$_4$ alkoxy, C$_1$-C$_4$ alkyl, cyclopropyl, CF$_3$, OCF$_3$, 5- or 6-membered heteroaryl, OH, OCHF$_2$, di-C$_1$-C$_4$-alkylamino, and cyano,
—(CHR$^{13}$)$_n$$^1$—C$_3$-C$_6$-cycloalkyl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
—(CHR$^{13}$)$_n$$^1$-4- to 10-membered-heterocyclyl substituted by 0 to 3 groups independently selected from the group consisting of halo, CF$_3$, OCF$_3$, 5- or 6-membered heteroaryl, OH, oxo, hydroxy-C$_1$-C$_4$-alkyl, and C$_1$-C$_4$ alkyl,
—(CHR$^{13}$)$_n$$^1$-5- to 10-membered-heteroaryl substituted by 0 to 3 groups independently selected from the group consisting of halo, CF$_3$, OCF$_3$, 5- or 6-membered heteroaryl, OH, hydroxy-C$_1$-C$_4$-alkyl, and C$_1$-C$_4$ alkyl,
di-C$_1$-C$_4$-alkylamino-C$_1$-C$_4$-alkyl,
di-C$_1$-C$_4$-alkoxy-C$_1$-C$_4$-alkyl,
hydroxy-C$_1$-C$_4$-alkyl,
cyano-C$_1$-C$_4$-alkyl,
C$_1$-C$_4$-alkoxy-C$_1$-C$_4$-alkyl,
C$_1$-C$_4$-alkoxycarbonyl-C$_1$-C$_4$-alkyl,
C$_1$-C$_4$-alkoxycarbonyl,
C$_1$-C$_4$-alkylcarbonyl,
phenylcarbonyl;
C$_1$-C$_4$-alkoxycarbonylamino-C$_1$-C$_4$-alkylcarbonyl, and di-C$_1$-C$_4$-alkylamino-C$_1$-C$_4$-alkylcarbonyl, alternatively, R$^6$ and R$^7$, when attached to the same nitrogen, combine to form a 4- to 8-membered heterocyclic ring containing carbon atoms substituted by 0 to 3 groups independently selected from the group consisting of halo, CF$_3$, CHF$_2$, OCF$_3$, OCHF$_2$, OCH$_2$F, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —$(CH_2)_{n^1}$phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino and —$(CH_2)_{n^1}$phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$n^1$, at each occurrence, is selected from 0, 1, 2 or 3; and
p, at each occurrence, is selected from 0, 1 and 2.

9. The compound of claim 8 wherein:
W is O;
$R^0$ is $R^1$ or $R^{1a}$;
Y is S or —$CR^8$=$CR^9$—;
$R^1$ is independently selected from the group consisting of:
  $C_1$-$C_2$ alkyl,
  $C_1$-$C_2$ alkoxy,
  $C_1$-$C_2$ alkylthio, and
  halo-$C_1$-$C_2$-alkyl, which contains 1 to 5 halogens, where halo is F or Cl;
$R^{1a}$ is independently selected from the group consisting of:
  H,
  fluoro,
  chloro,
  $C_1$-$C_2$ alkyl,
  $C_1$-$C_2$ alkoxy,
  $C_1$-$C_2$ alkylthio, and
  halo-$C_1$-$C_2$-alkyl, which contains 1 to 5 halogens, where halo is F or Cl;
$R^8$ and $R^9$ are independently selected from the group consisting of:
  H,
  fluoro,
  chloro,
  $CH_3$,
  $OCH_3$,
  $CF_3$, and
  $CHF_2$;
provided that at least one of $R^{1a}$, $R^8$ and $R^9$ is other than H;
$R^2$ is H;
$X^1$ is selected from the group consisting of CH or N;
$X^2$ and $X^4$ are CH;
$X^3$ is $CR^3$;
$R^3$ is selected from the group consisting of H, $C_1$-$C_3$ alkyl, $C_1$-$C_3$ alkoxy, fluoro, chloro, $OCF_3$, and halo-$C_1$-$C_2$-alkyl, which contains 1 to 5 halogens;
$R^4$ and $R^5$ are independently selected from H and $C_1$-$C_6$ alkyl;

is selected from the group consisting of phenyl, pyridyl, pyrazinyl, pyrimidinyl, pyridazinyl, and triazinyl;

Ⓑ is selected from the group consisting of phenyl, naphthyl pyridyl, pyrimidinyl, pyrrolyl, pyrazolyl, thienyl, thiazolyl,

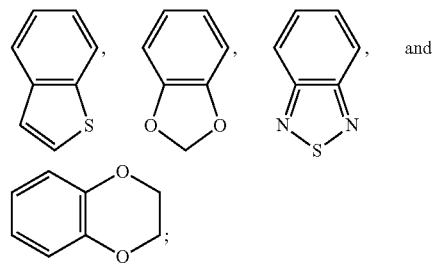

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, alkoxy-$C_1$-$C_4$ alkoxy, $C_1$-$C_4$ alkylsulfonyl, $C_1$-$C_4$ alkylsulfinyl, $S(=O)_2NR^6R^7$, $N(R^{13})$(C=O)$NR^6R^7$, $N(R^{13})$(C=O)$OR^{14}$, $N(R^{13})$(C=O)$R^{14}$, $NR^{13}S(O)R^{14}$, $NR^{13}SO_2R^{14}$, O(C=O)$NR^6R^7$, O(C=O)$OR^{14}$, O(C=O)$R^{14}$, (C=O)$OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cyclo alkyl, phenyl, and $C_1$-$C_4$ alkylthio;

$R^6$ and $R^7$ are independently, at each occurrence, selected from the group consisting of:
  H,
  $C_1$-$C_4$ alkyl,
  halo-$C_1$-$C_4$-alkyl,
  $C_2$-$C_4$ alkenyl,
  —$(CR^{14}R^{14})_{n^1}$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano,
  —$(CHR^{13})_{n^1}$—$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl,
  —$(CHR^{13})_{n^1}$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl,
  —$(CHR^{13})_{n^1}$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl, di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl,
$C_1$-$C_4$-alkoxycarbonyl,
$C_1$-$C_4$-alkylcarbonyl, and
phenylcarbonyl;

alternatively, $R^6$ and $R^7$, when attached to the same nitrogen, combine to form a 4- to 8-membered heterocyclic ring containing carbon atoms substituted by 0 to 3 groups independently selected from the group consisting of halo, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, and $C_1$-$C_3$ alkyl;

$R^{14}$ is independently, at each occurrence, selected from the group consisting of H, $C_1$-$C_3$ alkyl, and halo-$C_1$-$C_2$-alkyl;

$n^1$, at each occurrence, is selected from 0, 1, 2 or 3; and
p, at each occurrence, is selected from 0, 1 and 2.

10. The compound of claim 9 wherein:
W is O;
$R^0$ is $R^1$ or $R^{1a}$;
Y is S or —CH=CH—;
$R^1$ is independently selected from the group consisting of:
$CH_3$,
$OCH_3$,
$SCH_3$,
$CHFCH_3$, and
$CF_2CH_3$;
$R^{1a}$ is independently selected from the group consisting of:
chloro,
$CH_3$, and
$OCH_3$,
$R^2$ is H;
$X^1$ is CH;
$X^2$ and $X^4$ are CH;
$X^3$ is $CR^3$;
$R^3$ is selected from the group consisting of $OCH_3$, fluoro, and chloro;
$R^4$ and $R^5$ are independently selected from H and $CH_3$;

is selected from the group consisting of phenyl, pyridyl, pyrazinyl, pyrimidinyl, pyridazinyl, and triazinyl;

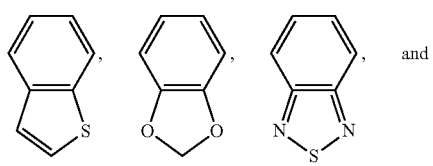

is selected from the group consisting of phenyl, naphthyl pyridyl, pyrimidinyl, pyrrolyl, pyrazolyl, thienyl, thiazolyl,

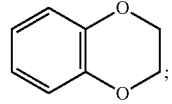

, and

;

$R^a$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^b$, at each occurrence, is independently selected from the group consisting of H, halo, halo-$C_1$-$C_4$ alkoxy, OH, CN, $NO_2$, $NR^6R^7$, COOH, $C_1$-$C_4$ alkoxy, $C_1$-$C_4$ alkylthio, $C_1$-$C_4$ alkoxycarbonyl, (C=O)$NR^6R^7$, $C_1$-$C_4$ alkoxy-$C_1$-$C_4$ alkoxy, $C_1$-$C_4$ alkylsulfonyl, $C_1$-$C_4$ alkylsulfinyl, $S(=O)_2NR^6R^7$, $N(R^{13})(C=O)NR^6R^7$, $N(R^{13})(C=O)OR^{14}$, $N(R^{13})(C=O)R^{14}$, $NR^{13}S(O)R^{14}$, $NR^{13}SO_2R^{14}$, $O(C=O)NR^6R^7$, $O(C=O)OR^{14}$, $O(C=O)R^{14}$, $(C=O)OR^{14}$, 5-6-membered heteroaryl, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, phenyl, and $C_1$-$C_4$ alkylthio;

$R^6$ and $R^7$ are independently, at each occurrence, selected from the group consisting of:
H,
$C_1$-$C_4$ alkyl,
halo-$C_1$-$C_4$-alkyl,
di-$C_1$-$C_4$-alkylamino-$C_1$-$C_4$-alkyl,
di-$C_1$-$C_4$-alkoxy-$C_1$-$C_4$-alkyl,
hydroxy-$C_1$-$C_4$-alkyl,
cyano-$C_1$-$C_4$-alkyl,
$C_1$-$C_4$-alkoxy-$C_1$-$C_4$-alkyl,
$C_1$-$C_4$-alkoxycarbonyl-$C_1$-$C_4$-alkyl, and
$C_1$-$C_4$-alkoxycarbonyl;

alternatively, $R^6$ and $R^7$, when attached to the same nitrogen, combine to form a 4- to 7-membered heterocyclic ring containing carbon atoms substituted by 0 to 2 groups independently selected from the group consisting of halo, $CF_3$, $CHF_2$, $OCF_3$, $OCHF_2$, $OCH_2F$, OH, oxo, hydroxy-$C_1$-$C_2$-alkyl, $C_1$-$C_3$ alkyl and $C_1$-$C_3$ alkoxy, and 0 to 2 additional heteroatoms selected from N, $NR^{13}$, O and $S(O)_p$;

$R^{13}$ is independently, at each occurrence, selected from the group consisting of H and $C_1$-$C_3$ alkyl;

$R^{14}$ is independently, at each occurrence, selected from the group consisting of H and $C_1$-$C_3$ alkyl $n^1$, at each occurrence, is selected from 0, 1, 2 or 3; and
p, at each occurrence, is selected from 0, 1 and 2.

11. The compound of claim 1, wherein:
$X_1$ is CH or N;
$R^1$ is $C_1$-$C_3$ alkoxy or halo-$C_1$-$C_2$-alkyl which contains 1 to 5 halogens;

$R^2$ is H;
$R^3$ is H, alkoxy or halogen;

is selected from the group consisting of phenyl, pyridyl and pyrimidinyl, all of which are substituted with 0 to 2 $R^a$ groups;

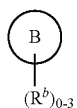

is selected from the group consisting of:
a) phenyl;
b) phenyl substituted with 1 to 2 $R^b$ substituents selected from halo, OH, halo-$C_1$-$C_2$-alkyl, which contains 1 to 5 halogens, CN, $NO_2$,

$N(C_1$-$C_4$ alkyl$)_2$, $CF_3$, $C_1$-$C_4$ alkyl, and $C_1$-$C_4$ alkoxy;
c) phenyl fused to a heterocyclo group;
d) monocyclic heteroaryl containing 5 or 6 ring members which contain:
1 oxygen atom,
2 nitrogen atoms,
2 sulfur atoms,
1 nitrogen atom,
1 sulfur atom,
1 oxygen atom,
or combinations thereof, which monocyclic heteroaryl is substituted with 0 to 2 $R^b$ substituents selected from halo, CN, $NO_2$, OH, $C_1$-$C_4$ alkyl, halo-$C_1$-$C_4$ alkyl, $C_1$-$C_4$ alkoxy, halo-$C_1$-$C_4$ alkoxy,

$N(C_1$-$C_4$ alkyl$)_2$, $C_1$-$C_4$ alkoxy-$C_1$-$C_4$ alkoxy, COOH, alkoxycarbonyl, heterocyclyl, or heterocyclylcarbonyl;
e) bicyclic heteroaryl containing 8 or 9 ring members and which contains a sulfur atom, nitrogen atoms or combinations thereof in the ring.

12. The compound of claim 1, wherein the compound is selected from:

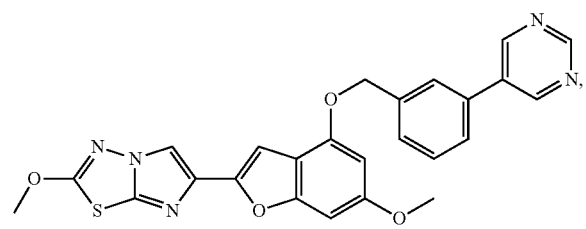

-continued

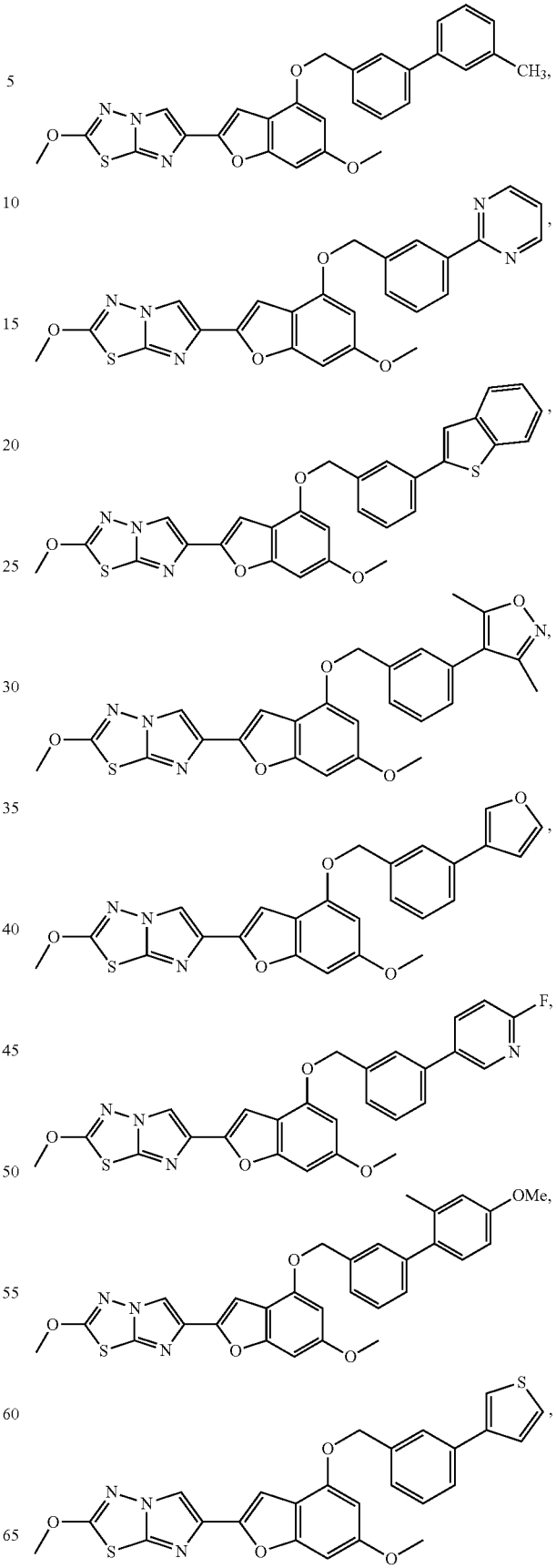

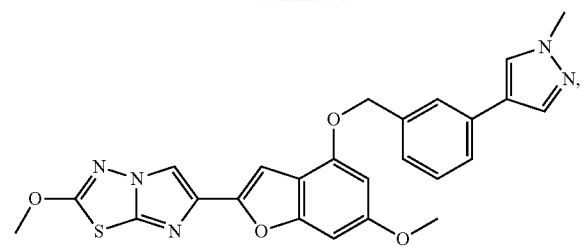
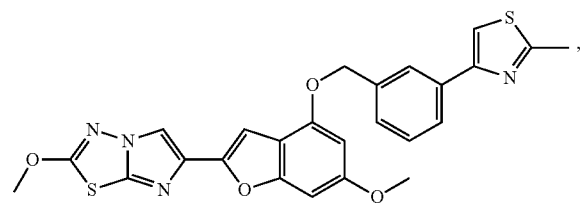
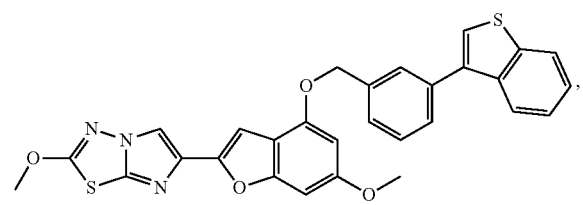
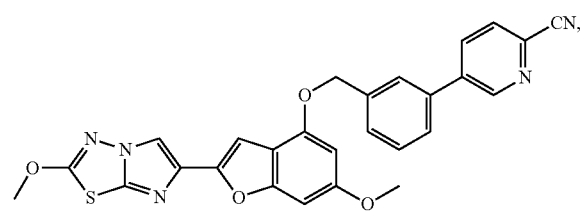
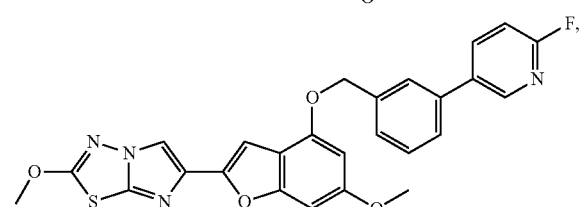
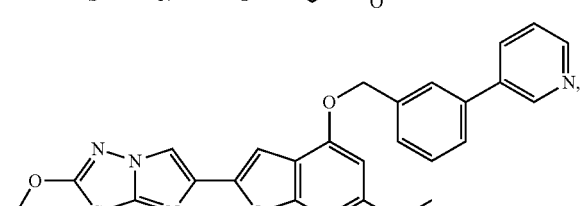
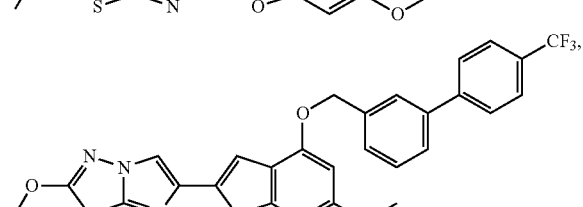
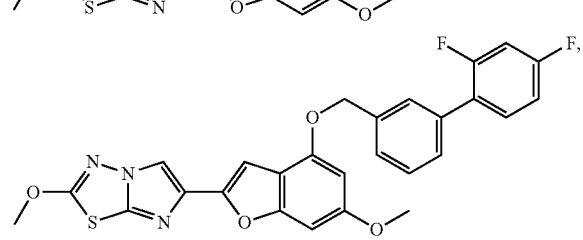
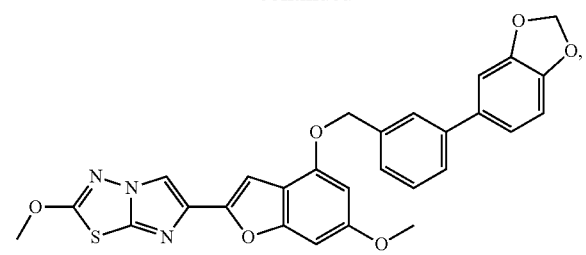
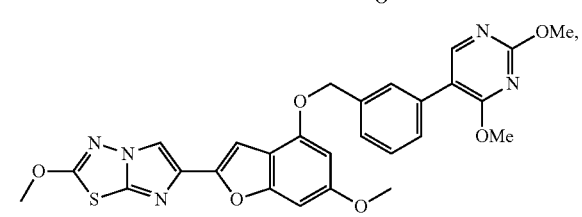
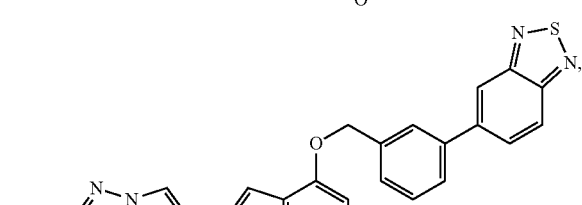
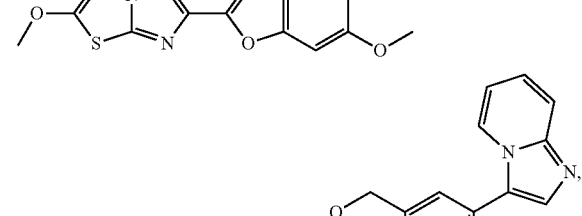
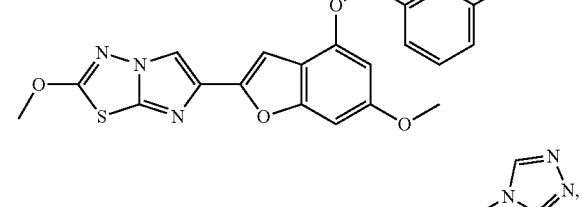
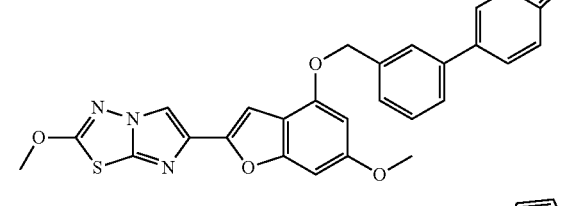
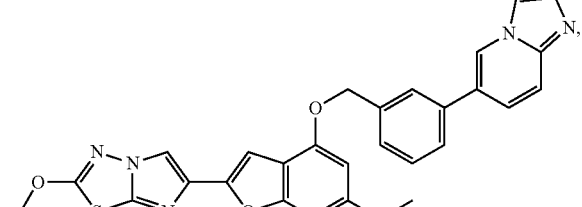
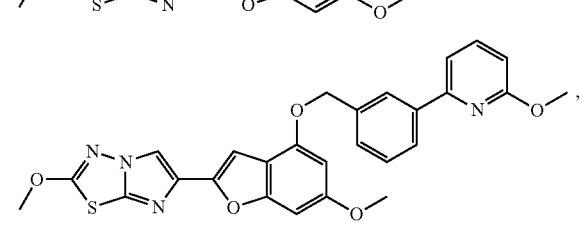

247
-continued
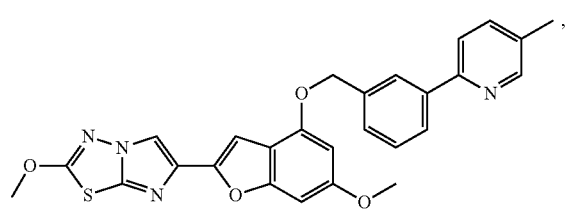
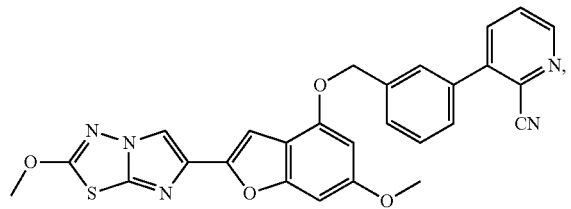
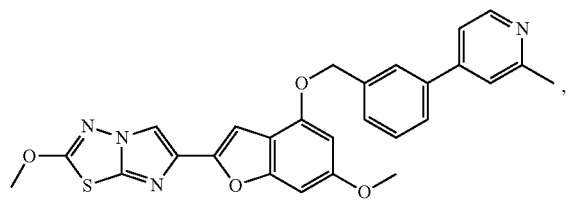
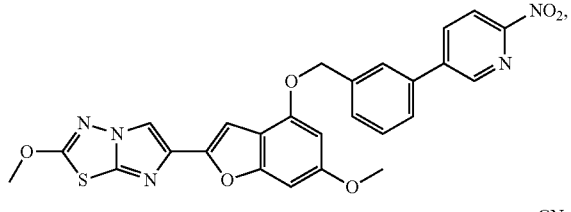
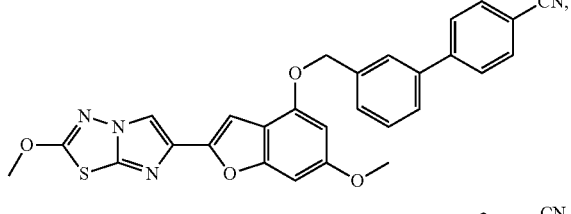
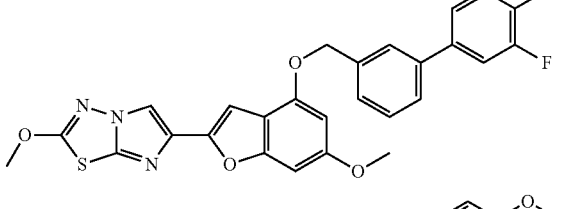
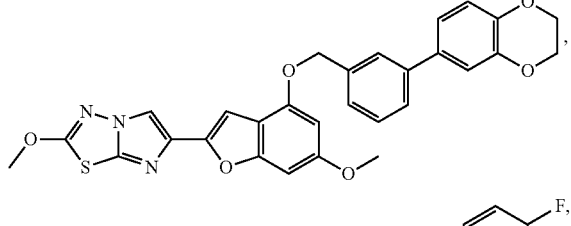
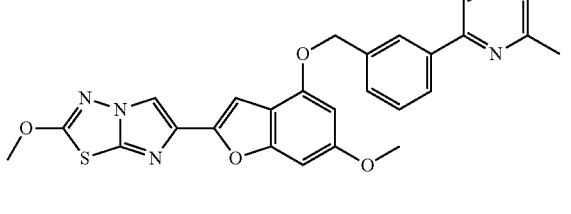
248
-continued
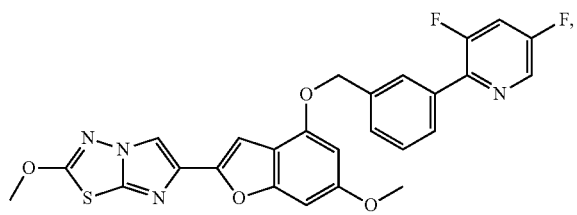
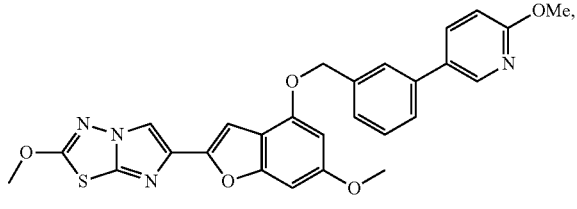
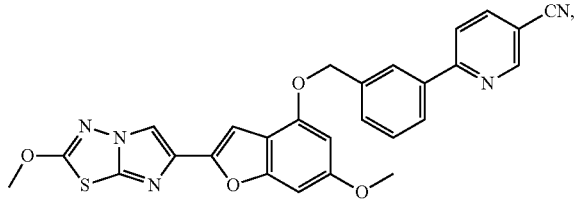
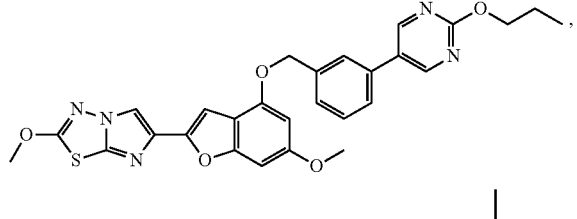
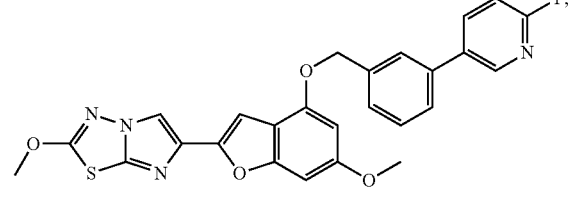
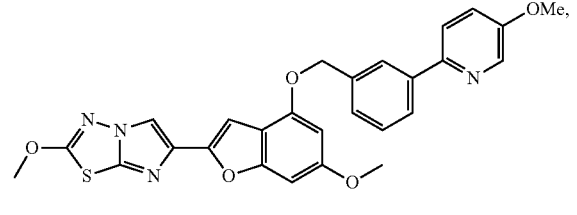

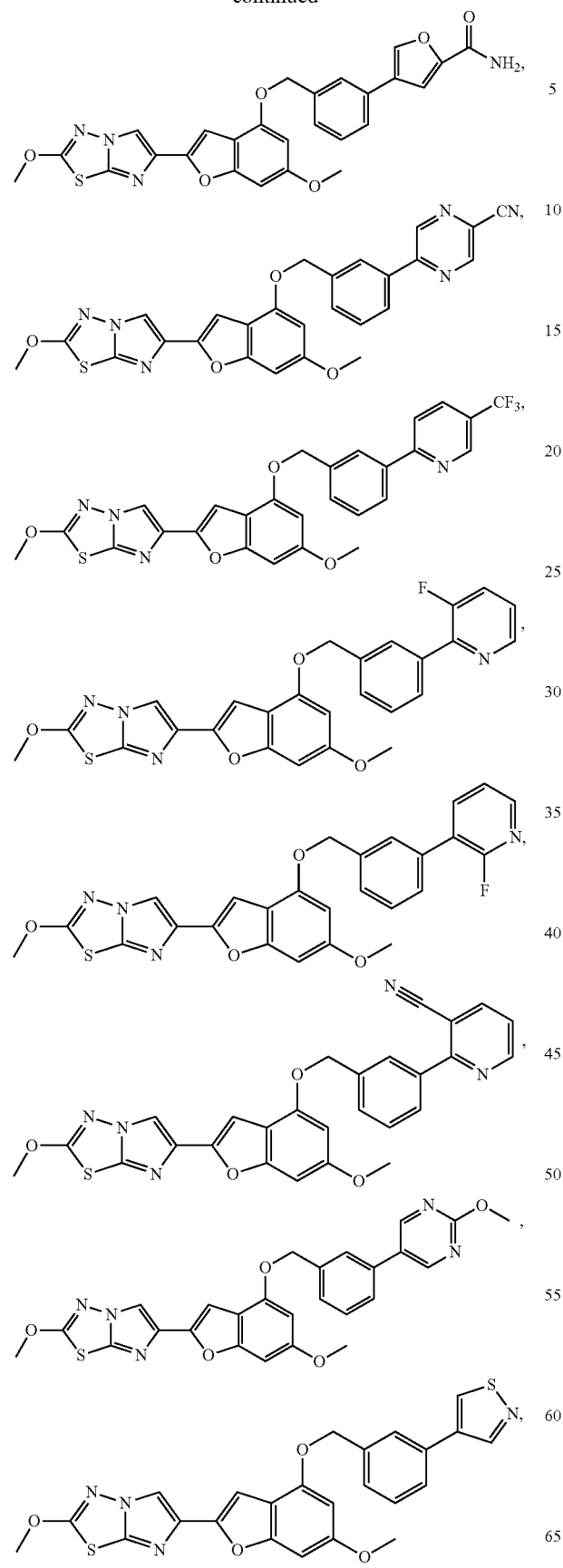
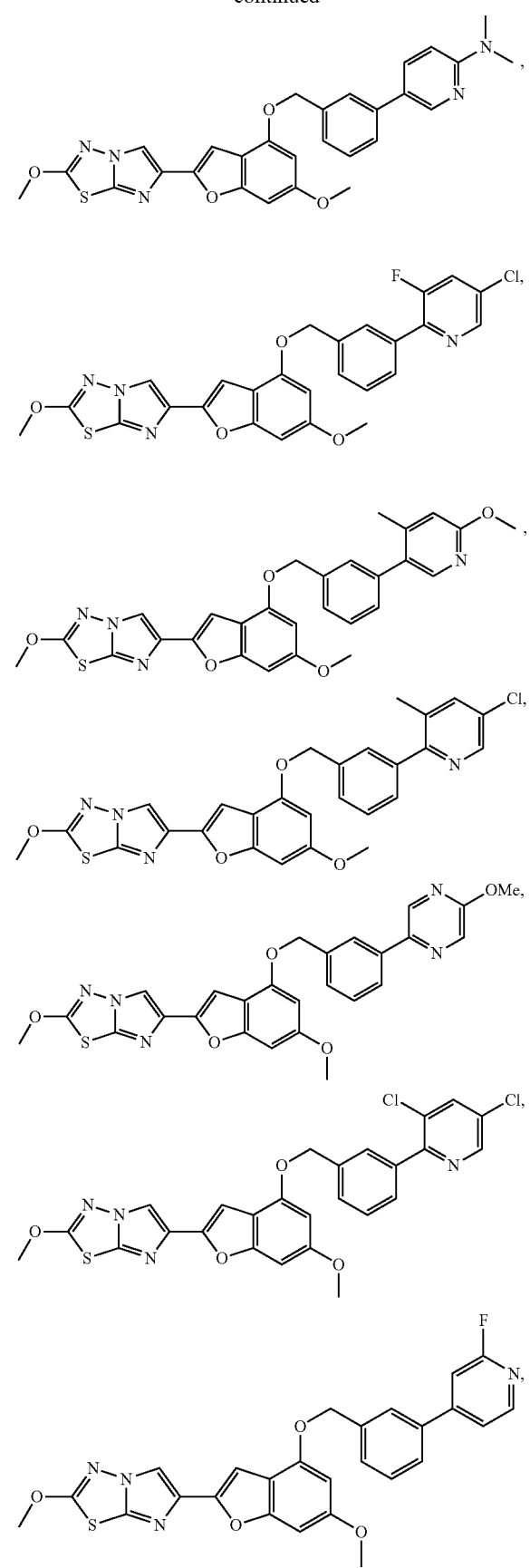

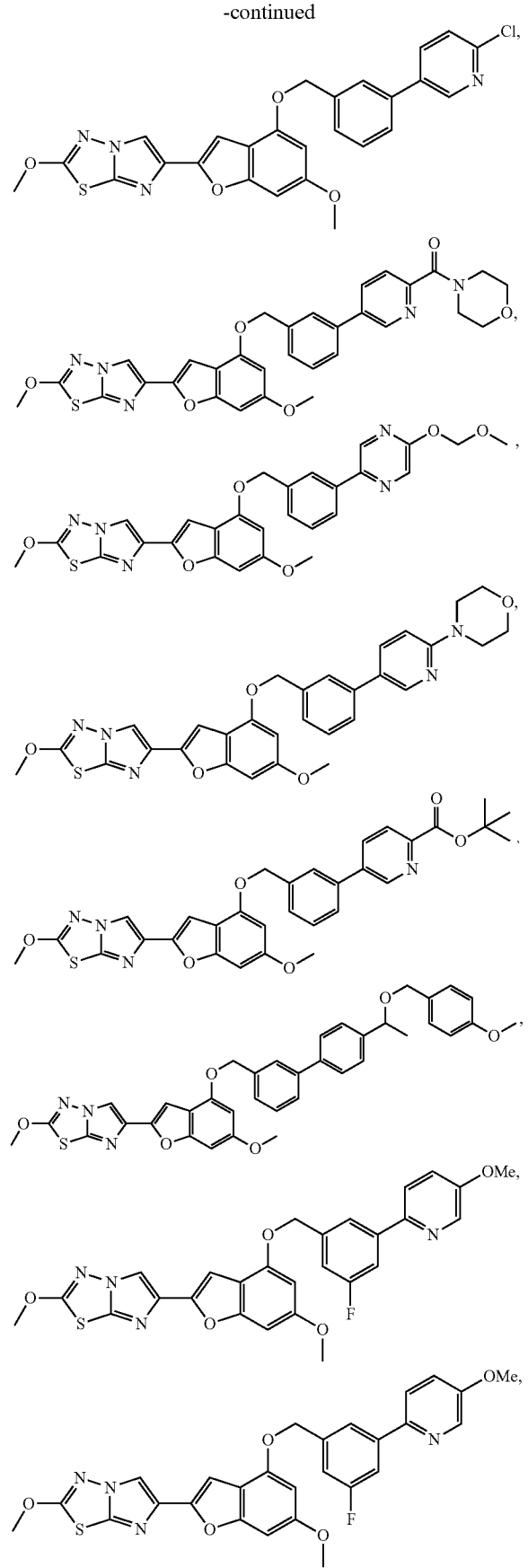
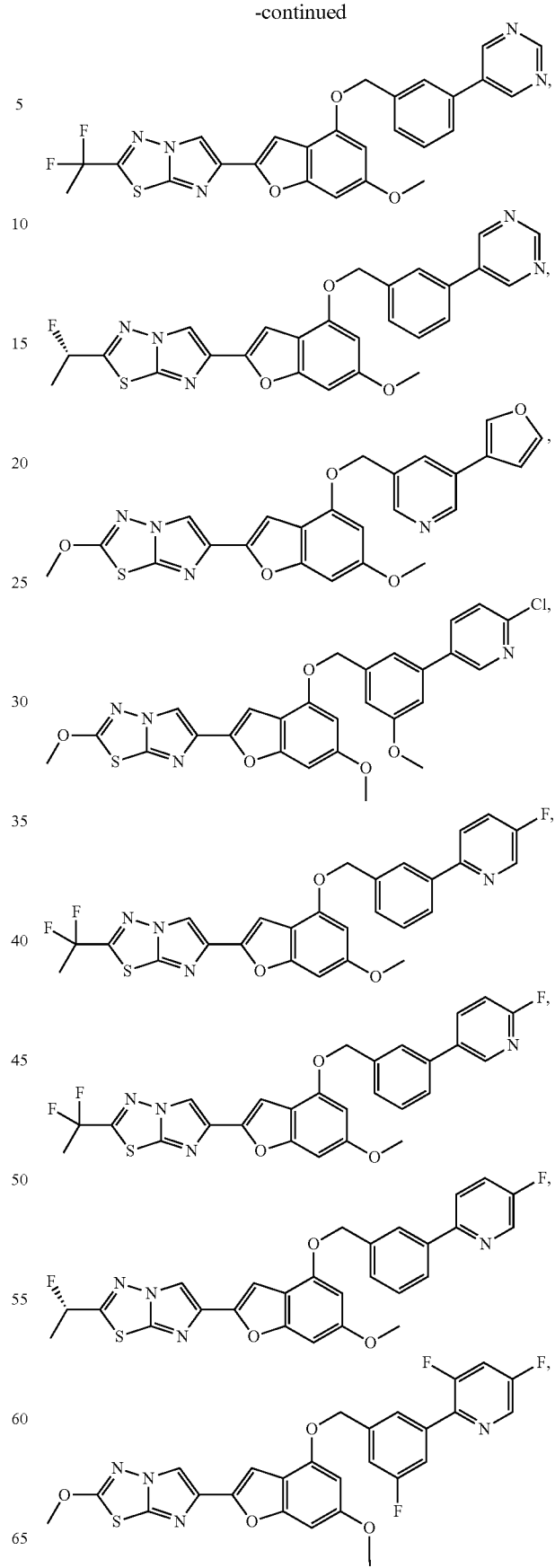

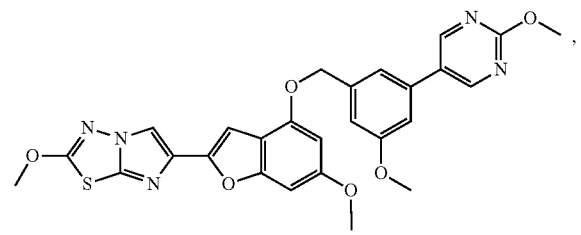,
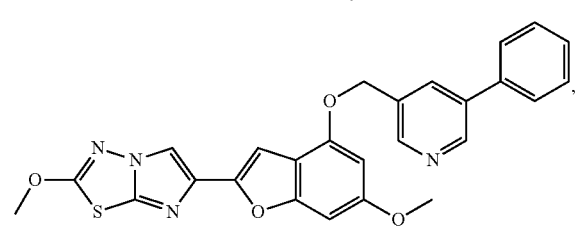,
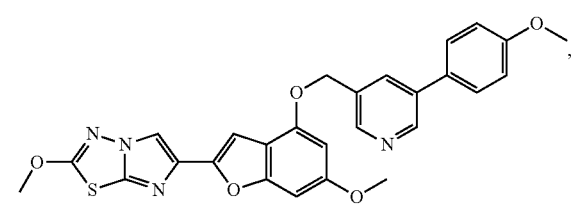,
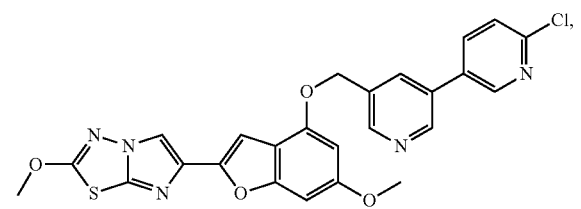,
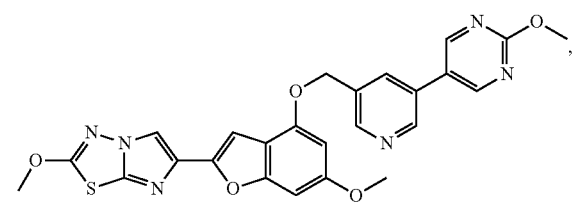,
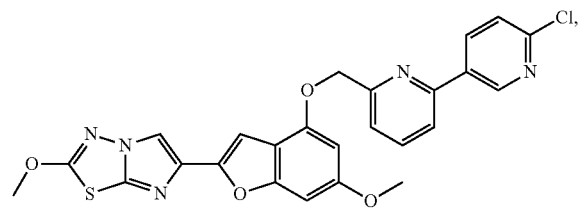,
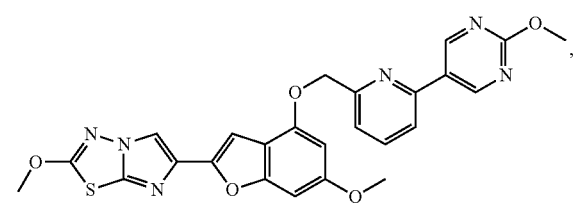,
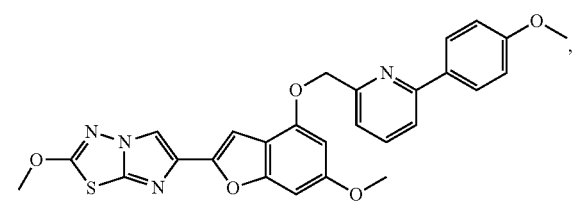,
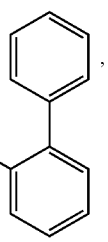,
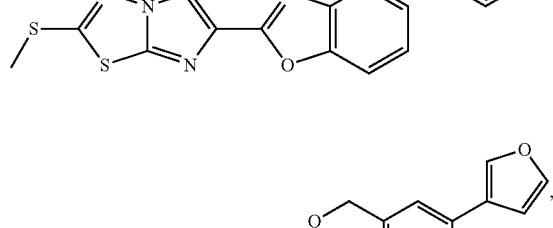,
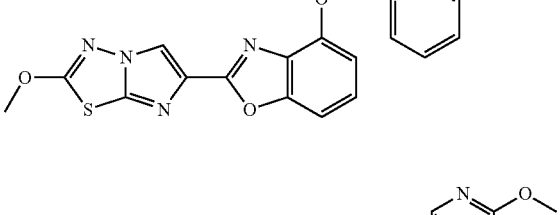,
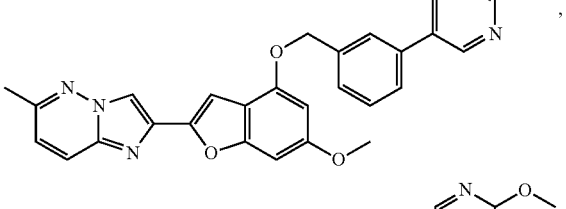,
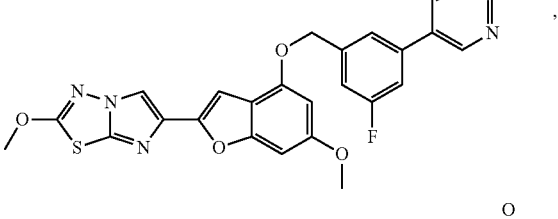,
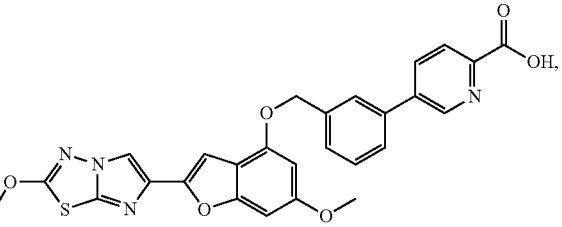,
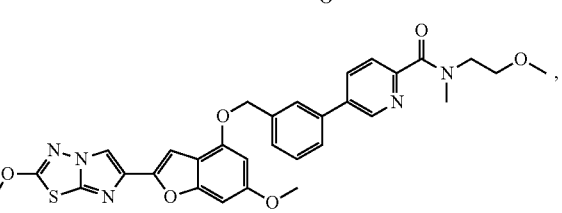,
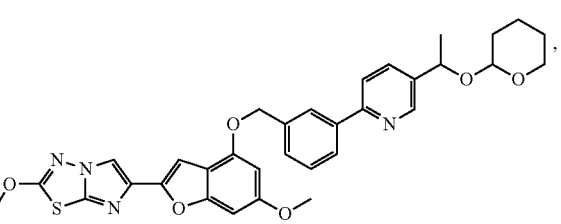, 255
-continued
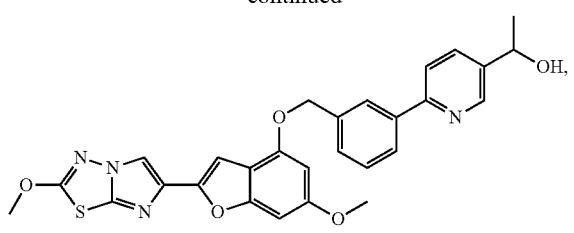
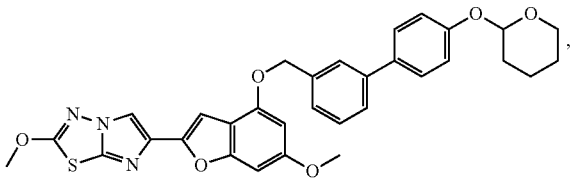
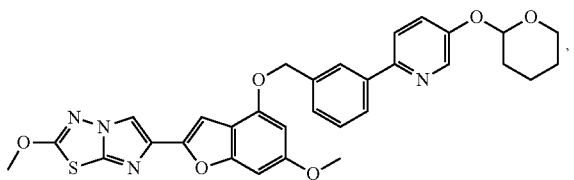
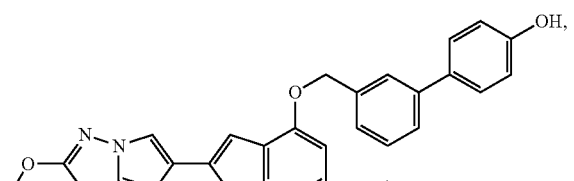
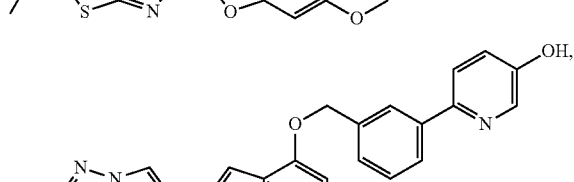
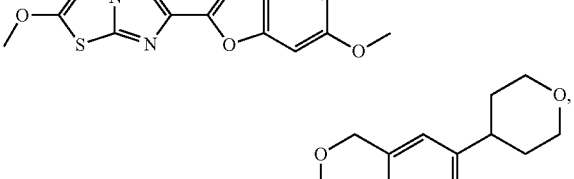
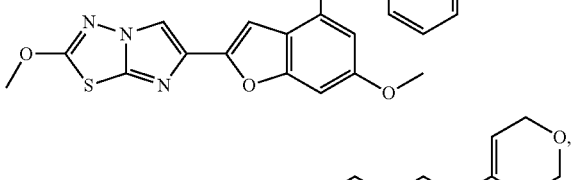
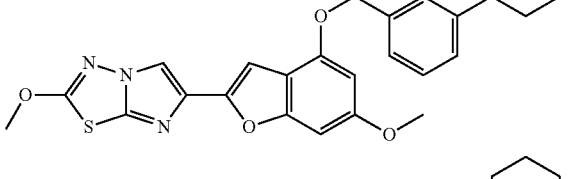
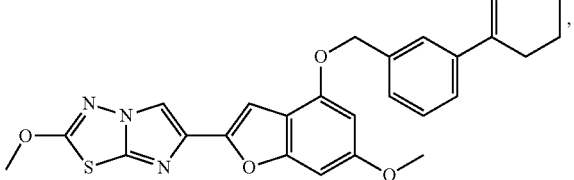
256
-continued
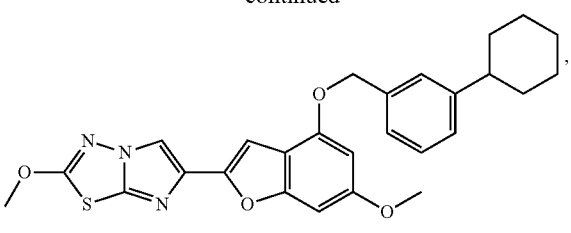
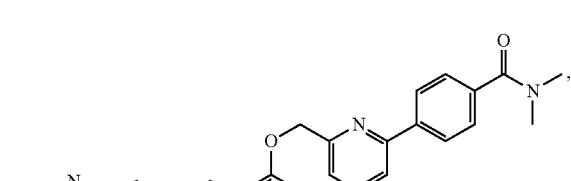
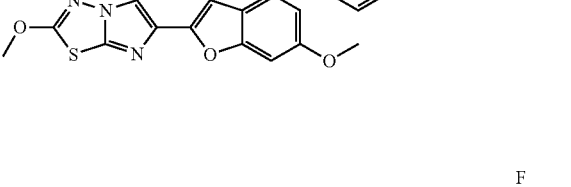
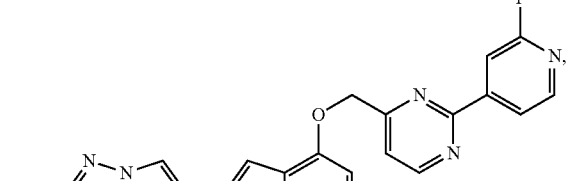
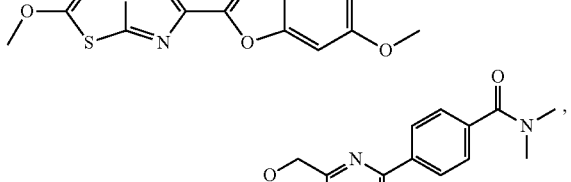
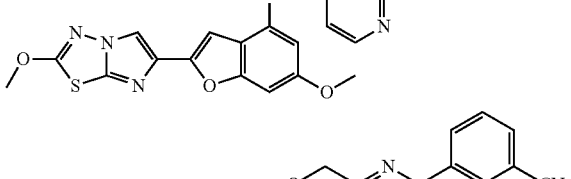
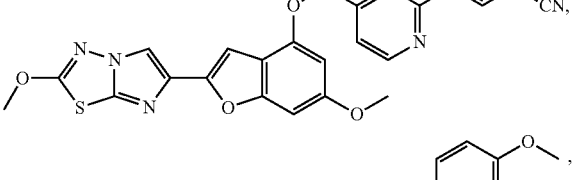
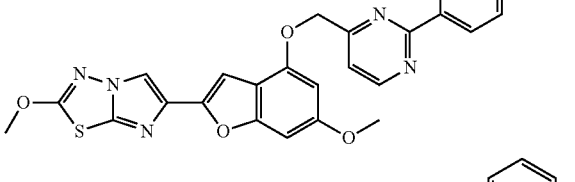
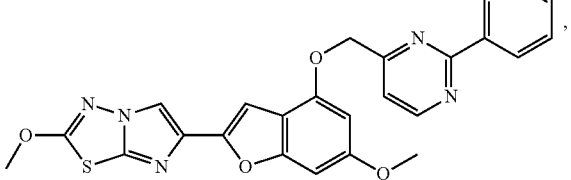

257
-continued

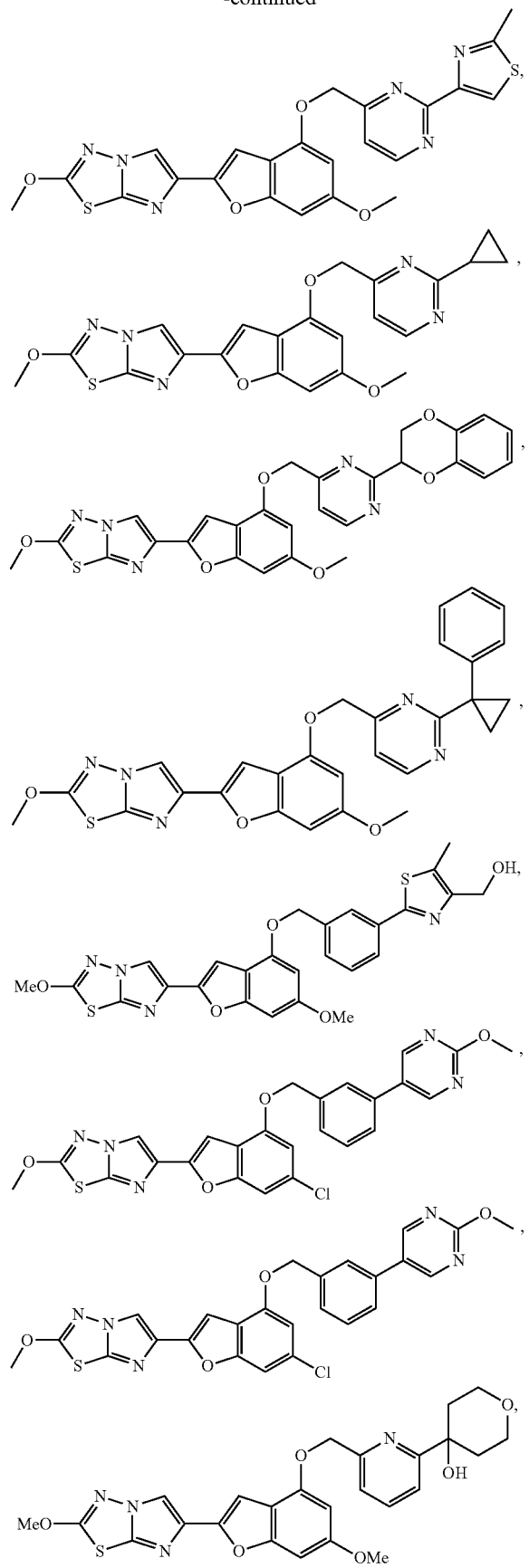

258
-continued

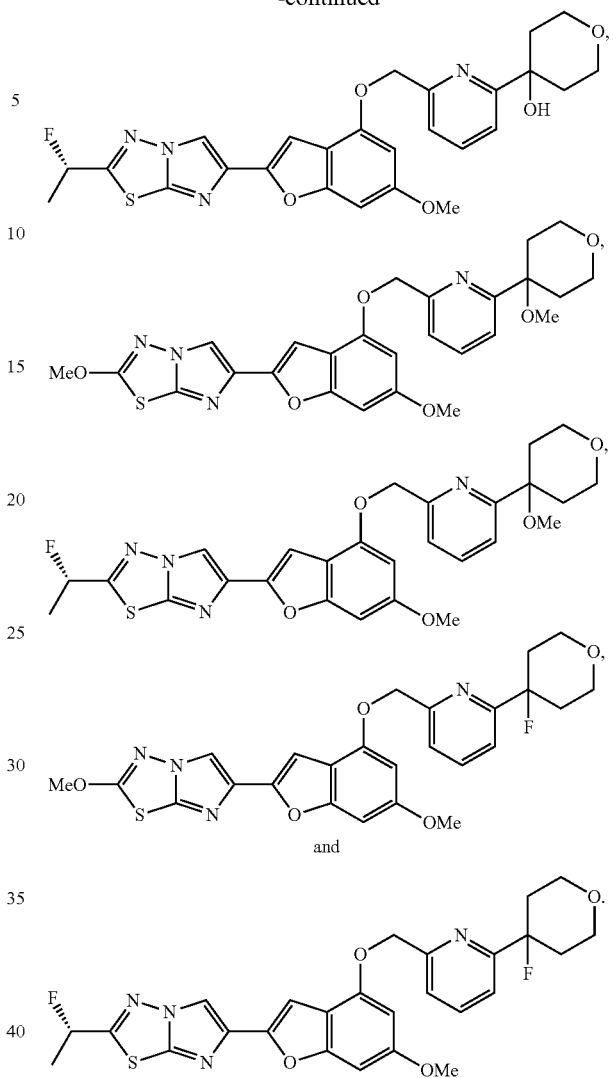

13. A pharmaceutical composition, which comprises a pharmaceutically acceptable carrier and a compound of claim 1, or stereoisomers, tautomers, pharmaceutically acceptable salts, or solvates thereof, alone or in combination with another therapeutic agent.

14. A method for the treatment of a thromboembolic disorder or the primary or secondary prophylaxis of a thromboembolic disorder, which comprises the steps of administering to a patient in need thereof a therapeutically effective amount of a compound of claim 1, or stereoisomers, tautomers, pharmaceutically acceptable salts, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

15. A method of inhibiting or preventing platelet aggregation, which comprises the step of administering to a subject in need thereof a therapeutically effective amount of a PAR4 antagonist, of claim 1.

16. A pharmaceutical composition, which comprises a pharmaceutically acceptable carrier and a compound of claim 12, or stereoisomers, tautomers, pharmaceutically acceptable salts, or solvates thereof, alone or in combination with another therapeutic agent.

17. A method for the treatment of a thromboembolic disorder or the primary or secondary prophylaxis of a thromboembolic disorder, which comprises the steps of administering to a patient in need thereof a therapeutically effective amount of a compound of claim 12, or stereoisomers, tautomers, pharmaceutically acceptable salts, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

18. A method of inhibiting or preventing platelet aggregation, which comprises the step of administering to a subject in need thereof a therapeutically effective amount of a PAR4 antagonist, of claim 12.

\* \* \* \* \*